US012460234B2

(12) United States Patent
Gonzalez et al.

(10) Patent No.: US 12,460,234 B2
(45) Date of Patent: Nov. 4, 2025

(54) SYNTHESIS OF ISOPRENOIDS AND DERIVATIVES

(71) Applicant: William Marsh Rice University, Houston, TX (US)

(72) Inventors: Ramon Gonzalez, Tampa, FL (US); James M. Clomburg, Houston, TX (US); Seokjung Cheong, Emeryville, CA (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 18/330,944

(22) Filed: Jun. 7, 2023

(65) Prior Publication Data

US 2024/0182932 A1 Jun. 6, 2024

Related U.S. Application Data

(62) Division of application No. 17/234,398, filed on Apr. 19, 2021, now abandoned, which is a division of application No. 16/081,756, filed as application No. PCT/US2017/022581 on Mar. 15, 2017, now Pat. No. 11,046,978.

(60) Provisional application No. 62/308,937, filed on Mar. 16, 2016, provisional application No. 62/343,598, filed on May 31, 2016.

(51) Int. Cl.
*C12P 7/42* (2006.01)

(52) U.S. Cl.
CPC .................................... *C12P 7/42* (2013.01)

(58) Field of Classification Search
None
See application file for complete search history.

(56) References Cited

U.S. PATENT DOCUMENTS

| | | | | |
|---|---|---|---|---|
| 8,546,362 | B2 | 10/2013 | Sulur et al. | |
| 8,884,100 | B2 | 11/2014 | Page et al. | |
| 8,895,307 | B2 | 11/2014 | Li et al. | |
| 9,416,364 | B2 | 8/2016 | Gonzalez et al. | |
| 9,611,460 | B2 | 4/2017 | Page et al. | |
| 9,994,881 | B2 | 6/2018 | Gonzalez et al. | |
| 11,046,978 | B2 * | 6/2021 | Gonzalez | C12P 7/24 |
| 2003/0125573 | A1 | 7/2003 | Millis et al. | |
| 2011/0229942 | A1 | 9/2011 | Cambbell et al. | |
| 2012/0144523 | A1 | 6/2012 | Page et al. | |
| 2013/0067619 | A1 | 3/2013 | Page et al. | |
| 2013/0072394 | A1 | 3/2013 | Li et al. | |
| 2013/0316413 | A1 | 11/2013 | Gonzalez et al. | |
| 2014/0141476 | A1 | 5/2014 | Page et al. | |
| 2014/0273110 | A1 | 9/2014 | Gonzalez et al. | |
| 2015/0284743 | A1 | 10/2015 | Markiere et al. | |

FOREIGN PATENT DOCUMENTS

| | | | |
|---|---|---|---|
| WO | 2013036812 | A1 | 3/2013 |
| WO | 2013053824 | A1 | 4/2013 |
| WO | 2012109176 | A2 | 11/2013 |
| WO | 2014076016 | A1 | 5/2014 |
| WO | 201519142 | A1 | 2/2015 |
| WO | 2015191422 | A1 | 12/2015 |
| WO | 2015191972 | A2 | 1/2016 |
| WO | 2016010827 | A1 | 1/2016 |
| WO | 2016007258 | A1 | 3/2016 |
| WO | 2017020043 | A2 | 7/2017 |

OTHER PUBLICATIONS

Atsumi, S.; Cann, A. F.; Connor, M. R.; Shen, C. R.; Smith, K. M.; Brynildsen, M. P.; Choou, K. J. Y.; Hanai, T.; Liao, J. C. "Metabolic engineering of *Escherichia coli* for 1-butanol production." Metab. Eng. 10, 305-311 (2008).

Baba, T.; Ara, T.; Hasegawa, M.; Takai, Y.; Okumura, Y.; Baba, M.; Datsenko, K. A.; Tomita, M.; Wanner, B. L.; Mori, H. "Construction of *Escherichia coli* K-12 in-frame, single-gene knockout mutants: the Keio collection." Mol Syst Biol 2 (2006).

Blecher, M. "Synthesis of long-chain fatty acyl-CoA thioesters using N-hydroxysuccinimide esters." Methods in Enzymology, 72, 404-408 (1981).

Chen, J.; Zhu, X.; Tan, Z.; Xu, H.; Tang, J.; Xiao, D.; Zhang, X. "Activating C4-dicarboxylate transporters DcuB and DcuC for improving succinate production." Appl. Microbiol. Biotechnol. 98, 2197-2205 (2014).

(Continued)

*Primary Examiner* — Christian L Fronda
(74) *Attorney, Agent, or Firm* — Baker, Donelson, Bearman, Caldwell, & Berkowitz, PC

(57) ABSTRACT

This disclosure generally relates to the use of enzyme combinations or recombinant microbes comprising same to make isoprenoid precursors, isoprenoids and derivatives thereof including prenylated aromatic compounds. Novel metabolic pathways exploiting Claisen, aldol, and acyloin condensations are used instead of the natural mevalonate (MVA) pathway or 1-deoxy-d-xylulose 5-phosphate (DXP) pathways for generating isoprenoid precursors such as isopentenyl pyrophosphate (IPP), dimethylallyl pyrophosphate (DMAPP), and geranyl pyrophosphate (GPP). These pathways have the potential for better carbon and or energy efficiency than native pathways. Both decarboxylative and non-carboxylative condensations are utilized, enabling product synthesis from a number of different starting compounds. These condensation reactions serve as a platform for the synthesis of isoprenoid precursors when utilized in combination with a variety of metabolic pathways and enzymes for carbon rearrangement and the addition/removal of functional groups. Isoprenoid alcohols are key intermediary products for the production of isoprenoid precursors in these novel synthetic metabolic pathways. These precursors can be modified to various isoprenoid products through prenyl transferase, terpene synthase, or terpene cyclases. The production of prenylated aromatic compounds is achieved through prenyl transfer of the hydrocarbon units of isoprenoid precursors to polyketides.

8 Claims, 88 Drawing Sheets

Specification includes a Sequence Listing.

(56) References Cited

OTHER PUBLICATIONS

Cheong, S.; Clomburg, J. M.; Gonzalez, R. Energy-and carbon-efficient synthesis of functionalized small molecules in bacteria using non-decarboxylative Claisen condensation reactions. Nat Biotech 34, 556-561 (2016).
Choi, S. Y.; Park, S. J.; Kim, W. J.; Yang, J. E.; Lee, H.; Shin, J.; Lee, S. Y. One-step fermentative production of poly(lactate-co-glycolate) from carbohydrates in *Escherichia coli*. Nat Biotech 34, 435-440 (2016).
Clomburg, J. M.; Vick, J. E.; Blanschien, M. D.; Rodriguez-Moya, M.; Gonzalez, R. "A synthetic biology approach to engineer a functional reversal of the beta-oxidation cycle." ACS Synthetic Biology 1, 541-554 (2012).
Cracan, V. R.; Banerjee, R. "Novel B12-dependent acyl-CoA mutases and their biotechnological potential." Biochemistry 51 (31), 6039-6046 (2012).
Dellomonaco, C.; Clomburg, J. M.; Miller, E. N.; Gonzalez, R. "Engineered reversal of the beta-oxidation cycle for the synthesis of fuels and chemicals." Nature 476, 355-359 (2011).
Gao, Y.; Honzatko, R. B.; Peters, R. J. "Terpenoid synthase structures: a so far incomplete view of complex catalysis." Natural Product Reports, 29, 1153-1175 (2012).
Haapalainen, A. M.; Merilainene, G.; Wierenga, R. K. "The thiolase superfamily: condensing enzymes with diverse reaction specificities. " Trends in Biochemical Sciences 31, 64-71 (2006).
Heath, R. J.; Rock, C. O. "The Claisen condensation in biology." Nat. Prod. Rep. 19, 581-596 (2002).
Iijima, Y.; Gang, D. R.; Freidman, E.; Lewinsohn, E.; Pichersky, E. "Characterization of Geraniol Synthase from the Peltate Glandsof Sweet Basil." Plant Physiol. 134, 370-379 (2004).
Jiang, C.; Kim, S. Y.; Suh, D-Y. "Divergent evolution of the thiolase superfamily and chalcone synthase family." Molecular Phylogenetics and Evolution 49, 691-701 (2008).
Jiang, Y.; Chen, B.; Duan, C.; Sun, B.; Yang, J.; Yang, S. "Multigene editing in the Escherichia coli genome via the CRISPR-Cas9 System." Appl. Environ. Microbiol. 81, 2506-2514 (2015).
Kim, J.; Darley, D.; Buckel, W. "2-Hydroxyisocaproyl-CoA dehydratase and its activator from Clostridium difficile." Febs J. 272, 550-561 (2005).
Kitagawa, M.; Ara, T.; Arifuzzaman, M.; Toka-Nakamichi, T.; Inamoto, E.; Toyonaca, H.; Mori, H. "Complete set of ORF clones of *Escherichia coli* ASKA library (A complete Set of *E. coli* K-12 ORF archive): Unique resources for biological research." DNA Res. 12, 291-299 (2005).
Kuzuyama, T.; Noel, J.; Richard, S. "Structural basis for the promiscuous biosynthetic prenylation of aromatic natural products." Nature 435, 983-987 (2005).
Liu, Y, et al. Improving the catalytic activity of isopentenyl phosphate kinase through protein coevolution analysis. Scientific Reports 6, 24117 (2016).
Mabanglo, M. F.; Pan, J-J.; Shakya, B.; Poulter, C. D. "Mutagenesis of isopentenyl phosphate kinase to enhance geranyl phosphate kinase activity." ACS Chem. Biol. 7, 1241-1246 (2012).
Magner, D. B.; Blankschien, M. D.; Lee< J. A.; Pennington, J. M.; Lupski, J. R.; Rosenberg, S. M. RecQ promotes toxic recombination in cells lacking recombination intermediate-removal proteins. Mol. Cell 26, 273-286 (2007).
Neidhardt, F. C.; Bloch, P. L.; Smith, D. F. "Culture medium for enterobacteria." J. Bacteriol. 119, 736-747 (1974).
Parasaran, T.; Tarbell, D. S. "Formic ethylcarbonic anhydride." The Journal of Organic Chemistry, 29(11), 3422-3423 (1964).
Reiling, K. K.; Yoshikuni, Y.; Martin, V. J. J.; Newman, J.; Bohlman, J.; Keasling, J. D. "Mono and diterpene production in *Escherichia coli*." Biotechnol Bioeng 87 (2004).
Sambrook, J."Molecular cloning: a laboratory manual." Edn. 3rd. (Cold Spring Harbor Laboratory Press., Cold Spring Harbor, N.Y.; 2001).
Schrader, J.; Bohlmann, J. "Biotechnology of isoprenoids." vol. 149. Springer, (2015).
Studier, F. W.; Moffatt, B. A. "Use of bacteriophage T7 RNA polymerase to direct selective high-level expression of cloned genes." J. Mol. Biol. 189, 113-130 (1986).
Thomason, L. C.; Sawitzke, J. A.; Li, X.; Costantino, N.; Court, D. L. "Recombineering: Genetic engineering in bacteria using homologous recombination." Current Protocols in Molecular Biology (John Wiley & Sons, Inc., 2001).
Vick, J. E.; Clomburg, J. M.; Blanschien, M. D.; Chou, A.; Kim, S.; Gonzalez, R. "*Escherichia coli* enoyl-acyl carrier protein reductase (Fabl) supports efficient operation of a functional reversal of the beta-oxidation cycle." Appl. Environ. Microbiol. 81, 1406-1416 (2015).
Vick, J. E.; Johnson, E. T.; Choudhary, S.; Bloch, S. E.; Lopez-Gallego, F.; Srivastava, P.; Tikh, H. B.; Wawrzyn, G. T.; Schmidt-Dannert, C. "Optimized compatible set of BioBrickTM vectors for metabolic pathway engineering." Appl. Microbiol. Biotechnol. 92, 1275-1286 (2011).
Yazdani, S. S.; Gonzalez, R. "Engineering *Escherichia coli* for the efficient conversion of glycerol to ethanol and co-products." Metab. Eng. 10, 340-351 (2008).
Shindo, K.; Tachibana, A.; Tanaka, A.; Toba, S.; Yuki, E.; Ozaki, T.; Kumano, T.; Nishiyama, M; Misawa, N.; Kuzuyama, T. "Production of novel antioxidative prenyl naphthalen-ols combinational bioconversion with dixugenase phnA1A2A3A4 and prenylktransferase NphB or SCO7190." Bioscience, Biotech., Biochem., 75, 3, 505-510 (2014).
Chica, R. A.; Doucet, N.; Pelletier, J. N. "Semi-rational approaches to engineering enzyme activity: combining the benefits of directed evolution and rational design." Curr. Opinion in Biotech., 16, 378-384 (2005).
Kumano, T.; Richard, S. B.; Noel, J. P.; Nishiyama, M.; Kuzuyama, T. "Chemoenzymatic synthesis of prenylated aromatic small molecules using Streptomyces prenyltransferases with relaxed substrate specificities." Bioorganic & Medicinal Chemistry, 16, 8117-8126 (2008).
Kizer, L.; Pitera, D. J.; Pfleger, B. F.; Keasling, J. D. "Application of functional genomics to pathway optimization for increased isoprenoid production." Applied ns Environ. Microbiol. 3229-3241 (2008).
Singh, R. K.; Lee, J-K., Selvaraj, C.; Singh, R.; Li, J.; Kim, S-Y.; Kalia, V. C. "Protein engineering approaches in the post-genomic era." Curr. Protein & Peptide Sci., 18, 1-11 (2017).
Edgar, S. M. "Metabolic engineering for the production of functionalized terpenoids in heterologous hosts." Thesis submitted to the Dept. Chem. Eng. Massachusetts Inst. Tech. (2017).
Prather, K. L. J.; Martin, C. H. "De novo biosynthetic pathways: rational design of microbial chemical factories." Curr. Opinion in Biotech. 19, 468-474 (2008).
Cheong, S. "Development of de novo biosynthetic pathways." Thesis submitted to the Dept. of Chem. Eng. at William Marsh Rice University, (2017).
Fitzpatrick, A. H.; Bhandari, J.; Crowell, D. N. "Farnesol kinase is involved in farnesol metabolism, ABA signaling and flower development in *Arabidopsis*." The Plant Journal, 66, 1078-1088 (2011).
Zheng, Y.; Liu, Q.; Li, L.; Qin, W.; Yang, J.; Zhang, H.; Jiang, X.; Cheng, T.; Liu, W.; Xu, X.; Xian, M. "Metabolic engineering of *Escherichia coli* for high-specificity production of isoprenol and prenol as next generation of biofuels." Biotechnology for Biofuels, 6, 57 (2013).
International Search Report and Written Opinion in International Application No. PCT/US2017/022581, mailed Jul. 26, 2017.
B. Markus Lange and Rodney Croteau, "Isopentenyl diphosphate biosynthesis via a mevalonate-independent pathway: Isopentenylrnonophosphate kinase catalyzes the terminal enzymatic step". In the Journal of Proceedings of the National Academy of Sciences, vol. 96, Issue 24, Sep. 13, 1999, pp. 13714-13719.

* cited by examiner

Continue to FIG. 1B

Continued from FIG. 1A acetyl-CoA + propionyl-CoA 2-methylacetoacetyl-CoA 3-hydroxy-2-methylbutanoyl-CoA 2-methyl-2-butenoyl-CoA (tiglyl-CoA)

FIG. 2A
primer
extender unit
thiolase
3-hydroxyacyl-CoA dehydrogenase
enoyl-CoA hydratase
mutase
thiolase
β-reduction
thiolase

3-methyl-2-butenoyl-CoA (3-methylcrotonyl-CoA)

acetyl-CoA 3-oxo-5-methyl-4-hexenoyl-coA 5-methyl-4-hexenoyl-coA propionyl-CoA 3-oxo-2,7-dimethyl-6-octenoyl-CoA Continue to FIG. 2B Continued from FIG. 2A Continue to FIG. 3B Continued from FIG. 3A propionyl-CoA glycolyl-CoA 2-hydroxy-3-oxopentanoyl-CoA 2,3-dihydroxypentanoyl-CoA 2-hydroxy-2-pentenoyl-CoA 2-hydroxypentanoyl-CoA 2-hydroxy-3-methylbutanoyl-CoA Continue to FIG. 4B Continued from FIG. 4A Continue to FIG. 5B Continued from FIG. 5A acetyl-CoA propionyl-CoA 2-methylacetoacetyl-CoA 3-hydroxy-2-methylbutanoyl-CoA 2-methyl-2-butenoyl-CoA (tiglyl-CoA)

Continue to FIG. 6B

Continued from FIG. 6A

Continue to FIG. 8B pyruvate
pyruvate
(S)-2-acetolactate
(2R)-2,3-dihydroxy-3-methylbutanoate
3-methyl-2-oxobutanoate (2-oxoisovalerate)
(2R)-3-methyl-2-hydroxybutanoate (2-hydroxyisovalerate)
(2R)-3-methyl-2-hydroxybutanoyl-CoA (2-hydroxyisovaleryl-CoA)
(2R)-3-methyl-2-hydroxybutanoate
(2R)-3-methyl-2-hydroxybutanal
(2R)-3-methyl-1,2-butanediol
3-methylbutanal Continue to FIG. 9B Continued from FIG. 9A Continue to FIG. 10B (2R)-3-methyl-2-hydroxybutanoyl-CoA
(2-hydroxyisovaleryl-CoA)

Continue to FIG. 11B, 11C

FIG. 11B
Continued from FIG. 11A
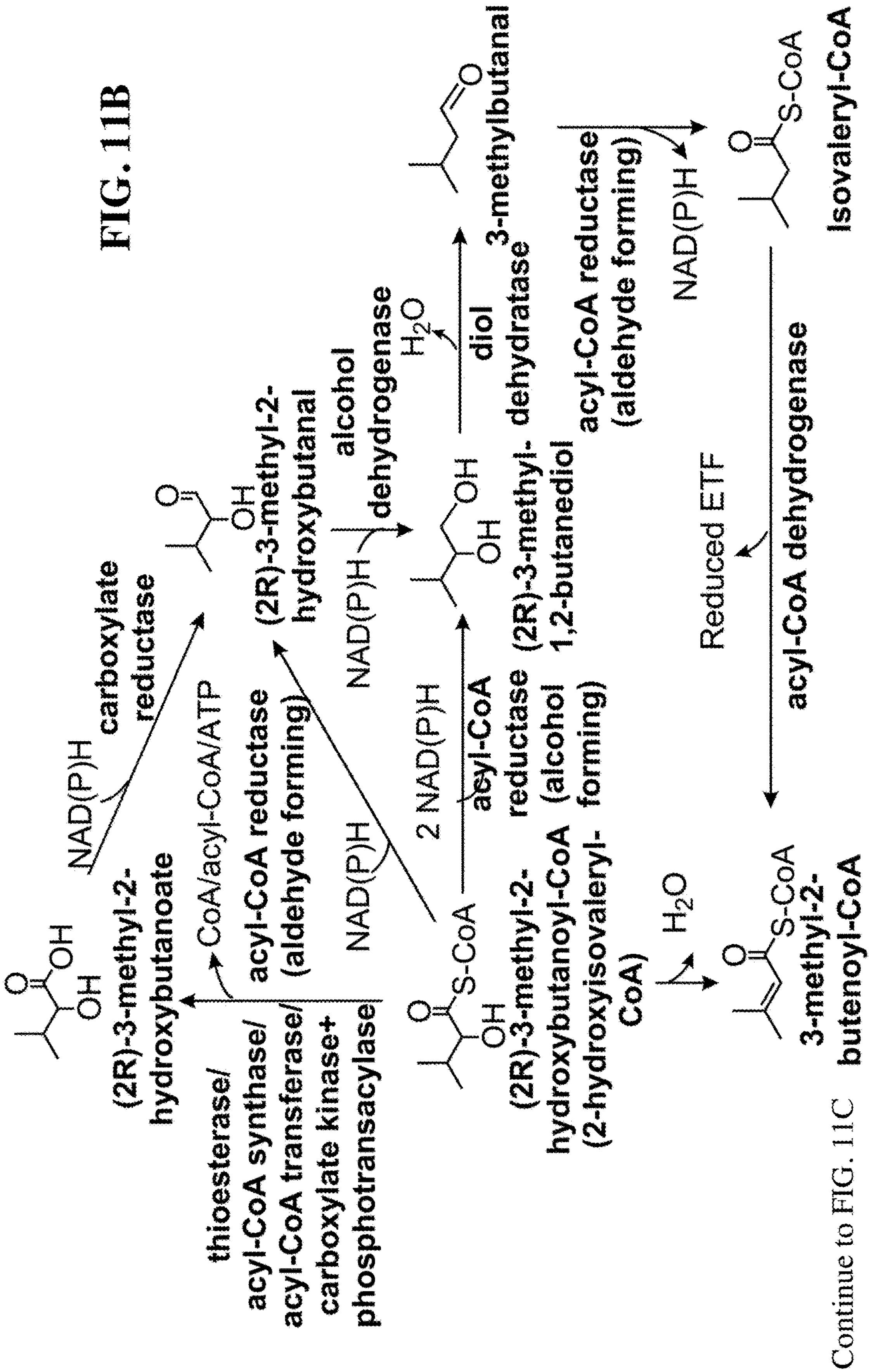
Continue to FIG. 11C

Continued from FIG. 13A

Continue to FIG. 14B

Continued from FIG. 14A

Continue to FIG. 16B

Continued from FIG. 16A

FIGURE 30A-1

| The invention includes any one or more of the following embodiment(s), in any combination(s) thereof: |
| --- |
| A genetically engineered microorganism producing prenylated aromatic compounds, said microorganism comprising:<br>a) at least one overexpressed thiolase able to catalyze a non-decarboxylative Claisen condensation of an acyl-CoA thioester primer and acyl-CoA thioester extender unit, β-reduction enzymes, acyl-CoA mutases and termination pathways to form isoprenoid precursors selected from a group comprising isopentenyl pyrophosphate (IPP), dimethylallyl pyrophosphate (DMAPP), geranyl pyrophosphate (GPP), or farnesyl pyrophosphate (FPP);<br>b) at least one overexpressed thiolase able to catalyze the non-decarboxylative Claisen condensation of an acyl-CoA thioester primer and acyl-CoA thioester extender unit, β-reduction enzymes, and termination pathways to form polyketide products;<br>c) at least one overexpressed aromatic prenyltransferase or 4-hydroxybenzoate grenyltransferase able to catalyze a prenyl transfer of said isoprenoid precursor to said polyketide product to form a prenylated aromatic compound; and,<br>d) a reduced expression of fermentation enzymes to reduced production of lactate, acetate, ethanol and succinate. |
| Any microorganism or method herein described, wherein the formation of said isoprenoid precursors comprises:<br>a) an overexpressed thiolase that catalyzes the non-decarboxylative Claisen condensation between an unsubstituted or functionalized acyl-CoA thioester primer and an unsubstituted or functionalized acyl-CoA thioester extender unit to form a β-keto-acyl-CoA thioester;<br>b) an overexpressed set of β-reduction enzymes that catalyzes the conversion of said β-keto-acyl-CoA thioester to a β-hydroxyacyl-CoA thioester, a trans-enoyl-CoA thioester, or an acyl-CoA thioester;<br>c) an overexpressed acyl-CoA mutase that catalyzes the carbon rearrangement of methyl branches on said β-keto-acyl-CoA thioester, β-hydroxy-acyl-CoA thioester, trans-enoyl-CoA thioester, or acyl-CoA thioester;<br>d) iterations of steps a, b, and c, wherein said iteration is achieved by utilizing the CoA thioesters generated in steps a, b, or c of the previous turn as a primer or an extender unit of step a in the next turn of iteration to elongate the CoA thioester chain by two carbons; and,<br>e) an overexpressed termination pathway that catalyzes the conversion of said β-keto-acyl-CoA thioester, β-hydroxy-acyl-CoA thioester, trans-enoyl-CoA thioester, or acyl-CoA thioester generated in steps a, b, c, or d into said isoprenoid precursors |

FIGURE 30A-2

| |
|---|
| Any microorganism or method herein described, wherein the formation of said polyketide products comprises:<br>a) an overexpressed thiolase that catalyzes the non-decarboxylative Claisen condensation between an acyl-CoA primer with an acyl-CoA thioester extender unit to form a polyketide CoA thioester;<br>b) iterations of step a, wherein said iteration is achieved by utilizing the polyketide CoA thioester generated in step a of the previous turn as a primer or an extender unit of step b in the next turn of iteration to elongate the polyketide chain by two carbons; and,<br>c) a termination pathway of the carbon chain elongation, wherein said termination pathway is consisting a CoA thioester removal hydrolysis reaction performed spontaneously or by an overexpressed thioesterase, and subsequent spontaneous reactions for the rearrangement or cycle generation of polyketide product. |
| Any microorganism or method herein described, wherein said acyl-CoA primer is an acyl-CoA thioester whose omega group is selected from the group consisting of hydrogen, alkyl group, hydroxyl group, carboxyl group, aryl group, halogen, amino group, hydroxyacyl group, carboxyacyl group, aminoacyl group, ketoacyl group, halogenated acyl group, and any other functionalized acyl groups. |
| Any microorganism or method herein described, wherein said acyl-CoA thioester extender unit is an acyl-CoA thioester whose omega group is selected from the group consisting of hydrogen, alkyl group, hydroxyl group, carboxyl group, aryl group, halogen, amino group, hydroxyacyl group, carboxyacyl group, aminoacyl group, ketoacyl group, halogenated acyl group, and any other functionalized acyl groups. |
| Any microorganism or method herein described, wherein said β-reduction enzymes are selected from the group consisting of:<br>a) an overexpressed 3-oxoacyl-[acyl-carrier-protein] reductase or overexpressed 3-hydroxyacyl-CoA dehydrogenase that catalyzes the reduction of a β-ketoacyl-CoA to a β-hydroxyacyl-CoA;<br>b) an overexpressed 3-hydroxyacyl-[acyl-carrier-protein] dehydratase or an overexpressed enoyl-CoA hydratase or 3-hydroxyacyl-CoA dehydratase that catalyzes the dehydration of a β-hydroxyacyl-CoA to a trans-enoyl-CoA; and,<br>c) an overexpressed enoyl-[acyl-carrier-protein] reductase or acyl-CoA dehydrogenase or trans-enoyl-CoA reductase that catalyzes the reduction of a transenoyl-CoA to an acyl-CoA. |
| Any microorganism or method herein described, wherein said termination pathway is selected from the group consisting of:<br>a) a thioesterase, or an acyl-CoA:acetyl-CoA transferase, or a phosphotransacylase and a carboxylate kinase;<br>b) an alcohol-forming coenzyme-A thioester reductase, or an aldehyde-forming CoA thioester reductase and an alcohol dehydrogenase;<br>c) an aldehyde-forming CoA thioester reductase;<br>d) an aldehyde-forming CoA thioester reductase and an aldehyde decarbonylase;<br>e) an alcohol dehydratase;<br>f) an alcohol kinase or an alcohol phosphotransferase; and,<br>g) an isopentenyl-diphosphate isomerase. |

FIGURE 30A-3

| |
|---|
| Any microorganism or method herein described, further comprising an overexpressed geranyl-, farnesyl- or, geranylgeranyl-diphosphate synthase catalyzing the head-to-tail or head-to-head condensation of said isoprenoid precursors. |
| Any microorganism or method herein described, wherein said isoprenoid precursor is geranyl pyrophosphate, said polyketide product is olivetolic acid, and said prenylated aromatic compound is cannabigerolic acid. |

FIGURE 30B-1

| The invention includes any one or more of the following embodiment(s), in any combination(s) thereof: |
|---|
| A genetically engineered microorganism comprising:<br>a) an overexpressed thiolase able to catalyze a non-decarboxylative Claisen condensation between an unsubstituted or functionalized acyl-CoA thioester primer and an unsubstituted or functionalized acyl-CoA thioester extender unit to form a β-keto-acyl-CoA thioester;<br>b) an overexpressed set of β-reduction enzymes able to catalyze the conversion of said β-keto-acyl-CoA thioester to a β-hydroxyacyl-CoA thioester, a trans-enoyl-CoA thioester, or an acyl-CoA thioester;<br>c) an overexpressed acyl-CoA mutase able to catalyze the carbon rearrangement of methyl branches within said β-keto-acyl-CoA thioester, β-hydroxy-acyl-CoA thioester, trans-enoyl-CoA thioester, or acyl-CoA thioester;<br>d) iterations of steps a, b, and c, wherein said iteration is achieved by utilizing the CoA thioesters generated in steps a, b, or c of the previous turn as a primer or an extender unit of step a in the next turn of iteration to elongate the CoA thioester chain by two carbons;<br>e) an overexpressed termination pathway that catalyzes the conversion of said β-keto-acyl-CoA thioester, β-hydroxy-acyl-CoA thioester, trans-enoyl-CoA thioester, or acyl-CoA thioester generated in steps a, b, c, or d into a isoprenoid precursor selected from the group comprising isopentenyl pyrophosphate (IPP), dimethylallyl pyrophosphate (DMAPP), geranyl pyrophosphate (GPP), or farnesyl pyrophosphate (FPP);<br>f) an overexpressed prenyl transferase, terpene synthase, or terpene cyclase able to catalyze the conversion of said isoprenoid precursors to desired isoprenoid products; and,<br>g) reduced expressions of fermentation enzymes leading to reduced production of lactate, acetate, ethanol and succinate. |
| Any microorganism or method herein described, wherein said acyl-CoA primer is an acyl CoA thioester whose omega group is selected from the group consisting of hydrogen, alkyl group, hydroxyl group, or carboxyl group. |
| Any microorganism or method herein described, wherein said omega-functionalized CoA thioester extender unit is an acyl CoA thioester whose omega group is selected from the group consisting of hydrogen, alkyl group, or hydroxyl group. |
| Any microorganism or method herein described, wherein said β-reduction enzymes are selected from the group consisting of:<br>a) an overexpressed 3-oxoacyl-[acyl-carrier-protein] reductase or overexpressed 3-hydroxyacyl-CoA dehydrogenase that catalyzes the reduction of a β-ketoacyl-CoA to a β-hydroxyacyl-CoA;<br>b) an overexpressed 3-hydroxyacyl-[acyl-carrier-protein] dehydratase or an overexpressed enoyl-CoA hydratase or 3-hydroxyacyl-CoA dehydratase that catalyzes the dehydration of a β-hydroxyacyl-CoA to a trans-enoyl-CoA; and,<br>c) an overexpressed enoyl-[acyl-carrier-protein] reductase or acyl-CoA dehydrogenase or trans-enoyl-CoA reductase that catalyzes the reduction of a transenoyl-CoA to an acyl-CoA. |

FIGURE 30B-2

| |
|---|
| Any microorganism or method herein described, said termination pathway is selected from the group consisting of:<br>a) a thioesterase, or an acyl-CoA:acetyl-CoA transferase, or a phosphotransacylase and a carboxylate kinase;<br>b) an alcohol-forming coenzyme-A thioester reductase, or an aldehyde-forming CoA thioester reductase and an alcohol dehydrogenase;<br>c) an aldehyde-forming CoA thioester reductase;<br>d) an aldehyde-forming CoA thioester reductase and an aldehyde decarbonylase;<br>e) an alcohol dehydratase;<br>f) an alcohol kinase; and,<br>g) an isopentenyl-diphosphate isomerase. |
| Any microorganism or method herein described, wherein said genetically engineered microorganism produces isoprenoids. |
| Any microorganism or method herein described, further comprising an overexpressed geranyl-, farnesyl- or, geranylgeranyl-diphosphate synthase catalyzing the head-to-tail or head-to-head condensation of isoprenoid precursors isopentenyl pyrophosphate (IPP), dimethylallyl pyrophosphate (DMAPP), geranyl pyrophosphate (GPP), or farnesyl pyrophosphate (FPP). |
| Any microorganism or method herein described, said aromatic prenyltransferase or 4-hydroxybenzoate grenyltransferase is encoded by a gene selected from the group consisting of Arabidopsis thaliana ppt1, Lithospermum erythrorhizon pgt-1, Lithospermum erythrorhizon pgt-2, Schizosaccharomyces pombe coq2, Cannabis sativa CsPT1, and other homologs and mutants. |
| Any microorganism or method herein described, said overexpressed thiolase is encoded by a gene(s) selected from the group consisting of E. coli atoB, E. coli yqeF, E. coli fadA, E. coli fadI, Ralstonia eutropha bktB, Pseudomonas sp. B13 catF, E coli paaJ, Rhodococcus opacus pcaF, Pseudomonas putida pcaF, Streptomyces sp. pcaF, P. putida fadAx, P. putida fadA, Ralstonia eutropha phaA, Acinetobacter sp. ADP1 dcaF, Clostridium acetobutylicum thlA, Clostridium acetobutylicum thlB, and other homologs and mutants. |
| Any microorganism or method herein described, wherein said overexpressed 3-hydroxyacyl-CoA dehydrogenase or 3-oxoacyl-[acyl-carrier-protein] reductase is encoded by a gene(s) selected from the group consisting of E. coli fabG, E. coli fadB, E. coli fadJ, E. coli paaH, P. putida fadB, P. putida fadB2x, Acinetobacter sp. ADP1 dcaH, Ralstonia eutrophus phaB, Clostridium acetobutylicum hbd and other homologs and mutants. |
| Any microorganism or method herein described, wherein said overexpressed enoyl-CoA hydratase, 3-hydroxyacyl-CoA dehydratase, or 3-hydroxyacyl-[acyl-carrier-protein] dehydratase is encoded by a gene(s) selected from the group consisting of E. coli fabA, E. coli fabZ, E. coli fadB, E. coli fadJ, E. coli paaF, P. putida fadB, P. putida fadB1x, Acinetobacter sp. ADP1 dcaE, Clostridium acetobutylicum crt, Aeromonas caviae phaJ, and other homologs and mutants. |

FIGURE 30B-3

| |
|---|
| Any microorganism or method herein described, wherein said acyl-CoA dehydrogenase, trans-enoyl-CoA reductase, or enoyl-[acyl-carrier-protein] reductase is encoded by a gene(s) selected from the group consisting of E. coli fadE, E. coli ydiO, Euglena gracilis TER, Treponema denticola TER, Clostridium acetobutylicum TER, E. coli fabI, Enterococcus faecalis fabK, Bacillus subtilis fabL, Vibrio cholerea fabV, and other homologs and mutants. |
| Any microorganism or method herein described, wherein said acyl-CoA mutase is encoded by a gene(s) selected from the group consisting Streptomyces cinnamonensis icmAB. Metallosphaera sedula Msed_0638, Msed_2055, Cupriavidus metallidurans icmF, Kyrpidia tusciae rcmAB, Rhodobacter sphaeroides meaA, and other homologs and mutants. |
| Any microorganism or method herein described, wherein said overexpressed thioesterase is encoded by a gene(s) selected from the group consisting of E. coli tesA, E. coli tesB, E. coli yciA, E. coli fadM, E. coli ydiI, E. coli ybgC, E. coli paaI, Mus musculus acot8, Alcanivorax borkumensis tesB2, Fibrobacter succinogenes Fs2108, Prevotella ruminicola Pr655, Prevotella ruminicola Pr1687, Lycopersicon hirsutum f glabratum mks2, and other homologs and mutants. |
| Any microorganism or method herein described, wherein said overexpressed acyl-CoA:acetyl-CoA transferase is encoded by a gene(s) selected from the group consisting of E. coli atoD, Clostridium kluyveri cat2, Clostridium acetobutylicum ctfAB, E. coli ydiF, and other homologs and mutants. |
| Any microorganism or method herein described, wherein said overexpressed phosphotransacylase is encoded by a gene(s) selected from the group consisting of Clostridium acetobutylicum ptb, Enterococcus faecalis ptb, Salmonella enterica pduL, and other homologs and mutants. |
| Any microorganism or method herein described, wherein said overexpressed carboxylate kinase is encoded by a gene(s) selected from the group consisting of Clostridium acetobutylicum buk, Enterococcus faecalis buk, Salmonella enterica pduW, and other homologs and mutants. |
| Any microorganism or method herein described, wherein said overexpressed alcohol-forming coenzyme-A thioester reductase is encoded by a gene(s) selected from the group consisting of Clostridium acetobutylicum adhE2, Arabidopsis thaliana At3g11980, Arabidopsis thaliana At3g44560, Arabidopsis thaliana At3g56700, Arabidopsis thaliana At5g22500, Arabidopsis thaliana CER4, Marinobacter aquaeolei VT8 maqu_2220, Marinobacter aquaeolei VT8 maqu_2507, and other homologs and mutants. |
| Any microorganism or method herein described, wherein said overexpressed aldehyde-forming CoA thioester reductase is encoded by a gene(s) selected from the group consisting of Acinetobacter calcoaceticus acr1, Acinetobacter sp Strain M-1 acrM, Clostridium beijerinckii ald, E. coli eutE, Salmonella enterica eutE, E. coli mhpF, and other homologs and mutants. |

FIGURE 30B-4

| |
|---|
| Any microorganism or method herein described, wherein said overexpressed alcohol dehydrogenase is encoded by a gene(s) selected from the group consisting of E. coli betA, E. coli dkgA, E. coli eutG, E. coli fucO, E. coli ucpA, E. coli yahK, E. coli ybbO, E. coli ybdH, E. coli yiaY, E. coli yjgB, and other homologs and mutants. |
| Any microorganism or method herein described, wherein said aldehyde decarbonylase is encoded by a gene(s) selected from the group consisting of Synechococcus elongatus PCC7942 orf1593, Nostoc punctiforme PCC73102 npun_R1711, Prochlorococcus marinus MIT9313 pmt1231, and other homologs and mutants. |
| Any microorganism or method herein described, wherein said alcohol dehydratase is encoded by a gene(s) selected from the group consisting of Elizabethkingia meningoseptica ohyA, and other homologs and mutants. |
| Any microorganism or method herein described, wherein said alcohol kinase or alcohol phosphotransferase is encoded by a gene(s) selected from the group consisting of Saccharomyces cerevisiae ERG12, Saccharomyces cerevisiae ERG8, Arabidopsis thaliana At5g58560, E. coli bacA, and other homologs and mutants. |
| Any microorganism or method herein described, wherein said isopentenyl diphosphate isomerase is encoded by a gene(s) selected from the group consisting of E. coli idi, and other homologs and mutants. |
| Any microorganism or method herein described, wherein said geranyl-, farnesyl- or, geranylgeranyl-diphosphate synthase is encoded by a gene(s) selected from the group consisting of E. coli ispA, Ips pini GPPS, Abies grandis GPPS2, and other homologs and mutants. |
| Any microorganism or method herein described, wherein said prenyl transferase, terpene synthase, or terpene cyclase is encoded by a gene selected from carbon lyases (EC 4.2.3.-). |
| Any microorganism or method herein described, wherein said reduced expressions of fermentation enzymes are ΔadhE, (Δpta or ΔackA or ΔackApta), ΔpoxB, ΔldhA, and ΔfrdA and less acetate, lactate, ethanol and succinate are thereby produced. |
| Any microorganism or method herein described, comprising one or more of the following mutations: fadR, atoC(c), ΔarcA, Δcrp, crp*. |

FIGURE 30B-5

| |
|---|
| A genetically engineered microorganism producing prenylated aromatic compounds, said microorganism comprising:<br>a) an overexpressed acetolactate synthase catalyzing the conversion of 2 molecules of pyruvate to acetolactate and enzymes converting said acetolactate to isoprenoid precursors isopentenyl pyrophosphate (IPP), dimethylallyl pyrophosphate (DMAPP), or geranyl pyrophosphate (GPP);<br>b) overexpressed thiolase(s) catalyzing the non-decarboxylative Claisen condensation of an acyl-CoA thioester primer and acyl-CoA thioester extender unit, β-reduction enzymes, and termination pathways leading to the generation of polyketide products;<br>c) an overexpressed aromatic prenyltransferase or 4-hydroxybenzoate grenyltransferase catalyzing a prenyl transfer from said isoprenoid precursor(s) to said polyketide product(s) forming a prenylated aromatic compound; and,<br>d) optionally comprising reduced expressions of fermentation enzymes leading to reduced production of lactate, acetate, ethanol and succinate. |
| Any microorganism or method herein described, wherein the generation of said isoprenoid precursors comprises:<br>a) an overexpressed acetolactate synthase that catalyzes conversion of 2 molecules of pyruvate to acetolactate;<br>b) an overexpressed acetohydroxyacid isomeroreductase catalyzing the conversion of said acetolactate to 2,3-dihydroxy-3-methylbutanoate;<br>c) an overexpressed dihydroxyacid dehydratase catalyzing the conversion of said 2,3-dihydroxy-3-methylbutanoate to 3-methyl-2-oxobutanoate;<br>d) an overexpressed 2-hydroxyacid dehydrogenase catalyzing the conversion of said 3-methyl-2-oxobutanoate to 3-methyl-2-hydroxybutanoate;<br>e) one or more overexpressed enzymes converting said 3-methyl-2-hydroxybutanoate to dimethylallyl phosphate, wherein said enzyme(s) is selected from:<br>i) a 2-hydroxyacid dehydratase and a carboxylate kinase;<br>ii) an acyl-CoA synthase, acyl-CoA transferase, or carboxylate kinase and phosphotransacylase, a 2-hydroxyacyl-CoA dehydratase, a thioesterase, acyl-CoA transferase, or phosphotransacylase and carboxylate kinase, and a carboxylate kinase;<br>iii) an acyl-CoA synthase, acyl-CoA transferase, or carboxylate kinase and phosphotransacylase, a 2-hydroxyacyl-CoA dehydratase, and a phosphotransacylase;<br>iv) an acyl-CoA synthase, acyl-CoA transferase, or carboxylate kinase and phosphotransacylase, a 2-hydroxyacyl-CoA dehydratase, an alcohol forming acyl-CoA reductase, and an alcohol kinase;<br>v) an acyl-CoA synthase, acyl-CoA transferase, or carboxylate kinase and phosphotransacylase, a 2-hydroxyacyl-CoA dehydratase, an aldehyde forming acyl-CoA reductase, an alcohol dehydrogenase, and an alcohol kinase;<br>f) an overexpressed phosphate kinase catalyzing the conversion of said dimethylallyl phosphate to dimethylallyl pyrophosphate (DMAPP);<br>g) an overexpressed isopentenyl diphosphate isomerase catalyzing the conversion of said dimethylallyl pyrophosphate to isopentenyl pyrophosphate (IPP); and,<br>h) an overexpressed geranyl pyrophosphate synthase catalyzing the conversion of said dimethylallyl pyrophosphate and isopentenyl pyrophosphate to geranyl pyrophosphate (GPP); |

FIGURE 30B-6

| |
|---|
| Any microorganism or method herein described, wherein said generation of polyketide products comprises:<br>a) an overexpressed thiolase that catalyzes the non-decarboxylative Claisen condensation between an acyl-CoA primer with an acyl-CoA thioester extender unit to form a polyketide CoA thioester;<br>b) an overexpressed 3-hydroxyacyl-CoA dehydrogenase or 3-oxoacyl-[acyl-carrier-protein] reductase that catalyzes the reduction of β-keto group of said polyketide CoA thioester to ß-hydroxy group;<br>c) an overexpressed enoyl-CoA hydratase, 3-hydroxyacyl-CoA dehydratase, or 3-hydroxyacyl-[acyl-carrier-protein] dehydratase that catalyzes the dehydration of said β-keto group formed in step a to form a double bond between the alpha and beta sites of said polyketide CoA thioester;<br>d) an overexpressed acyl-CoA dehydrogenase, trans-enoyl-CoA reductase, or enoyl-[acyl-carrier-protein] reductase that catalyzes the reduction of said double bond formed in step b to a single bond between the alpha and beta sites of said polyketide CoA thioester;<br>e) iterations of reaction a, wherein said iteration is achieved by utilizing the polyketide CoA thioester generated in steps a, b, c, or d of the previous turn as a primer or an extender unit of step a in the next turn of iteration to elongate the polyketide chain by two carbons; and,<br>f) a termination pathway of the carbon chain elongation, wherein said termination pathway is consisting a CoA thioester removal hydrolysis reaction performed spontaneously or by an overexpressed thioesterase, and subsequent spontaneous reactions for the rearrangement or cycle generation of polyketide product. |
| Any microorganism or method herein described, wherein said acyl-CoA primer is an acyl-CoA thioester whose omega group is selected from the group consisting of hydrogen, alkyl group, hydroxyl group, carboxyl group, aryl group, halogen, amino group, hydroxyacyl group, carboxyacyl group, aminoacyl group, ketoacyl group, halogenated acyl group, and any other functionalized acyl groups. |
| Any microorganism or method herein described, said acyl-CoA thioester extender unit is an acyl-CoA thioester whose omega group is selected from the group consisting of hydrogen, alkyl group, hydroxyl group, carboxyl group, aryl group, halogen, amino group, hydroxyacyl group, carboxyacyl group, aminoacyl group, ketoacyl group, halogenated acyl group, and any other functionalized acyl groups. |
| Any microorganism or method herein described, further comprising an overexpressed geranyl-, farnesyl- or, geranylgeranyl-diphosphate synthase catalyzing the head-to-tail or head-to-head condensation of isoprenoid precursors isopentenyl pyrophosphate (IPP), dimethylallyl pyrophosphate (DMAPP), geranyl pyrophosphate (GPP), or farnesyl pyrophosphate (FPP). |
| Any microorganism or method herein described, wherein said isoprenoid precursor is geranyl pyrophosphate, said polyketide product is olivetolic acid, and said prenylated aromatic compound is cannabigerolic acid. |
| Any microorganism or method herein described, further comprising an overexpressed tetrahydrocannabinolic acid synthase, cannabidiolic acid synthase, cannabichromenic acid synthase catalyzing the conversion of cannabigerolic acid to tetrahydrocannabinolic acid, cannabidiolic acid, or cannabichromenic acid. |
| Any microorganism or method herein described, wherein said genetically engineered microorganism produces tetrahydrocannabinolic acid, cannabidiolic acid, or cannabichromenic acid. |

FIGURE 30B-7

| |
|---|
| A genetically engineered microorganism comprising:<br>a) an overexpressed acetolactate synthase that catalyzes conversion of 2 molecules of pyruvate to acetolactate;<br>b) an overexpressed acetohydroxyacid isomeroreductase catalyzing the conversion of said acetolactate to 2,3-dihydroxy-3-methylbutanoate;<br>c) an overexpressed dihydroxyacid dehydratase catalyzing the conversion of said 2,3-dihydroxy-3-methylbutanoate to 3-methyl-2-oxobutanoate;<br>d) an overexpressed 2-hydroxyacid dehydrogenase catalyzing the conversion of said 3-methyl-2-oxobutanoate to 3-methyl-2-hydroxybutanoate;<br>e) one or more overexpressed enzymes converting said 3-methyl-2-hydroxybutanoate to dimethylallyl phosphate, wherein said enzyme(s) is selected from:<br>i) a 2-hydroxyacid dehydratase and a carboxylate kinase;<br>ii) an acyl-CoA synthase, acyl-CoA transferase, or carboxylate kinase and phosphotransacylase, a 2-hydroxyacyl-CoA dehydratase, a thioesterase, acyl-CoA transferase, or phosphotransacylase and carboxylate kinase, and a carboxylate kinase;<br>iii) an acyl-CoA synthase, acyl-CoA transferase, or carboxylate kinase and phosphotransacylase, a 2-hydroxyacyl-CoA dehydratase, and a phosphotransacylase;<br>iv) an acyl-CoA synthase, acyl-CoA transferase, or carboxylate kinase and phosphotransacylase, a 2-hydroxyacyl-CoA dehydratase, an alcohol forming acyl-CoA reductase, and an alcohol kinase;<br>v) an acyl-CoA synthase, acyl-CoA transferase, or carboxylate kinase and phosphotransacylase, a 2-hydroxyacyl-CoA dehydratase, an aldehyde forming acyl-CoA reductase, an alcohol dehydrogenase, and an alcohol kinase;<br>f) an overexpressed phosphate kinase catalyzing the conversion of said dimethylallyl phosphate to dimethylallyl pyrophosphate (DMAPP);<br>g) an overexpressed isopentenyl diphosphate isomerase catalyzing the conversion of said dimethylallyl pyrophosphate to isopentenyl pyrophosphate (IPP);<br>h) an overexpressed geranyl-, farnesyl- or, geranylgeranyl-diphosphate synthase catalyzing the head-to-tail or head-to-head condensation of isoprenoid precursors isopentenyl pyrophosphate (IPP), dimethylallyl pyrophosphate (DMAPP), geranyl pyrophosphate (GPP), or farnesyl pyrophosphate (FPP);<br>i) an overexpressed prenyl transferase, terpene synthase, or terpene cyclase catalyzing the conversion of said isoprenoid precursors to desired isoprenoid products; and,<br>j) reduced expressions of fermentation enzymes leading to reduced production of lactate, acetate, ethanol and succinate. |
| Any microorganism or method herein described, wherein said genetically engineered microorganism produces isoprenoids. |
| Any microorganism or method herein described, wherein said acetolactate synthase is encoded by a gene(s) selected from the group consisting of *E. coli ilvBN*, *E. coli ilvIH*, and other homologs and mutants. |
| Any microorganism or method herein described, wherein said acetohydroxyacid isomeroreductase is encoded by a gene(s) selected from the group consisting of *E. coli ilvC* and other homologs and mutants. |
| Any microorganism or method herein described, wherein said 2-hydroxyacid dehydrogenase is encoded by a gene(s) selected from the group consisting of *Acidaminococcus fermentans hgdH*, *Methanocaldococcus jannaschii mdh*, *M. jannaschii comC*, *E. coli mdh*, *E. coli serA*, *E. coli ldhA*, *Haloferax mediterranei ddh*, and other homologs and mutants. |
| Any microorganism or method herein described, wherein said 2-hydroxyacid dehydratase is encoded by a gene(s) selected from the group consisting of *E. coli fumA*, |

FIGURE 30B-8

| |
|---|
| *E. coli fumB*, *E. coli fumC*, and other homologs and mutants. |
| Any microorganism or method herein described, wherein said carboxylate kinase is encoded by a gene(s) selected from the group consisting of *Clostridium acetobutylicum buk*, *Enterococcus faecalis buk*, *Salmonella enterica pduW*, and other homologs and mutants. |
| Any microorganism or method herein described, wherein said overexpressed acyl-CoA synthase is encoded by a gene(s) selected from the group consisting of *E. coli sucC*, *E. coli sucD*, *E. coli paaK*, *E. coli prpE*, *E. coli menE*, *E. coli fadK*, *E. coli fadD*, *Penicillium chrysogenum phl*, *Salmonella typhimurium LT2 prpE*, *Bacillus subtilis bioW*, *Cupriavidus basilensis hmfD*, *Rhodopseudomonas palustris badA*, *R. palustris hbaA*, *Pseudomonas aeruginosa* PAO1 *pqsA*, *Arabidopsis thaliana 4cl*, and other homologs and mutants. |
| Any microorganism or method herein described, wherein said overexpressed acyl-CoA transferase is encoded by a gene(s) selected from the group consisting of *E. coli atoD*, *E. coli scpC*, *E. coli ydiF*, *E. coli atoA*, *E. coli atoD*, *Clostridium acetobutylicum ctfA*, *C. acetobutylicum ctfB*, *Clostridium kluyveri cat2*, *C. kluyveri cat1*, *P. putida pcaI*, *P. putida pcaJ*, *Megasphaera elsdenii pct*, *Acidaminococcus fermentans gctA*, *Acidaminococcus fermentans gctB*, *Acetobacter aceti aarC*, and other homologs and mutants. |
| Any microorganism or method herein described, wherein said overexpressed phosphotransacylase is encoded by a gene(s) selected from the group consisting of *Clostridium acetobutylicum ptb*, *Enterococcus faecalis ptb*, *Salmonella enterica pduL*, and other homologs and mutants. |
| Any microorganism or method herein described, wherein said 2-hydroxyacyl-CoA dehydratase is encoded by a gene(s) selected from the group consisting of *Acidaminococcus fermentans hgdCAB*, *Clostridium symbiosum hgdCAB*, *Fusobacterium nucleatum hgdCAB*, *Peptoclostridium difficile hadIBC*, *Clostridium propionicum lcdCAB*, and other homologs and mutants. |
| Any microorganism or method herein described, wherein said overexpressed thioesterase is encoded by a gene(s) selected from the group consisting of *E. coli tesA*, *E. coli tesB*, *E. coli yciA*, *E. coli fadM*, *E. coli ydiI*, *E. coli ybgC*, *E. coli paaI*, *Mus musculus acot8*, *Alcanivorax borkumensis tesB2*, *Fibrobacter succinogenes Fs2108*, *Prevotella ruminicola Pr655*, *Prevotella ruminicola Pr1687*, *Lycopersicon hirsutum* f *glabratum mks2*, and other homologs and mutants. |
| Any microorganism or method herein described, wherein said overexpressed alcohol-forming coenzyme-A thioester reductase is encoded by a gene(s) selected from the group consisting of *Clostridium acetobutylicum adhE2*, *Arabidopsis thaliana At3g11980*, *Arabidopsis thaliana At3g44560*, *Arabidopsis thaliana At3g56700*, *Arabidopsis thaliana At5g22500*, *Arabidopsis thaliana CER4*, *Marinobacter aquaeolei* VT8 *maqu_2220*, *Marinobacter aquaeolei* VT8 *maqu_2507*, and other homologs and mutants. |
| Any microorganism or method herein described, wherein said overexpressed aldehyde-forming CoA thioester reductase is encoded by a gene(s) selected from the group consisting of *Acinetobacter calcoaceticus acr1*, *Acinetobacter sp Strain M-1 acrM*, *Clostridium beijerinckii ald*, *E. coli eutE*, *Salmonella enterica eutE*, *E. coli mhpF*, and other homologs and mutants. |
| Any microorganism or method herein described, wherein said overexpressed alcohol dehydrogenase is encoded by a gene(s) selected from the group consisting of *E. coli betA*, *E. coli dkgA*, *E. coli eutG*, *E. coli fucO*, *E. coli ucpA*, *E. coli yahK*, *E. coli ybbO*, *E. coli ybdH*, *E. coli yiaY*, *E. coli yjgB*, and other homologs and mutants. |
| Any microorganism or method herein described, wherein said alcohol kinase or alcohol phosphotransferase is encoded by a gene(s) selected from the group consisting of |

FIGURE 30B-9

| |
|---|
| *Saccharomyces cerevisiae* ERG12, *Saccharomyces cerevisiae* ERG8, *Arabidopsis thaliana* At5g58560, *Mentha x piperita ipk*, *Methanocaldococcus jannaschi mvk*, *Arabidopsis thaliana mvk*, *E. coli ispE*, *E. coli glpK*, and other homologs and mutants. |
| Any microorganism or method herein described, wherein said phosphate kinase is encoded by a gene(s) selected from the group consisting of *Methanothermobacter thermautotrophicus MTH_47*, *Thermoplasma acidophilum* Ta0103, *Enterococcus faecalis mvaK2*, *Streptococcus pneumoniae mvaK2*, *Staphylococcus aureus mvaK2*, and other homologs and mutants. |
| Any microorganism or method herein described, wherein said isopentenyl diphosphate isomerase is encoded by a gene(s) selected from the group consisting of *E. coli idi*, *Arabidopsis thaliana IPP1*, *Arabidopsis thaliana IPP2*, *Bacillus subtilis idi*, *Saccharomyces cerevisiae IDI1*, *Staphylococcus aureus fni*, and other homologs and mutants. |
| Any microorganism or method herein described, wherein said geranyl pyrophosphate synthase is encoded by a gene(s) selected from the group consisting of *E. coli ispA*, *Ips pini GPPS*, *Abies grandis GPPS2*, and other homologs and mutants. |
| Any microorganism or method herein described, wherein said overexpressed thiolase is encoded by a gene(s) selected from the group consisting of *E. coli atoB*, *E. coli yqeF*, *E. coli fadA*, *E. coli fadI*, *Ralstonia eutropha bktB*, *Pseudomonas* sp. B13 *catF*, *E coli paaJ*, *Rhodococcus opacus pcaF*, *Pseudomonas putida pcaF*, *Streptomyces* sp. *pcaF*, *P. putida fadAx*, *P. putida fadA*, *Ralstonia eutropha phaA*, *Acinetobacter* sp. ADP1 *dcaF*, *Clostridium acetobutylicum thlA*, *Clostridium acetobutylicum thlB*, and other homologs and mutants. |
| Any microorganism or method herein described, wherein said overexpressed 3-hydroxyacyl-CoA dehydrogenase or 3-oxoacyl-[acyl-carrier-protein] reductase is encoded by a gene(s) selected from the group consisting of *E. coli fabG*, *E. coli fadB*, *E. coli fadJ*, *E. coli paaH*, *P. putida fadB*, *P. putida fadB2x*, *Acinetobacter* sp. ADP1 *dcaH*, *Ralstonia eutrophus phaB*, *Clostridium acetobutylicum hbd* and other homologs and mutants. |
| Any microorganism or method herein described, wherein said overexpressed enoyl-CoA hydratase, 3-hydroxyacyl-CoA dehydratase, or 3-hydroxyacyl-[acyl-carrier-protein] dehydratase is encoded by a gene(s) selected from the group consisting of *E. coli fabA*, *E. coli fabZ*, *E. coli fadB*, *E. coli fadJ*, *E. coli paaF*, *P. putida fadB*, *P. putida fadB1x*, *Acinetobacter* sp. ADP1 *dcaE*, *Clostridium acetobutylicum crt*, *Aeromonas caviae phaJ*, and other homologs and mutants. |
| Any microorganism or method herein described, wherein said acyl-CoA dehydrogenase, trans-enoyl-CoA reductase, or enoyl-[acyl-carrier-protein] reductase is encoded by a gene(s) selected from the group consisting of *E. coli fadE*, *E. coli ydiO*, *Euglena gracilis* TER, *Treponema denticola* TER, *Clostridium acetobutylicum* TER, *E. coli fabI*, *Enterococcus faecalis fabK*, *Bacillus subtilis fabL*, *Vibrio cholerea fabV*, and other homologs and mutants. |
| Any microorganism or method herein described, wherein said aromatic prenyltransferase or 4-hydroxybenzoate grenyltransferase is encoded by a gene(s) selected from the group consisting of *Arabidopsis thaliana ppt1*, *Lithospermum erythrorhizon pgt-1*, *Lithospermum erythrorhizon pgt-2*, *Schizosaccharomyces pombe coq2*, *Cannabis sativa CsPT1*, and other homologs and mutants. |
| Any microorganism or method herein described, wherein said geranyl-, farnesyl- or, geranylgeranyl-diphosphate synthase is encoded by a gene(s) selected from the group consisting of *E. coli ispA*, *Ips pini GPPS*, *Abies grandis GPPS2*, and other homologs and mutants. |
| Any microorganism or method herein described, wherein said prenyl transferase, terpene synthase, or terpene cyclase is encoded by a gene(s) selected from the group |

FIGURE 30B-10

| |
|---|
| consisting *Arabidopsis thaliana AT3G25820*, *Picea abies TPS-Lim*, *Solanum lycopersicum MTS2*, *Lavandula angustifolia LaLINS*, *Streptomyces exfoliates penA*, *Nostoc punctiforme Npun_R3832*, *Mentha aquatic linS*, *Solanum lycopersicum MTS1*, and other homologs and mutants. |
| Any microorganism or method herein described, wherein said reduced expressions of fermentation enzymes are Δ*adhE*, (Δ*pta* or Δ*ackA* or Δ*ackApta*), Δ*poxB*, Δ*ldhA*, and Δ*frdA* and less acetate, lactate, ethanol and succinate are thereby produced. |
| Any microorganism or method herein described, comprising one or more of the following mutations: *fadR*, *atoC*(c), Δ*arcA*, Δ*crp*, *crp**. |
| A method of producing isoprenoid precursors or products from isoprenoid precursors, comprising growing the microorganism of any one of claims 1-38 in a culture medium for a time and under conditions to produce isoprenoid precursors or products from isoprenoid precursors, and isolating said isoprenoid precursors or products from isoprenoid precursors. |
| A method of producing dimethylallyl pyrophosphate (DMAPP) and isopentenyl pyrophosphate (IPP), or products from said DMAPP and IPP, comprising growing a microorganism in a culture medium for a time and under conditions sufficient to produce DMAPP and IPP or products from said DMAPP and IPP, and isolating said DMAPP and IPP, or products from said DMAPP and IPP, wherein said microorganism comprises:<br>a) an overexpressed acetolactate synthase that catalyzes conversion of 2 molecules of pyruvate to acetolactate;<br>b) an overexpressed acetohydroxyacid isomeroreductase catalyzing the conversion of said acetolactate to 2,3-dihydroxy-3-methylbutanoate;<br>c) an overexpressed dihydroxyacid dehydratase catalyzing the conversion of said 2,3-dihydroxy-3-methylbutanoate to 3-methyl-2-oxobutanoate;<br>d) an overexpressed 2-hydroxyacid dehydrogenase catalyzing the conversion of said 3-methyl-2-oxobutanoate to 3-methyl-2-hydroxybutanoate;<br>e) one or more overexpressed enzymes for converting said 3-methyl-2-hydroxybutanoate to dimethylallyl phosphate;<br>f) an overexpressed phosphate kinase catalyzing the conversion of said dimethylallyl phosphate to DMAPP; and<br>g) an overexpressed isopentenyl diphosphate isomerase catalyzing the conversion of said DMAPP to IPP. |
| A method of producing dimethylallyl pyrophosphate (DMAPP) and isopentenyl pyrophosphate (IPP), or products from said DMAPP and IPP, comprising growing a microorganism in a culture medium for a time and under conditions sufficient to produce DMAPP AND IPP or products from said DMAPP and IPP, and isolating said DMAPP and IPP, or products from said DMAPP and IPP, wherein said microorganism comprises:<br>a) an overexpressed acetolactate synthase that catalyzes conversion of 2 molecules of pyruvate to acetolactate;<br>b) an overexpressed acetohydroxyacid isomeroreductase catalyzing the conversion of said acetolactate to 2,3-dihydroxy-3-methylbutanoate;<br>c) an overexpressed dihydroxyacid dehydratase catalyzing the conversion of said 2,3-dihydroxy-3-methylbutanoate to 3-methyl-2-oxobutanoate;<br>d) an overexpressed 2-hydroxyacid dehydrogenase catalyzing the conversion of said 3-methyl-2-oxobutanoate to 3-methyl-2-hydroxybutanoate;<br>e) one or more overexpressed enzyme(s) for converting said 3-methyl-2-hydroxybutanoate to dimethylallyl phosphate, , wherein said enzyme(s) is selected from:<br>i) a 2-hydroxyacid dehydratase and a carboxylate kinase; |

FIGURE 30B-11 ii) an acyl-CoA synthase, acyl-CoA transferase, or carboxylate kinase and phosphotransacylase, a 2-hydroxyacyl-CoA dehydratase, a thioesterase, acyl-CoA transferase, or phosphotransacylase and carboxylate kinase, and a carboxylate kinase;
iii) an acyl-CoA synthase, acyl-CoA transferase, or carboxylate kinase and phosphotransacylase, a 2-hydroxyacyl-CoA dehydratase, and a phosphotransacylase;
iv) an acyl-CoA synthase, acyl-CoA transferase, or carboxylate kinase and phosphotransacylase, a 2-hydroxyacyl-CoA dehydratase, an alcohol forming acyl-CoA reductase, and an alcohol kinase;
v) an acyl-CoA synthase, acyl-CoA transferase, or carboxylate kinase and phosphotransacylase, a 2-hydroxyacyl-CoA dehydratase, an aldehyde forming acyl-CoA reductase, an alcohol dehydrogenase, and an alcohol kinase;

f) an overexpressed phosphate kinase catalyzing the conversion of said dimethylallyl phosphate to DMAPP; and,
g) an overexpressed isopentenyl diphosphate isomerase catalyzing the conversion of said DMAPP to IPP.

FIGURE 30C-1

| The invention includes any one or more of the following embodiment(s), in any combination(s) thereof: |
|---|
| A recombinant microorganism producing an isoprenoid precursor(s), or optionally an isoprenoid(s) or a derivative(s) thereof, said recombinant microorganism comprising:<br>a) one or more condensation product(s) selected from:<br>a. a beta-ketoacyl-CoA produced by an enzyme-catalyzed non-decarboxylative Claisen condensation of an acyl-CoA plus a second acyl-CoA;<br>b. a beta-ketoacyl-CoA produced by an enzyme-catalyzed decarboxylative Claisen condensation of an acyl-CoA plus a beta-carboxylic acyl-CoA;<br>c. an aldol produced by an enzyme-catalyzed aldol condensation of an aldehyde plus a ketone, or an aldehyde plus a second aldehyde, or an aldehyde plus a carboxylic acid;<br>d. an acyloin produced by an enzyme-catalyzed non-decarboxylative acyloin condensation of a ketone and an aldehyde, or an aldehyde and a second aldehyde; or<br>e. an acyloin produced by an enzyme-catalyzed decarboxylative acyloin condensation of a ketone and an alpha-keto acid, or an aldehyde and an alpha-keto acid, or an alpha-keto acid and a second alpha-keto acid;<br>b) three (or two, or one) or more enzymes to convert said condensation product(s) to an isoprenoid alcohol(s), with at least three (or two, or one) of said enzymes selected from an acetohydroxy acid isomeroreductase, an acetoacetate decarboxylate, an acyl-CoA dehydrogenase, an acyl-CoA reductase, an acyl-CoA synthase, an acyl-CoA transferase, an alcohol dehydratase, an alcohol dehydrogenase, an aldehyde decarboxylase, an alpha-keto acid decarboxylase, an alpha-keto acid dehydrogenase, a carboxylate kinase, a carboxylate reductase, a dehydratase, a dihydroxyacid dehydratase, a diol dehydratase, an enoate hydratase, an enoyl-CoA hydratase, an enoyl-CoA reductase, a glutaconyl-CoA decarboxylase, an hydroxyacid dehydratase, an hydroxyacid dehydrogenase, an hydroxyacyl-CoA dehydratase, an hydroxyacyl-CoA dehydrogenase, an hydroxymethylacyl-CoA synthase, an isomeroreductase, an isopropylmalate dehydrogenase, an isopropylmalate isomerase, an isopropylmalate synthase, a mutase, an omega-oxidation enzyme, a phosphotransacylase, a thioesterase, or a thiolase, where said conversion optionally proceeds through an isoprenoid acyl-CoA;<br>c) one or more phosphorylation enzyme(s) to convert said isoprenoid alcohol(s) to an isoprenoid precursor(s); and<br>d) optionally one or more enzyme(s) to convert said isoprenoid precursor(s) to another isoprenoid precursor(s) or an isoprenoid(s) or a derivative(s) thereof;<br>wherein one or more of said enzyme(s) is heterologous. |

FIGURE 30C-2

| |
|---|
| A recombinant microorganism producing an isoprenoid precursor(s), or optionally an isoprenoid(s) or a derivative(s) thereof, said recombinant microorganism comprising:<br>a) one or more condensation product(s) selected from:<br>a. a beta-ketoacyl-CoA produced by an enzyme-catalyzed non-decarboxylative Claisen condensation of an acyl-CoA plus a second acyl-CoA;<br>b. a beta-ketoacyl-CoA produced by an enzyme-catalyzed decarboxylative Claisen condensation of an acyl-CoA plus a beta-carboxylic acyl-CoA;<br>c. an aldol produced by an enzyme-catalyzed aldol condensation of an aldehyde plus a ketone, or an aldehyde plus a second aldehyde, or an aldehyde plus a carboxylic acid;<br>d. an acyloin produced by an enzyme-catalyzed non-decarboxylative acyloin condensation of a ketone and an aldehyde, or an aldehyde and a second aldehyde; or<br>e. an acyloin produced by an enzyme-catalyzed decarboxylative acyloin condensation of a ketone and an alpha-keto acid, or an aldehyde and an alpha-keto acid, or an alpha-keto acid and a second alpha-keto acid;<br>b) three (or two, or one) or more enzymes to convert said condensation product(s) to an isoprenoid alcohol(s), with at least one of said enzymes comprising an alcohol forming termination enzyme(s);<br>c) one or more phosphorylation enzyme(s) to convert said isoprenoid alcohol(s) to an isoprenoid precursor(s); and<br>d) optionally one or more enzyme(s) to convert said isoprenoid precursor(s) to another isoprenoid precursor(s) or an isoprenoid(s) or a derivative(s) thereof;<br>wherein one or more of said enzyme(s) is heterologous. |
| A recombinant microorganism comprising one or more enzyme-produced intermediate products selected from 2-acetolactate, 2 hydroxy-isovalerate, 2-oxo-isocaproate, 3-methyl-3-hydroxybutyryl-CoA, 4-hydroxy-2-methylbutanoyl-CoA, 3-methylcrotonyl-CoA, 3-methyl-3-butenoyl-CoA, 3-methyl-2-buten-1-al, geranyl-CoA, 3-methyl-2-buten-1-ol, 3-methyl-3-buten-1-ol, 4-hydroxy-2-oxo-4-methylpentanoate, geraniol, or dimethylallyl phosphate. |
| A recombinant microorganism comprising:<br>a) one or more enzyme-produced intermediate products selected from 2-acetolactate, 2 hydroxy-isovalerate, 2-oxo-isocaproate, 3-methyl-3-hydroxybutyryl-CoA, 4-hydroxy-2-methylbutanoyl-CoA, 3-methylcrotonyl-CoA, 3-methyl-3-butenoyl-CoA, 3-methyl-2-buten-1-al, geranyl-CoA, 3-methyl-2-buten-1-ol, 3-methyl-3-buten-1-ol, 4-hydroxy-2-oxo-4-methylpentanoate, geraniol, or dimethylallyl phosphate.<br>b) one or more enzyme(s) to convert said intermediate product(s) to an isoprenoid alcohol(s), except in the case of intermediate products 3-methyl-2-buten-1-ol or 3-methyl-3-buten-1-ol which are isoprenoid alcohols and proceed directly to step c), or dimethylallyl phosphate which proceeds directly to step d);<br>c) one or more phosphorylation enzyme(s) to convert said isoprenoid alcohol(s) to an isoprenoid precursor(s); and<br>d) optionally one or more enzyme(s) to convert said isoprenoid precursor(s) to another isoprenoid precursor(s) or an isoprenoid(s) or a derivative(s) thereof;<br>wherein one or more of said enzyme(s) is heterologous. |

FIGURE 30C-3

| |
|---|
| A recombinant microorganism comprising:<br>a) one or more condensation product(s) selected from:<br>a. a beta-ketoacyl-CoA produced by an enzyme-catalyzed non-decarboxylative Claisen condensation of an acyl-CoA plus a second acyl-CoA;<br>b. a beta-ketoacyl-CoA produced by an enzyme-catalyzed decarboxylative Claisen condensation of an acyl-CoA plus a beta-carboxylic acyl-CoA;<br>c. an aldol produced by an enzyme-catalyzed aldol condensation of an aldehyde plus a ketone, or an aldehyde plus a second aldehyde, or an aldehyde plus a carboxylic acid;<br>d. an acyloin produced by an enzyme-catalyzed non-decarboxylative acyloin condensation of a ketone and an aldehyde, or an aldehyde and a second aldehyde; or<br>e. an acyloin produced by an enzyme-catalyzed decarboxylative acyloin condensation of a ketone and an alpha-keto acid, or an aldehyde and an alpha-keto acid, or an alpha-keto acid and a second alpha-keto acid;<br>b) one or more enzymes to convert said condensation product(s) to an intermediate product(s) selected from 2 hydroxy-isovalerate, 2-oxo-isocaproate, 3-methyl-3-hydroxybutyryl-CoA, 4-hydroxy-2-methylbutanoyl-CoA, 3-methylcrotonyl-CoA, 3-methyl-3-butenoyl-CoA, 3-methyl-2-buten-1-al, geranyl-CoA, 3-methyl-2-buten-1-ol, 3-methyl-3-buten-1-ol, 4-hydroxy-2-oxo-4-methylpentanoate, geraniol, or dimethylallyl phosphate;<br>c) one or more enzyme(s) to convert said intermediate product(s) to an isoprenoid alcohol(s), except in the case of intermediate products 3-methyl-2-buten-1-ol or 3-methyl-3-buten-1-ol which are isoprenoid alcohols and proceed directly to step d), or dimethylallyl phosphate which proceeds directly to step e);<br>d) one or more phosphorylation enzyme(s) to convert said isoprenoid alcohol(s) to an isoprenoid precursor(s); and<br>e) optionally one or more enzyme(s) to convert said isoprenoid precursor(s) to another isoprenoid precursor(s) or an isoprenoid(s) or a derivative(s) thereof;<br>wherein one or more of said enzyme(s) is heterologous. |
| A recombinant microorganism comprising:<br>a) an enzyme-produced isoprenoid alcohol(s);<br>b) one or more phosphorylation enzyme(s) to convert said isoprenoid alcohol(s) to an isoprenoid precursor(s); and<br>c) optionally one or more enzymes to convert said isoprenoid precursor(s) to another isoprenoid precursor(s) or an isoprenoid(s) or a derivative(s) thereof. |

FIGURE 30C-4

| |
|---|
| A recombinant microorganism comprising:<br>a) a thiolase or a ketoacetyl-CoA synthase enzyme catalyzing a condensation of an acyl-CoA plus a second acyl-CoA to form a beta-ketoacyl CoA, each said acyl-CoA selected from acetyl-CoA, glycolyl-CoA, propionyl-CoA, malonyl-CoA, an unsubstituted acyl-CoA, or a functionalized acyl-CoA;<br>b) optionally one or more iteration(s) wherein said beta-ketoacyl CoA is modified using one or more enzymes and then used as an acyl-CoA primer unit for a new condensation iteration of step a);<br>c) three (or two, or one) or more enzyme(s) to convert said beta-ketoacyl CoA to an isoprenoid alcohol, said enzyme(s) comprising a beta-reduction enzyme(s), and an alcohol forming termination enzyme(s);<br>d) one or more phosphorylation enzyme(s) to convert said isoprenoid alcohol(s) to an isoprenoid precursor(s); and<br>e) optionally one or more enzyme(s) to convert said isoprenoid precursor(s) to another isoprenoid precursor(s) or an isoprenoid(s) or a derivative(s) thereof;<br>wherein one or more said enzyme(s) is heterologous. |
| A recombinant microorganism comprising:<br>a) an acetolactate synthase enzyme catalyzing a decarboxylative condensation between two pyruvates to form 2-acetolactate;<br>b) an acetohydroxy acid isomeroreductase plus a dihydroxy acid dehydratase to convert said 2-acetolactate to 2-oxoisovalerate;<br>c) four (or three, or two, or one) or more enzymes to convert said 2-oxoisovalerate to an isoprenoid alcohol(s), with at least four (or three, or two, or one) of said enzymes selected from an acetohydroxy acid isomeroreductase, an acetoacetate decarboxylate, an acyl-CoA dehydrogenase, an acyl-CoA reductase, an acyl-CoA synthase, an acyl-CoA transferase, an alcohol dehydratase, an alcohol dehydrogenase, an aldehyde decarboxylase, an alpha-keto acid decarboxylase, an alpha-keto acid dehydrogenase, a carboxylate kinase, a carboxylate reductase, a dehydratase, a dihydroxyacid dehydratase, a diol dehydratase, an enoate hydratase, an enoyl-CoA hydratase, an enoyl-CoA reductase, a glutaconyl-CoA decarboxylase, an hydroxyacid dehydratase, an hydroxyacid dehydrogenase, an hydroxyacyl-CoA dehydratase, an hydroxyacyl-CoA dehydrogenase, an hydroxymethylacyl-CoA synthase, an isomeroreductase, an isopropylmalate dehydrogenase, an isopropylmalate isomerase, an isopropylmalate synthase, a mutase, an omega-oxidation enzyme, a phosphotransacylase, a thioesterase, or a thiolase, where said conversion optionally proceeds through an isoprenoid acyl-CoA;<br>d) one or more phosphorylation enzyme(s) to convert said isoprenoid alcohol to an isoprenoid precursor(s); and<br>e) optionally one or more enzyme(s) to convert said isoprenoid precursor(s) to another isoprenoid precursor(s) or an isoprenoid(s) or a derivative(s) thereof;<br>wherein one or more said enzyme(s) is heterologous. |

FIGURE 30C-5

| |
|---|
| A recombinant microorganism comprising:<br>a) an acetolactate synthase enzyme catalyzing a decarboxylative condensation between two pyruvates to form 2-acetolactate;<br>b) an acetohydroxy acid isomeroreductase plus a dihydroxy acid dehydratase to convert said 2-acetolactate to 2-oxoisovalerate;<br>c) four (or three, or two, or one) or more enzymes to convert said 2-oxoisovalerate to an isoprenoid alcohol(s), with at least one of said enzymes comprising an alcohol forming termination enzyme(s);<br>d) one or more phosphorylation enzyme(s) to convert said isoprenoid alcohol to an isoprenoid precursor(s); and<br>e) optionally one or more enzyme(s) to convert said isoprenoid precursor(s) to another isoprenoid precursor(s) or an isoprenoid(s) or a derivative(s) thereof;<br>wherein one or more said enzyme(s) is heterologous. |
| Any recombinant microorganism or process (or method) herein described, that comprises<br>a) a thiolase catalyzing conversion of an acetyl-CoA and a propionyl-CoA to 2-methylacetoacetyl-CoA;<br>b) a 3-hydroxyacyl-CoA dehydrogenase catalyzing conversion of said 2-methylacetoacetyl-CoA to 3-hydroxy-2-methylbutanoyl-CoA;<br>c) an enoyl-CoA hydratase catalyzing conversion of said 3-hydroxy-2-methylbutanoyl-CoA to 2-methyl-2-butenoyl-CoA;<br>d) a mutase catalyzing conversion of said 2-methyl-2-butenoyl-CoA to 3-methyl-2-butenoyl-CoA;<br>e) a thiolase catalyzing conversion of said 3-methyl-2-butenoyl-CoA and an acetyl-CoA to 3-oxo-5-methyl-4-hexenoyl-CoA;<br>f) a 3-hydroxyacyl-CoA dehydrogenase plus a 3-hydroxyacyl-CoA dehydratase plus an enoyl-CoA reductase catalyzing conversion of said 3-oxo-5-methyl-4-hexenoyl-CoA to 5-methyl-4-hexenoyl-CoA;<br>g) a thiolase catalyzing conversion of said 5-methyl-4-hexenoyl-CoA plus a propionyl-CoA to 3-oxo-2,7-dimethyl-6-octenoyl-CoA;<br>h) a 3-hydroxyacyl-CoA dehydrogenase plus a 3-hydroxyacyl-CoA dehydratase plus an enoyl-CoA reductase catalyzing conversion of said 3-oxo-2,7-dimethyl-6-octenoyl-CoA to 2,7-dimethyl-2,6-octadienoyl-CoA;<br>i) a mutase catalyzing conversion of said 2,7-dimethyl-2,6-octadienoyl-CoA to 3,7-dimethyl-2,6-octadienoyl-CoA;<br>j) one or more enzyme(s) catalyzing conversion of said 3,7-dimethyl-2,6-octadienoyl-CoA to geraniol, wherein said enzyme(s) is selected from:<br>a. an alcohol-forming acyl-CoA reductase;<br>b. an aldehyde forming acyl-CoA reductase plus an alcohol dehydrogenase; or<br>c. a carboxylate reductase plus an alcohol dehydrogenase plus an enzyme(s) selected from an acyl-CoA synthase, an acyl-CoA transferase, a thioesterase, or a carboxylate kinase plus a phosphotransacylase; and<br>k) one or more enzyme(s) catalyzing conversion of said geraniol to GPP, said enzyme(s) selected from an alcohol kinase plus a phosphate kinase, or an alcohol diphosphokinase. |

FIGURE 30C-6

Any recombinant microorganism or method herein described, that comprises:

a) a thiolase catalyzing conversion of a glycolyl-CoA plus a propionyl-CoA to 4-hydroxy-3-oxo-2-methylbutanoyl-CoA;
b) a 3-hydroxyacyl-CoA dehydrogenase catalyzing conversion of said hydroxy-3-oxo-2-methylbutanoyl-CoA to 3,4-dihydroxy-2-methylbutanoyl-CoA;
c) an enoyl-CoA hydratase 3 catalyzing conversion of said 3,4-dihydroxy-2-methylbutanoyl-CoA to 4-hydroxy-2-methyl-2-butenoyl-CoA;
d) an enoyl-CoA reductase catalyzing conversion of said 4-hydroxy-2-methyl-2-butenoyl-CoA to 4-hydroxy-2-methylbutanoyl-CoA;
e) one or more enzyme(s) catalyzing conversion of said 4-hydroxy-2-methylbutanoyl-CoA to 2-methyl-1,4-butanediol, wherein said enzyme(s) is selected from:
    a. an alcohol-forming acyl-CoA reductase;
    b. an aldehyde forming acyl-CoA reductase plus an alcohol dehydrogenase; or
    c. a carboxylate reductase plus an alcohol dehydrogenase plus an enzyme(s) selected from an acyl-CoA synthase, an acyl-CoA transferase, a thioesterase, or a carboxylate kinase plus a phosphotransacylase;
f) a dehydratase catalyzing conversion of said 2-methyl-1,4-butanediol to 3-methyl-3-buten-1-ol;
g) one or more enzyme(s) catalyzing conversion of said 3-methyl-3-buten-1-ol to IP or IPP, wherein said enzyme(s) is selected from:
    a. an alcohol kinase;
    b. an alcohol kinase plus a phosphate kinase; or
    c. an alcohol diphosphokinase;
h) optionally, an isopentenyl diphosphate isomerase catalyzing conversion of said IPP to DMAPP; and
i) optionally a geranyl pyrophosphate synthase catalyzing conversion of said DMAPP and IPP to GPP.

FIGURE 30C-7

Any recombinant microorganism or process herein described, that comprises:

a) a thiolase catalyzing conversion of a glycolyl-CoA and a propionyl-CoA to 2-hydroxy-3-oxopentanoyl-CoA;
b) a 3-hydroxyacyl-CoA dehydrogenase catalyzing conversion of said 2-hydroxy-3-oxopentanoyl-CoA to 2,3-dihydroxypentanoyl-CoA;
c) an enoyl-CoA hydratase catalyzing conversion of said 2,3-dihydroxypentanoyl-CoA to 2-hydroxy-2-pentenoyl-CoA;
d) an enoyl-CoA reductase catalyzing conversion of said 2-hydroxy-2-pentenoyl-CoA to 2-hydroxypentanoyl-CoA;
e) a mutase catalyzing conversion of said 2-hydroxypentanoyl-CoA to 2-hydroxy-3-methylbutanoyl-CoA;
f) a dehydratase catalyzing conversion of said 2-hydroxy-3-methylbutanoyl-CoA to 3-methyl-2-butenoyl-CoA;
g) one or more enzyme(s) catalyzing conversion of said 3-methyl-2-butenoyl-CoA to 3-methyl-2-buten-1-ol, wherein said enzyme(s) is selected from:
    a. an alcohol-forming acyl-CoA reductase;
    b. an aldehyde forming acyl-CoA reductase plus an alcohol dehydrogenase; or
    c. a carboxylate reductase plus an alcohol dehydrogenase plus an enzyme(s) selected from an acyl-CoA synthase, an acyl-CoA transferase, a thioesterase, or a carboxylate kinase plus a phosphotransacylase;
h) one or more enzyme(s) catalyzing conversion of said 3-methyl-2-buten-1-ol to DMAP or DMAPP, wherein said enzyme(s) is selected from:
    a. an alcohol kinase;
    b. an alcohol kinase plus a phosphate kinase; or
    c. an alcohol diphosphokinase;
i) optionally, an isopentenyl diphosphate isomerase catalyzing conversion of said DMAPP to IPP; and
j) optionally a geranyl pyrophosphate synthase catalyzing conversion of said DMAPP and IPP to GPP.

FIGURE 30C-8

| |
|---|
| Any recombinant microorganism or process herein described, that comprises:<br>a) a thiolase catalyzing conversion of an acetyl-CoA and a propionyl-CoA to 3-oxopentanoyl-CoA;<br>b) a 3-hydroxyacyl-CoA dehydrogenase catalyzing conversion of said 3-oxopentanoyl-CoA to 3-hydroxypentanoyl-CoA;<br>c) a mutase catalyzing conversion of said 3-hydroxypentanoyl-CoA to 3-hydroxy-3-methylbutanoyl-CoA;<br>d) an enoyl-CoA hydratase catalyzing conversion of said 3-hydroxy-3-methylbutanoyl-CoA to 3-methyl-2-butenoyl-CoA;<br>e) one or more enzyme(s) catalyzing conversion of said 3-methyl-2-butenoyl-CoA to 3-methyl-2-buten-1-ol, wherein said enzyme(s) is selected from:<br>a. an alcohol-forming acyl-CoA reductase;<br>b. an aldehyde forming acyl-CoA reductase plus an alcohol dehydrogenase; or<br>c. a carboxylate reductase plus an alcohol dehydrogenase plus an enzyme(s) selected from an acyl-CoA synthase, an acyl-CoA transferase, a thioesterase, or a carboxylate kinase plus a phosphotransacylase;<br>f) one or more enzyme(s) catalyzing conversion of said 3-methyl-2-buten-1-ol to DMAP or DMAPP, wherein said enzyme(s) is selected from:<br>a. an alcohol kinase;<br>b. an alcohol kinase plus a phosphate kinase; or<br>c. an alcohol diphosphokinase;<br>g) optionally, an isopentenyl diphosphate isomerase catalyzing conversion of said DMAPP to IPP; and<br>h) optionally a geranyl pyrophosphate synthase catalyzing conversion of said DMAPP and IPP to GPP. |
| Any recombinant microorganism or process herein described,, that comprises:<br>a) a thiolase catalyzing conversion of an acetyl-CoA and a propionyl-CoA to 2-methylacetoacetyl-CoA;<br>b) a 3-hydroxyacyl-CoA dehydrogenase catalyzing conversion of said 2-methylacetoacetyl-CoA to 3-hydroxy-2-methylbutanoyl-CoA;<br>c) an enoyl-CoA hydratase catalyzing conversion of said 3-hydroxy-2-methylbutanoyl-CoA to 2-methyl-2-butenoyl-CoA;<br>d) a mutase catalyzing conversion of said 2-methyl-2-butenoyl-CoA to 3-methyl-2-butenoyl-CoA;<br>e) one or more enzyme(s) catalyzing conversion of said 3-methyl-2-butenoyl-CoA to 3-methyl-2-buten-1-ol, wherein said enzyme(s) is selected from:<br>a. an alcohol-forming acyl-CoA reductase;<br>b. an aldehyde forming acyl-CoA reductase plus an alcohol dehydrogenase; or<br>c. a carboxylate reductase plus an alcohol dehydrogenase plus an enzyme(s) selected from an acyl-CoA synthase, an acyl-CoA transferase, a thioesterase, or a carboxylate kinase plus a phosphotransacylase;<br>f) one or more enzyme(s) catalyzing conversion of said 3-methyl-2-buten-1-ol to DMAP or DMAPP, wherein said enzyme(s) is selected from:<br>a. an alcohol kinase;<br>b. an alcohol kinase plus a phosphate kinase; or<br>c. an alcohol diphosphokinase;<br>g) optionally, an isopentenyl diphosphate isomerase catalyzing conversion of said DMAPP to IPP; and<br>h) optionally a geranyl pyrophosphate synthase catalyzing conversion of said DMAPP and IPP to GPP. |

FIGURE 30C-9

Any recombinant microorganism or process herein described, that comprises:

a) a thiolase catalyzing conversion of 2 molecules of acetyl-CoA to acetoacetyl-CoA or a ketoacyl-CoA synthase catalyzing conversion of malonyl-CoA plus acetyl-Co to acetoacetyl-CoA;
b) a hydroxymethylglutaryl-CoA synthase catalyzing conversion of said acetoacetyl-CoA plus acetyl-CoA to 3-hydroxy-3-methylglutaryl-CoA;
c) an enoyl-CoA hydratase catalyzing conversion of said 3-hydroxy-3-methylglutaryl-CoA to 3-methylglutaconyl-CoA;
d) a glutaconyl-CoA decarboxylase catalyzing conversion of said 3-methylglutaconyl-CoA to 3-methyl-2-butenoyl-CoA;
e) one or more enzyme(s) catalyzing conversion of said 3-methyl-2-butenoyl-CoA to 3-methyl-2-buten-1-ol, wherein said enzyme(s) is selected from:
    a. an alcohol-forming acyl-CoA reductase;
    b. an aldehyde forming acyl-CoA reductase plus an alcohol dehydrogenase; or
    c. a carboxylate reductase plus an alcohol dehydrogenase plus an enzyme(s) selected from an acyl-CoA synthase, an acyl-CoA transferase, a thioesterase, or a carboxylate kinase plus a phosphotransacylase;
f) one or more enzyme(s) catalyzing conversion of said 3-methyl-2-buten-1-ol to DMAP or DMAPP, wherein said enzyme(s) is selected from:
    a. an alcohol kinase;
    b. an alcohol kinase plus a phosphate kinase; or
    c. an alcohol diphosphokinase;
g) optionally, an isopentenyl diphosphate isomerase catalyzing conversion of said DMAPP to IPP; and
h) optionally a geranyl pyrophosphate synthase catalyzing conversion of said DMAPP and IPP to GPP.

FIGURE 30C-10

Any recombinant microorganism or process herein described, with metabolic pathways that comprise:

a) a thiolase catalyzing conversion of 2 molecules of acetyl-CoA to acetoacetyl-CoA or a ketoacyl-CoA synthase catalyzing conversion of malonyl-CoA plus acetyl-Co to acetoacetyl-CoA;
b) an acyl-CoA synthase, or an acyl-CoA transferase, or a thioesterase, or a carboxylate kinase plus phosphotransacylase catalyzing conversion of said acetoacetyl-CoA to acetoacetate;
c) an acetoacetate decarboxylase or a spontaneous reaction catalyzing conversion of said acetoacetate to acetone;
d) a thiolase or hydroxymethylglutaryl-CoA synthase catalyzing a non-decarboxylative condensation of said acetone and acetyl-CoA to 3-methyl-3-hydroxybutyryl-CoA;
e) an enoyl-CoA hydratase catalyzing conversion of said 3-methyl-3-hydroxybutyryl-CoA to 3-methyl-2-butenoyl-CoA;
f) one or more enzyme(s) catalyzing conversion of said 3-methyl-2-butenoyl-CoA to 3-methyl-2-buten-1-ol, wherein said enzyme(s) is selected from:
    a. an alcohol-forming acyl-CoA reductase;
    b. an aldehyde forming acyl-CoA reductase plus an alcohol dehydrogenase; or
    c. a carboxylate reductase plus an alcohol dehydrogenase plus an enzyme(s) selected from an acyl-CoA synthase, an acyl-CoA transferase, a thioesterase, or a carboxylate kinase plus a phosphotransacylase;
g) one or more enzyme(s) catalyzing conversion of said 3-methyl-2-buten-1-ol to DMAP or DMAPP, wherein said enzyme(s) is selected from:
    a. an alcohol kinase;
    b. an alcohol kinase plus a phosphate kinase; or
    c. an alcohol diphosphokinase;
h) optionally, an isopentenyl diphosphate isomerase catalyzing conversion of said DMAPP to IPP; and
i) optionally a geranyl pyrophosphate synthase catalyzing conversion of said DMAPP and IPP to GPP.

FIGURE 30C-11

Any recombinant microorganism or process herein described, that comprises:

a) an acetolactate synthase catalyzing conversion of 2 molecules of pyruvate to acetolactate;
b) an acetohydroxyacid isomeroreductase catalyzing conversion of said acetolactate to 2,3-dihydroxy-3-methylbutanoate;
c) a dihydroxyacid dehydratase catalyzing conversion of said 2,3-dihydroxy-3-methylbutanoate to 3-methyl-2-oxobutanoate;
d) a 2-hydroxyacid dehydrogenase catalyzing conversion of said 3-methyl-2-oxobutanoate to 3-methyl-2-hydroxybutanoate;
e) one or more enzyme(s) catalyzing conversion of said 3-methyl-2-hydroxybutanoate to 3-methyl-2-buten-1-ol, wherein said enzymes(s) is selected from:
    a. a 2-hydroxyacid dehydratase plus a carboxylate reductase plus an alcohol dehydrogenase;
    b. a 2-hydroxyacid dehydratase plus an alcohol forming acyl-CoA reductase plus one or more enzyme(s) selected from a thioesterase, an acyl-CoA synthase, an acyl-CoA transferase, or a carboxylate kinase plus a phosphotransacylase;
    c. a 2-hydroxyacid dehydratase plus an aldehyde forming acyl-CoA reductase plus an alcohol dehydrogenase plus one or more enzyme(s) selected from a thioesterase, an acyl-CoA synthase, an acyl-CoA transferase, or a carboxylate kinase plus a phosphotransacylase; or
    d. a 2-hydroxyacyl-CoA dehydratase plus an alcohol forming acyl-CoA reductase plus a diol dehydratase plus an aldehyde forming acyl-CoA reductase plus an acyl-CoA dehydrogenase plus one or more additional enzyme(s) selected from:
        a. an acyl-CoA synthase;
        b. an acyl-CoA transferase; or
        c. a carboxylate kinase plus a phosphotransacylase, plus one or more additional enzyme(s) selected from:
        a. an alcohol forming acyl-CoA reductase;
        b. an aldehyde forming acyl-CoA reductase plus an alcohol dehydrogenase; or
        c. a carboxylate reductase plus an alcohol dehydrogenase plus one or more enzyme(s) selected from a thioesterase, an acyl-CoA synthase, an acyl-CoA transferase, or a carboxylate kinase plus a phosphotransacylase;

f) one or more enzyme(s) catalyzing conversion of said 3-methyl-2-buten-1-ol to DMAP or DMAPP, wherein said enzyme(s) is selected from:
    a. an alcohol kinase;
    b. an alcohol kinase plus a phosphate kinase; or
    c. an alcohol diphosphokinase;
g) optionally, an isopentenyl diphosphate isomerase catalyzing conversion of said DMAPP to IPP; and
h) optionally a geranyl pyrophosphate synthase catalyzing conversion of said DMAPP and IPP to GPP.

FIGURE 30C-12

Any recombinant microorganism or process herein described, that comprises (FIG 9-7):

a) an acetolactate synthase catalyzing conversion of 2 molecules of pyruvate to acetolactate;
b) an acetohydroxyacid isomeroreductase catalyzing conversion of said acetolactate to 2,3-dihydroxy-3-methylbutanoate;
c) a dihydroxyacid dehydratase catalyzing conversion of said 2,3-dihydroxy-3-methylbutanoate to 3-methyl-2-oxobutanoate;
d) an isopropylmalate synthase catalyzing conversion of said 3-methyl-2-oxobutanoate to 2-isopropylmalate;
e) an isopropylmalate isomerase catalyzing conversion of said 2-isopropylmalate to 3-isopropylmalate;
f) an isopropylmalate dehydrogenase catalyzing conversion of said 3-isopropylmalate to 4-methyl-2-oxopentanoate;
g) one or more enzyme(s) catalyzing conversion of said 4-methyl-2-oxopentanoate to isovaleryl-CoA, wherein said enzyme(s) is selected from:
    a. an alpha-keto acid dehydrogenase; or
    b. an alpha-keto acid decarboxylase plus an aldehyde forming acyl-CoA reductase;
h) an acyl-CoA dehydrogenase catalyzing conversion of said isovaleryl-CoA to 3-methyl-2-butenoyl-CoA;
i) one or more enzyme(s) catalyzing conversion of said 3-methyl-2-butenoyl-CoA to 3-methyl-2-buten-1-ol, wherein said enzyme(s) is selected from:
    a. an alcohol-forming acyl-CoA reductase;
    b. an aldehyde forming acyl-CoA reductase plus an alcohol dehydrogenase; or
    c. a carboxylate reductase plus an alcohol dehydrogenase plus an enzyme(s) selected from an acyl-CoA synthase, an acyl-CoA transferase, a thioesterase, and a carboxylate kinase plus a phosphotransacylase;
j) one or more enzyme(s) catalyzing conversion of said 3-methyl-2-buten-1-ol to DMAP or DMAPP, wherein said enzyme(s) is selected from:
    a. an alcohol kinase;
    b. an alcohol kinase plus a phosphate kinase; or
    c. an alcohol diphosphokinase;
k) optionally, an isopentenyl diphosphate isomerase catalyzing conversion of said DMAPP to IPP; and
l) optionally a geranyl pyrophosphate synthase catalyzing conversion of said DMAPP and IPP to GPP.

FIGURE 30C-13

Any recombinant microorganism or process herein described, that comprises:

a) a thiolase catalyzing conversion of 2 molecules of acetyl-CoA to acetoacetyl-CoA or a ketoacyl-CoA synthase catalyzing conversion of malonyl-CoA plus acetyl-Co to acetoacetyl-CoA;
b) a 3-hydroxyacyl-CoA dehydrogenase catalyzing conversion of said acetoacetyl-CoA to 3-hydroxybutyryl-CoA;
c) an enoyl-CoA hydratase catalyzing conversion of said 3-hydroxybutyryl-CoA to crotonyl-CoA;
d) an enoyl-CoA reductase catalyzing conversion of said crotonyl-CoA to crotonyl-CoA to butyryl-CoA;
e) a mutase catalyzing conversion of said butyryl-CoA to isobutyryl-CoA;
f) an aldehyde forming acyl-CoA reductase catalyzing conversion of said isobutyryl-CoA to isobutanal;
g) a 2-hydroxyacyl-CoA lyase catalyzing conversion of said isobutanal and formyl-CoA to 3-methyl-2-hydroxybutanoyl-CoA;
h) one or more enzyme(s) catalyzing conversion of said 3-methyl-2-hydroxybutanoyl-CoA to 3-methyl-2-butenoyl-CoA, wherein said enzyme(s) is selected from:
    a. a 2-hydroxyacyl-CoA dehydratase; or
    b. an aldehyde forming acyl-CoA reductase plus an acyl-CoA dehydrogenase plus a diol dehydratase plus one or more additional enzyme(s) selected from:
        a. an alcohol forming acyl-CoA reductase;
        b. an alcohol dehydrogenase; or
        c. a carboxylate reductase plus an alcohol dehydrogenase plus an enzyme(s) selected from an acyl-CoA synthase, an acyl-CoA transferase, a thioesterase, or a carboxylate kinase plus a phosphotransacylase;
i) one or more enzyme(s) catalyzing conversion of said 3-methyl-2-butenoyl-CoA to 3-methyl-2-buten-1-ol, wherein said enzyme(s) is selected from:
    a. an alcohol-forming acyl-CoA reductase;
    b. an aldehyde forming acyl-CoA reductase plus an alcohol dehydrogenase; or
    c. a carboxylate reductase plus an alcohol dehydrogenase plus an enzyme(s) selected from an acyl-CoA synthase, an acyl-CoA transferase, a thioesterase, or a carboxylate kinase plus a phosphotransacylase;
j) one or more enzyme(s) catalyzing conversion of said 3-methyl-2-buten-1-ol to DMAP or DMAPP, wherein said enzyme(s) is selected from:
    a. an alcohol kinase;
    b. an alcohol kinase plus a phosphate kinase; or
    c. an alcohol diphosphokinase;
k) optionally, an isopentenyl diphosphate isomerase catalyzing conversion of said DMAPP to IPP; and
l) optionally a geranyl pyrophosphate synthase catalyzing conversion of said DMAPP and IPP to GPP.

FIGURE 30C-14

Any recombinant microorganism or process herein described, that comprises:

a) an aldolase catalyzing conversion of pyruvate and acetaldehyde to 4-hydroxy-2-oxopentanoate;
b) a mutase catalyzing conversion of said 4-hydroxy-2-oxopentanoate to 3-hydroxy-2-oxo-3-methylbutanoate;
c) a 2-hydroxyacid dehydrogenase catalyzing conversion of said 3-hydroxy-2-oxo-3-methylbutanoate to 2,3-dihydroxy-3-methylbutanoate;
d) a dihydroxyacid dehydratase catalyzing conversion of said 2,3-dihydroxy-3-methylbutanoate to 3-methyl-2-oxobutanoate;
e) a 2-hydroxyacid dehydrogenase catalyzing conversion of said 3-methyl-2-oxobutanoate to 3-methyl-2-hydroxybutanoate;
f) one or more enzyme(s) catalyzing conversion of said 3-methyl-2-hydroxybutanoate to 3-methyl-2-buten-1-ol, wherein said enzymes(s) is selected from:
    a. a 2-hydroxyacid dehydratase plus a carboxylate reductase plus an alcohol dehydrogenase;
    b. a 2-hydroxyacid dehydratase plus an alcohol forming acyl-CoA reductase plus one or more enzyme(s) selected from thioesterase, acyl-CoA synthase, acyl-CoA transferase, or a carboxylate kinase plus a phosphotransacylase;
    c. a 2-hydroxyacid dehydratase plus an aldehyde forming acyl-CoA reductase plus an alcohol dehydrogenase plus one or more enzyme(s) selected from a thioesterase, an acyl-CoA synthase, an acyl-CoA transferase, or a carboxylate kinase plus a phosphotransacylase; or
    d. a 2-hydroxyacyl-CoA dehydratase plus an alcohol forming acyl-CoA reductase plus a diol dehydratase plus an aldehyde forming acyl-CoA reductase plus an acyl-CoA dehydrogenase plus one or more additional enzyme(s) selected from:
        a. an acyl-CoA synthase;
        b. an acyl-CoA transferase; or
        c. a carboxylate kinase plus a phosphotransacylase, plus one or more additional enzyme(s) selected from:
        a. an alcohol forming acyl-CoA reductase;
        b. an aldehyde forming acyl-CoA reductase plus an alcohol dehydrogenase; or
        c. a carboxylate reductase plus an alcohol dehydrogenase plus one or more enzyme(s) selected from a thioesterase, an acyl-CoA synthase, an acyl-CoA transferase, or a carboxylate kinase plus a phosphotransacylase;

g) one or more enzyme(s) catalyzing conversion of said 3-methyl-2-buten-1-ol to DMAP or DMAPP, wherein said enzyme(s) is selected from:
    a. an alcohol kinase;
    b. an alcohol kinase plus a phosphate kinase; or
    c. an alcohol diphosphokinase;
h) optionally, an isopentenyl diphosphate isomerase catalyzing conversion of said DMAPP to IPP; and
i) optionally a geranyl pyrophosphate synthase catalyzing conversion of said DMAPP and IPP to GPP.

FIGURE 30C-15

Any recombinant microorganism or process herein described, that comprises:

a) an aldolase catalyzing conversion of pyruvate and acetaldehyde to 4-hydroxy-2-oxopentanoate;
b) a mutase catalyzing conversion of said 4-hydroxy-2-oxopentanoate to 3-hydroxy-2-oxo-3-methylbutanoate;
c) a 2-hydroxyacid dehydrogenase catalyzing conversion of said 3-hydroxy-2-oxo-3-methylbutanoate to 2,3-dihydroxy-3-methylbutanoate;
d) a dihydroxyacid dehydratase catalyzing conversion of said 2,3-dihydroxy-3-methylbutanoate to 3-methyl-2-oxobutanoate;
e) an isopropylmalate synthase catalyzing conversion of said 3-methyl-2-oxobutanoate to 2-isopropylmalate;
f) an isopropylmalate isomerase catalyzing conversion of said 2-isopropylmalate to 3-isopropylmalate;
g) an isopropylmalate dehydrogenase catalyzing conversion of said 3-isopropylmalate to 4-methyl-2-oxopentanoate;
h) one or more enzyme(s) catalyzing conversion of said 4-methyl-2-oxopentanoate to isovaleryl-CoA, wherein said enzyme(s) is selected from:
   a. an alpha-keto acid dehydrogenase; or
   b. an alpha-keto acid decarboxylase plus an aldehyde forming acyl-CoA reductase;
i) an acyl-CoA dehydrogenase catalyzing conversion of said isovaleryl-CoA to 3-methyl-2-butenoyl-CoA;
j) one or more enzyme(s) catalyzing conversion of said 3-methyl-2-butenoyl-CoA to 3-methyl-2-buten-1-ol, wherein said enzyme(s) is selected from:
   a. an alcohol-forming acyl-CoA reductase;
   b. an aldehyde forming acyl-CoA reductase plus an alcohol dehydrogenase; or
   c. a carboxylate reductase plus an alcohol dehydrogenase plus an enzyme(s) selected from an acyl-CoA synthase, an acyl-CoA transferase, a thioesterase, or a carboxylate kinase plus a phosphotransacylase;
k) one or more enzyme(s) catalyzing conversion of said 3-methyl-2-buten-1-ol to DMAP or DMAPP, wherein said enzyme(s) is selected from:
   a. an alcohol kinase;
   b. an alcohol kinase plus a phosphate kinase; or
   c. an alcohol diphosphokinase;
l) optionally, an isopentenyl diphosphate isomerase catalyzing conversion of said DMAPP to IPP; and
m) optionally a geranyl pyrophosphate synthase catalyzing conversion of said DMAPP and IPP to GPP.

FIGURE 30C-16

| |
|---|
| Any recombinant microorganism or process herein described,, that comprises:<br>a) an aldolase catalyzing conversion of 2-oxobutanoate and acetaldehyde to 4-hydroxy-2-oxo-3-methylpentanoate;<br>b) a mutase catalyzing conversion of said 4-hydroxy-2-oxo-3-methylpentanoate to 4-hydroxy-2-oxo-4-methylpentanoate;<br>c) a 2-oxopent-4-enoate hydratase catalyzing conversion of said 4-hydroxy-2-oxo-4-methylpentanoate to 4-methyl-2-oxopent-4-enoate;<br>d) one or more enzyme(s) catalyzing conversion of said 4-methyl-2-oxopent-4-enoate to 3-methyl-3-buten-1-ol, wherein said enzymes(s) is selected from:<br>a. an alpha-ketoacid decarboxylase plus an alcohol dehydrogenase;<br>b. an alpha-ketoacid dehydrogenase plus an alcohol forming acyl-CoA reductase;<br>c. an alpha-ketoacid dehydrogenase plus an aldehyde forming acyl-CoA reductase plus an alcohol dehydrogenase; or<br>d. an alpha-ketoacid dehydrogenase plus a carboxylate reductase plus an alcohol dehydrogenase plus an enzyme(s) selected from a thioesterase, an acyl-CoA synthase, an acyl-CoA transferase, or a carboxylate kinase plus a phosphotransacylase;<br>e) one or more enzyme(s) catalyzing conversion of said 3-methyl-3-buten-1-ol to IP or IPP, wherein said enzyme(s) is selected from:<br>a. an alcohol kinase;<br>b. an alcohol kinase plus a phosphate kinase; or<br>c. an alcohol diphosphokinase;<br>f) optionally, an isopentenyl diphosphate isomerase catalyzing conversion of said IPP to DMAPP; and<br>g) optionally a geranyl pyrophosphate synthase catalyzing conversion of said DMAPP and IPP to GPP. |
| Any recombinant microorganism or process herein described,, wherein said isoprenoid precursor(s) is selected from dimethylallyl phosphate (DMAP), isopentenyl phosphate (IP), isopentenyl pyrophosphate (IPP), dimethylallyl pyrophosphate (DMAPP), geranyl pyrophosphate (GPP), farnesyl pyrophosphate (FPP), or geranylgeranyl diphosphate (GGPP). |
| Any recombinant microorganism or process herein described,, comprising one or more enzyme(s) selected from a prenyl transferase, a terpene synthase, or a terpene cyclase catalyzing conversion of said isoprenoid precursor(s) to an isoprenoid(s) or a derivative(s) thereof. |
| Any recombinant microorganism or process herein described,, wherein said isoprenoid(s) is selected from hemiterpenoid(s), monoterpenoid(s), sesquiterpenoid(s), diterpenoid(s), sesterterpenoid(s), triterpenoid(s), tetraterpenoid(s), polyterpenoid(s), or a derivative(s) thereof. |
| Any recombinant microorganism or process herein described,, wherein said isoprenoid derivative(s) is a prenylated aromatic compound(s). |

FIGURE 30C-17

| |
|---|
| Any recombinant microorganism or process herein described,, wherein said isoprenoid derivative(s) is a prenylated aromatic compound(s), said recombinant microorganism comprising:<br>a) an aromatic prenyltransferase or a 4-hydroxybenzoate geranyltransferase enzyme catalyzing a prenyl transfer from an isoprenoid precursor(s) to an aromatic polyketide(s) forming a prenylated aromatic compound(s);<br>b) a metabolic pathway for the production of an aromatic polyketide(s) or an extracellular source of an aromatic polyketide(s), where optionally said metabolic pathway is a thiolase enzyme(s) catalyzing one or multiple iterative non-decarboxylative condensation(s) of an acyl-CoA and acyl-CoA plus beta-reduction enzyme(s) plus termination pathway enzyme(s); and<br>c) optionally one or more enzymes catalyzing conversion of said prenylated aromatic compound(s) to another prenylated aromatic compound(s) or a derivative(s) thereof. |
| A recombinant microorganism producing a prenylated aromatic compound(s), said recombinant microorganism comprising:<br>a) an aromatic prenyltransferase enzyme catalyzing a prenyl transfer from an isoprenoid precursor(s) to an aromatic polyketide(s) forming a prenylated aromatic compound(s), said enzyme encoded by a gene(s) selected from *Arabidopsis thaliana ppt1, Lithospermum erythrorhizon pgt-1, Lithospermum erythrorhizon pgt-2, Schizosaccharomyces pombe coq2, E. coli ubiA, Streptomyces sp. strain CL190 nphB, Streptomyces sp. CNQ-509 cnqp3, Phleum pretense phl p4, Streptomyces Coelicolor SCO7190, Streptomyces Coelicolor SCO7190 or Phleum pretense phl p4*;<br>b) a metabolic pathway for the production of an aromatic polyketide(s) or an extracellular source of an aromatic polyketide(s), where optionally said metabolic pathway is a thiolase enzyme(s) catalyzing one or multiple iterative non-decarboxylative condensation(s) of an acyl-CoA and acyl-CoA plus beta-reduction enzyme(s) plus termination pathway enzyme(s); and<br>c) optionally one or more enzymes catalyzing conversion of said prenylated aromatic compound(s) to another prenylated aromatic compound(s) or a derivative(s) thereof.<br>wherein said enzyme(s) or gene(s) includes its homolog(s). |
| Any recombinant microorganism or process herein described,, wherein said isoprenoid precursor is GPP, said one or more aromatic polyketide product(s) is selected from olivetolic acid, olivetol, divarinolic acid or divarinol. |
| Any recombinant microorganism or process herein described,, wherein said isoprenoid derivative(s) is a cannabinoid(s). |
| Any recombinant microorganism or process herein described,, further comprising one or more enzyme(s) selected from tetrahydrocannabinolic acid synthase, cannabidiolic acid synthase, cannabichromenic acid synthase, tetrahydrocannabivarinic acid synthase, cannabidivarinic acid synthase, or cannabichrovarinic acid synthase. |
| Any recombinant microorganism or process herein described,, wherein said cannabinoid(s) is selected from cannabigerolic acid (CBGA), cannabigerol (CBG), cannabigerovarinic acid (CBGVA), and cannabigerovarin (CBGV), tetrahydrocannabinolic acid (THCA), tetrahydrocannabinol (THC), cannabidiolic acid (CBDA), cannabidiol (CBD), cannabichromenic acid (CBCA), cannabichromene (CBC), tetrahydrocannabivarinic acid (THCVA), tetrahydrocannabivarin (THCV), cannabidivarinic acid (CBDVA), cannabidivarin (CBDV), cannabichrovarinic acid (CBCVA), cannabichrovarin (CBCV), cannabinolic acid (CBNA), cannabinol (CBN); cannabivarinic acid (CBVA), or cannabivarin (CBV). |

FIGURE 30C-18

| |
|---|
| Any recombinant microorganism or process herein described,, that comprises one or more enzymes selected from:<br>a) a thiolase encoded by a gene(s) selected from *E. coli atoB, E. coli yqeF, E. coli fadA, E. coli fadI, Ralstonia eutropha bktB, Pseudomonas sp. B13 catF, E coli paaJ, Rhodococcus opacus pcaF, Pseudomonas putida pcaF, Streptomyces sp. pcaF, P. putida fadAx, P. putida fadA, Ralstonia eutropha phaA, Acinetobacter sp. ADP1 dcaF, Clostridium acetobutylicum thlA, or Clostridium acetobutylicum thlB;*<br>b) an acetolactate synthase or an acyloin condensation enzyme encoded by a gene(s) selected from *E. coli ilvBN, B. subtilis alsS*, or *E. coli ilvIH*;<br>c) a 2-hydroxyacyl-CoA lyase encoded by a gene(s) selected from *Homo sapiens hacl1, Rattus norvegicus hacl1, Dictyostelium discoideum hacl1*, or *Mus musculus hacl1*;<br>d) an aldolase encoded by a gene(s) selected from *E. coli mhpE, Pseudomonas putida xylK*, or *Pseudomonas* sp. CF600 *dmpG*;<br>e) a ketoacyl-CoA synthase encoded by a gene(s) selected from *Gluconobacter oxydans GOX0115, Pseudomonas aeruginosa fabH2, Streptomyces* sp. MMG1121 *PRK09352, Streptomyces tendae acs2, Streptomyces* sp. strain CL190 *nphT7, Physaria fendleri KCS3, Saccharomyces cerevisiae ELO2, Arabidopsis thaliana col KCS1, Arabidopsis thaliana col FAE1*, or *Arabidopsis thaliana col CER6*;<br>f) a prenyltransferase or 4-hydroxybenzoate geranyltransferase encoded by a gene(s) selected from *Arabidopsis thaliana ppt1, Lithospermum erythrorhizon pgt-1, Lithospermum erythrorhizon pgt-2, Schizosaccharomyces pombe coq2, Cannabis sativa CsPT1, E. coli ubiA, Streptomyces sp. strain CL190 nphB, Streptomyces sp. CNQ-509 cnqp3, Phleum pretense phl p4, Streptomyces Coelicolor SCO7190, Streptomyces Coelicolor SCO7190 or Phleum pretense phl p4*;<br>wherein said enzyme(s) or gene(s) includes its homolog(s). |
| Any recombinant microorganism or process herein described, that further comprises reduced expression of gene(s) encoding one or more fermentation enzymes leading to reduced production of one or more of lactate, acetate, ethanol or succinate. |
| Any recombinant microorganism or process herein described, that comprises a homologous chromosomal expression of one or more enzyme(s) selected from an acetolactate synthase, a ketoacyl-CoA synthase, a 2-hydroxyacyl-CoA lyase, an aldolase, an acyloin synthase, an acetohydroxy acid isomeroreductase, an acetoacetate decarboxylate, an acyl-CoA dehydrogenase, an acyl-CoA reductase, an acyl-CoA synthase, an acyl-CoA transferase, an alcohol dehydratase, an alcohol dehydrogenase, an alpha-keto acid decarboxylase, an alpha-keto acid dehydrogenase, a carboxylate kinase, a carboxylate reductase, a dehydratase, a dihydroxyacid dehydratase, a diol dehydratase, an enoyl-CoA hydratase, an enoyl-CoA reductase, a glutaconyl-CoA decarboxylase, an hydroxyacid dehydratase, an hydroxyacid dehydrogenase, an hydroxyacyl-CoA dehydratase, an hydroxyacyl-CoA dehydrogenase, an hydroxymethylacyl-CoA synthase, an isomeroreductase, an isopropylmalate dehydrogenase, an isopropylmalate isomerase, an isopropylmalate synthase, a mutase, a phosphotransacylase, a thioesterase, or a thiolase, an aromatic prenyltransferase, a 4-hydroxybenzoate geranyltransferase, an alcohol kinase, a phosphate kinase, or an alcohol diphosphokinase. |

FIGURE 30C-19

| |
|---|
| Any recombinant microorganism or process herein described, that comprises a recombinant vector expressing one or more enzyme(s) selected from an acetolactate synthase, a ketoacyl-CoA synthase, a 2-hydroxyacyl-CoA lyase, an aldolase, an acyloin synthase, an acetohydroxy acid isomeroreductase, an acetoacetate decarboxylate, an acyl-CoA dehydrogenase, an acyl-CoA reductase, an acyl-CoA synthase, an acyl-CoA transferase, an alcohol dehydratase, an alcohol dehydrogenase, an alpha-keto acid decarboxylase, an alpha-keto acid dehydrogenase, a carboxylate kinase, a carboxylate reductase, a dehydratase, a dihydroxyacid dehydratase, a diol dehydratase, an enoyl-CoA hydratase, an enoyl-CoA reductase, a glutaconyl-CoA decarboxylase, an hydroxyacid dehydratase, an hydroxyacid dehydrogenase, an hydroxyacyl-CoA dehydratase, an hydroxyacyl-CoA dehydrogenase, an hydroxymethylacyl-CoA synthase, an isomeroreductase, an isopropylmalate dehydrogenase, an isopropylmalate isomerase, an isopropylmalate synthase, a mutase, a phosphotransacylase, a thioesterase, or a thiolase, an aromatic prenyltransferase, a 4-hydroxybenzoate geranyltransferase, an alcohol kinase, a phosphate kinase, or an alcohol diphosphokinase. |
| Any recombinant microorganism or process herein described, wherein said vector is a prokaryotic vector, a viral vector, or a eukaryotic vector. |
| Any recombinant microorganism or process herein described, wherein said vector is an *Escherichia coli* expression vector. |
| Any recombinant microorganism or process herein described, wherein said recombinant microorganism is a bacteria or yeast cell. Insect, plant, algal and mammalian cells could also be used. *Escherichia* and *Escherichia coli* cells are preferred. |
| A method of producing an isoprenoid precursor(s), or optionally an isoprenoid(s) or a derivative(s) thereof, said method comprising growing any recombinant microorganism herein described in a culture medium for a time and under conditions to produce an isoprenoid(s), an isoprenoid precursor(s), or a derivative(s) thereof. |
| Any recombinant microorganism or process herein described, wherein said isoprenoid precursor(s), isoprenoid(s), or derivative(s) thereof is isolated from the culture medium or said recombinant microorganism or both. |
| Any recombinant microorganism or process herein described, wherein said isoprenoid derivative(s) is a prenylated aromatic compound(s). |
| Any recombinant microorganism or process herein described, wherein said isoprenoid derivative(s) is a cannabinoid(s). |

FIGURE 30C-20

A process for the production of an isoprenoid precursor(s), or optionally an isoprenoid(s) or a derivative(s) thereof, said process comprising:

a) catalyzing condensation of two compounds to form a condensation product(s) selected from:
   a. a non-decarboxylative Claisen condensation of an acyl-CoA plus a second acyl-CoA to form a beta-ketoacyl-CoA;
   b. a decarboxylative Claisen condensation of an acyl-CoA plus a beta-carboxylic acyl-CoA to form a beta-ketoacyl-CoA;
   c. an aldol condensation of an aldehyde plus a ketone, or an aldehyde plus a second aldehyde, or an aldehyde plus a carboxylic acid to form an aldol;
   d. a non-decarboxylative acyloin condensation of a ketone plus an aldehyde, or an aldehyde plus a second aldehyde to form an acyloin; or
   e. a decarboxylative acyloin condensation of a ketone plus an alpha-keto acid, an aldehyde plus an alpha-keto acid, or an alpha-keto acid plus a second alpha-keto acid to form an acyloin;

b) catalyzing conversion of said condensation product(s) to an isoprenoid alcohol(s) using three (or two, or one) or more enzymes, with at least three (or two, or one) of said enzymes selected from an acetohydroxy acid isomeroreductase, an acetoacetate decarboxylate, an acyl-CoA dehydrogenase, an acyl-CoA reductase, an acyl-CoA synthase, an acyl-CoA transferase, an alcohol dehydratase, an alcohol dehydrogenase, an aldehyde decarboxylase, an alpha-keto acid decarboxylase, an alpha-keto acid dehydrogenase, a carboxylate kinase, a carboxylate reductase, a dehydratase, a dihydroxyacid dehydratase, a diol dehydratase, an enoate hydratase, an enoyl-CoA hydratase, an enoyl-CoA reductase, a glutaconyl-CoA decarboxylase, an hydroxyacid dehydratase, an hydroxyacid dehydrogenase, an hydroxyacyl-CoA dehydratase, an hydroxyacyl-CoA dehydrogenase, an hydroxymethylacyl-CoA synthase, an isomeroreductase, an isopropylmalate dehydrogenase, an isopropylmalate isomerase, an isopropylmalate synthase, a mutase, an omega-oxidation enzyme, a phosphotransacylase, a thioesterase, or a thiolase, where said conversion optionally proceeds through an isoprenoid acyl-CoA;

c) catalyzing conversion of said isoprenoid alcohol(s) to an isoprenoid precursor(s) using one or more phosphorylation enzyme(s); and d) optionally catalyzing conversion of said isoprenoid precursor(s) to another isoprenoid precursor(s) or an isoprenoid(s) or a derivative(s) thereof using one or more enzyme(s).

FIGURE 30C-21

| |
|---|
| A process for the production of an isoprenoid precursor(s), or optionally an isoprenoid(s) or a derivative(s) thereof, said process comprising:<br>a) catalyzing condensation of two compounds to form a condensation product(s) selected from:<br>a. a non-decarboxylative Claisen condensation of an acyl-CoA plus a second acyl-CoA to form a beta-ketoacyl-CoA;<br>b. a decarboxylative Claisen condensation of an acyl-CoA plus a beta-carboxylic acyl-CoA to form a beta-ketoacyl-CoA;<br>c. an aldol condensation of an aldehyde plus a ketone, or an aldehyde plus a second aldehyde, or an aldehyde plus a carboxylic acid to form an aldol;<br>d. a non-decarboxylative acyloin condensation of a ketone plus an aldehyde, or an aldehyde plus a second aldehyde to form an acyloin; or<br>e. a decarboxylative acyloin condensation of a ketone plus an alpha-keto acid, an aldehyde plus an alpha-keto acid, or an alpha-keto acid plus a second alpha-keto acid to form an acyloin;<br>b) catalyzing conversion of said condensation product(s) to an isoprenoid alcohol(s) using three (or two, or one) or more enzymes with at least one of said enzyme(s) comprising an alcohol forming termination enzyme(s).<br>c) catalyzing conversion of said isoprenoid alcohol(s) to an isoprenoid precursor(s) using one or more phosphorylation enzyme(s); and<br>d) optionally catalyzing conversion of said isoprenoid precursor(s) to another isoprenoid precursor(s) or an isoprenoid(s) or a derivative(s) thereof using one or more enzyme(s). |
| A process for the production of an isoprenoid precursor(s), or optionally an isoprenoid(s) or a derivative(s) thereof, said process comprising one or more enzyme-produced intermediate products selected from 2-acetolactate, 2-hydroxy-isovalerate, 2-oxo-isocaproate, 3-methyl-3-hydroxybutyryl-CoA, 4-hydroxy-2-methylbutanoyl-CoA, 3-methylcrotonyl-CoA, 3-methyl-3-butenoyl-CoA, 3-methyl-2-buten-1-al, geranyl-CoA, 3-methyl-2-buten-1-ol, 3-methyl-3-buten-1-ol, 4-hydroxy-2-oxo-4-methylpentanoate, geraniol, or dimethylallyl phosphate. |
| A process for the production of an isoprenoid precursor(s), or optionally an isoprenoid(s) or a derivative(s) thereof, said process comprising:<br>a) one or more enzyme-produced intermediate products selected from 2-acetolactate, 2 hydroxy-isovalerate, 2-oxo-isocaproate, 3-methyl-3-hydroxybutyryl-CoA, 4-hydroxy-2-methylbutanoyl-CoA, 3-methylcrotonyl-CoA, 3-methyl-3-butenoyl-CoA, 3-methyl-2-buten-1-al, geranyl-CoA, 3-methyl-2-buten-1-ol, 3-methyl-3-buten-1-ol, 4-hydroxy-2-oxo-4-methylpentanoate, geraniol, or dimethylallyl phosphate;<br>b) catalyzing conversion of said intermediate product(s) to an isoprenoid alcohol(s) using one or more enzyme(s), except in the case of intermediate products 3-methyl-2-buten-1-ol or 3-methyl-3-buten-1-ol which are isoprenoid alcohols and proceed directly to step c), or dimethylallyl phosphate which proceeds directly to step d);<br>c) catalyzing conversion of said isoprenoid alcohol(s) to an isoprenoid precursor(s) using one or more phosphorylation enzyme(s); and<br>d) optionally catalyzing conversion of said isoprenoid precursor(s) to another isoprenoid precursor(s) or an isoprenoid(s) or a derivative(s) thereof using one or more enzyme(s). |

FIGURE 30C-22

| |
|---|
| A process for the production of an isoprenoid precursor(s), or optionally an isoprenoid(s) or a derivative(s) thereof, said process comprising:<br>a) catalyzing condensation of two compounds to form a condensation product(s) selected from:<br>a. a non-decarboxylative Claisen condensation of an acyl-CoA plus a second acyl-CoA to form a beta-ketoacyl-CoA;<br>b. a decarboxylative Claisen condensation of an acyl-CoA plus a beta-carboxylic acyl-CoA to form a beta-ketoacyl-CoA;<br>c. an aldol condensation of an aldehyde plus a ketone, or an aldehyde plus a second aldehyde, or an aldehyde plus a carboxylic acid to form an aldol;<br>d. a non-decarboxylative acyloin condensation of a ketone plus an aldehyde, or an aldehyde plus a second aldehyde to form an acyloin; or<br>e. a decarboxylative acyloin condensation of a ketone plus an alpha-keto acid, an aldehyde plus an alpha-keto acid, or an alpha-keto acid plus a second alpha-keto acid to form an acyloin;<br>b) catalyzing conversion of said condensation product(s) to an intermediate product(s) selected from 2 hydroxy-isovalerate, 2-oxo-isocaproate, 3-methyl-3-hydroxybutyryl-CoA, 4-hydroxy-2-methylbutanoyl-CoA, 3-methylcrotonyl-CoA, 3-methyl-3-butenoyl-CoA, 3-methyl-2-buten-1-al, geranyl-CoA, 3-methyl-2-buten-1-ol, 3-methyl-3-buten-1-ol, 4-hydroxy-2-oxo-4-methylpentanoate, geraniol, or dimethylallyl phosphate, using one or more enzyme(s);<br>c) catalyzing conversion of said intermediate product(s) to an isoprenoid alcohol(s) using one or more enzyme(s), except in the case of intermediate products 3-methyl-2-buten-1-ol or 3-methyl-3-buten-1-ol which are isoprenoid alcohols and proceed directly to step d), or dimethylallyl phosphate which proceeds directly to step e);<br>d) catalyzing conversion of said isoprenoid alcohol(s) to an isoprenoid precursor(s) using one or more phosphorylation enzyme(s); and<br>e) optionally catalyzing conversion of said isoprenoid precursor(s) to another isoprenoid precursor(s) or an isoprenoid(s) or a derivative(s) thereof using one or more enzyme(s). |
| A process for the production of an isoprenoid precursor(s), or optionally an isoprenoid(s) or a derivative(s) thereof, said process comprising:<br>a) one or more enzyme-produced isoprenoid alcohols(s);<br>b) catalyzing conversion of said isoprenoid alcohol(s) to an isoprenoid precursor(s) using one or more phosphorylation enzyme(s); and<br>c) optionally catalyzing conversion of said isoprenoid precursor(s) to another isoprenoid precursor(s) or an isoprenoid(s) or a derivative(s) thereof using one or more enzyme(s). |

FIGURE 30C-23

| |
|---|
| A process for the production of an isoprenoid precursor(s), or optionally an isoprenoid(s) or a derivative(s) thereof, said process comprising:<br>a) catalyzing condensation between an acyl-CoA plus a second acyl-CoA, each said acyl-CoA selected from acetyl-CoA, glycolyl-CoA, propionyl-CoA, malonyl-CoA, an unsubstituted acyl-CoA, or a functionalized acyl-CoA to form a beta-ketoacyl CoA using an enzyme selected from a thiolase or a ketoacetyl-CoA synthase;<br>b) optionally one or more iteration(s) wherein said beta-ketoacyl CoA is modified using one or more enzymes and then used as an acyl-CoA primer unit for a new condensation iteration of step a);<br>c) catalyzing conversion of said beta-ketoacyl CoA to an isoprenoid alcohol using three (or two, or one) or more enzyme(s) comprising a beta-reduction enzyme(s), and an alcohol forming termination enzyme(s);<br>d) catalyzing conversion of said isoprenoid alcohol to an isoprenoid precursor(s) using or more phosphorylation enzyme(s); and<br>e) optionally catalyzing conversion of said isoprenoid precursor(s) to another isoprenoid precursor(s) or an isoprenoid(s) or a derivative(s) thereof using one or more enzyme(s). |
| A process for the production of an isoprenoid precursor(s), or optionally an isoprenoid(s) or a derivative(s) thereof, said process comprising:<br>a) catalyzing condensation of two pyruvates to form 2-acetolactate using acetolactate synthase;<br>b) catalyzing conversion of said 2-acetolactate to 2-oxoisovalerate using acetohydroxy acid isomeroreductase plus dihydroxyacid dehydratase;<br>c) catalyzing conversion of 2-oxoisovalerate to an isoprenoid alcohol(s) using four (or three, or two, or one) or more enzymes, with at least four (or three, or two, or one) of said enzymes selected from an acetohydroxy acid isomeroreductase, an acetoacetate decarboxylate, an acyl-CoA dehydrogenase, an acyl-CoA reductase, an acyl-CoA synthase, an acyl-CoA transferase, an alcohol dehydratase, an alcohol dehydrogenase, an aldehyde decarboxylase, an alpha-keto acid decarboxylase, an alpha-keto acid dehydrogenase, a carboxylate kinase, a carboxylate reductase, a dehydratase, a dihydroxyacid dehydratase, a diol dehydratase, an enoate hydratase, an enoyl-CoA hydratase, an enoyl-CoA reductase, a glutaconyl-CoA decarboxylase, an hydroxyacid dehydratase, an hydroxyacid dehydrogenase, an hydroxyacyl-CoA dehydratase, an hydroxyacyl-CoA dehydrogenase, an hydroxymethylacyl-CoA synthase, an isomeroreductase, an isopropylmalate dehydrogenase, an isopropylmalate isomerase, an isopropylmalate synthase, a mutase, an omega-oxidation enzyme, a phosphotransacylase, a thioesterase, or a thiolase, where said conversion optionally proceeds through an isoprenoid acyl-CoA;<br>d) catalyzing conversion of said isoprenoid alcohol to an isoprenoid precursor(s) using one or more phosphorylation enzyme(s); and<br>e) optionally catalyzing conversion of said isoprenoid precursor(s) to another isoprenoid precursor(s) or an isoprenoid(s) or a derivative(s) thereof using one or more enzyme(s). |

FIGURE 30C-24

| |
|---|
| A process for the production of an isoprenoid precursor(s), or optionally an isoprenoid(s) or a derivative(s) thereof, said process comprising:<br>a) catalyzing condensation of two pyruvates to form 2-acetolactate using acetolactate synthase;<br>b) catalyzing conversion of said 2-acetolactate to 2-oxoisovalerate using acetohydroxy acid isomeroreductase plus dihydroxyacid dehydratase;<br>c) catalyzing conversion of 2-oxoisovalerate to an isoprenoid alcohol(s) using four (or three, or two, or one) or more enzymes with at least one of said enzyme(s) comprising an alcohol forming termination enzyme(s);<br>d) catalyzing conversion of said isoprenoid alcohol to an isoprenoid precursor(s) using one or more phosphorylation enzyme(s); and<br>e) optionally catalyzing conversion of said isoprenoid precursor(s) to another isoprenoid precursor(s) or an isoprenoid(s) or a derivative(s) thereof using one or more enzyme(s). |
| Any method or process herein described, wherein said isoprenoid precursor is selected from dimethylallyl phosphate (DMAP), isopentenyl phosphate (IP), isopentenyl pyrophosphate (IPP), dimethylallyl pyrophosphate (DMAPP), geranyl pyrophosphate (GPP), farnesyl pyrophosphate (FPP), or geranylgeranyl diphosphate (GGPP). |
| Any method or process herein described, comprising one or more enzyme(s) selected from a prenyl transferase, a terpene synthase, or a terpene cyclase catalyzing conversion of said isoprenoid precursor(s) to an isoprenoid(s) and a derivative(s) thereof. |
| Any method or process herein described,wherein said isoprenoid(s) is selected from hemiterpenoid(s), monoterpenoid(s), sesquiterpenoid(s), diterpenoid(s), sesterterpenoid(s), triterpenoid(s), tetraterpenoid(s), polyterpenoid(s), or a derivative(s) thereof. |
| Any method or process herein described,wherein said isoprenoid derivative(s) is a prenylated aromatic compound. |
| Any method or process herein described, wherein:<br>a) said isoprenoid derivative(s) is a prenylated aromatic compound(s); and<br>b) said process further comprising:<br>a. catalyzing a prenyl transfer from an isoprenoid precursor(s) to an aromatic polyketide(s) forming a prenylated aromatic compound(s) using an aromatic prenyltransferase or a 4-hydroxybenzoate geranyltransferase;<br>b. optionally said aromatic polyketide(s) is formed by catalyzing one or multiple iterative non-decarboxylative condensation(s) of an acyl-CoA and a second acyl-CoA plus beta-reduction enzyme(s) plus termination pathway enzyme(s); and<br>c. optionally catalyzing conversion of said prenylated aromatic compound(s) to another prenylated aromatic compound(s) or a derivative(s) thereof using one or more enzymes. |

FIGURE 30C-25

| |
|---|
| A process for the production of a prenylated aromatic compound(s), said process comprising:<br>a) catalyzing a prenyl transfer from an isoprenoid precursor(s) to an aromatic polyketide(s) forming a prenylated aromatic compound(s) using an aromatic prenyltransferase enzyme, said enzyme encoded by a gene(s) selected from *Arabidopsis thaliana ppt1, Lithospermum erythrorhizon pgt-1, Lithospermum erythrorhizon pgt-2, Schizosaccharomyces pombe coq2, Cannabis sativa CsPT1, E. coli ubiA, Streptomyces sp. strain CL190 nphB, Streptomyces sp. CNQ-509 cnqp3, Phleum pretense phl p4, Streptomyces Coelicolor SCO7190, Streptomyces Coelicolor SCO7190 or Phleum pretense phl p4*;<br>b) optionally said aromatic polyketide(s) is formed by catalyzing one or multiple iterative non-decarboxylative condensation(s) of an acyl-CoA and a second acyl-CoA plus beta-reduction enzyme(s) plus termination pathway enzyme(s); and<br>c) optionally catalyzing conversion of said prenylated aromatic compound(s) to another prenylated aromatic compound(s) or a derivative(s) thereof using one or more enzymes;<br>) wherein said enzyme(s) or gene(s) includes its homolog(s). |
| Any method or process herein described, wherein said isoprenoid derivative(s) is a cannabinoid(s). |
| Any method or process herein described,wherein said cannabinoid(s) is selected from cannabigerolic acid (CBGA), cannabigerol (CBG), cannabigerovarinic acid (CBGVA), and cannabigerovarin (CBGV), tetrahydrocannabinolic acid (THCA), tetrahydrocannabinol (THC), cannabidiolic acid (CBDA), cannabidiol (CBD), cannabichromenic acid (CBCA), cannabichromene (CBC), tetrahydrocannabivarinic acid (THCVA), tetrahydrocannabivarin (THCV), cannabidivarinic acid (CBDVA), cannabidivarin (CBDV), cannabichrovarinic acid (CBCVA), cannabichrovarin (CBCV), cannabinolic acid (CBNA), cannabinol (CBN); cannabivarinic acid (CBVA), or cannabivarin (CBV). |
| Any method or process herein described,wherein each of said enzyme(s) is purified, or partially purified, or is contained in a recombinant microorganism producing said enzyme(s) or a lysate thereof, or combinations thereof, and wherein said isoprenoid precursor(s), isoprenoid(s) or derivative(s) thereof is optionally isolated. |

FIGURE 30C-26

A bacteria comprising Δ*fadE bktB*$^{CT5}$ Δ*atoB fadB*$^{CT5}$ Δ*fadA egter*$^{CT5}$ or Δ*fadE bktB*$^{CT5}$ Δ*atoB fadB*$^{CT5}$ Δ*fadA egter*$^{CT5}$ AccABCD+ or bkdF+ bkdG+ bkdH+ lplA+ lpdA1+ leuA+ leuB+ or HMGS+ aibA+ aibB+ liuC or HMGS+ aibA+ aibB+ liuC maqu_2507 or atoB$^{CT5}$ ΔfadB HMGS+ aibAB+ cbjALD+ liuC + or HMGS+ aibAB+ cbjALD+ liuC+ yjgB+ or HMGS+ aibAB+ cbjALD+ liuC+ yahK+ or idi+ trGPPS2+ ges+ ychB+ mtipk+ or MK+ HMGS+ HMGR+ or MK+ PMK+ PMD+ HMGS+ HMGR+ or idi+ trGPPS2+ CymR+ CT5+ NphB+ or idi+ trGPPS2+ CymR+ NphB+ or ΔglcD bktB+ phaB1+ phaJ+ pct+ tdter+ or fadB2x+ fadB1x+ ydiI+ or idi+ trGPPS2+ ges+ or idi+ trGPPS2+ ges+ ychB+ mtipk or idi+ trGPPS2+ ges+ thaipk+ mtipk+ or bktB+ phaB1+ phaJ+ or pct+ tdter+ or bktB+ or phaB1+ phaJ+ or ilvC+ ilvD+ alsS+ panE+ or bkdF+ bkdG+ bkdH+ lplA+ lpdA1+ or leuABCD+ or HMGS+ or aibAB+ P2-liuC+ or JC01(DE3): MG1655 (DE3) ΔldhA ΔpoxB Δpta ΔadhE ΔfrdA or JST06 (DE3): MG1655 (DE3) ΔldhA ΔpoxB Δpta ΔadhE ΔfrdA ΔyciA ΔybgC ΔydiI ΔtesA ΔfadM ΔtesB or JST06 (DE3) atoBCT5: MG1655 (DE3) atoBCT5 ΔldhA ΔpoxB Δpta ΔadhE ΔfrdA ΔyciA ΔybgC ΔydiI ΔtesA ΔfadM ΔtesB or JST06 (DE3) atoBCT5 ΔfadB: MG1655 (DE3) atoBCT5 ΔfadB ΔldhA ΔpoxB Δpta ΔadhE ΔfrdA ΔyciA ΔybgC ΔydiI ΔtesA ΔfadM ΔtesB or JST10 (DE3): MG1655 (DE3) bktBCT5 ΔatoB fadBCT5 ΔfadA egTERCT5 ΔldhA ΔpoxB Δpta ΔadhE ΔfrdA ΔyciA ΔybgC ΔydiI ΔtesA ΔfadM ΔtesB ΔfadE or ΔldhA ΔpoxB Δpta ΔadhE ΔfrdA ΔyciA ΔybgC ΔydiI ΔtesA ΔfadM ΔtesB or atoB$^{CT5}$ ΔldhA ΔpoxB Δpta ΔadhE ΔfrdA ΔyciA ΔybgC ΔydiI ΔtesA ΔfadM ΔtesB or atoBCT5 ΔfadB ΔldhA ΔpoxB Δpta ΔadhE ΔfrdA ΔyciA ΔybgC ΔydiI ΔtesA ΔfadM ΔtesB or bktBCT5 ΔatoB fadBCT5 ΔfadA egTERCT5 ΔldhA ΔpoxB Δpta ΔadhE ΔfrdA ΔyciA ΔybgC ΔydiI ΔtesA ΔfadM ΔtesB ΔfadE or any of the bacteria descried herein, or any combination(s) thereof or any bacteria with any of the plasmids described herein added thereto.

SYNTHESIS OF ISOPRENOIDS AND DERIVATIVES

PRIOR RELATED APPLICATIONS

This application is a divisional application of U.S. Ser. No. 17/234,398, filed Apr. 19, 2021 which is a divisional application of U.S. Ser. No. 16/081,756, filed Aug. 31, 2018 (now US patent U.S. Ser. No. 11/046,978) which is a National Phase filing under 35 U.S.C. § 371 of International Application PCT/US2017/022581, filed Mar. 15, 2017 which claims priority to US Serial Nos. 62/308,937, filed Mar. 16, 2016, titled SYNTHESIS OF ISOPRENOIDS AND DERIVATIVES THROUGH THIOLASE-CATALYZED NON-DECARBOXYLATIVE CONDENSATION REACTIONS, and 62/343,598, filed May 31, 2016, titled BIOLOGICAL SYNTHESIS OF ISOPRENOIDS AND PRENYLATED AROMATICS, each of which are incorporated by reference herein in its entirety for all purposes.

REFERENCE TO ELECTRONIC SEQUENCE LISTING

The application contains Sequence Listing which has been submitted electronically in .XML format and is hereby incorporated by reference in its entirety. Said .XML copy, created on Oct. 6, 2023, is named "RICE2016-060-08USDIV2.xml" and is 189,059 bytes in size. The sequence listing contained in this .XML file is part of the specification and is hereby incorporated by reference herein in its entirety.

FIELD OF THE DISCLOSURE

This disclosure generally relates to the use of enzyme combinations or recombinant microorganisms comprising same to make various isoprenoid precursors, isoprenoids and derivatives thereof including prenylated aromatic compounds. Novel enzymes and cells for making cannabinoids and olivoteic acid are also provided.

BACKGROUND OF THE DISCLOSURE

The biosynthesis of fatty acids, polyketides, isoprenoids, and many other molecules with applications ranging from biofuels and green chemicals to therapeutic agents, rely on reactions catalyzing the formation of carbon-carbon bonds. Small precursor metabolites serve as building blocks for these pathways, which are subsequently condensed and modified until the desired chain length and functionality are achieved.

Isoprenoids represent one of the largest and most diverse classes of these natural products, with more than 40,000 different structures found in all kingdoms of life. These natural products have a wide range of ecological, physiological and structural functions and have been utilized for their very different properties in applications such as medicines, flavors, and fragrances. Furthermore, modem industry has harnessed these compounds as pharmaceuticals, components of personal hygiene and cosmetic products, antimicrobial agents, solvents, and commodity materials such natural rubbers and biofuels.

Despite this high diversity and product functionality, all isoprenoids are formed from the 5-carbon ($C_5$) building blocks isopentenyl pyrophosphate (IPP) and dimethylallyl pyrophosphate (DMAPP). These two building blocks are formed from one of two native pathways: the mevalonate (MVA) pathway (native to most archaea and eukaryotes) or the 2-C-methyl-D-erythritol 4-phosphate/1-deoxy-D-xylulose 5-phosphate (DXP/MEP) pathway (native to most bacteria). The MVA pathway utilizes 3 acetyl-CoA molecules for the formation of the $C_5$ intermediates, while the 3-carbon intermediates pyruvate and glyceraldehyde-3-phosphate serve as the starting point in the DXP pathway. Following the synthesis of IPP and DMAPP through either pathway, these intermediates are condensed and modified by various combinations of for example geranyl-, farnesyl- or, geranylgeranyl-diphosphate synthases, prenyl transferase, terpene synthases, or terpene cyclases to form thousands of products.

While these native pathways have been exploited for the synthesis of various isoprenoid products, there are limitations in using the native pathways. For example, the synthesis of the required $C_5$ building blocks from either the MVA or DXP pathway results in the inevitable loss of carbon from the starting intermediates (3 acetyl-CoA molecules or pyruvate and glyceraldehyde-3-phosphate). Furthermore, both the MVA and DXP pathways are energy (ATP) intensive, with the net consumption of 3 ATP equivalents from starting intermediates. Thus, there exists a need for methods to overcome the inherently low carbon and energy efficiency of natural isoprenoid precursor synthesis pathways. Preferably, such pathways would further diversify the range of products, and provide a more carbon and energy efficient route.

SUMMARY OF THE DISCLOSURE

This disclosure generally relates to the use of either enzyme combinations or recombinant microbes expressing those enzyme combinations to make isoprenoid precursors, isoprenoids and derivatives thereof including prenylated aromatic compounds through novel synthetic metabolic pathways instead of the natural mevalonate (MVA) pathway or 1-deoxy-d-xylulose 5-phosphate (DXP) pathways, that can be exploited to achieve better carbon and or energy efficiency than the natural pathways.

Several approaches are described herein. In one approach, the enzymes are made and combined in one or more in vitro reactions to make the desired products. In another approach, recombinant cells are harvested and used as temporary bioreactors containing the enzymes to do all or part of the reactions for as long as the enzymes remain active. In another approach, the cells are lysed, and the lysate is used to catalyze the needed reactions. In yet another approach, recombinant cells are used in a growing, living system to continually make products. Combinations of the various approaches can also be used.

Further, there are three basic products types made herein, a) isoprenoid precursors, b) isoprenoids and derivatives thereof including prenylated aromatic compounds, and c) polyketides. Prenylated aromatic compounds are made by condensing isoprenoid precursors and aromatic polyketides, which can be made either by the methods of the invention or can be purchased or made by prior art recombinant synthesis methods.

As described herein, the novel pathways for the synthesis of these products exploit enzymes catalyzing Claisen, aldol, or acyloin condensation reactions for the generation of longer chain length intermediates from central carbon metabolites (FIG. 1). Both decarboxylative and non-carboxylative condensations are utilized, enabling product synthesis from a number of different starting compounds. These condensation reactions serve as a platform for the synthesis of isoprenoid precursors, isoprenoids and derivatives thereof, polyketides, and prenylated aromatic compounds when utilized in combination with a variety of metabolic pathways and enzymes for carbon rearrangement and the addition/removal of functional groups (FIG. 1).

One aspect of the invention is a CoA-dependent elongation platform based on the use of Claisen condensations, which accept functionalized acyl-CoAs as primers and extender units in a reverse beta-oxidation like pathway. Products can be pulled out at any point, and further modified if desired. In other aspects of the invention, aldol or acyloin condensations serve as the starting condensation reaction to enable product synthesis from central carbon metabolites such as pyruvate through various enzyme combinations (FIG. 1). Isoprenoid acyl-CoAs, such as 3-methyl-but-2-enoyl-CoA and 3-methyl-but-3-enoyl-CoA, and isoprenoid alcohols, such as prenol and isoprenol, are key pathway intermediates that can be converted to isoprenoid precursors, such as isopentenyl phosphate (IP), dimethylallyl phosphate (DMAP), IPP and DMAPP, through phosphorylation enzymes (FIG. 1). As above, any of the products can be further modified if desired.

In one embodiment, native or engineered thiolases catalyze the condensation between an acyl-CoA primer and another acyl-CoA serving as the extender unit, forming a beta-keto acyl-CoA. FIG. 1 demonstrates the general CoA-dependent elongation platform, which can also utilize decarboxylative Clasien condensation reactions catalyzed by ketoacyl-CoA synthases. Primers and extender units can be omega-functionalized to add required functionalities to the carbon chain. The beta-keto group of the beta-keto acyl-CoA formed via condensation can be reduced and modified step-wise by the beta-reduction reactions catalyzed by dehydrogenase(s), dehydratase(s) and/or reductase(s). Dehydrogenases reduce the beta-keto group of a CoA intermediate synthesized by the condensation(s) to a beta-hydroxy group. Dehydratases catalyze the dehydration of beta-keto group to an alpha, beta double bond. Reductases reduce the alpha, beta double bond to the single bond. Furthermore, various carbon re-arrangement enzymes, such as acyl-CoA mutases, can be employed to modify the carbon structure and branching of the acyl-CoAs. These CoA intermediates can then serve as the primer for the next round of condensation with the extender unit or as direct intermediates to IP, DMAP, IPP, DMAPP, or other isoprenoid precursors. After termination by spontaneous or enzyme-catalyzed CoA removal, reduction, and/or phosphorylation, and subsequent structure rearrangement, isoprenoids precursors (e.g., IPP, DMAPP, GPP, GGPP, FPP) are produced, and isoprenoids and derivatives thereof can be produced from those. Examples of pathways based on these Clasien condensation reactions are shown in FIGS. 2-6.

In another embodiment, either non-decarboxylative or decarboxylative Claisen condensation is used to form acetoacetyl-CoA as an intermediate. In one such pathway, acetoacetyl-CoA is subsequently converted to 3-hydroxy-3-methylglutaryl-CoA, which is then dehydrated and decarboxylated to form the isoprenoid acyl-CoA 3-methyl-2-butenoyl-CoA (FIG. 7). In another pathway from acetoacetyl-CoA, acetone generated from the decarboxylation of acetoacetic acid is converted to 3-methyl-3-hydroxy-butyryl-CoA through a non-decarboxylative Claisen condensation, which is then dehydrated to form 3-methyl-2-butenoyl-CoA (FIG. 8). 3-methyl-2-butenoyl-CoA can then be converted to prenol through various alcohol forming termination pathways (FIG. 7 and FIG. 8). This 5-carbon isoprenoid alcohol is then converted to DMAPP through a two-step phosphorylation with DMAP as an intermediate, or a one step diphosphorylation catalyzed by an alcohol diphosphokinase. DMAPP can be isomerized into IPP, generating the two required $C_5$ isoprenoid precursors.

Isoprenoid precursors, such as DMAPP, IPP, and GPP, can be condensed and modified by various combinations of geranyl-, farnesyl- or, geranylgeranyl-diphosphate synthases, prenyl transferase, terpene synthases, or terpene cyclases to form numerous isoprenoid products and derivatives thereof (FIG. 15). Combining this route for isoprenoid precursor formation for example with a route to aromatic polyketides enables the production of prenylated aromatic compounds through prenyl transfer of hydrocarbon units of isoprenoid intermediates to aromatic polyketides.

Examples of routes to polyketides include those based on thiolase-catalyzed condensation reactions or polyketide synthases. The route to polyketides via condensation and beta-reduction reactions involves the use of native or engineered thiolases that catalyze the non-decarboxylative condensation in an iterative manner (i.e. a single or multiple turns of the cycle) between two either unsubstituted or functionalized acyl-CoAs each serving as the primer and the extender unit to generate and elongate polyketide CoA intermediates. Before the next round of thiolase reaction, the beta-keto group of the polyketide chain can be reduced and modified step-wise by dehydrogenase or dehydratase or reductase reactions. Dehydrogenase reaction converts the beta-keto group to beta-hydroxy group. Dehydratase reaction converts the beta-hydroxy group to alpha-beta-double-bond. Reductase reaction converts the alpha-beta-double-bond to a single bond. Spontaneous or enzymatically catalyzed termination reaction(s) terminate the elongation of polyketide chain at any point through CoA removal and spontaneous rearrangement of the structure, generating the final functional polyketide products. This approach is the subject of patent application WO2017020043, BIOSYNTHESIS OF POLYKETIDES, filed Aug. 1, 2016, and 62/198,764, filed Jul. 30, 2015.

Alternatively, polyketide molecules can be formed through polyketide synthases (PKS). This large class of secondary metabolites formed by bacteria, fungi and plant are synthesized through these multi-domain enzymes or enzyme complexes. From a relatively small set of starting and extending molecules, these enzymes are capable of producing a vast array of complex metabolites through combinatorial and iterative carbon-carbon bond formation. Here, PKSs can be exploited for the synthesis of targeted polyketide molecules that can be further combined with isoprenoids and isoprenoid precursors synthesized through various pathways to form different molecules. This includes prenyl transfer of the hydrocarbon moiety of isoprenoid precursors to aromatic polyketides, forming prenylated aromatic compounds.

This disclosure also relates to the use of enzyme combinations or recombinant microbes to make isoprenoid precursors, isoprenoids and derivatives thereof including prenylated aromatic compounds through acyloin condensation reactions (FIG. 1). Certain examples involve using valine biosynthetic enzymes through acetolactate as an intermediate (FIG. 9 and FIG. 10). The pathway begins from a central carbon intermediate, in which two molecules of pyruvate are combined to form acetolactate through decarboxylative acyloin condensation, followed by subsequent isomeroreduction and dehydration to form 3-methyl-2-oxobutanoate. These reactions, catalyzed by acetolactate synthase, acetohydroxyacid isomeroreductase, and dihydroxyacid dehydratase, respectively, are part of the ubiquitous valine biosynthesis pathway.

Following initial use of this amino acid synthesis pathway for the generation of 3-methyl-2-oxobutanoate, several metabolic routes to isoprenoid precursors can be exploited. One such pathway involves a keto-reduction and combinations of dehydration and phosphorylation, either converting the free acid intermediate or its CoA derivative to prenol (FIG. 9). Alternatively, the addition of 2-carbons to 3-methyl-2-oxobutanoate, followed by subsequent isomerization, and decarboxylation results in the generation of isovaleryl-CoA, which can then be converted to prenol through a series of reactions (FIG. 10). For either pathway, prenol is then converted to DMAPP, which can be isomerized into IPP generating the two required $C_5$ isoprenoid precursors. As with the above pathways, DMAPP and IPP can be condensed and modified by various combinations of geranyl-, farnesyl- or, geranylgeranyl-diphosphate synthases, prenyl transferase, terpene synthases, or terpene cyclases to form numerous isoprenoid products and derivatives thereof, including prenylated aromatic compounds.

In another embodiment, the non-decarboxylative acyloin condensation of isobutanal and formyl-CoA to 3-methyl-2-hydroxybutanoyl-CoA catalyzed by 2-hydroxyacyl-CoA lyase is utilized (FIG. 11). Isobutanal is generated through the use of Claisen condensation and beta-reduction reactions, with carbon rearrangement and an aldehyde forming termination pathway. Formyl-CoA can be generated directly from formate or formaldehyde. Following acyloin condensation, 3-methyl-2-hydroxybutanoyl-CoA is converted to prenol through various pathways (FIG. 11). As with the above pathways, prenol is subsequently converted into DMAPP and IPP, which can be condensed and modified by various combinations of geranyl-, farnesyl- or, geranylgeranyl-diphosphate synthases, prenyl transferase, terpene synthases, or terpene cyclases to form numerous isoprenoid products and derivatives thereof, including prenylated aromatic compounds.

This disclosure also relates to the use of enzyme combinations or recombinant microbes to make isoprenoid precursors, isoprenoids and derivatives thereof including prenylated aromatic compounds through aldol condensation reactions (FIG. 1). Pathways exploiting this reaction utilize an aldolase catalyzing the aldol condensation of a ketone, aldehyde, or carboxylic acid with an aldehyde to produce an aldol product. Depending on the compounds undergoing aldol condensation, a variety of metabolic pathways and enzymes for carbon rearrangement and the addition/removal of functional groups can be utilized for the synthesis of key isoprenoid intermediates including isoprenoid acyl-CoAs, such as 3-methyl-but-2-enoyl-CoA and 3-methyl-but-3-enoyl-CoA, and isoprenoid alcohols, such as prenol and isoprenol (FIG. 1). These intermediates are subsequently converted to isoprenoid precursors.

In one embodiment, an aldolase catalyzes the aldol condensation of pyruvate and acetaldehyde forming 4-hydroxy-2-oxopentanoate (FIG. 12 and FIG. 13). Carbon rearrangement catalyzed by a mutase and reduction through the action of a 2-hydroxyacid dehydrogenase converts 4-hydroxy-2-oxopentanoate to 2,3-dihydroxy-3-methylbutanoate, an intermediate of the aforementioned valine biosythensis pathway. Following dehydration to 3-methyl-2-oxobutanoate, several metabolic routes to isoprenoid precursors can be exploited, including keto-reduction and combinations of dehydration and phosphorylation, either converting the free acid intermediate or its CoA derivative to prenol (FIG. 12). Alternatively, the addition of 2-carbons to 3-methyl-2-oxobutanoate, followed by subsequent isomerization, and decarboxylation results in the generation of isovaleryl-CoA, which can then be converted to prenol through a series of reactions (FIG. 13). For either pathway, prenol is then converted to DMAPP, which can be isomerized into IPP generating the two required $C_5$ isoprenoid precursors.

In another embodiment, an aldolase catalyzes the aldol condensation of 2-oxobutanoate and acetaldehyde forming 4-hydroxy-2-oxo-3-methylpentanoate (FIG. 14). Conversion of this intermediate to 4-methyl-2-oxopent-4-enoate, through the action of a mutase and a dehydratase, enables the use of a number of pathways to generate isoprenol from 4-methyl-2-oxopent-4-enoate. This 5-carbon isoprenoid alcohol is then converted to IPP through a two-step phosphorylation with IP as an intermediate, or a one step diphosphorylation catalyzed by an alcohol diphosphokinase. IPP can be isomerized into DMAPP generating the two $C_5$ isoprenoid precursors. As with the above pathways, IPP and DMAPP can be condensed and modified by various combinations of geranyl-, farnesyl- or, geranylgeranyl-diphosphate synthases, prenyl transferase, terpene synthases, or terpene cyclases to form numerous isoprenoid products and derivatives thereof, including prenylated aromatic compounds.

The in vivo process involves for example performing traditional fermentations using industrial organisms (for example bacteria or yeast, such as *E. coli, B. subtillis, S. cerevisiae, P. pastoris* and the like) that convert different feedstocks into isoprenoid precursors, isoprenoids, and derivatives thereof including prenylated aromatic compounds. These organisms are considered workhorses of modern biotechnology. Media preparation, sterilization, inoculum preparation, fermentation and product recovery are some of the main steps of the process.

As an alternative to the in vivo expression of the pathway(s), a cell free, in vitro, version of the pathway(s) can be constructed. By purifying, or partially purifying, the relevant enzyme for each reaction step, the overall pathway can be assembled by combining the necessary enzymes. Alternatively, crude protein extract of cells expressing the pathway(s) can be utilized. With the addition of the relevant cofactors and substrates, the pathway can be assessed for its performance independently of a host. As yet another alternative, whole wet or dried cells can be used as bioreactors.

As used herein, a "primer" is a starting molecule for a Claisen condensation reaction to add one or multiple carbon extender units to a growing acyl-CoA. The reactions can be performed once or can be repeated in a cycle for increased carbon chain length. The typical "initial" or "initiating" primer is either acetyl-CoA or propionyl-CoA, but as the chain grows by adding extender units in each cycle, the primer will accordingly increase in size. In some cases, recombinant microbes or enzyme systems can also be provided with larger primers, e.g, $C_4$ primers, etc. added to the media or obtained from other cell pathways. In this invention, non-traditional primers can also be used in which the primer is functionalized, e.g., the terminal omega carbon has been functionalized (i.e., omega-hydroxylated, omega-carboxylated, etc).

It should be noted that there is a second type of primer used herein, which are the short oligonucleotides used in amplification reactions. These should not be confused with the "primer" used in the carbon chain elongation cycles described herein.

As used herein, the "extender unit" is an acyl-CoA that reacts with the primer in one or more condensations to add carbons on the acyl-CoA primer. In biological systems, the extender unit is typically acetyl-CoA. In this invention, traditional extenders or non-traditional extender units can be used, for example, when the terminal omega carbon has been functionalized (e.g., omega-hydroxylated extender unit, omega-carboxylated extender unit, etc).

Thiolases are ubiquitous enzymes that have key roles in many vital biochemical pathways, including the beta-oxidation pathway of fatty acid degradation and various biosynthetic pathways. Members of the thiolase family can be divided into two broad categories: degradative thiolases (EC 2.3.1.16), and biosynthetic thiolases (EC 2.3.1.9). The forward and reverse reactions are shown below:

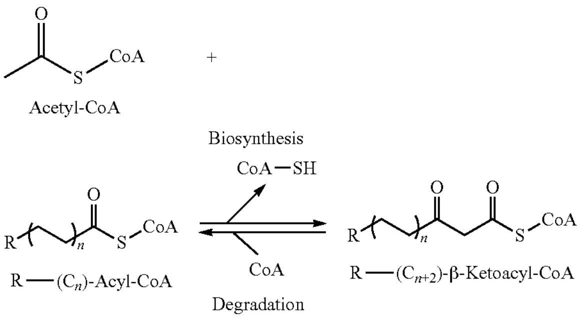

Acetyl-CoA

R—($C_n$)-Acyl-CoA

R—($C_{n+2}$)-β-Ketoacyl-CoA

These two different types of thiolases are found both in eukaryotes and prokaryotes: for example acetoacetyl-CoA thiolase (EC:2.3.1.9) and 3-ketoacyl-CoA thiolase (EC: 2.3.1.16). 3-ketoacyl-CoA thiolase (also called thiolase I) has a broad chain-length specificity for its substrates and is involved in degradative pathways such as fatty acid beta-oxidation. Acetoacetyl-CoA thiolase (also called thiolase II) is specific for the thiolysis of acetoacetyl-CoA and is involved in biosynthetic pathways such as poly beta-hydroxybutyric acid synthesis.

The degradative thiolases can be made to run in the forward direction by building up the level of left-hand side reactants (primer and extender unit), thus driving the equilibrium in the forward direction and/or by overexpressing same or by expressing a mutant of same.

As used herein, a "thiolase" is an enzyme that catalyzes the condensation of an either unsubstituted or functionalized acyl-CoA as the primer and another either unsubstituted or functionalized acyl-CoA for chain elongation to produce a beta-keto acyl-CoA in a non-decarboxylative condensation reaction:

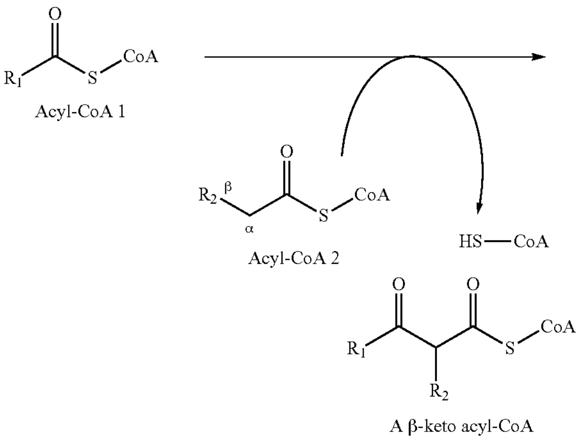

Acyl-CoA 1

Acyl-CoA 2

A β-keto acyl-CoA wherein $R_1$ or $R_2$ throughout are independently an hydrogen, alkyl group, hydroxyl group, carboxyl group, aryl group, halogen, amino group, hydroxyacyl group, carboxyacyl group, aminoacyl group, ketoacyl group, halogenated acyl group, or any other functionalized acyl groups.

As used herein, a "ketoacyl-CoA synthase" is an enzyme that catalyzes the condensation of an either unsubstituted or functionalized acyl-CoA as the primer and either unsubstituted or functionalized beta-carboxylic acyl-CoA for chain elongation to produce a beta-keto acyl-CoA in a decarboxylative condensation reaction:

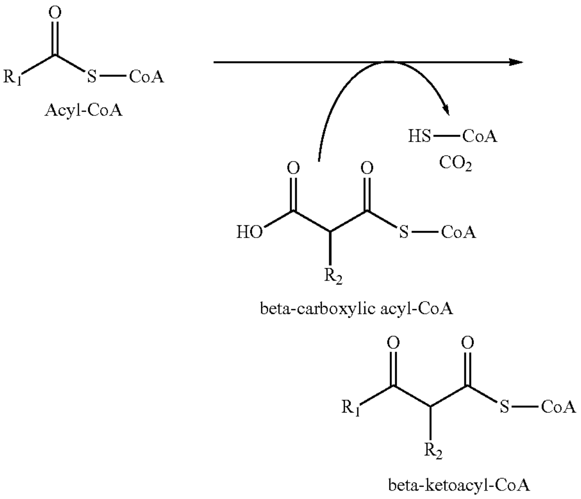

Acyl-CoA beta-carboxylic acyl-CoA beta-ketoacyl-CoA

As used herein, a "hydroxyacyl-CoA dehydrogenase (HACD)" is an enzyme that catalyzes the reduction of a beta-keto acyl-CoA to a beta-hydroxy acyl-CoA:

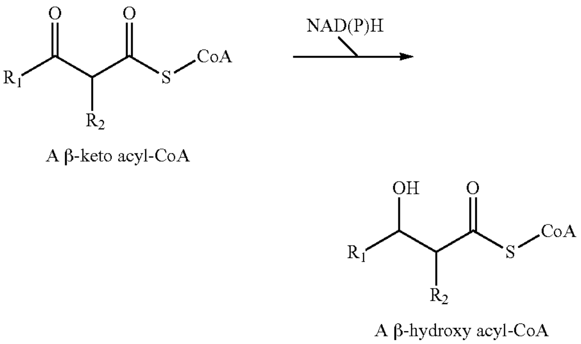

A β-keto acyl-CoA

A β-hydroxy acyl-CoA

As used herein, "enoyl-CoA hydratase (ECH)" is an enzyme that catalyzes the dehydration of a beta-hydroxy acyl-CoA to an enoyl-CoA:

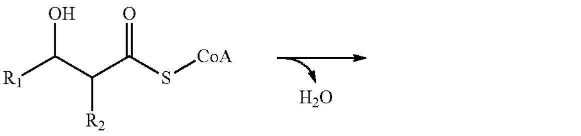

-continued

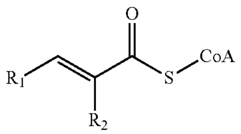

As used herein, an "enoyl-CoA reductase (ECR)" is an enzyme that catalyzes the reduction of an enoyl-CoA to an acyl-CoA:

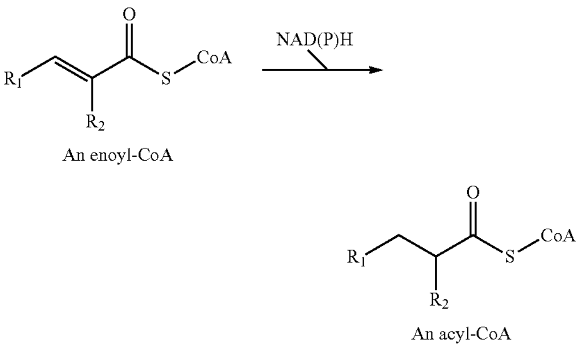

As used herein, the "beta-reduction enzymes" include HACD, ECH and ECR.

As used herein, an "acyloin condensation enzyme" is an enzyme that catalyzes the acyloin condensation of a ketone or aldehyde with either an alpha-ketoacid or an aldehyde to produce an acyloin product:

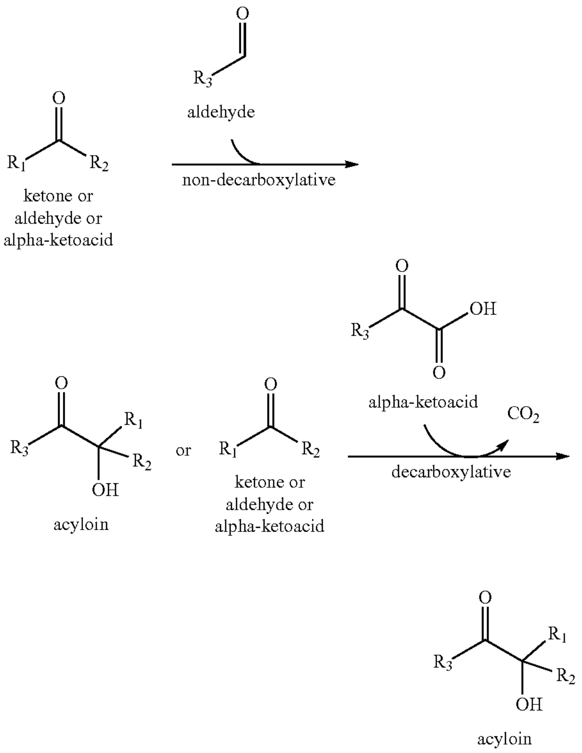

As used herein, "acetalactate synthase" or "ALS" enzyme (also known as acetohydroxy acid synthase, or AHAS) (EC 2.2.1.6) is a protein found in plants and micro-organisms. ALS catalyzes the first step in the synthesis of the branched-chain amino acids (valine, leucine, and isoleucine) through a decarboxylative acyloin condensation between two pyruvate molecules. "Acetohydroxyacid isomeroreductase" or "AHAIR" (EC1.1.1.86) (also known as (ketol-acid reductoisomerase or "KARI") is the second enzyme in the pathway for valine production. "Dihydroxyacid dehydratase" (EC 4.2.1.9) is the third enzyme in the valine pathway. Table E provides a variety of examples of these enzymes.

As used herein, an "aldolase" is an enzyme that catalyzes the aldol condensation of a ketone, aldehyde, or carboxylic acid with an aldehyde to produce an aldol product:

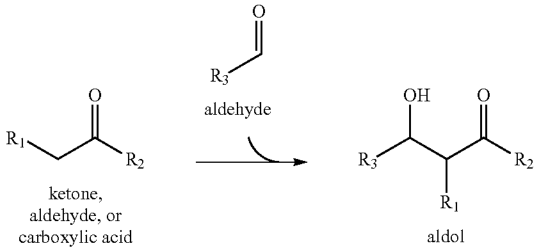

As used herein, a "termination pathway" or "termination enzymes" refers to one or more enzymes (or genes encoding same) that convert a CoA intermediate to a direct product (e.g. acid, alcohol, etc.)

As used herein, an "alcohol forming termination enzyme" refers to one or more enzymes (or genes encoding same) that converts an acyl-CoA to an alcohol, for example:

a) Alcohol forming acyl-CoA reductase;

b) Aldehyde forming acyl-CoA reductase plus alcohol dehydrogenase;

c) The transformation of acyl-CoA to a carboxylic acid (for example through a thioesterase, acyl-CoA transferase or phosphostransacyclase plus carboxylate kinase), a carboxylic acid reductase plus an alcohol dehydrogenase;

d) Aldehyde forming acyl-CoA reductase, an aldehyde decarboxylase, plus an omega-oxidation enzyme.

As used herein, a "phosphorylation enzyme" refers to one or more enzymes (or genes encoding same) that convert an alcohol to a phosphate or diphosphate. For example, an alcohol kinase, an alcohol kinase plus a phosphate kinase, or an alcohol diphosphokinase.

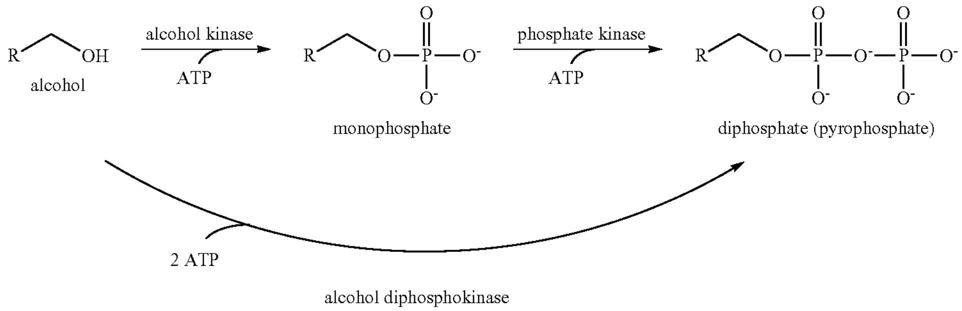

alcohol monophosphate diphosphate (pyrophosphate)

As used herein, "isoprenoid acyl-CoAs" are a class of intermediate products including 3-methyl-but-2-enoyl-CoA (3-methylcrotonyl-CoA), 3-methyl-but-3-enoyl-CoA, and intermediates with one or more prenyl (3-methyl-but-2-en-1-yl) or isoprenyl (3-methyl-but-3-en-1-yl) units attached to 3-methyl-but-2-enoyl-CoA or 3-methyl-but-3-enoyl-CoA:

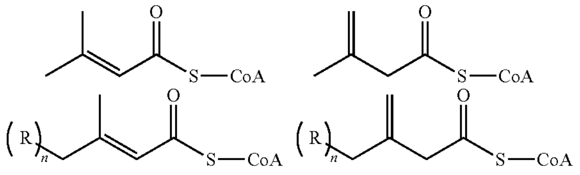

isoprenoid acyl-CoAs where R = 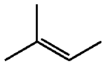 or 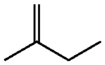 for n = 1, 2, 3, 4 ...

-continued where R = 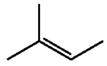 or 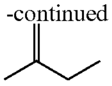 for n = 1, 2, 3, 4 ...

As used herein, "isoprenoid alcohols" are a class of intermediate products including 3-methyl-but-2-en-1-ol (prenol), 3-methyl-but-3-en-1-ol (isoprenol), and products with one or more prenyl (3-methyl-but-2-en-1-yl) or isoprenyl (3-methyl-but-3-en-1-yl) units attached to 3-methyl-but-2-en-1-ol or 3-methyl-but-3-en-1-ol:

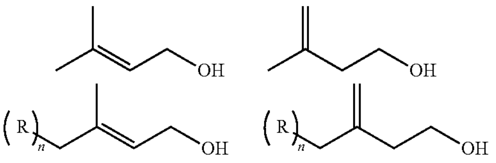

isoprenoid alcohols

As used herein, "dimethylallyl pyrophosphate" or "DMAPP" is an intermediate product of both mevalonic acid (MVA) pathway and the 2-C-methyl-D-erythritol 4-phosphate/1-deoxy-D-xylulose 5-phosphate pathway (DXP/MEP) pathway. It is an isomer of isopentenyl pyrophosphate (IPP) and exists in virtually all life forms.

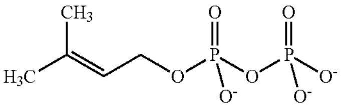

DMAPP

As used herein, "isopentenyl pyrophosphate" or "IPP" is an intermediate product of both mevalonic acid (MVA) pathway and the 2-C-methyl-D-erythritol 4-phosphate/I-deoxy-D-xylulose 5-phosphate pathway (DXP/MEP) pathway.

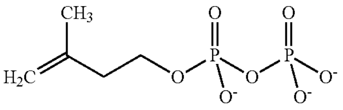

IPP

Isopentenyl pyrophosphate isomerase (IPP isomerase) catalyzes the interconversion of the relatively un-reactive IPP and the more-reactive electrophile DMAPP:

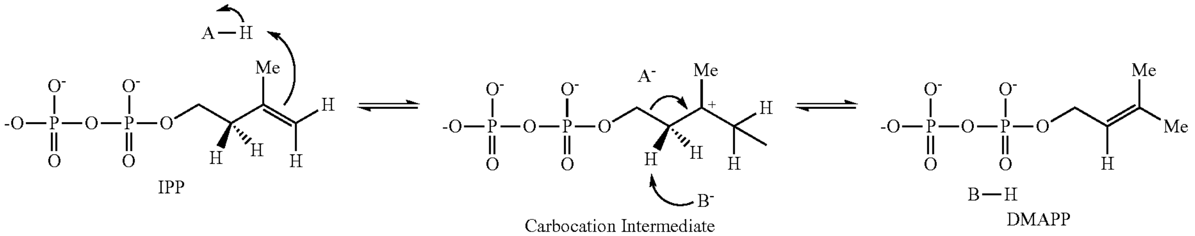

IPP

Carbocation Intermediate

DMAPP

As used herein, "geranyl pyrophosphate" or "GPP", also known as geranyl diphosphate (GDP), is an intermediate used by organisms in the biosynthesis of farnesyl pyrophosphate, geranylgeranyl pyrophosphate, cholesterol, terpenes, prenylated aromatic compounds, terpenoids and the like:

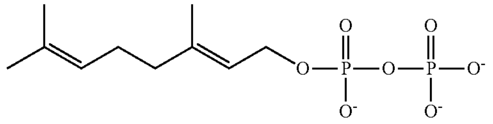

GPP

IPP and DMAPP are condensed to make GPP:

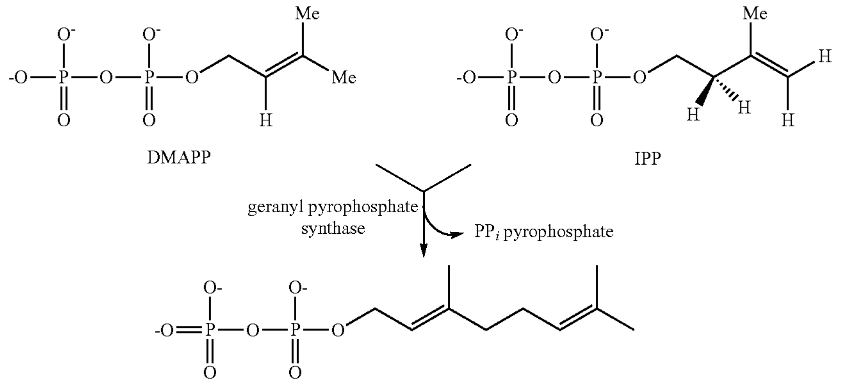

DMAPP

IPP geranyl pyrophosphate (GGP)

As used herein, references to cells or bacteria or strains and all such similar designations include progeny thereof. The use of the singular "cell" does not imply that a single cell is to be used in any method, but includes all progeny produced by growing such cell. It is also understood that all progeny may not be precisely identical in DNA content, due to deliberate or inadvertent mutations that have been added to the parent. Mutant progeny that have the same function or biological activity as screened for in the originally transformed cell are included. Where distinct designations are intended, it will be clear from the context.

The terms "operably associated" or "operably linked," as used herein, refer to functionally coupled nucleic acid sequences.

DMAPP and IPP—also known as "isoprenoid precursors" herein—can be further condensed and modified to make a wide range of products, including prenylated aromatic compounds and terpenoids. "Isoprenoid precursors" also includes isoprenoid monophosphates, such as dimethylallyl phosphate (DMAP) and isopentenyl phosphate (IP), as well as longer chain length intermediates with a hydrocarbon chain bound to a mono- or pyro-phosphate, such as geranyl pyrophophosphate (GPP), farnesyl pyrophosphate (FPP), and geranylgeranyl pyrophosphate (GGPP) which can be formed through iterative condensation(s) of DMAPP and IPP. The terpenoids—also called "isoprenoids"—are a large and diverse class of naturally occurring organic chemicals derived from five-carbon isoprene units assembled and modified in thousands of ways.

As used herein, a "prenylated aromatic compound" is a derivative of an isoprenoid containing one or more prenyl units (3-methyl-but-2-en-1-yl) attached to a compound containing one or more aromatic group.

As used herein, a "cannabinoid" is a prenylated aromatic compound naturally found in the *Cannabis sativa* L plant, or a derivative thereof. Over 60 cannabinoids have been identified to date. Many of the more common cannabinoids have either 21 or 22 carbon atoms. Examples of cannabinoids include (CBGA), cannabigerol (CBG), cannabigerovarinic acid (CBGVA), cannabigerovarin (CBGV), tetrahydrocannabinolic acid (THCA), tetrahydrocannabinol (THC), cannabidiolic acid (CBDA), cannabidiol (CBD), cannbichromenic acid (CBCA), cannbichromene (CBC), tetrahydrocannabivarinic acid (THCVA), tetrahydrocannabivarin (THCV), cannabidivarinic acid (CBDVA), cannabidivarin (CBDV), cannabichrovarinic acid (CBCVA), and cannabichrovarin (CBCV).

As used herein "recombinant" or "engineered" is relating to, derived from, or containing genetic material that has been intentionally altered by the action on man.

"Reduced activity" or "inactivation" is defined herein to be at least a 75% reduction in protein activity, as compared with an appropriate control species, usually wild type of that gene. Preferably, at least 80, 85, 90, 95% reduction in activity is attained, and in the most preferred embodiment, the activity is eliminated (100%, aka a "knock-out" or "null" mutants). Proteins can be inactivated with inhibitors, by mutation, or by suppression of expression or translation, and the like. Use of a frame shift mutation, early stop codon, deletions or insertions, gene editing, e.g., with CRISPR/cas9 and the like, or point mutations of critical residues, and the like, can completely inactivate (100%) of a gene product by completely preventing transcription and/or translation of the active protein.

"Overexpression" or "overexpressed" is defined herein to be at least 150% of protein activity as compared with an appropriate control species (e.g., wild type of the gene in question), and preferably 200, 500, 1000% or more. Any expression in a host species that otherwise lacks the gene would be overexpression. Overexpression can be achieved by mutating the protein to produce a more active form or a form that is resistant to inhibition, by removing inhibitors, by gene editing, e.g, with CRISPR/cas9 and the like, or adding activators, and the like. Overexpression can also be achieved by removing repressors, adding multiple copies of the gene to the cell, or upregulating the endogenous gene, and the like.

The term "heterologous" as used herein means containing or derived from a polymer of nucleic acids wherein at least one of the following is true: (a) the sequence of nucleic acids is foreign to (i.e., not naturally found in) a given cell; (b) the sequence may be naturally found in a given cell, but in an unnatural (e.g., greater than expected) amount; or (c) the sequence of nucleic acids comprises two or more subsequences that are not naturally found in the same relationship to each other in a given host. For example, regarding instance (c), a heterologous nucleic acid sequence that is recombinantly produced will have two or more sequences from unrelated genes arranged to make a new functional nucleic acid. The unrelated genes of part (c) may be either foreign to or naturally found in the recombinant microorganism. A heterologous enzyme is one that is produced by the transcription and translation of heterologous DNA. Overexpression and reduced expression is typically achieved through heterologous DNA The microbes of the invention are generally made by transforming the host cell with an expression vector encoding one or more of the proteins, but the genes can also be added to the chromosome by recombineering, homologous recombination, and similar techniques. Where the needed protein is endogenous, as is the case in some instances, it may suffice as is, but it is usually overexpressed for better functionality and control over the level of active enzyme. The symbol "@" is used to indicate where a gene is inserted into the genome, otherwise it is placed into the native locus.

The term "endogenous" or "native" means that a gene originated from the species in question, without regard to subspecies or strain, although that gene may be naturally or intentionally mutated, or placed under the control of a promoter that results in overexpression or controlled expression of said gene. Thus, genes from Clostridia would not be endogenous to *Escherichia*, but a plasmid expressing a gene from *E. coli* would be considered to be endogenous to any genus of *Escherichia*, even though it may now be overexpressed. By contrast, a "heterogenous" gene would come from a different species.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, background mutations that do not effect the invention, and the like.

As used herein, reference to the accession number of an enzyme or its gene is intended to include the sequence data incorporated therein, as well as all known homologs linked thereto. Furthermore, reference to any protein by accession number includes all those homologs that catalyze the same reaction, although Km and Kcat can vary. Bacterial homologs preferably have >50% amino acid identity, but mammalian homologs are typically >80%.

In calculating "% identity," the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova TA & Madden TL (1999) FEMS Microbiol. Lett. 174:247-250. The default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 1 1 for proteins; E Cost to extend gap [Integer] default=2 for nucleotides, 1 for proteins; q Penalty for nucleotide mismatch [Integer] default=−3; r reward for nucleotide match [Integer] default=1; e expect value [Real] default=10; W word size [Integer] default=1 1 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs. This program is available online at NCBI™ (ncbi.nlm.nih.gov/BLAST/).

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

FIG. 11A-C: Pathways for the synthesis of isoprenoid precursors IPP, DMAPP and GPP from the non-decarboxylative acyloin condensation of isobutanol and formyl-CoA. Exemplary enzymes for each step shown in Table G.

FIG. 24A, the result of assay on degradation of 2-hydroxyhexadecaonyl-CoA to formyl-CoA and pentadecanal; FIG. 24B: the result of assay on acyloin condensation of pentadecanal and formyl-CoA to 2-hydroxyhexadecanoyl-CoA, which is hydrolyzed to 2-hydroxyhexadecanoic acid; FIG. 24C: the result of assay on acyloin condensation between formyl-CoA and acetaldehyde to lactyl-CoA, which is hydrolyzed to lactate; FIG. 24D: the result of assay on acyloin condensation between formaldehyde and formyl-CoA to glycolyl-CoA, which is hydrolyzed to glycolate.

FIGS. 30A-1 to 30A-3, 30B-1 to 30B-11, 30C-1 to 30-26: Embodiments of the invention.

DETAILED DESCRIPTION

Figure 1A:
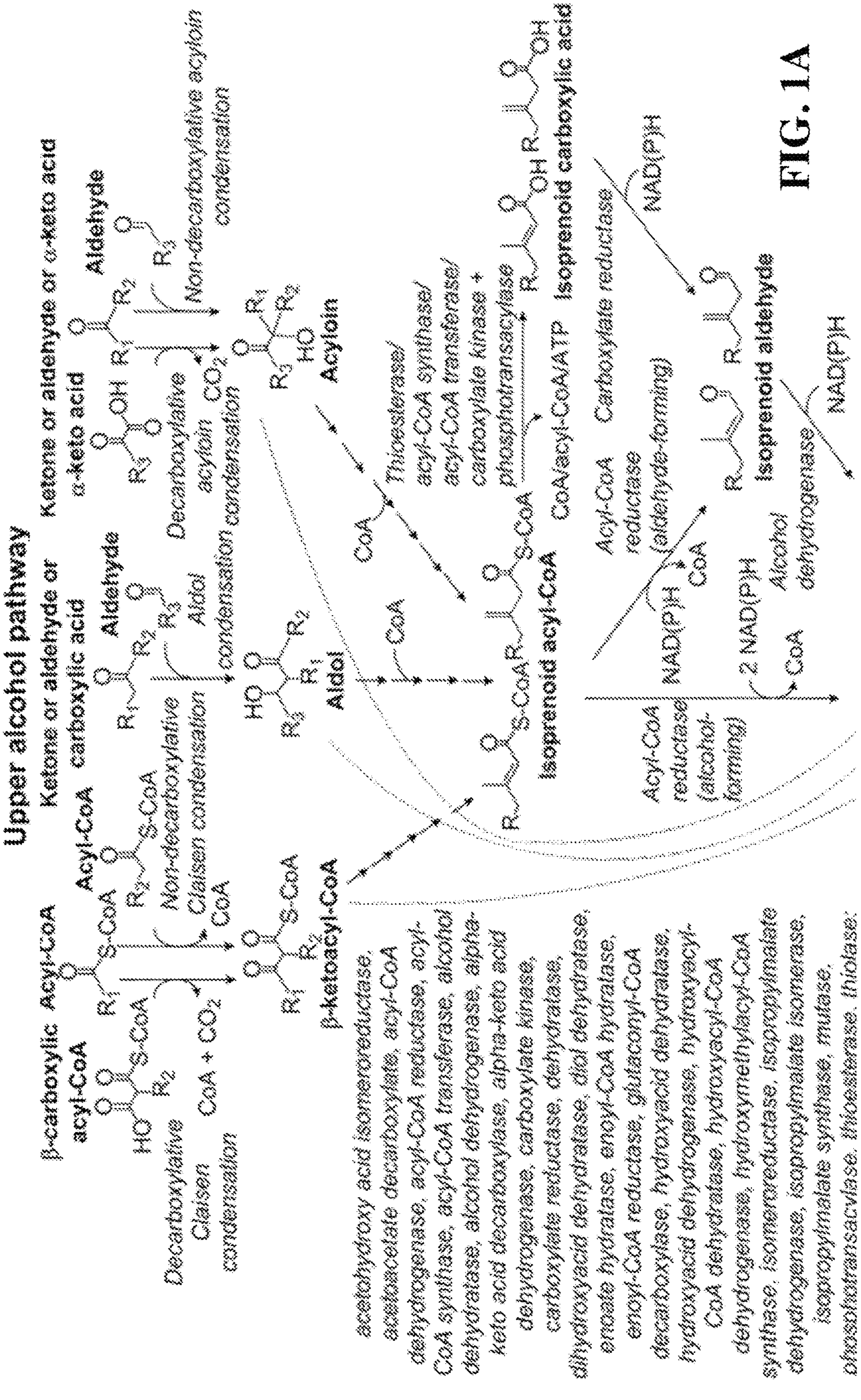
FIG. 1A-B: Synthesis of isoprenoid precursors, isoprenoids and derivatives thereof, and prenylated aromatic compounds using Claisen, aldol, or acyloin condensation reactions. Thiolases catalyze the non-decarboxylative condensation between an acyl-CoA, serving as the primer, and another acyl-CoA, serving as the extender unit, forming beta-keto acyl-CoA. Ketoacyl-CoA synthases catalyze the decarboxylative condensation between acyl-CoA and a beta-carboxylic acyl-CoA to form a beta-ketoacyl-CoA forming a beta-keto acyl-CoA. Aldolases or 2-hydroxyacyl-CoA lyases catalyze the aldol condensation of an aldehyde and a ketone, or an aldehyde and a second aldehyde, or an aldehyde and a carboxylic acid to form an aldol. Acyloin synthases or acetolactate synthase catalyze the non-decarboxylative acyloin condensation of a ketone and an aldehyde, or an aldehyde and a second aldehyde, or the decarboxylative acyloin condensation of a ketone and an alpha-keto acid, an aldehyde and an alpha keto acid, or an alpha-keto acid and a second alpha-keto acid to form an acyloin. Following condensation of starting compounds to initiate a given pathway, a variety of metabolic pathways and enzymes (dotted lines or multiple arrows) for carbon rearrangement and the addition/removal of functional groups can be utilized for the synthesis of key isoprenoid intermediates including isoprenoid acyl-CoAs, such as 3-methyl-but-2-enoyl-CoA and 3-methyl-but-3-enoyl-CoA, and isoprenoid alcohols, such as prenol and isoprenol. Isoprenoid alcohols are then converted to isoprenoid precursors such as DMAPP, IPP, and GPP. Prenylated aromatic compounds are formed from the prenyl transfer of the hydrocarbon units of isoprenoid precursors to aromatic polyketides. Isoprenoids and derivatives thereof can be formed from the isoprenoid precursors via prenyl transferase, terpene synthase, or terpene cyclases.
Figure 1B:
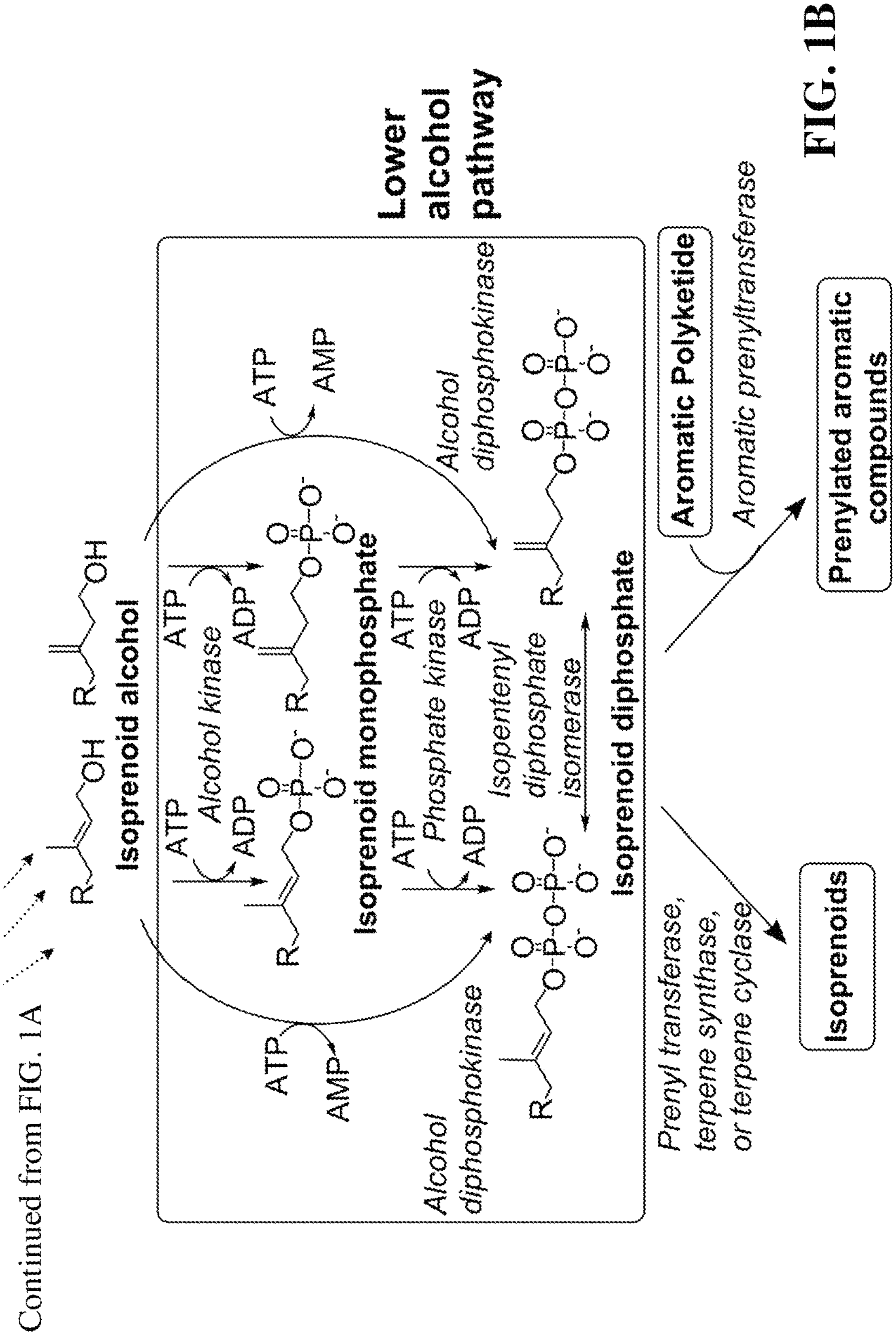

This disclosure generally relates to the use of enzyme combinations or recombinant microbes comprising the same to make isoprenoid precursors, isoprenoids and derivatives thereof including prenylated aromatic compounds through novel synthetic metabolic pathways. As described herein, the novel pathways for the synthesis of these products exploit enzymes catalyzing Claisen, aldol, or acyloin condensation reactions for the generation of longer chain length intermediates from central carbon metabolites (FIG. 1). Both decarboxylative and non-carboxylative condensations are utilized, enabling product synthesis from a number of different starting compounds. These condensation reactions serve as a platform for the synthesis of isoprenoid precursors, isoprenoids and derivatives thereof, polyketides, and prenylated aromatic compounds when utilized in combination with a variety of metabolic pathways and enzymes for carbon rearrangement and the addition/removal of functional groups (FIG. 1). Isoprenoid alcohols are key intermediary products for the production of isoprenoid precursors in these novel synthetic metabolic pathways.

One such pathway employs native or engineered thiolases that catalyze the condensation between an acyl-CoA, serving as the primer, and another acyl-CoA, serving as the extender unit, enabling the formation of beta-keto acyl-CoA intermediate (FIG. 1). Primers and extender units can be omega-functionalized to add required functionalities to the carbon chain, which can be further modified to form isoprenoid intermediates. The beta-keto group of the beta-keto acyl-CoA formed via condensation can be reduced and modified step-wise by one or more of the beta-reduction enzymes-dehydrogenase, dehydratase, and/or reductase reactions. Furthermore, various carbon re-arrangement enzymes, such as acyl-CoA mutases, can be employed to modify the carbon structure and branching of the acyl-CoAs. These CoA intermediates can then serve as the primer for the next round of condensation with the extender unit or as direct precursors to IPP, DMAPP, or other isoprenoid intermediates. After the termination by spontaneous or enzyme-catalyzed CoA removal, reduction, and/or phosphorylation, and subsequent structure re-arrangement, isoprenoids precursors (e.g. IPP and DMAPP), isoprenoids and derivatives thereof are produced. Many examples of thiolase enzymes which can potentially catalyze the condensation of an acyl-CoA primer and acyl-CoA extender unit are provided herein and the following Table A provides several additional examples which can also serve as templates for engineered variants. In another embodiment, ketoacyl-CoA synthetases can be employed in place of thiolases, catalyzing decarboxylative Claisen condensations.

By employing these thiolase- or ketoacyl-CoA synthase catalyzed condensations with unsubstituted or functionalized acyl-CoAs serving as the primer and the extender unit, various beta-keto acyl-CoAs can be generated that through additional beta-reduction and carbon rearrangement modifications serve as direct precursors to the $C_5$ isoprenoid intermediates IPP or DMAPP. For example, FIGS. 2-6 depict various primer/extender unit combinations that through condensation and beta-reduction/carbon rearrangement reaction form CoAs that can be converted to IPP and DMAPP through various termination pathways. These building blocks can then be converted to longer chain length isoprenoid intermediates and products through, for example, known geranyl-, farnesyl- or, geranylgeranyl-diphosphate synthases, such as the formation of the $C_{10}$ intermediate geranyl pyrophosphate (GPP) from IPP and DMAPP by GPP synthase.

Figure 2A:
FIG. 2A-B: Generation of isoprenoid precursor GPP through non-decarboxylative condensations, beta-reductions, acyl-CoA mutases, and termination pathways starting with acetyl-CoA as the primer and propionyl-CoA as the extender unit.
Figure 2B:
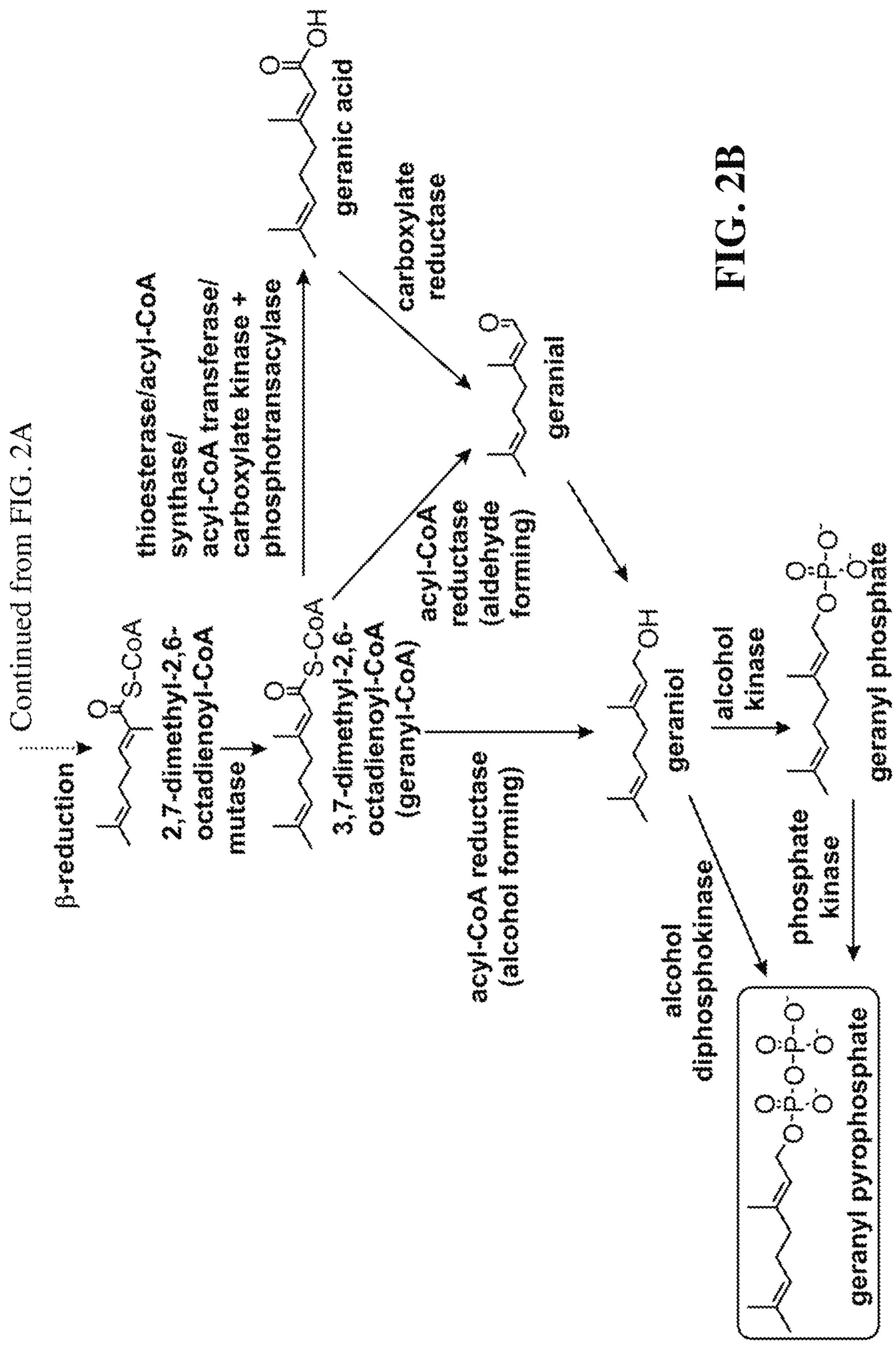
Figure 3A:
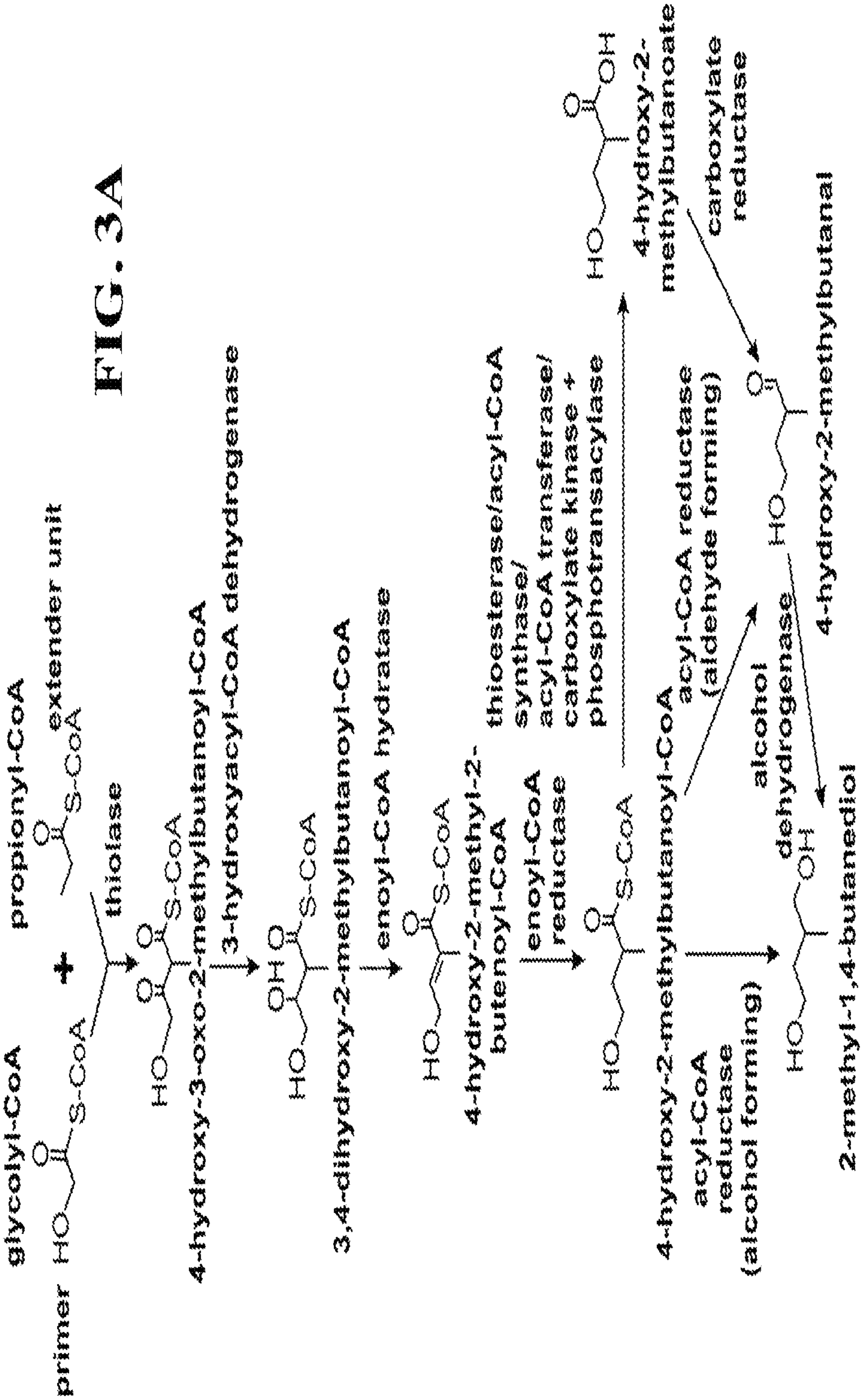
FIG. 3A-B: Generation of isoprenoid precursors IPP, DMAPP, and GPP through non-decarboxylative condensation, beta-reductions, and termination pathways starting with glycolyl-CoA as the primer and propionyl-CoA as the extender unit.
Figure 3B:
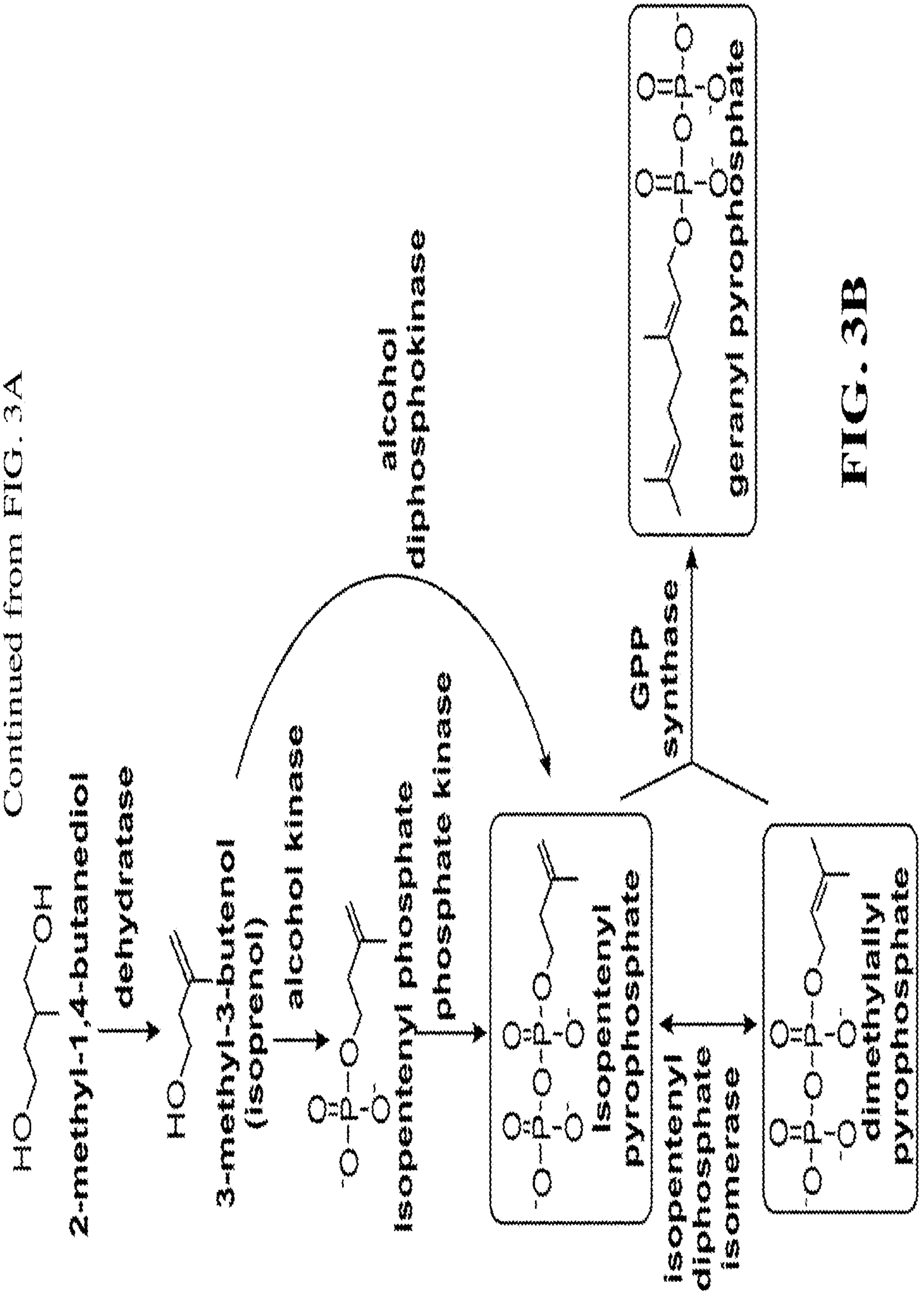
Figure 4A:
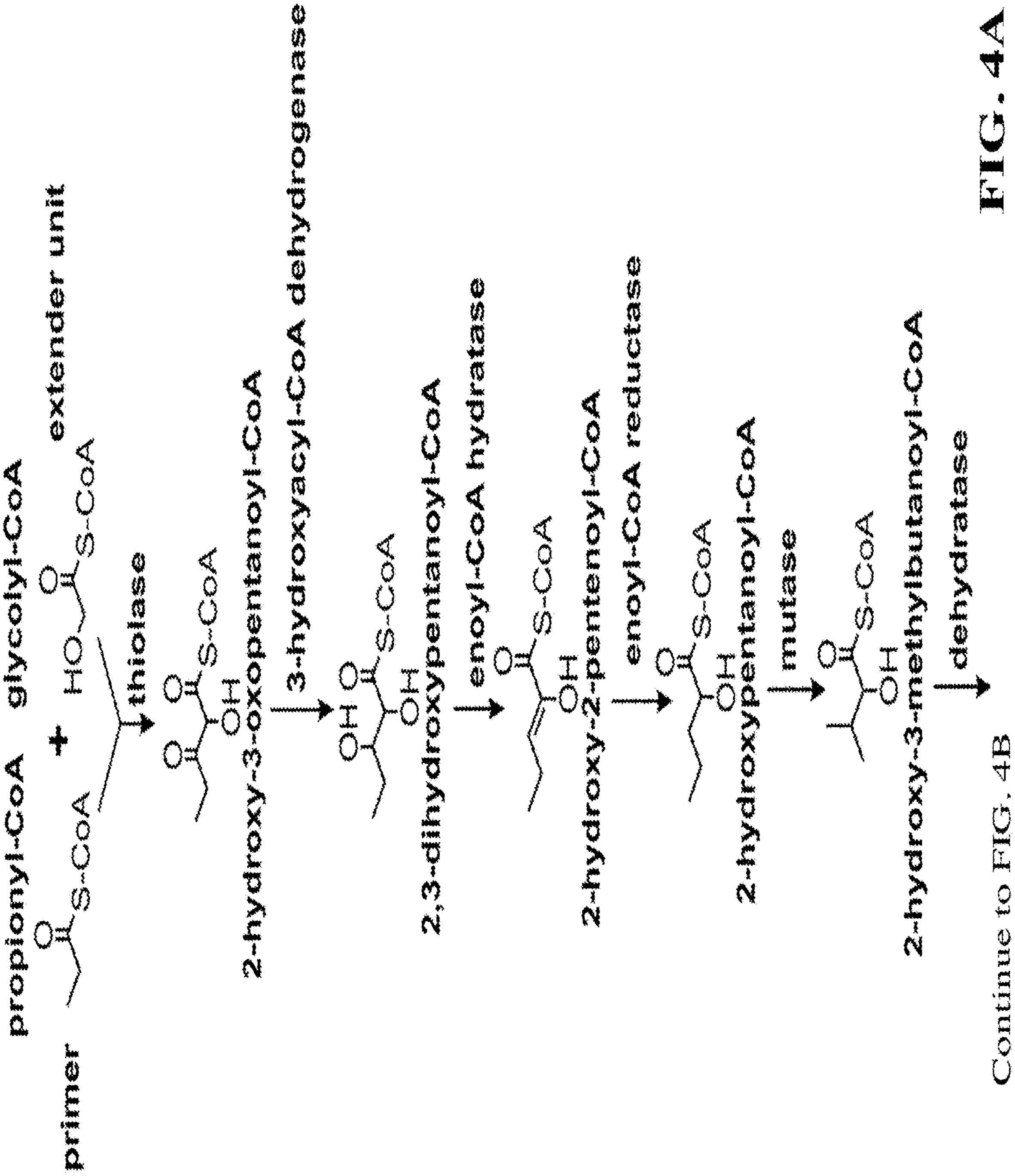
FIG. 4A-B: Generation of isoprenoid precursors IPP, DMAPP and GPP through non-decarboxylative condensation, beta-reductions, acyl-CoA mutase, and termination pathways starting with propionyl-CoA as the primer and glycolyl-CoA as the extender unit.
Figure 4B:
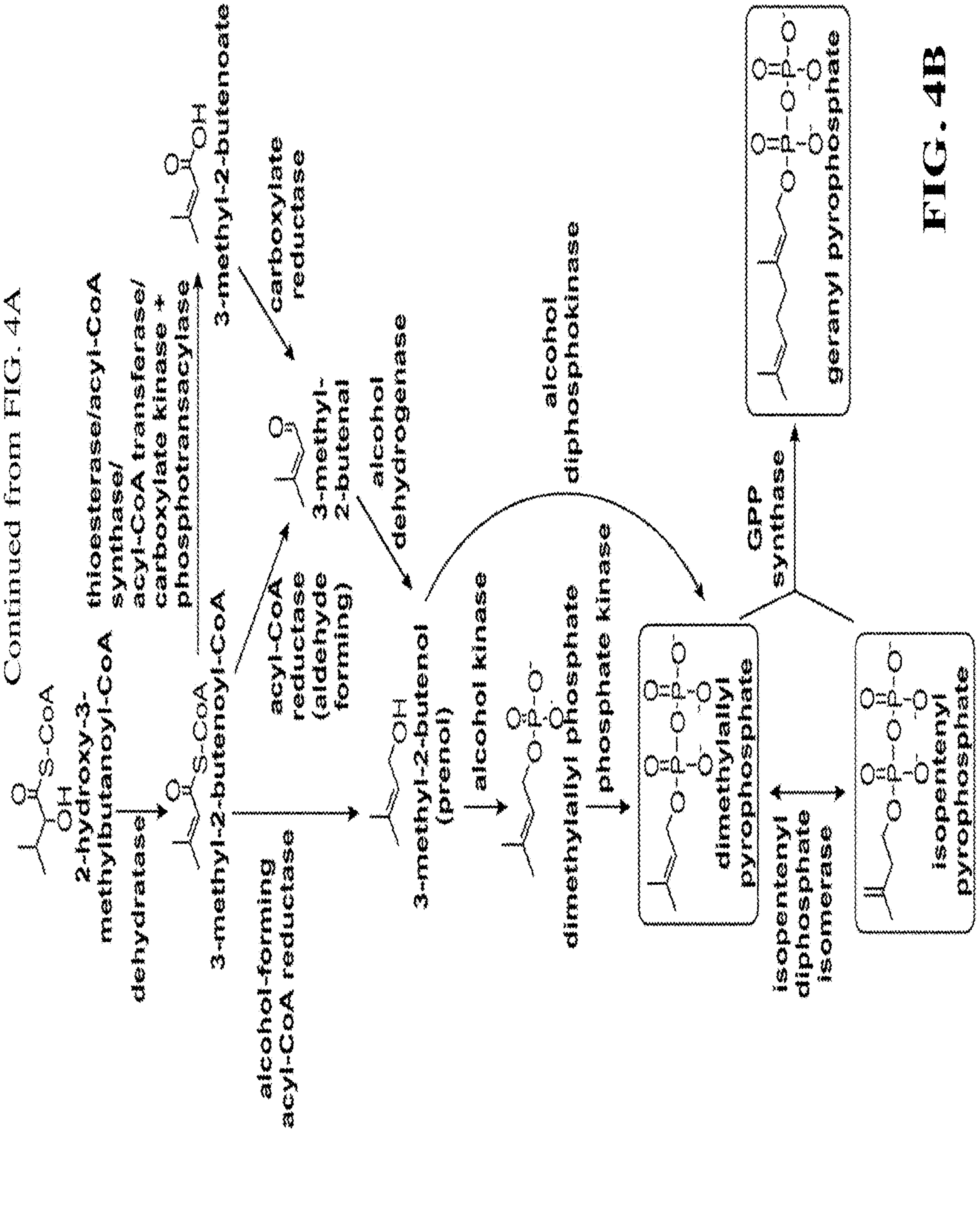
Figure 5A:
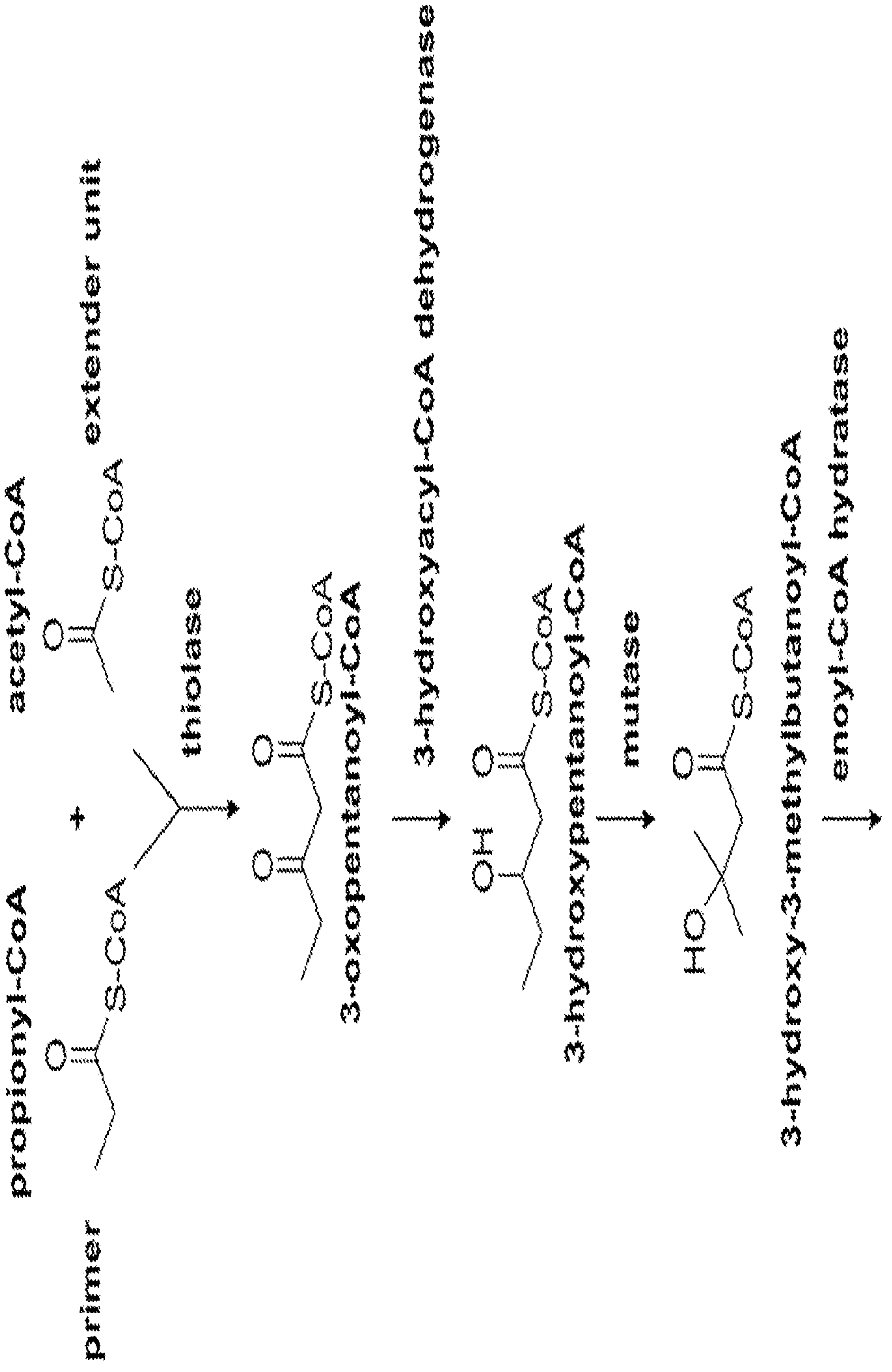
FIG. 5A-B: Generation of isoprenoid precursors IPP, DMAPP and GPP through non-decarboxylative condensations, beta-reductions, acyl-CoA mutase, and termination pathways starting with propionyl-CoA as the primer and acetyl-CoA as the extender unit.
Figure 5B:
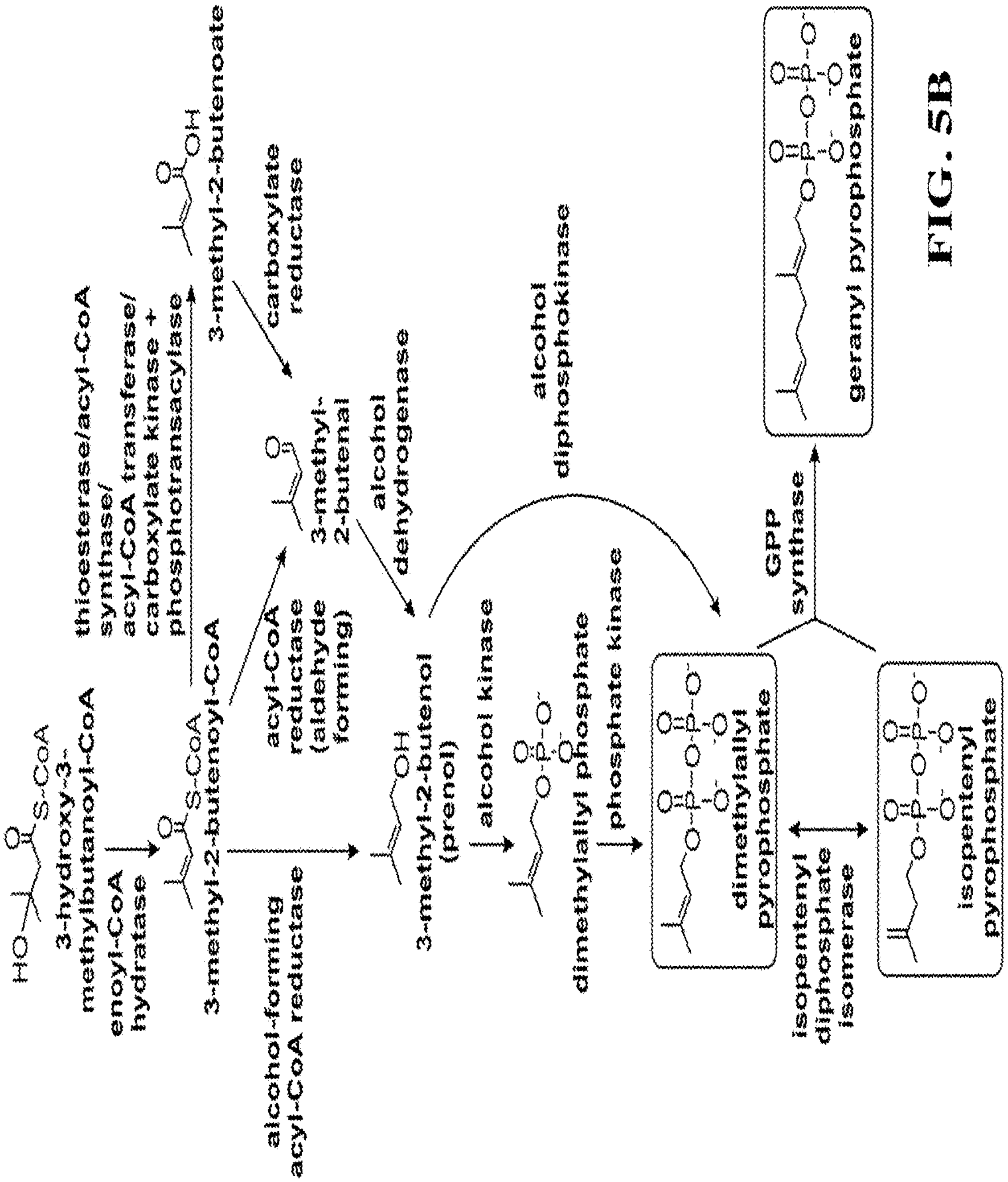
Figure 6A:
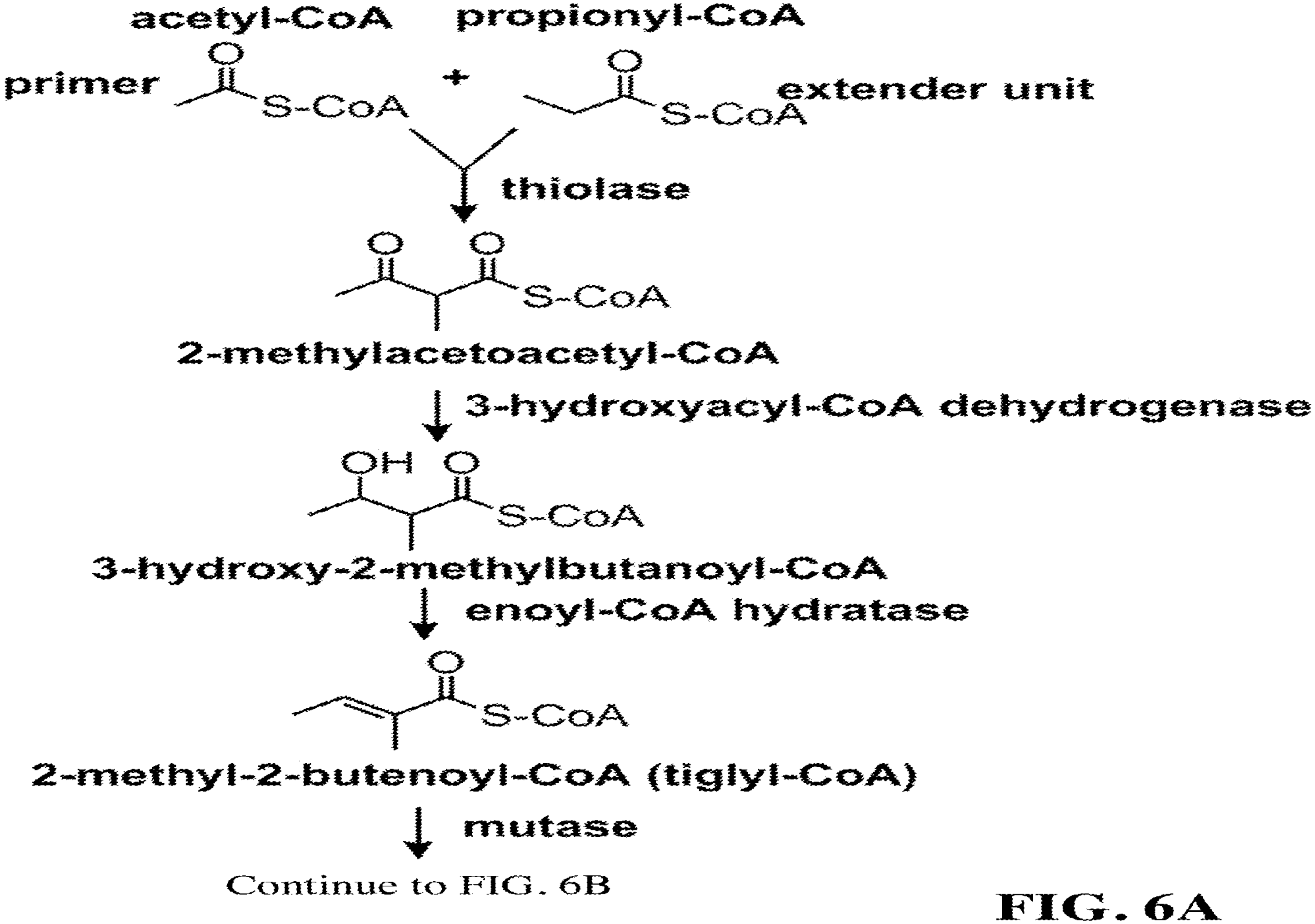
FIG. 6A-B: Generation of isoprenoid precursors IPP, DMAPP and GPP through non-decarboxylative condensation, beta-reductions, acyl-CoA mutase, and termination pathways starting with acetyl-CoA as the primer and propionyl-CoA as the extender unit.
Figure 6B:
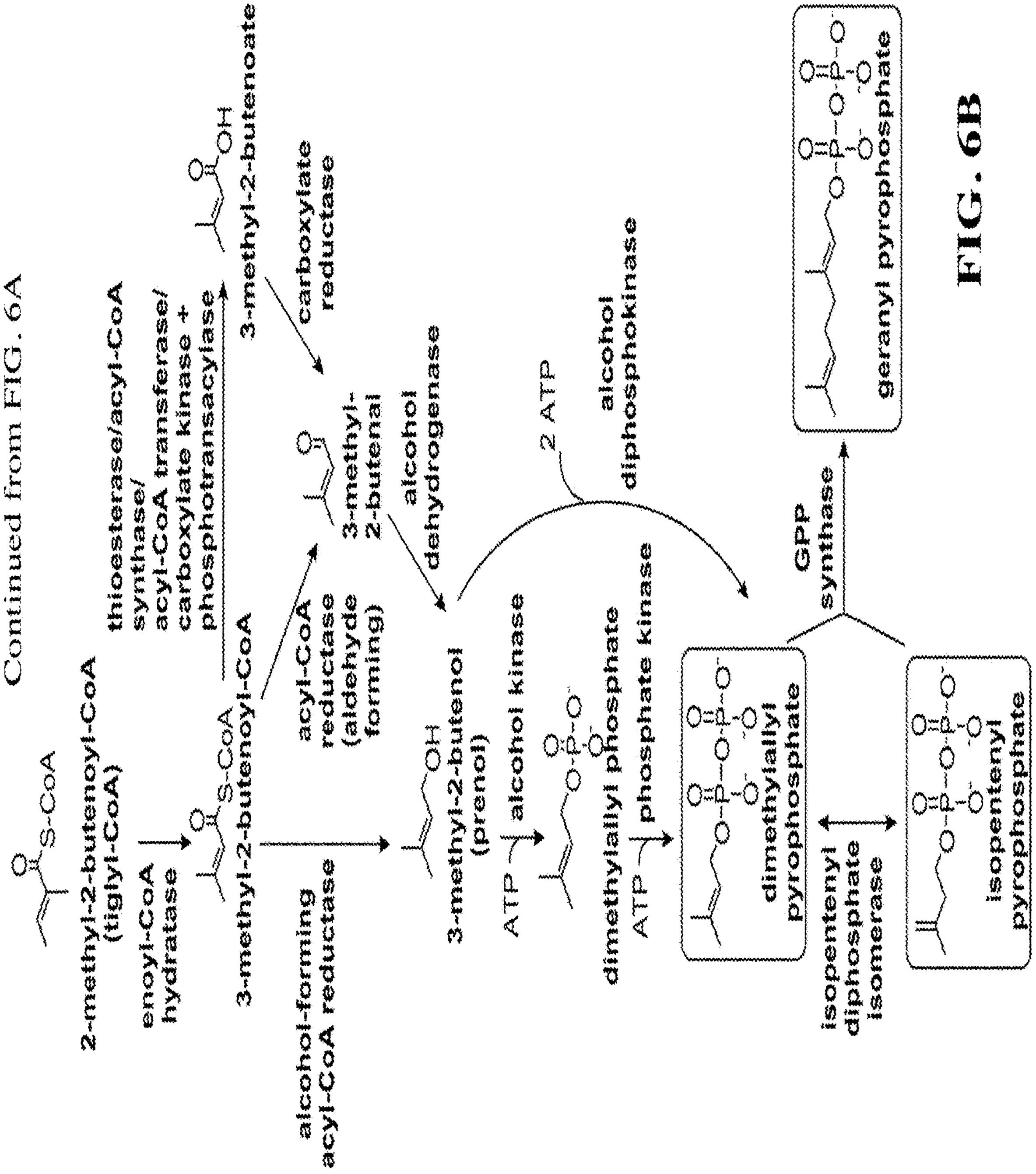

In addition to serving as precursors to IPP and DMAPP, the above described acyl-CoA intermediates can also serve as a primer for the next round of condensation with an extender unit enabling the synthesis of longer chain beta-keto acyl-CoAs. Additional rounds of elongation/beta-reduction/carbon rearrangement result in CoA intermediates that can be converted to longer chain length (e.g. $C_{10}$, $C_{15}$, etc.) isoprenoid intermediates. For example, FIG. 2 depicts the direct synthesis of GPP through condensation and beta-reduction/carbon rearrangement formation of an isoprenoid acyl-CoA that can be converted to GPP. This type of strategy can be utilized to target not only $C_{10}$ isoprenoid intermediates, but also longer chain length compounds as well. Following either route to isoprenoid precursors various prenyl transferases, terpene synthases, or terpene cyclases can be used to convert the isoprenoid precursors into desired isoprenoid products and derivatives thereof. Exemplary materials that can be used with the invention include those in Tables A and B.

Figure 7A:
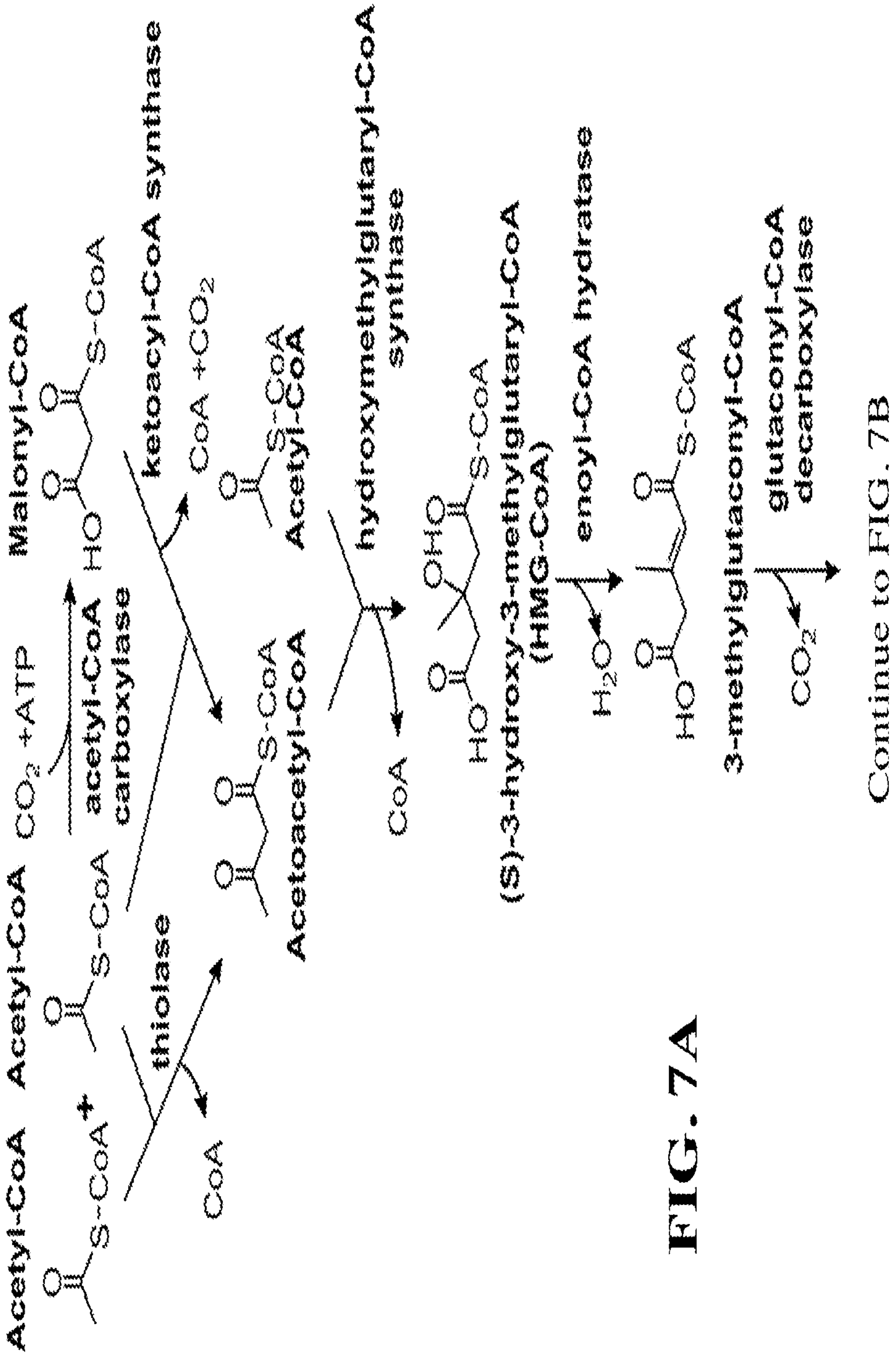
FIG. 7A-B: Pathways for the synthesis of isoprenoid precursors IPP, DMAPP and GPP from the central carbon intermediate acetyl-CoA through decarboxylative or non-decarboxylative Claisen condensation. Conversion of 2 acetyl-CoA or an acetyl-CoA and a malonyl-CoA to acetoacetyl-CoA initiates the pathway, which then proceeds through 3-hydroxy-3-methylglutaryl-CoA as an intermediate. Exemplary enzymes for each step shown in Table C.
Figure 7B:
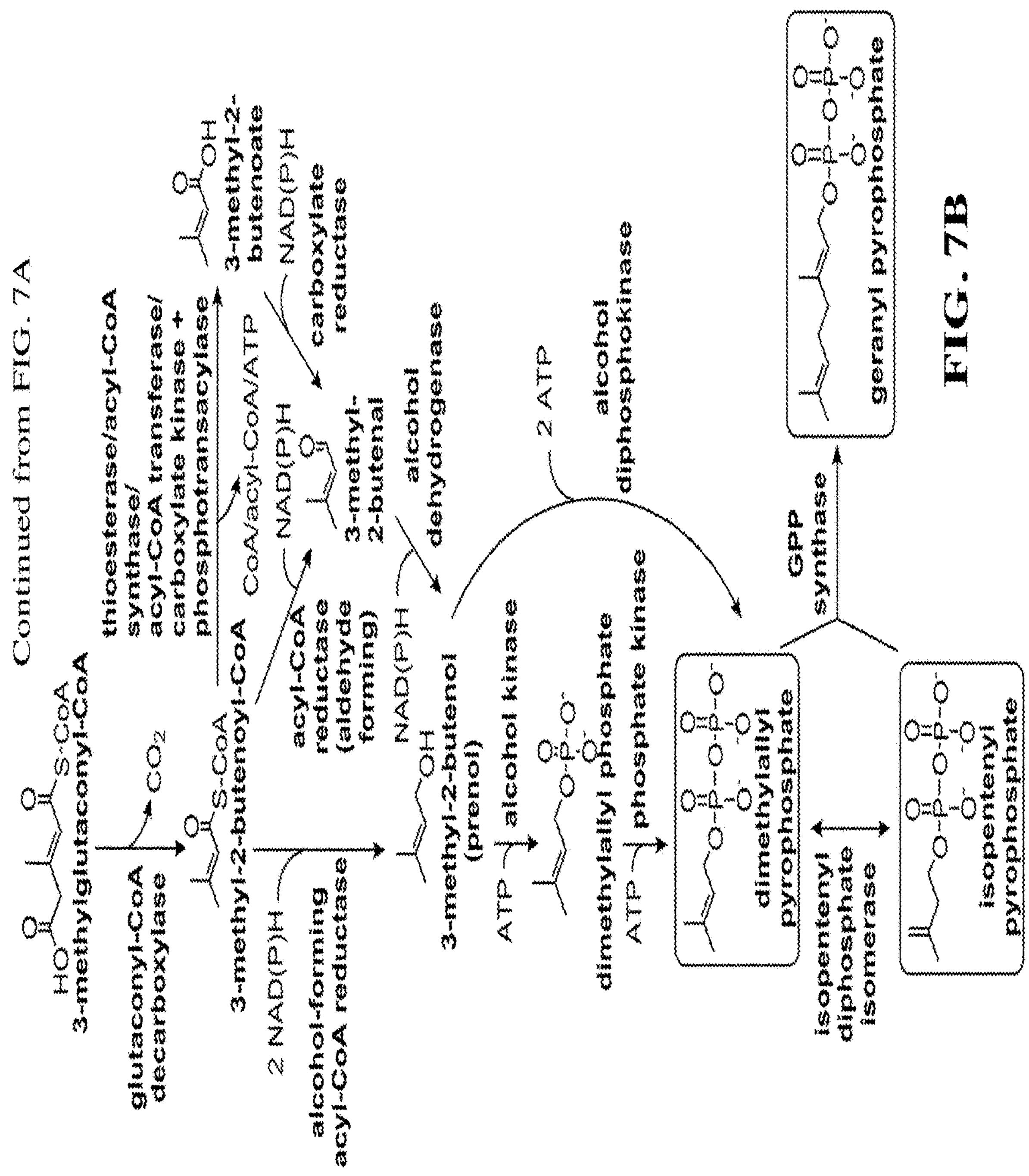

In another embodiment, the formation of isoprenoid precursors, isoprenoids and derivatives thereof including prenylated aromatic compounds proceeds from acetoacetyl-CoA formed as an intermediate through the non-decarboxylative condensation of 2 acetyl-CoA molecules catalyzed by thiolase(s) or decarboxylative condensation of acetyl-CoA and malonyl-CoA catalyzed by keto-acyl-CoA synthase(s). In one such pathway, acetoacetyl-CoA is first converted to 3-hydroxy-3-methylglutaryl-CoA by hydroxymethylglutaryl-CoA synthase (FIG. 7). 3-hydroxy-3-methylglutaryl-CoA is then dehydrated and decarboxylated through the action of an enoyl-CoA hydratase and glutaconyl-CoA decarboxylase, respectively, to form 3-methyl-2-butenoyl-CoA (FIG. 7). From 3-methyl-2-butenoyl-CoA, a number of routes are available leading to the formation of dimethylallyl phosphate. The formation of the isoprenoid precursors IPP and DMAPP then proceeds as described. These pathways are depicted in FIG. 7 and Table C provides examples of enzymes that can be used.

Figure 8A:
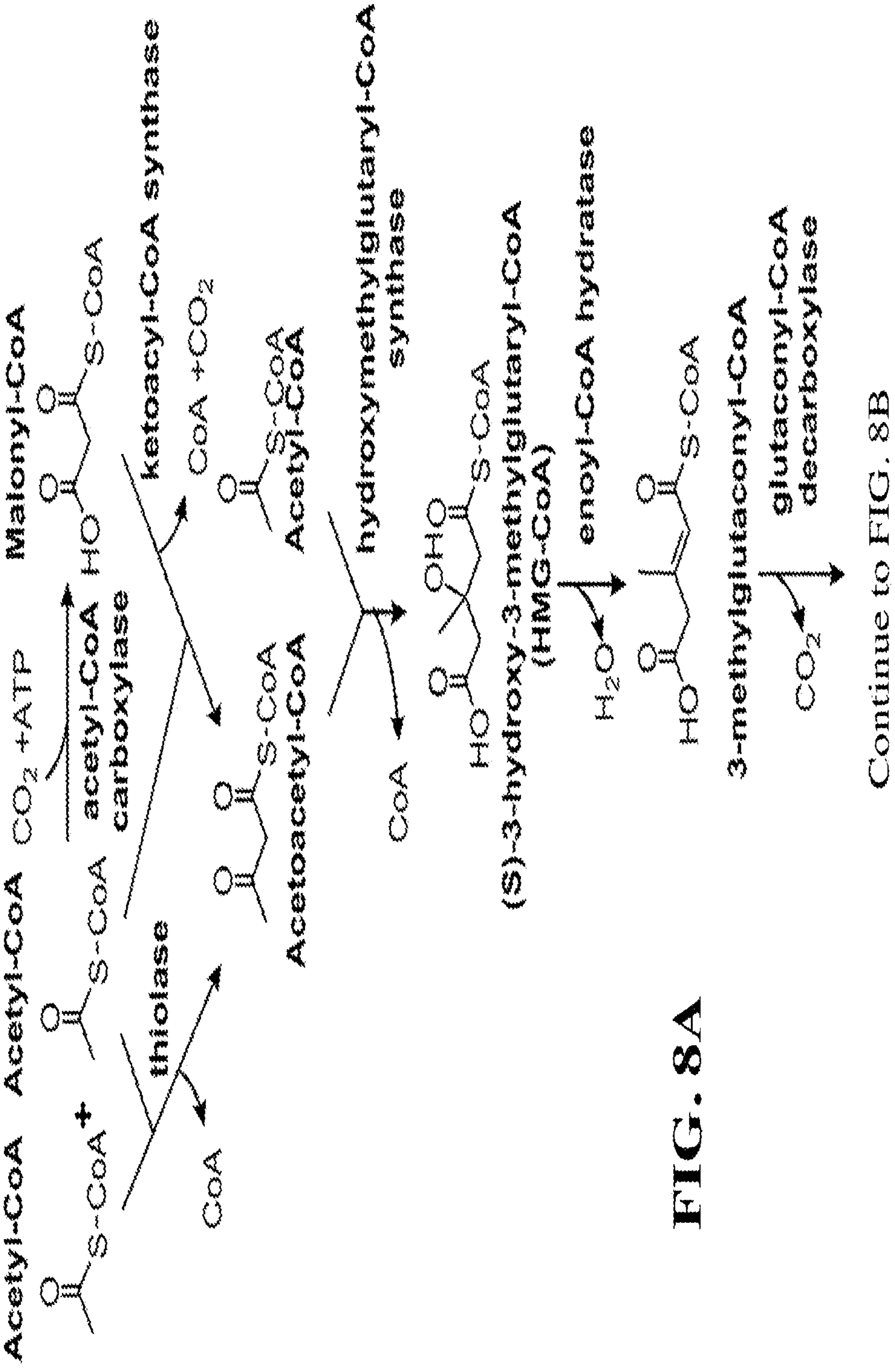
FIG. 8A-B: Pathways for the synthesis of isoprenoid precursors IPP, DMAPP and GPP from the central carbon intermediate acetyl-CoA CoA through decarboxylative or non-decarboxylative Claisen condensation. Conversion of 2 acetyl-CoA or an acetyl-CoA and a malonyl-CoA to acetoacetyl-CoA initiates the pathway, which proceeds through 3-hydroxy-3-methylbutyryl-CoA as an intermediate. Exemplary enzymes for each step shown in Table D.
Figure 8B:
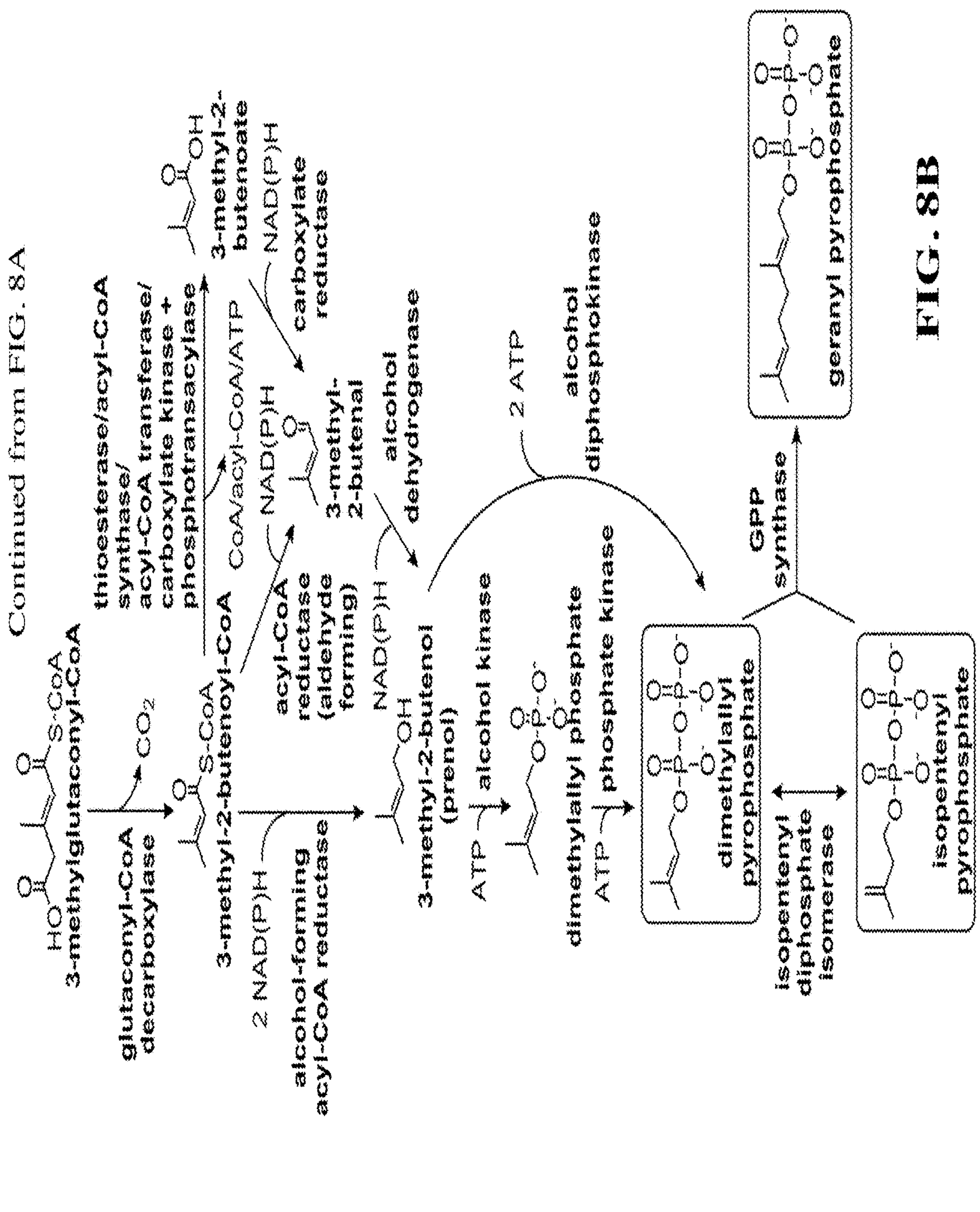

In another pathway from acetoacetyl-CoA, acetone generated from the decarboxylation of acetoacetic acid is converted to 3-methyl-3-hydroxy-butyryl-CoA through a condensation (FIG. 8). Dehydration of 3-methyl-3-hydroxy-butyryl-CoA through the action of an enoyl-CoA hydratase then forms 3-methyl-2-butenoyl-CoA. From 3-methyl-2-butenoyl-CoA, a number of routes are available leading to the formation of dimethylallyl phosphate, and then to IPP and DMAPP as described. These pathways are depicted in FIG. 8 and Table D provides examples of enzymes that can be used.

Figure 9A:
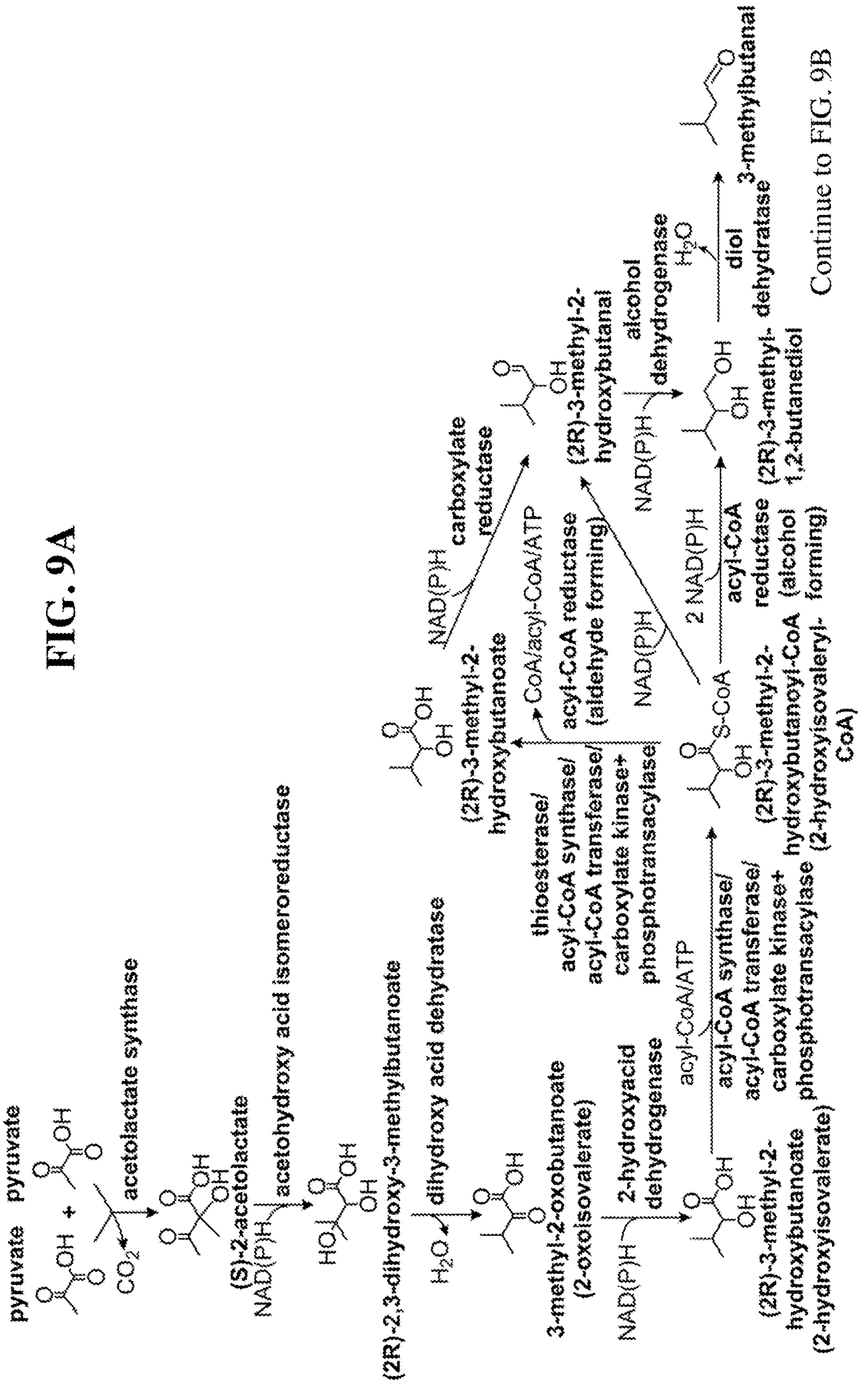
FIG. 9A-B: Pathways for the synthesis of isoprenoid precursors IPP, DMAPP and GPP from the acyloin condensation of the central carbon intermediate pyruvate. Conversion of 2 pyruvate to acetolactate initiates the pathway, which proceeds through 2-hydroxyisovalerate as an intermediate. Exemplary enzymes for each step shown in Table E.
Figure 9B:
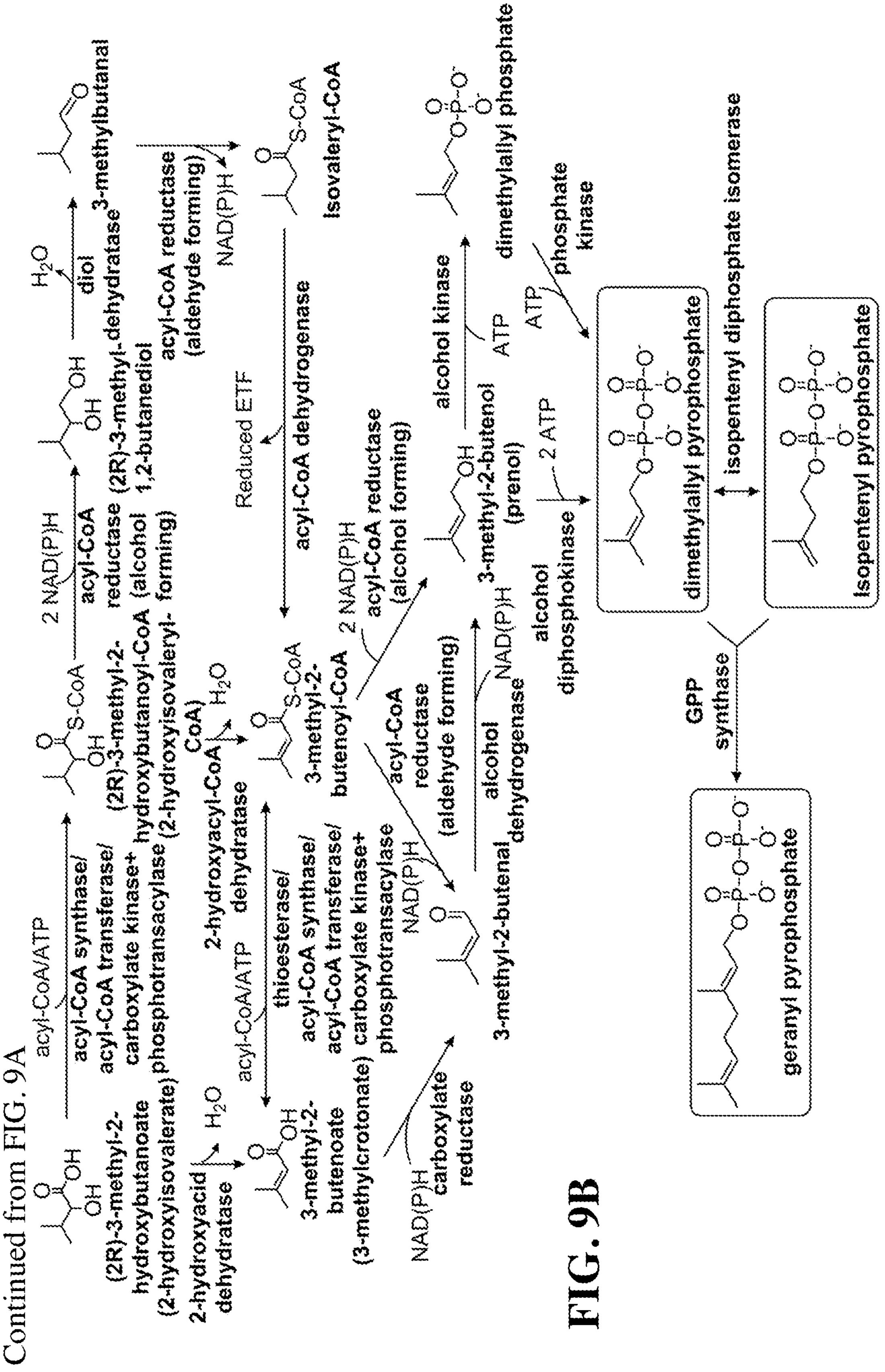
Figure 10A:
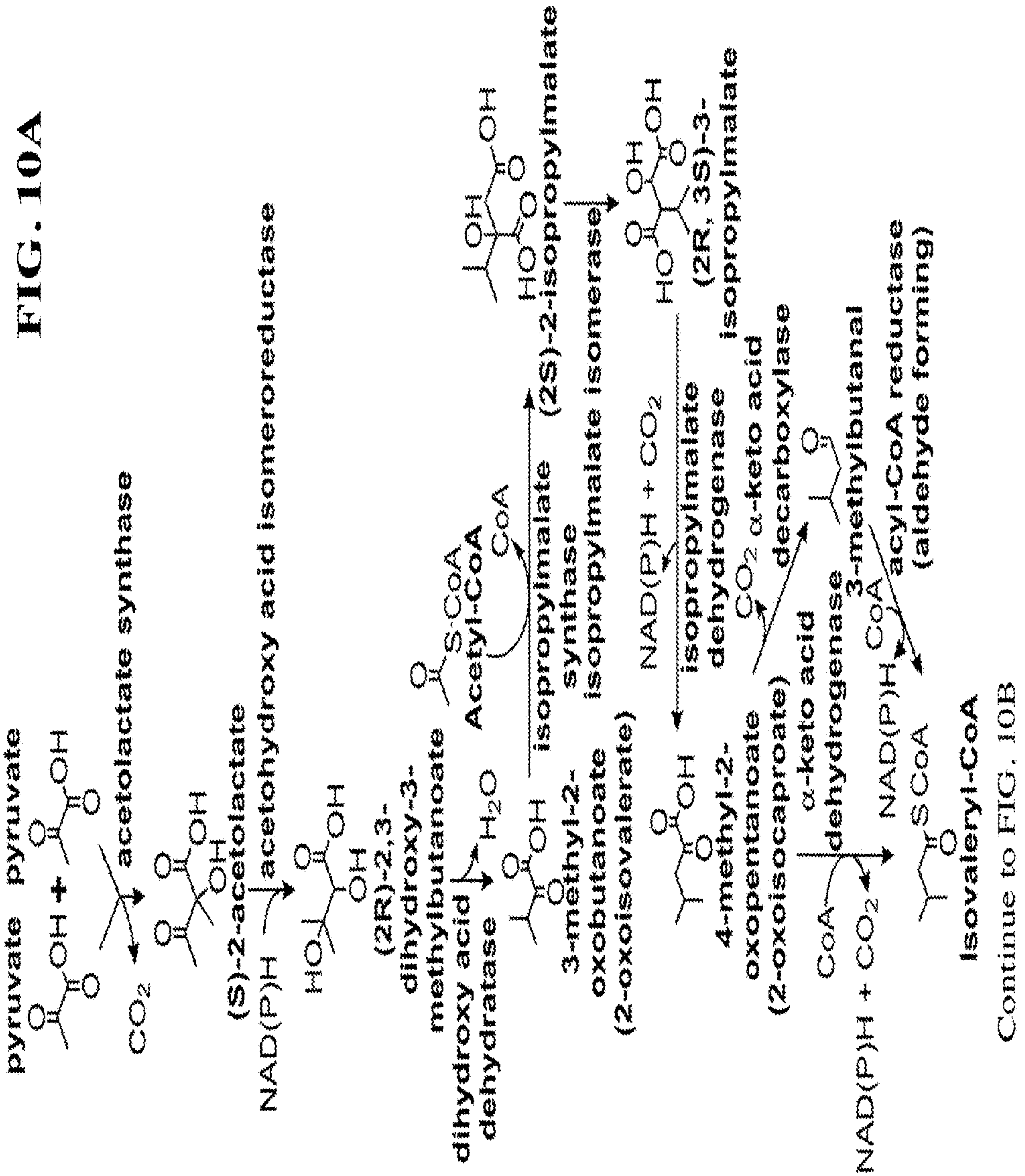
FIG. 10A-B: Pathways for the synthesis of isoprenoid precursors IPP, DMAPP and GPP from the acyloin condensation of the central carbon intermediate pyruvate. Conversion of 2 pyruvate to acetolactate initiates the pathway, which proceeds through 2-isopropylmalate as an intermediate. Exemplary enzymes for each step shown in Table F.
Figure 10B:
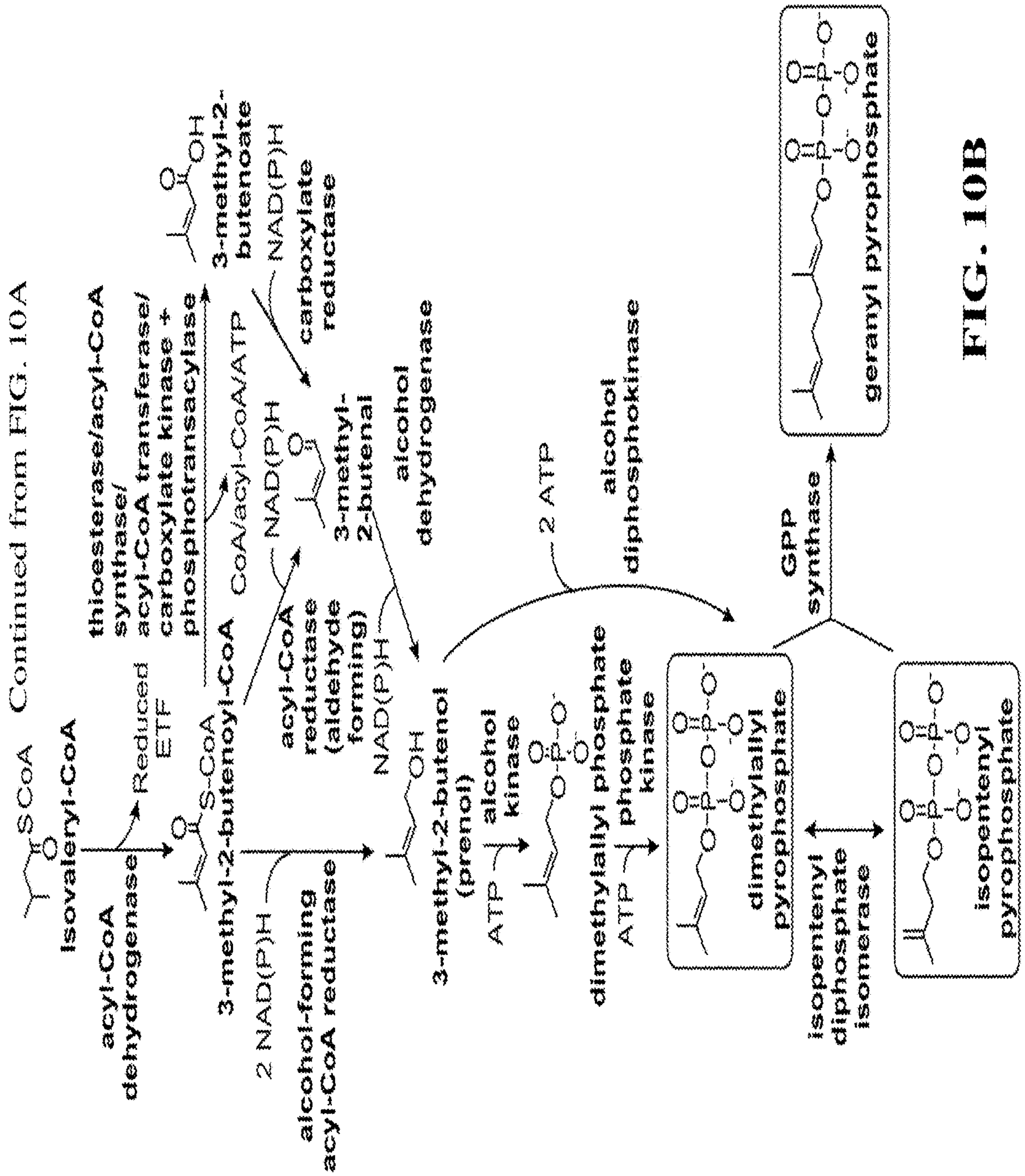

This disclosure also relates to the use of enzyme combinations or recombinant microbes to make isoprenoid precursors, isoprenoids and derivatives thereof including prenylated aromatic compounds through acyloin condensation reactions (FIG. 1). In one embodiment, the pathway begins from the central carbon intermediate pyruvate, with a decarboxylative acyloin condensation of 2 molecules of pyruvate forming acetolactate. Subsequent isomeroreduction and dehydration convert acetolactate to 3-methyl-2-oxobutanoate (FIG. 9 and FIG. 10). These first 3 reactions are catalyzed by acetalactate synthase, acetohydroxyacid isomeroreductase, and dihydroxyacid dehydratase, respectively.

Following the formation of 3-methyl-2-oxobutanoate, several potential pathways can be exploited for the conversion of 3-methyl-2-oxobutanoate to isoprenoid precursors. One such pathway to isoprenoid precursors involves a keto-reduction to 3-methyl-2-hydroxybutanoate, catalyzed by 2-hydroxyacid dehydrogenase. A series of different reactions can then be employed to convert 3-methyl-2-hydroxybutanoate into prenol (FIG. 9). In general, these steps involve the dehydration and phosphorylation of either the acid intermediate (3-methyl-2-hydroxybutanoate) or its CoA derivative to into prenol. Conversion of the acid intermediate requires a 2-hydroxyacid dehydratase for the formation of an alpha-beta-double bond, and the subsequent conversion to 3-methyl-2-butenoyl-CoA through the action of any of an acyl-CoA synthetase, an acyl-CoA transferase, or the combination of a carboxylate kinase and phosphotransacylase (FIG. 9). From 3-methyl-2-butenoyl-CoA, a number of routes are available leading to the formation of prenol. The formation of the isoprenoid precursors IPP and DMAPP then proceeds from prenol through an alcohol kinase and phosphate kinase or an alcohol diphosphokinase to form DMAPP, with isopentenyl diphosphate isomerase able to interconvert DMAPP and IPP. These pathways are also depicted in FIG. 9 and Table E.

Alternatively, 3-methyl-2-hydroxybutanoate can be converted into its CoA derivative (3-methyl-2-hydroxybutanoyl-CoA) before the dehydration reaction. This can be accomplished through any of an acyl-CoA synthetase, an acyl-CoA transferase, or the combination of a carboxylate kinase and phosphotransacylase. Following activation to 3-methyl-2-hydroxybutanoyl-CoA, the dehydration reaction forms 3-methyl-2-butenoyl-CoA, which is catalyzed by a 2-hydroxyacyl-CoA dehydratase, for which a number of candidate enzymes are available (Table E). From 3-methyl-2-butenoyl-CoA, a number of routes are available leading to the formation of prenol. The formation of the isoprenoid precursors IPP and DMAPP proceeds as described. These pathways are also depicted in FIG. 9 and Table E.

An alternative route from 3-methyl-2-oxobutanoate involves the addition of 2 carbons (with acetyl-CoA as the donor) through the action of isopropylmalate synthases to form (2S)-isopropylmalate (FIG. 10). Isopropylmalate isomerase and isopropylmalate dehydrogenase then convert (2S)-isopropylmalate to 4-methyl-2-oxopentanoate, which is subsequently converted to 3-methyl-2-butenoyl-CoA through a branched chain alpha-keto acid dehydrogenase and an acyl-CoA dehydrogenase (FIG. 10). From 3-methyl-2-butenoyl-CoA, a number of routes are available leading to the formation of prenol. The formation of the isoprenoid precursors IPP and DMAPP is as described above. These pathways are depicted in FIG. 10 and Table F provides examples of enzymes that can be used.

Figure 11A:
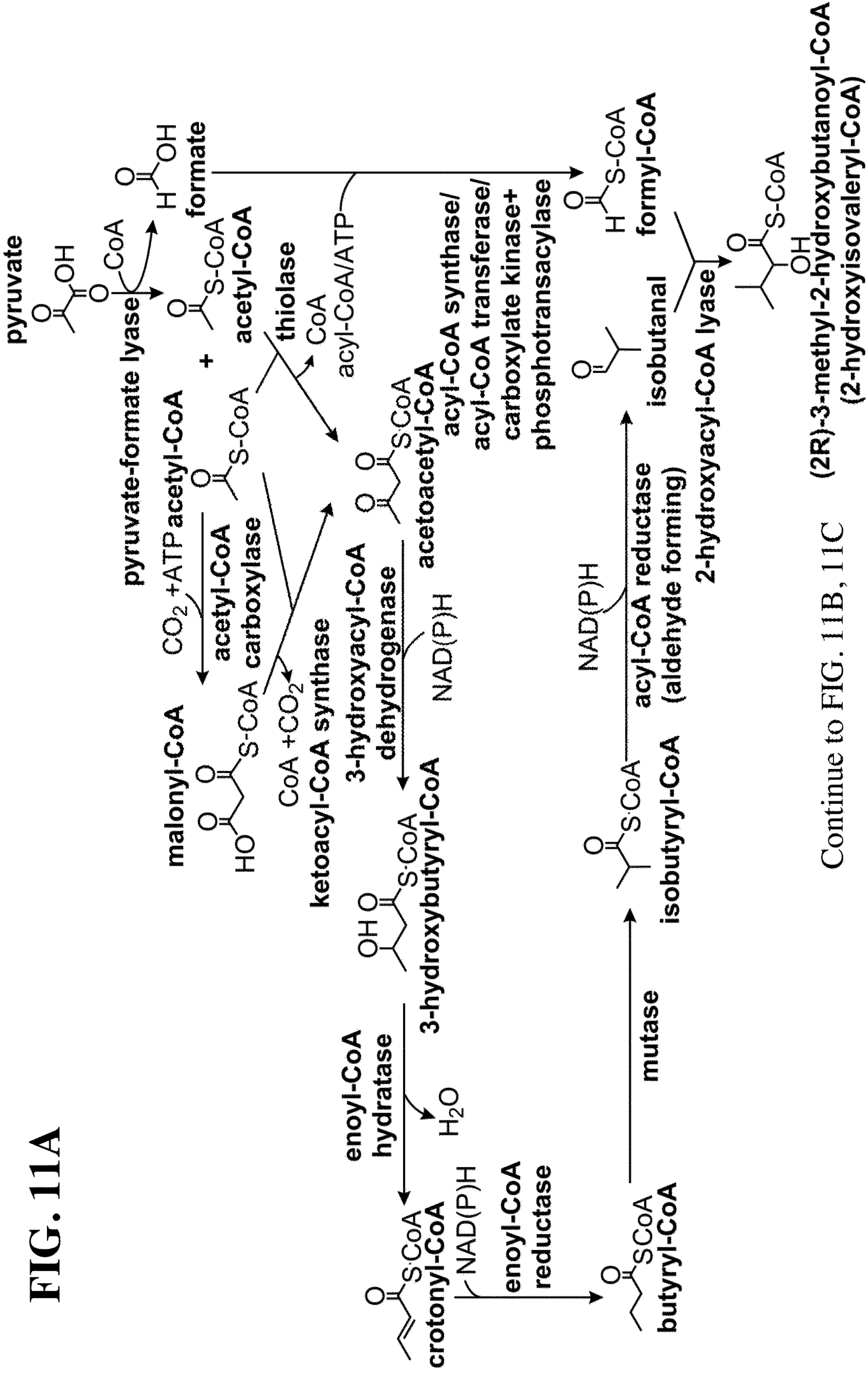
Figure 11C:
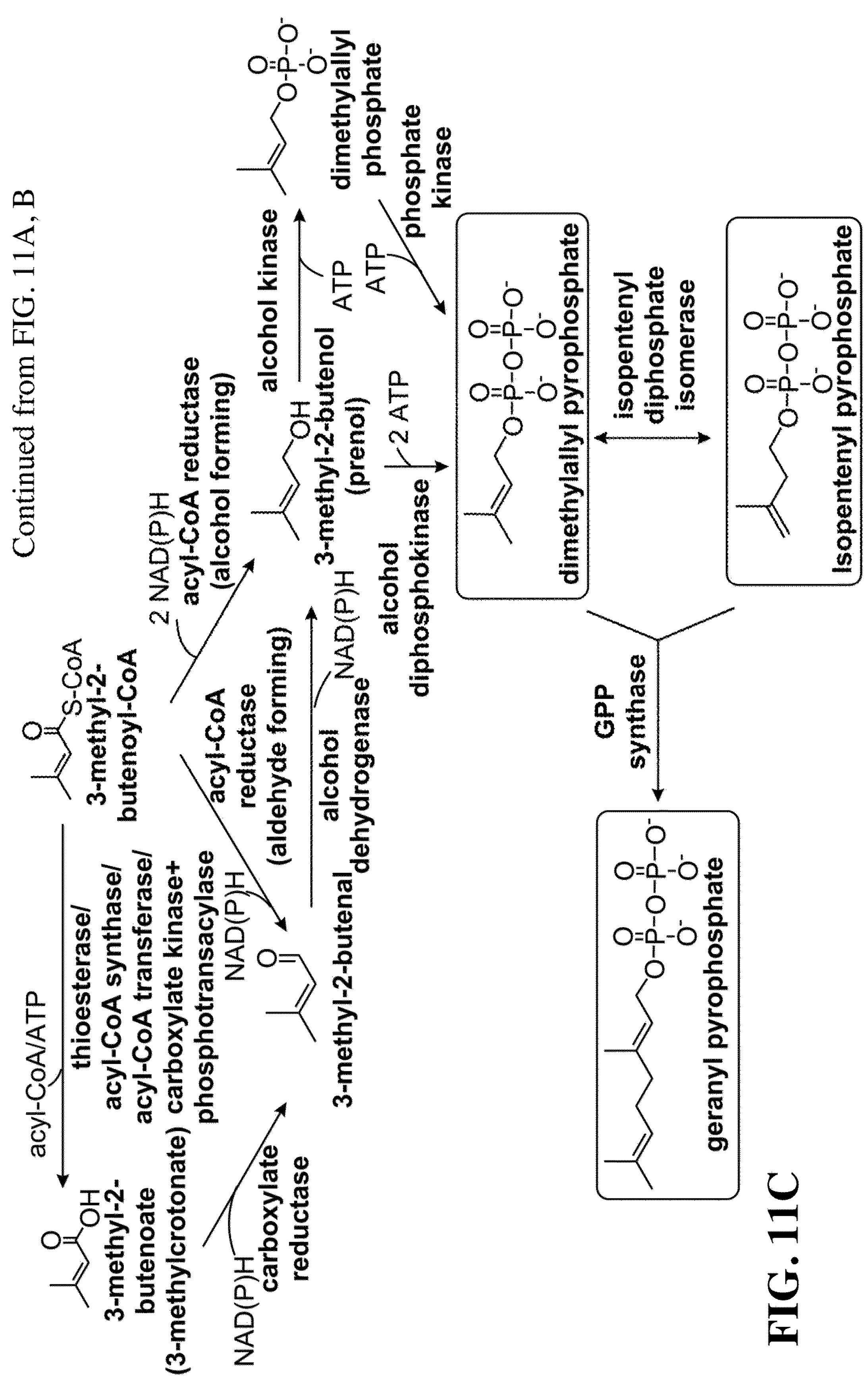

In another embodiment, the non-decarboxylative acyloin condensation of isobutanal and formyl-CoA to 3-methyl-2-hydroxybutanoyl-CoA catalyzed by 2-hydroxyacyl-CoA lyase is utilized (FIG. 11). Isobutanal is generated through the use of Claisen condensation and beta-reduction reactions, with carbon rearrangement and an aldehyde forming termination pathway. Formyl-CoA can be generated directly from formate or formaldehyde. Following acyloin condensation, 3-methyl-2-hydroxybutanoyl-CoA is converted to prenol through various pathways (FIG. 11). Prenol is subsequently converted into DMAPP and IPP. These pathways are depicted in FIG. 11 and Table G provides examples of enzymes that can be used.

Figure 12A:
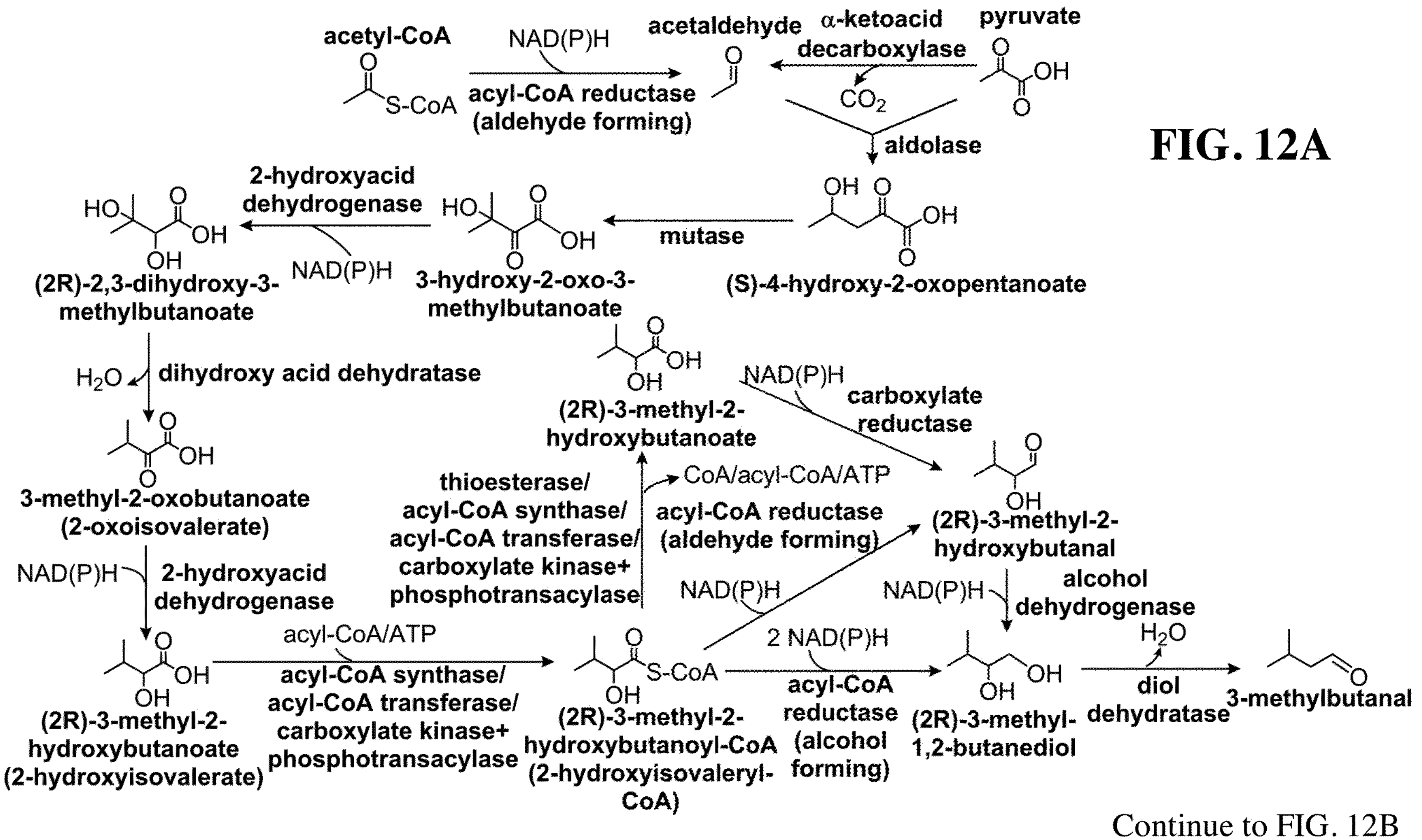
FIG. 12A-B: Pathways for the synthesis of isoprenoid precursors IPP, DMAPP and GPP from the aldol condensation of acetaldehyde and pyruvate. Condensation to 4-hydroxy-2-oxopentanote initiates the pathway, which proceeds through 2-hydroxyisovalerate as an intermediate. Exemplary enzymes for each step shown in Table H.
Figure 12B:
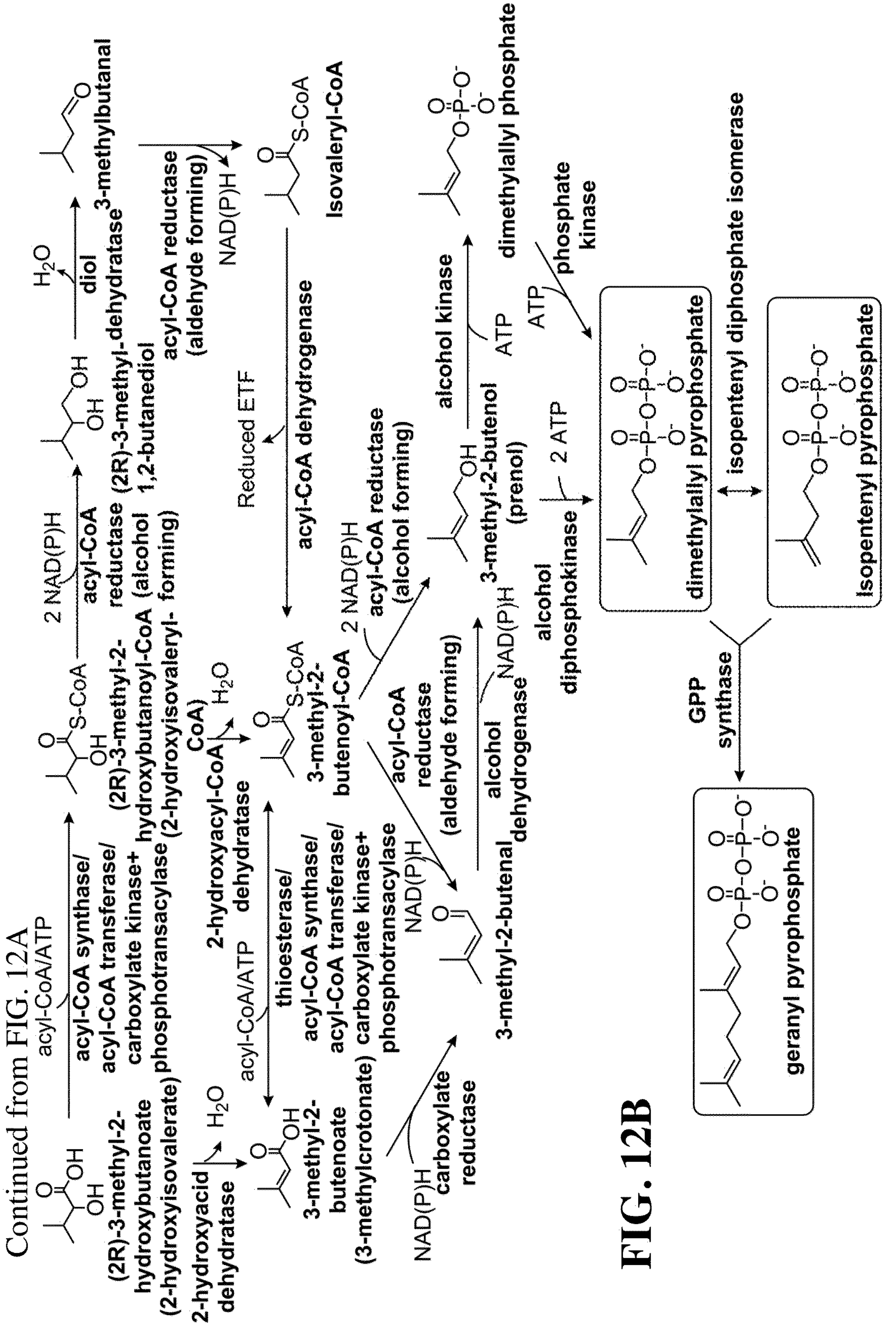

This disclosure also relates to the use of enzyme combinations or recombinant microbes to make isoprenoid precursors, isoprenoids and derivatives thereof including prenylated aromatic compounds through acyloin condensation reactions (FIG. 1). In one embodiment, the pathway begins from the central carbon intermediate pyruvate, which is condensed with acetealdeyhde in an aldol condensation to form 4-hydroxy-2-oxopentanoate (FIG. 12). Carbon rearrangement catalyzed by a mutase and reduction through the action of a 2-hydroxyacid dehydrogenase converts 4-hydroxy-2-oxopentanoate to 2,3-dihydroxy-3-methylbutanoate, an intermediate of the aforementioned valine biosynthesis pathway. Following dehydration to 3-methyl-2-oxobutanoate, several metabolic routes to isoprenoid precursors can be exploited, including keto-reduction and combinations of dehydration and phosphorylation, either converting the free acid intermediate or its CoA derivative to prenol (FIG. 12). Prenol is subsequently converted into DMAPP and IPP. These pathways are depicted in FIG. 12 and Table H below provides examples of enzymes that can be used.

Figure 13A:
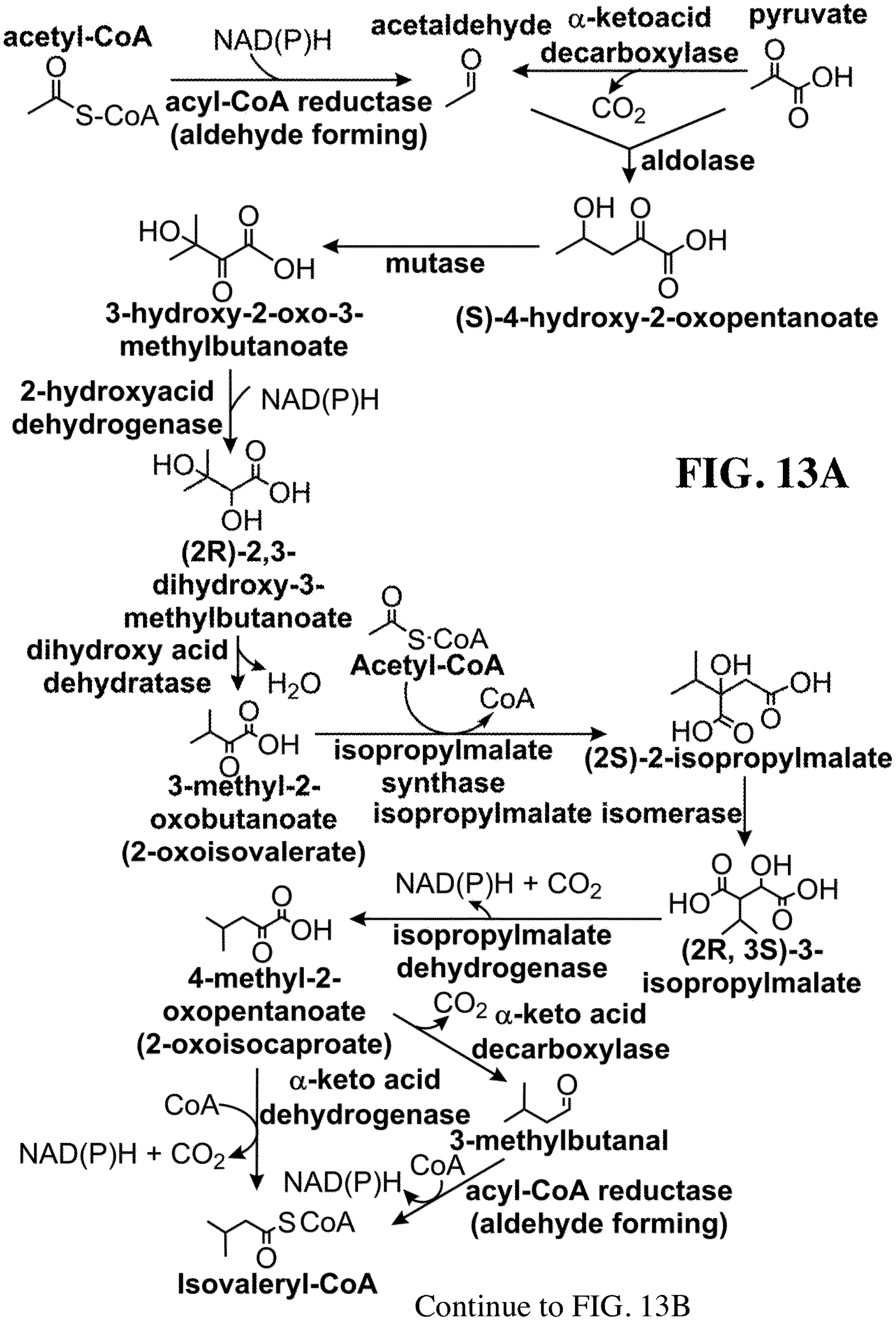
FIG. 13A-B: Pathways for the synthesis of isoprenoid precursors IPP, DMAPP and GPP from the aldol condensation of acetaldehyde and pyruvate. Condensation to 4-hydroxy-2-oxopentanote initiates the pathway, which proceeds through 2-isopropylmalate as an intermediate. Exemplary enzymes for each step shown in Table I.
Figure 13B:
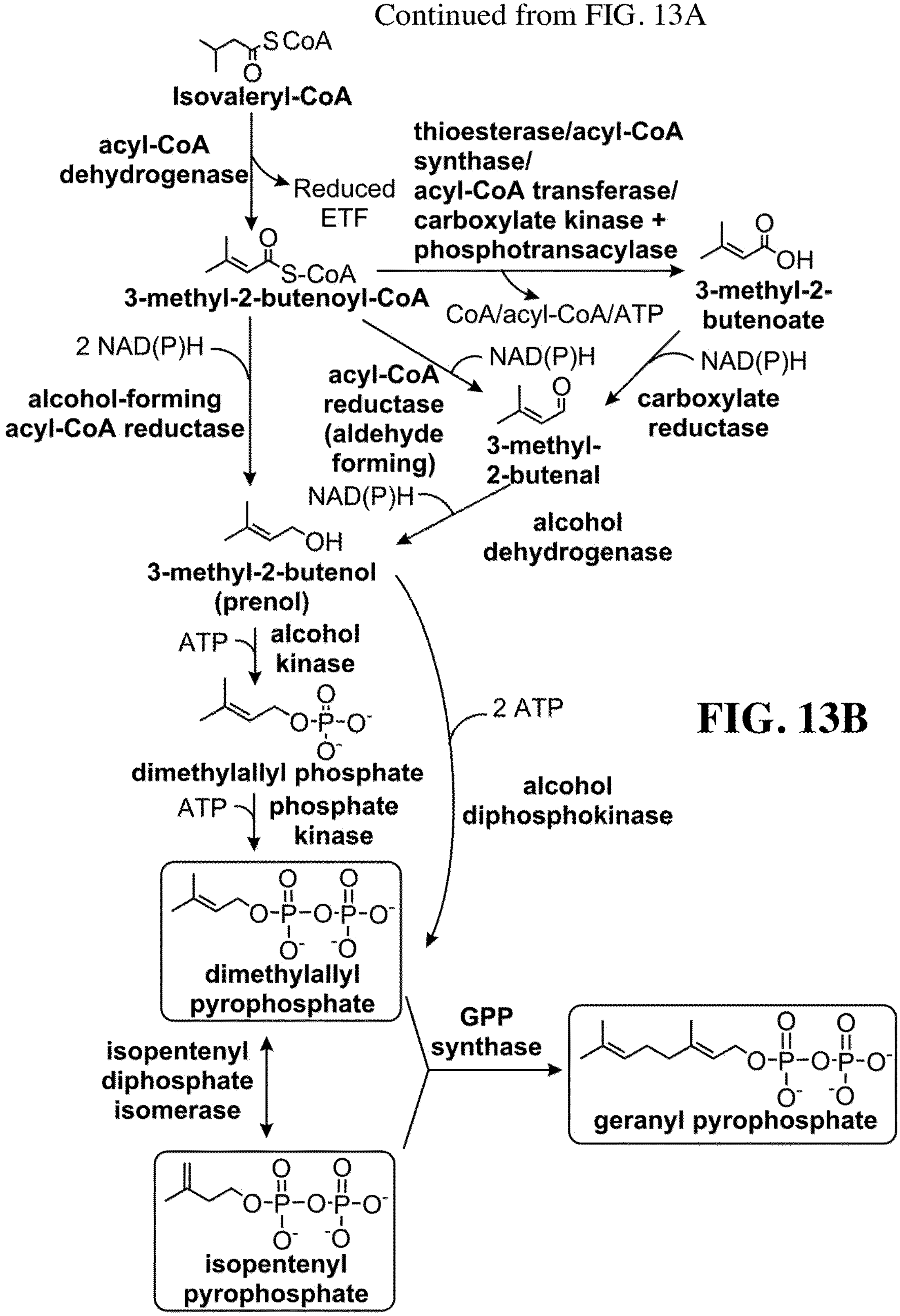

Alternatively, the addition of 2-carbons to 3-methyl-2-oxobutanoate, followed by subsequent isomerization, and decarboxylation results in the generation of isovaleryl-CoA, which can then be converted to prenol through a series of reactions (FIG. 13). Prenol is then converted to DMAPP, which can be isomerized into IPP generating the two $C_5$ isoprenoid precursors. These pathways are depicted in FIG. 13 and Table I below provides examples of enzymes that can be used.

Figure 14A:
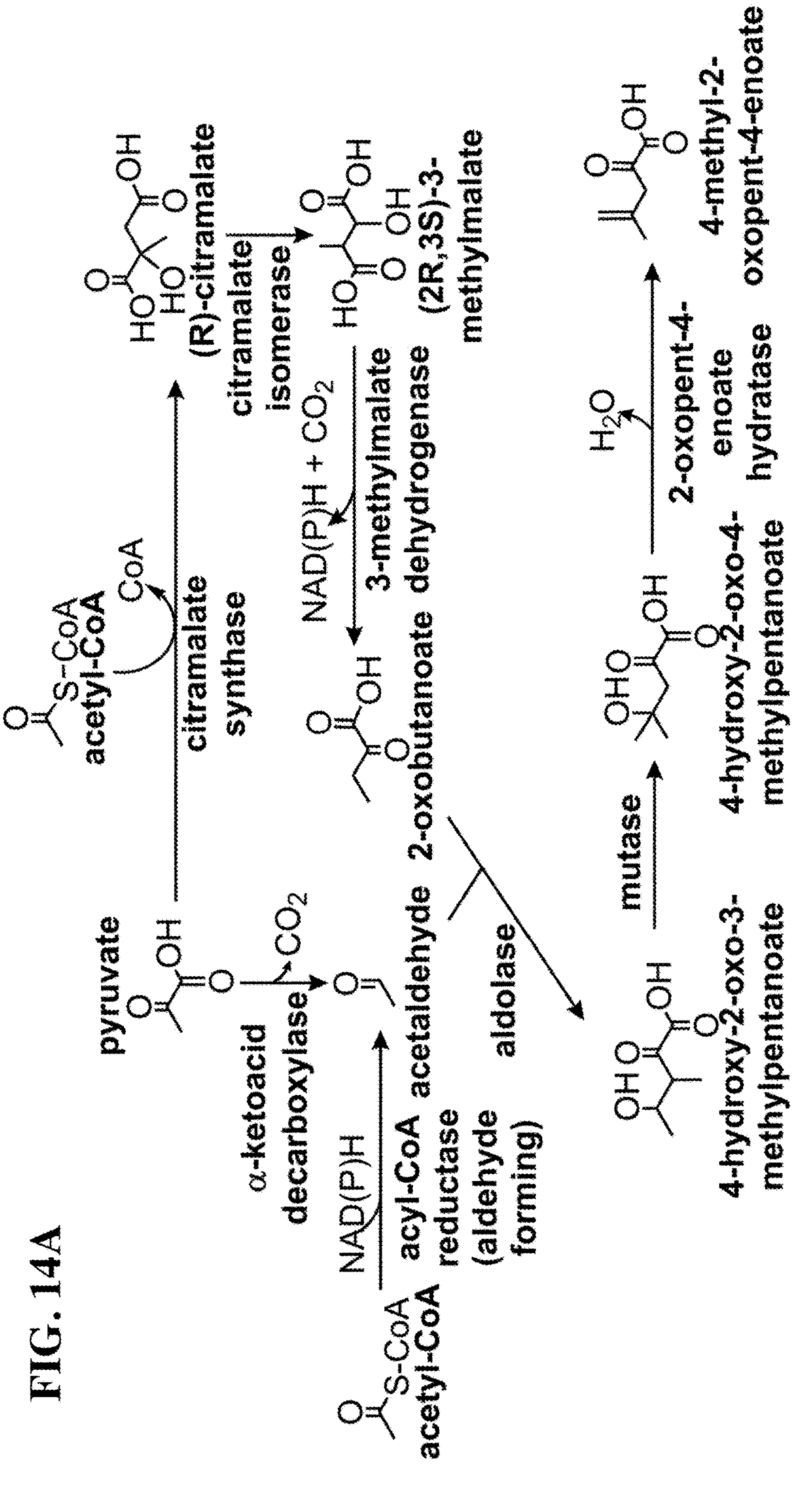
FIG. 14A-B: Pathways for the synthesis of isoprenoid precursors IPP, DMAPP and GPP from the aldol condensation of acetaldehyde and 2-oxobutanoate. Exemplary enzymes for each step shown in Table J.
Figure 14B:
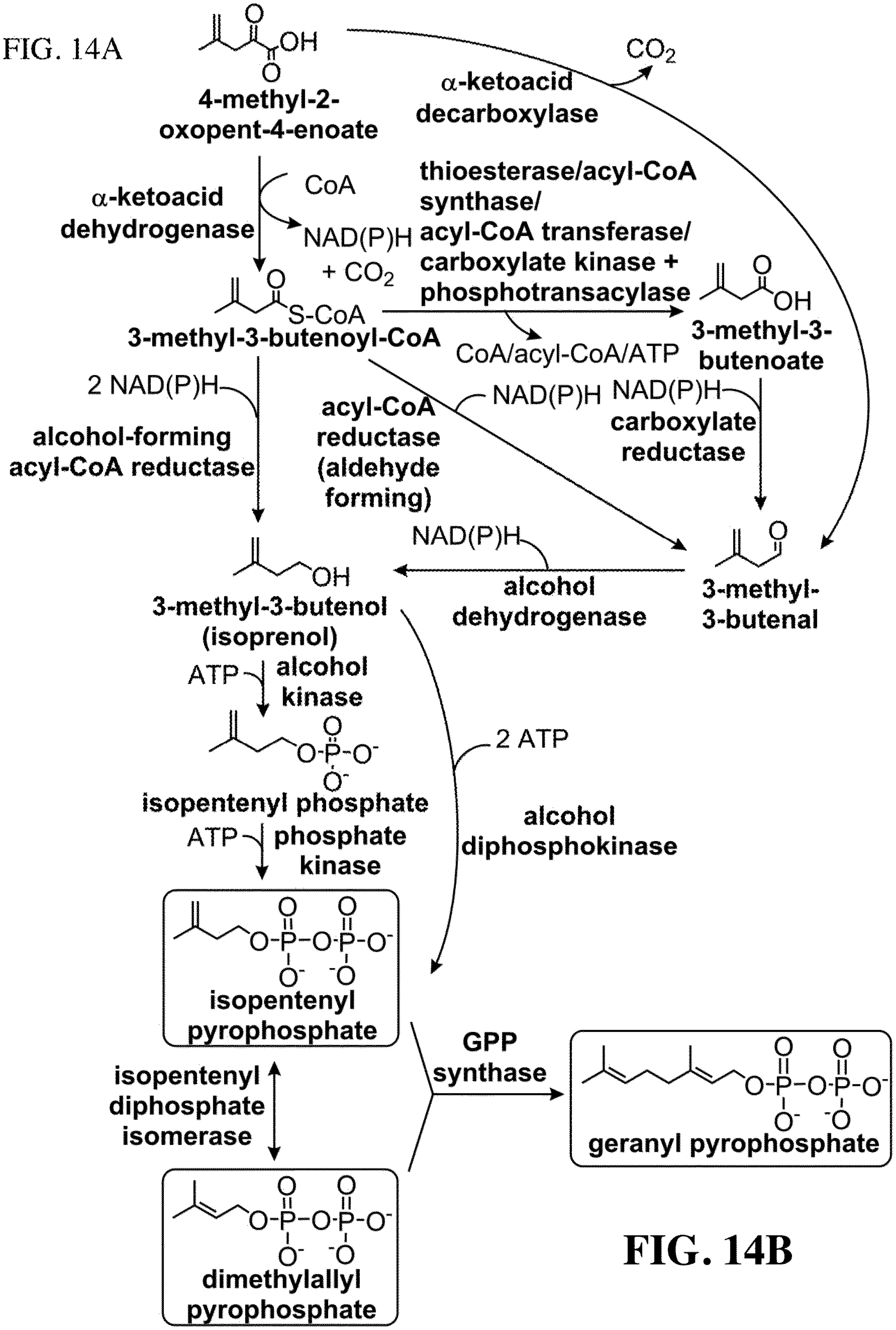

In another embodiment, an aldolase catalyzes the aldol condensation of 2-oxobutanoate and acetaldehyde forming 4-hydroxy-2-oxo-3-methylpentanoate (FIG. 14). Conversion of this intermediate to 4-methyl-2-oxopent-4-enoate, through the action of a mutase and a dehydratase, enables the use of a number of pathways to generate isoprenol from 4-methyl-2-oxopent-4-enoate. This 5-carbon isoprenoid alcohol is then converted to IPP through a two-step phosphorylation with IP as an intermediate, or a one step diphosphorylation catalyzed by an alcohol diphosphokinase. IPP can be isomerized into DMAPP generating the two $C_5$ isoprenoid precursors. These pathways are depicted in FIG. 14 and Table J below provides examples of enzymes that can be used.

Figure 15:
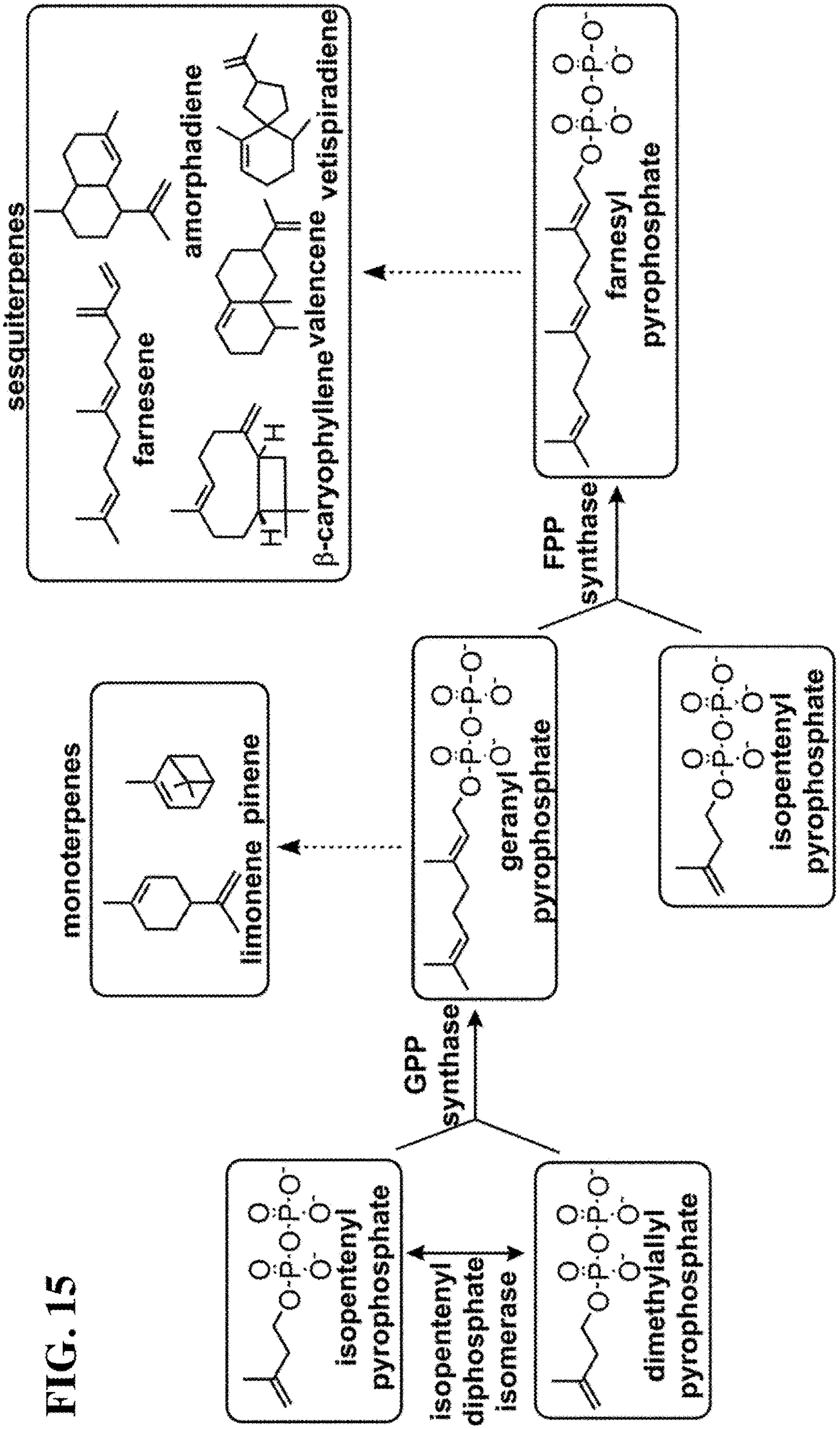
FIG. 15: Pathways for the synthesis of isoprenoids from isoprenoid precursors such as DMAPP, IPP, GPP, and FPP. Generation of isoprenoid precursors through described routes can be combined with various isoprenoid forming enzymes such as prenyl transferases, terpene synthases, or terpene cyclases to synthesize isoprenoids and derivatives thereof. Exemplary enzymes for each step shown in Table K.

The synthesis of IPP, DMAPP, GPP, FPP or other isoprenoid precursors can then be combined with the rearrangement of these intermediates into the desired isoprenoid product. The 5-carbon isomers IPP and DMAPP are the fundamental building blocks of isoprenoid products. From these $C_5$ units, an immense number of products can be synthesized through the action of for example prenyl transferases, terpene synthases, or terpene cyclases, which involves the prenyl transfer, head-to-tail condensation, head-to-head condensation, tail-to-tail condensation, or cyclization, among other biochemical reactions, of IPP, DMAPP, and other longer chain isoprenoid precursors synthesized from the $C_5$ building blocks. As such, the generation of these intermediates can enable the synthesis of for example a variety of monoterpenes ($C_{10}$), sesquiterpenes ($C_{15}$), diterpenes ($C_{20}$), sesterterpenes ($C_{25}$), triterpenes ($C_{30}$), sesquarterpenes ($C_{35}$), and tetraterpenes ($C_{40}$), among other isoprenoid compounds and derivatives thereof (FIG. 15). Table K below provides examples of enzymes that can be used.

The isoprenoid precursors synthesized through these routes can also be exploited for the synthesis of hybrid products, which contain as an example, the $C_5$ (dimethylallyl), $C_{10}$ (geranyl), or $C_{15}$ (farnesyl) isoprenoid attached to an aromatic core structure. The prenylation of these aromatic compounds with the isoprenoid units offers another route to diverse products. One route to polyketides involves native or engineered thiolases catalyzing the condensation in an iterative manner (i.e. one or multiple rounds) between two either unsubstituted or functionalized acyl-CoAs each serving as the primer and the extender unit to generate and elongate polyketide CoAs. Before an optional next round of thiolase reaction, the beta-keto group of the polyketide chain can be reduced and modified step-wise by the beta-reduction reactions. Spontaneous or enzymatically catalyzed termination reaction terminates the elongation of the polyketide chain at any point through CoA removal and reactions rearranging the structure, generating the final functional polyketide products. Examples of enzymes that can be used for these key reactions are shown in Tables A and B. This approach is the subject of patent application WO2017020043, BIOSYNTHESIS OF POLYKETIDES, filed Aug. 1, 2016, and 62/198,764, filed Jul. 30, 2015.

Figure 16A:
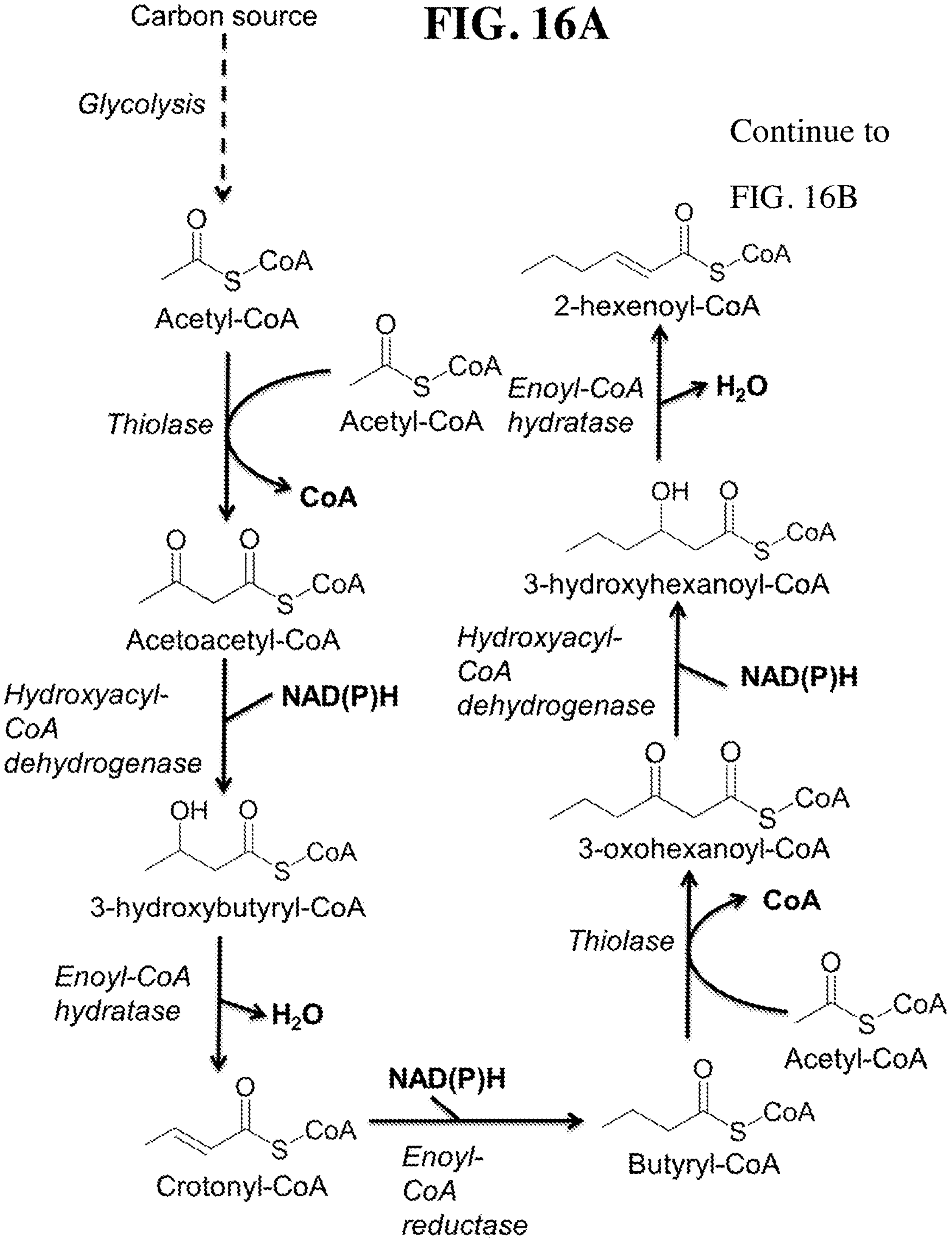
FIG. 16A-B: Pathways for the synthesis of polyketides, olivetolic acid and olivetol, through thiolases-catalyzed non-decarboxylative condensations, beta-reductions, and termination pathways.
Figure 16B:
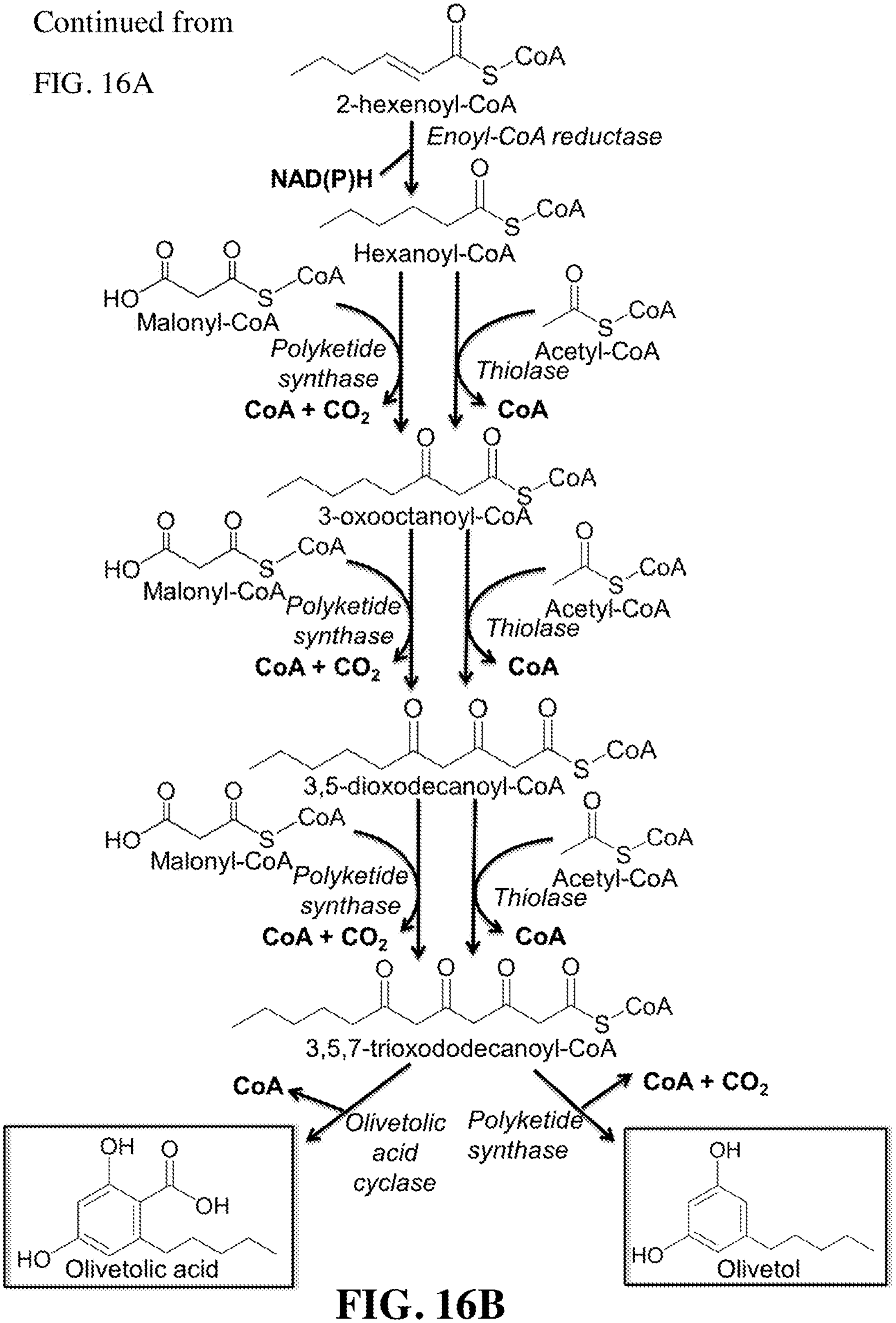
Figure 17:
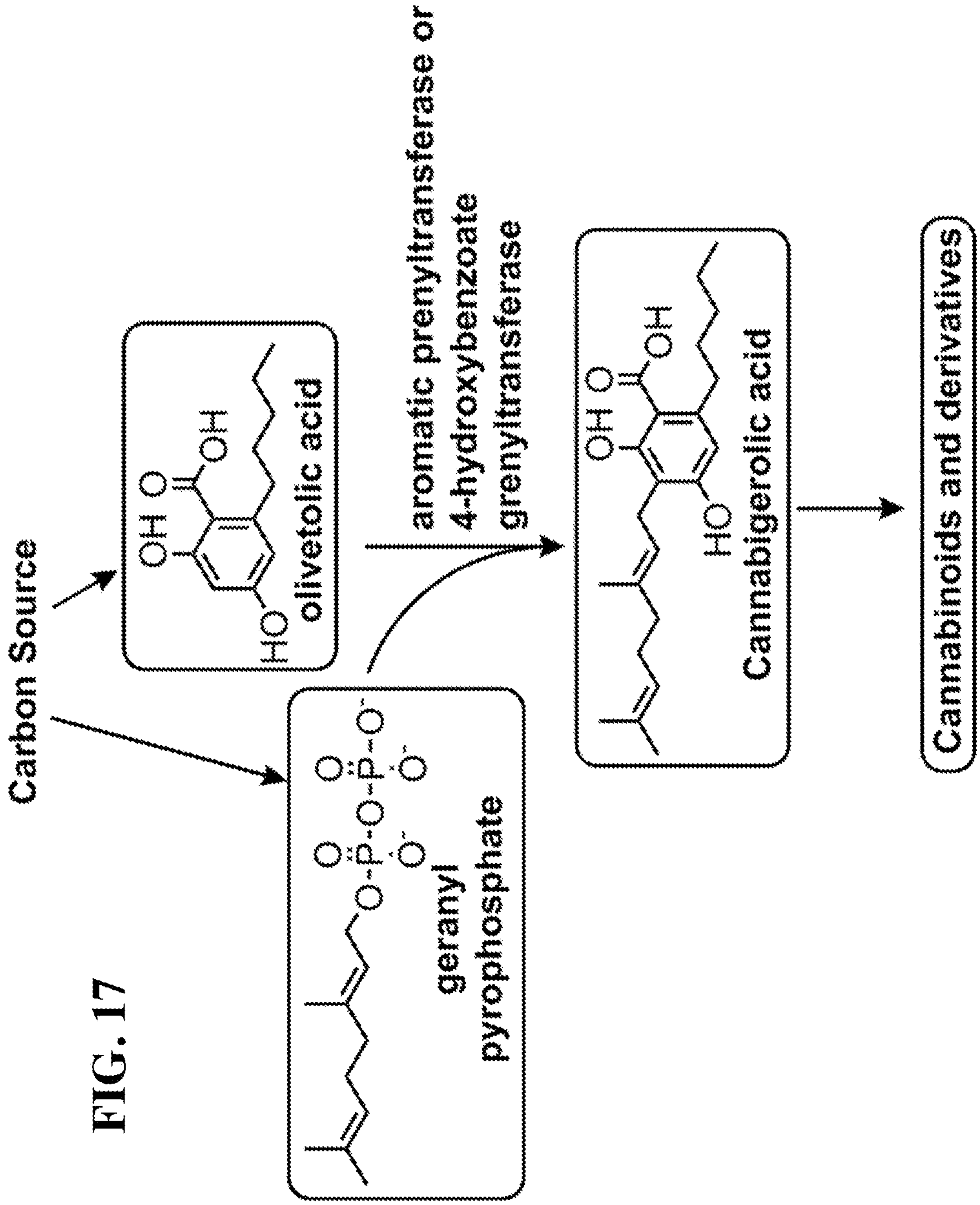
FIG. 17: Synthesis of prenylated aromatic compound cannabigerolic acid through olivetolic acid prenylation with the hydrocarbon unit of geranyl pyrophosphate. Geranyl pyrophosphate generated through various example routes as shown in FIG. 2-14, or through native pathways such as MVA or DXP pathway or commercial sources. Olivetolic acid generated through thiolases-catalyzed non-decarboxylative condensations, beta-reductions, and termination pathways, with examples shown in FIG. 16 or through alternative pathways or from commercial sources. Exemplary enzymes prenyl transfer step shown in Table L.

The polyketides synthesized through this route or other routes such as polyketide synthases can be combined with isoprenoid precursors for the formation of prenylated aromatic compounds. For example, FIG. 16 demonstrates olivetolic acid generation through condensation and beta-reduction reactions and generation of isoprenoid precursor geranyl pyrophosphate, which when combined through the action of an aromatic prenyltransferase or 4-hydroxybenzoate grenyltransferase, enables the synthesis of the cannabinoid cannabigerolic acid (FIG. 17). Cannabigerolic acid can then be converted into a number of other cannabinoids, including $\Delta^9$-tetrahydrocannabinolic acid, cannabidiolic acid, and cannabichromenic acid. Examples of enzymes that can be used for these key reactions are shown in Table L.

As such, through the use of these novel pathways based on Claisen, aldol, or acyloin condensation, this platform can be exploited to make not only isoprenoids precursors, isoprenoids and derivatives thereof, but also diverse hybrid products with wide ranging applications.

(Prophetic) GPP Biosynthesis Through Utilization of Beta-Oxidation Reversal and Methyl Group Transferring Mutase The purpose of this example is to demonstrate the biosynthesis of GPP through a novel pathway that recruits condensation and beta-reduction reactions as well as a mutase that moves the methyl group by one carbon. *E. coli* serves as the host organism. This pathway starts from non-decarboxylative Claisen condensation between acetyl-CoA, which serves as the primer, and propionyl-CoA, which serves as the extender unit, by thiolase FadAx (AAK18171.1) from *P. putida*. In the pathway, propionyl-CoA is activated from propionic acid, which is either supplemented or synthesized through overexpressed native pathway of conversion of succinate to propionic acid, catalyzed by *M. elsdenii* acyl-CoA transferase Pct (BAU59368.1). After two beta-reduction steps catalyzed by hydroxyacyl-CoA dehydrogenase FadB2x (AAK18170.1) and enoyl-CoA hydratase FadB1x (AAK18173.1), both from *P. putida*, 2-methylcrotonyl-CoA (tiglyl-CoA) is generated. Then, mutase moves the methyl group from alpha-site to beta-site on tiglyl-CoA, generating 3-methyl-2-butenoyl-CoA (3-methylcrotonyl-CoA). 3-methylcrotonyl-CoA is converted to prenol by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. Alcohol-forming acyl-CoA reductase is selected from the group consisting *C. acetobutylicum* AdhE2 (YP_009076789.1) and *M. aquaeolei* VT8 Maqu_2507 (YP_959769.1). CbjALD from *C. beijerinckii* aldehyde forming acyl-CoA reductase (AAT66436.1) is selected for conversion of 3-methylcrotonyl-CoA to prenol. Alcohol dehydrogenase is selected from the group consisting *E. coli* YahK (NP_414859.1), *E. coli* YjgB (NP_418690.4) and *Acinetobacter* sp. SE19 ChnD (BAC80217.1).

Prenol is then converted to DMAPP by one or two steps of phosphorylation. If phosphorylated by two steps, the first step is catalyzed by *E. coli* alcohol kinase YchB (NP_415726.1) or *Thermoplasma acidophilum* phosphate kinase ThaIPK (WP_010900530.1, V73I, Y141V and K204G mutations to increase specificity on prenol. Liu et al. 2016) and the second is by *M. thermautotrophicus* phosphate kinase MtIPK (AAB84554.1). The one step phosphorylation is catalyzed by alcohol diphosphokinase. *E. coli* isopentenyl pyrophosphate isomerase Idi (NP_417365.1) converts DMAPP to IPP. Then, DMAPP and IPP are condensed to GPP catalyzed by *E. coli* GPP synthase IspA (NP_414955.1, with S80F mutation to make the enzyme exclusive active on GPP synthesis, Reiling et al. 2004) or *Abies grandis* GPP synthase GPPS2 (AAN01134.1, N-terminal 84 aa truncation to improve the activity). 3-methylcrotonyl-CoA can also serve as the primer for the next iteration composed of reactions by thiolase, hydroxyacyl-CoA dehydrogenase, enoyl-CoA hydratase and enoyl-CoA reductase, with acetyl-CoA as the extender unit, generating 5-methyl-4-hexenoyl-CoA. 5-methyl-4-hexenoyl-CoA, serving as the primer, is condensed with extender unit propionyl-CoA through condensation by *P. putida* thiolase FadAx. After two beta-reduction steps catalyzed by *P. putida* hydroxyacyl-CoA dehydrogenase FadB2x and enoyl-CoA hydratase FadB1x, 2,7-dimethyl-2,6-octadienoyl-CoA is formed. Then, mutase moves the methyl group from alpha-site to beta-site, converting 2,7-dimethyl-2,6-octadienoyl-CoA to 3,7-dimethyl-2,6-octadienoyl-CoA, namely geranyl-CoA. Geranyl-CoA is converted to geraniol by alcohol-forming acyl-CoA reductase or aldehyde forming acyl-CoA reductase and alcohol dehydrogenase. Geraniol is then converted to GPP by one or two steps of phosphorylation. If phosphorylated through two steps, the first step is catalyzed by *Arabidopsis thaliana* alcohol kinase AT5G58560 (NP_200664.1) and the second step is catalyzed by Thermoplasma *acidophilum* phosphate kinase ThaIPK (WP_010900530.1, Y70A, V130A and 1130A mutations to increase specificity on geranyl phosphate over isopentenyl phosphate, Mabanglo et al. 2012). The one-step phosphorylation is catalyzed by alcohol diphosphokinase. *Ocimum basilicum* geraniol synthase GES (AR11765.1, with N-terminal 65 aa truncated to improve the activity, lijima et al. 2004) converts GPP to geraniol, which serves as the proxy product of GPP to demonstrate the synthesis pathway.

JST06(DE3) serves as the *E. coli* host strain for demonstration of this novel pathway. JST06(DE3) (MG1655(DE3) ΔldhA ΔpoxB Δpta ΔadhE ΔfrdA ΔyciA ΔybgC ΔydiI ΔtesA ΔfadM ΔtesB) (Cheong et al. 2016) is an *E. coli* strain deficient in mixed-acid fermentation pathways due to deletions of genes ldhA, poxB, pta, adhE and frdA, which maximize the supply of acetyl-CoA, and deletions of genes encoding major thioesterases (yciA, ybgC, ydiI, tesA, fadM and tesB), which minimize the hydrolysis of CoA intermediates.

The genes for overexpression are either cloned into appropriate vectors or inserted into chromosome with strong synthetic constitutive promoter, such as M1-93. When cloned into vectors, these genes are amplified through PCR using appropriate primers to append homology on each end for recombination into the vector backbone with e.g., Phusion polymerase (Thermo Scientific, Waltham, MA) to serve as the gene insert. Plasmids are linearized by the appropriate restriction enzymes (New England Biolabs, Ipswich, MA, USA) and recombined with the gene inserts using the In-Fusion HD Eco-Dry Cloning system. The mixture is subsequently transformed into Stellar competent cells. Transformants that grow on solid media (LB+Agar) supplemented with the appropriate antibiotic are isolated and screened for the gene insert by PCR. Plasmids from verified transformants are isolated and the sequence of the gene insert is further confirmed by DNA sequencing. The sequence confirmed plasmids are then introduced to host strain through electroporation.

When inserted into chromosome, CRISPR is used and genetic sites of tesB, adhE and ldhA are suitable loci, although others could be used. CRISPR method is based on the method developed by Jiang et al. (Jiang et al. 2015). First, the host strain is transformed with plasmid pCas, the vector for expression of Cas9 and λ-red recombinase. The resulting strain is grown under 30° C. with L-arabinose for induction of λ-red recombinase expression, and when OD reaches ~0.6, competent cells are prepared and transformed with pTargetF (AddGene 62226) expressing sgRNA and N20 spacer targeting the locus and template of insertion of target gene. The template is the inserted gene plus MI-93 promoter with ~500 bp sequences homologous with upstream and downstream of the insertion locus, constructed through overlap PCR with usage of Phusion polymerase or synthesized by GenScript (Piscataway, NJ) or GeneArt® (Life Technologies, Carlsbad, CA). The way to switch N20 spacer of pTargetF plasmid is inverse PCR with the modified N20 sequence hanging at the 5' end of primers with usage of Phusion polymerase and followed by self-ligation with usage of T4 DNA ligase and T4 polynucleotide kinase (New England Biolabs, Ipswich, MA, USA). Transformants that grow under 30° C. on solid media (LB+Agar) supplemented with spectinomycin and kanamycin (or other suitable antibiotic) are isolated and screened for the chromosomal gene insert by PCR. The sequence of the gene insert, which is amplified from genomic DNA through PCR using Phusion polymerase, is further confirmed by DNA sequencing. The pTargetF can then be cured through IPTG induction, and pCas can be cured through growth under higher temperature like 37-42° C.

All molecular biology techniques are performed with standard methods (Miller, 1972; Sambrook et al., 2001) or by manufacturer protocol. Strains are stored in glycerol stocks at −80° C. Plates are prepared using LB medium containing 1.5% agar, and appropriate antibiotics are included at the following concentrations: ampicillin (100 μg/mL), kanamycin (50 μg/mL), spectinomycin (50 μg/mL) and chloramphenicol (12.5 μg/mL).

MOPS minimal medium (Neidhardt et al., 1974) with 125 mM MOPS and $Na_2HPO_4$ in place of $K_2HPO_4$ (2.8 mM), supplemented with 20 g/L glycerol or 40 g/L glucose, 10 g/L tryptone, 5 g/L yeast extract, 100 μM $FeSO_4$, 5 mM calcium pantothenate, 5 mM $(NH_4)_2SO_4$, and 30 mM $NH_4Cl$ is used for fermentations. If required, 55 g/L of $CaCO_3$ is also supplemented as pH buffer. 20 mM propionic acid is supplemented, if it is not synthesized intracellularly and needed for the experiment. Antibiotics (50 μg/mL carbenicillin, 50 μg/mL spectinomycin and 50 μg/mL kanamycin) are included when appropriate. All chemicals are obtained from Fisher Scientific Co. (Pittsburgh, PA) and Sigma-Aldrich Co. (St. Louis, MO).

Fermentations are performed in 25 mL Pyrex Erlenmeyer flasks (narrow mouth/heavy duty rim, Corning Inc., Corning, NY) filled with appropriate volume of fermentation medium and sealed with foam plugs filling the necks. A single colony of the desired strain is cultivated overnight (14-16 hrs) in LB medium with appropriate antibiotics and used as the inoculum with initial $OD_{550}$ as ~0.05. After inoculation, flasks are incubated in a NBS 124 Benchtop Incubator Shaker (New Brunswick Scientific Co., Inc., Edison, NJ) at 200 rpm and 37° C. or 30° C. When optical density (550 nm, $OD_{550}$) reached ~0.3-0.5, appropriate concentration of isopropyl beta-D-1-thiogalactopyranoside (IPTG) (or other suitable inducer) is added for plasmid gene induction. Additional fermentations are conducted in a SixFors multi-fermentation system (Infors HT, Bottmingen, Switzerland) with an air flowrate of 2 N L/hr, independent control of temperature (37° C.), pH (controlled at 7.0 with NaOH and $H_2SO_4$), and appropriate stirrer speed. Precultures are grown in 25 mL Pyrex Erlenmeyer flasks as described above and incubated for 4 hours post-induction. An appropriate amount of this pre-culture is centrifuged, washed twice with fresh media, and used for inoculation (400 mL initial volume). The fermentations in bioreactor use described fermentation media with 30 g/L glycerol or 40 g/L glucose, with the optional inclusion of 5 μM sodium selenite to promote FHL activity, and appropriate IPTG and antibiotics. If required, propionic acid (20 mM) is added at 0, 24, and 48 hours.

After the fermentation, the supernatant obtained through 5000 g, 5 min centrifuge in an Optima L-80XP Ultracentrifuge (Beckman-Coulter, Schaumburg, IL) of 2 mL culture is prepared for GC-FID/GC-MS analysis of geraniol. The supernatant aliquots of 2 mL are transferred to 5 mL glass vials (Fisher Scientific Co., Pittsburgh, PA). Then, organic solvent (typically hexane) is added at a 1:1 ratio to a fermentation broth sample (e.g. 2 mL for a 2 mL aqueous solution) for extraction. Following an appropriate extraction (vortex samples for 15 seconds, spin on a rotator at 60 rpm for 2 hours, and vortex again for 15 seconds), 1 mL of the organic phase is removed. 50 μL pyridine and 50 uL BSTFA are then added to the 1 mL organic phase for derivatization, with the reaction allowed to proceed at 70° C. for 30 minutes. After cooling to room temperature, this mixture is used for GC analysis.

GC analysis is conducted on an Agilent 7890B Series Custom Gas Chromatography system equipped with a 5977B Inert Plus Mass Selective Detector Turbo EI Bundle (for identification) or a Flame Ionization Detector (for quantification) and an Agilent HP-5 capillary column (0.25 mm internal diameter, 0.25 m film thickness, 30 m length). The following temperature profile is used with helium as the carrier gas at a flowrate of 1.5 mL/min: Initial 5° C. (hold 3 min); ramp at 20° C./min to 270° C. (hold 6 min). The injector and detector temperature are 250° C. and 350° C., respectively. 1 μL of sample is injected with a 4:1 split ratio.

Figure 18:
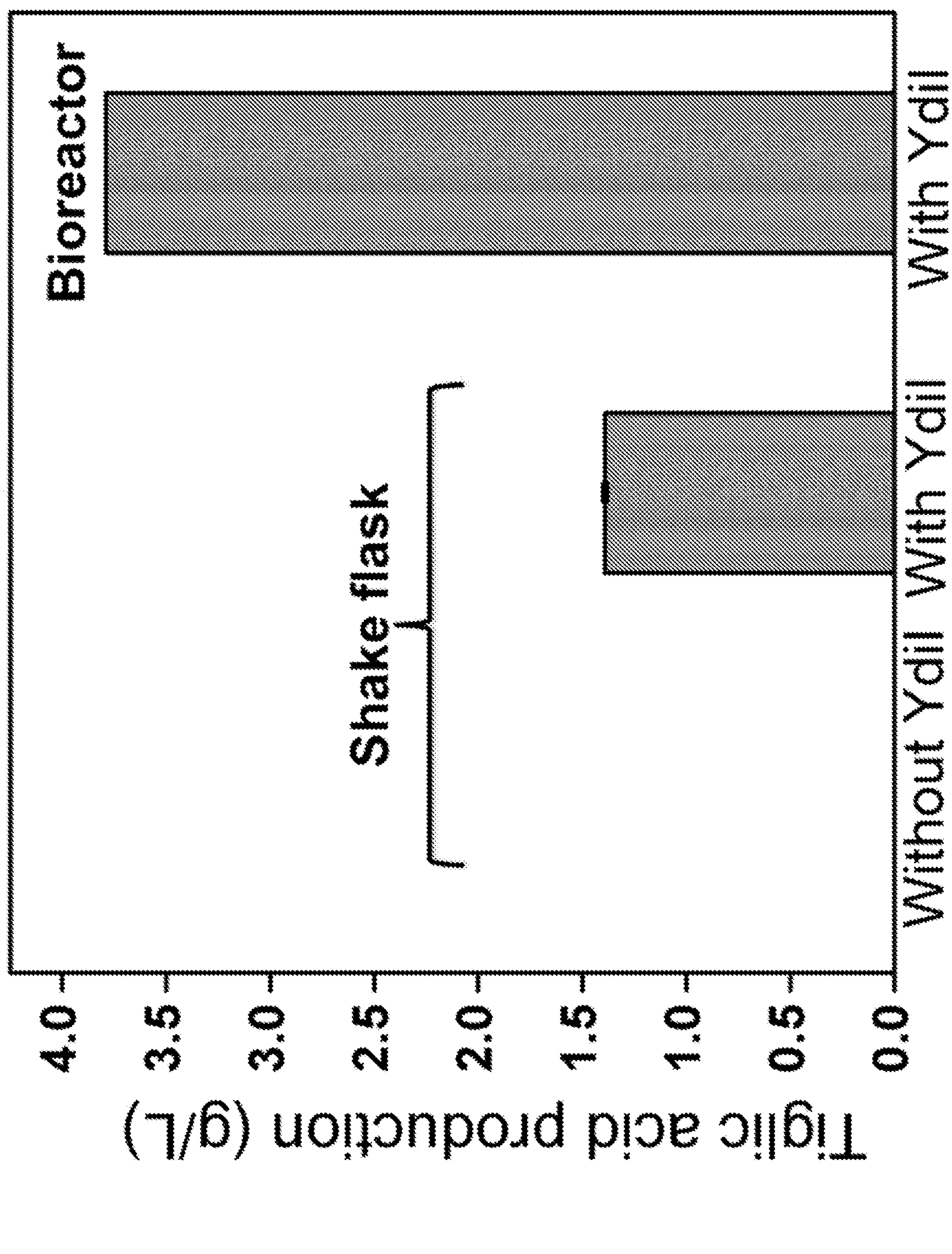
FIG. 18: Titers of tiglic acid of JST06(DE3) strain overexpressing thiolase FadAx, hydroxyacyl-CoA dehydrogenase FadB2x and enoyl-CoA hydratase FadB1x along with acyl-CoA transferase Pct with or without thioesterase YdiI in shake flasks or bioreactor.

Among above enzymes, the activities of thiolase FadAx, hydroxyacyl-CoA dehydrogenase FadB2x and enoyl-CoA hydratase FadB1x, required for the above described GPP synthesizing reverse beta-oxidation pathways, have already been demonstrated in vivo. JST06(DE3) overexpressing these enzymes along with *E. coli* thioesterase YdiI (NP_416201.1) and Pet have been grown in shake flasks with 20 g/L glycerol and 20 mM propionic acid for 48 hours at 20 mL volume and in a controlled bioreactor for 72 hours with 30 g/L glycerol and supplementation of 20 mM propionic acid every 24 hours, both induced by induced by 5 μM IPTG at 37° C., leading to production of 1.39 g/L of 2-methyl-2-butenoic acid or tiglic acid in shake flasks, and 3.79 g/L of tiglic acid in bioreactors (FIG. 18). If YdiI is not overexpressed, no tiglic acid production was detected, indicating that YdiI is able to hydrolyze 2-methyl-2-butenoyl-CoA (tiglyl-CoA), generated through FadAx condensation between primer acetyl-CoA and extender unit propionyl-CoA and subsequent beta-reduction steps by FadB2x and FadB1x, to tiglic acid.

In the above demonstration, the genes encoding FadAx and Pct were expressed from pCDF-P1-pct-fadAx and the genes encoding FadB1x, FadB2x and YdiI were expressed from pET-P1-fadB2x-fadB1x-P2-ydiI. The primers used in constructions of these plasmids are listed in Table M. For the construction of pCDF-P1-pct-fadAx, the pct gene insert was first PCR amplified with pct-f1/pct-r1 primers and inserted into vector pCDFDuet-1 (Novagen, Darmstadt, Germany) cleaved by NcoI and EcoRI through In-Fusion HD Eco-Dry Cloning system (Clontech Lab., CA) to construct pCDF-P1-pct. Then, the fadAx gene insert was PCR amplified with fadAx-f1/fadAx-r1 and inserted into vector pCDF-PI-pct cleaved by EcoRI through In-Fusion cloning, generating pCDF-P1-pct-fadAx. For the construction of pET-P1-fadB2x-fadB1x-P2-ydiI, the fadB2x gene insert was first PCR amplified with fadB2x-f1/fadB2x-r1 primers and inserted into vector pETDuet-1 (Novagen, Darmstadt, Germany) cleaved by NcoI and EcoRI through In-Fusion cloning, generating pET-P1-fadB2x. Then, the fadB1x gene insert was PCR amplified with fadB1x-f1/fadB1x-r1 primers and inserted into pET-P1-fadB2x cleaved by EcoRI through In-Fusion cloning, generating pET-P1-fadB2x-fadB1x. Finally, the ydiI gene insert was PCR amplified with ydiI-f1/ydiI-r1 primers and inserted into pET-P1-fadB2x-fadB1x cleaved by NdeI (New England Biolabs, Ipswich, MA, USA) through In-Fusion cloning, generating pET-P2-fadB2x-fadB1x-P2-ydiI. Before the introduction to host strain, the sequences of constructed plasmids were confirmed by DNA sequencing.

Two plasmids for expressing the pathway that converts prenol to GPP and geraniol (or "Lower alcohol pathway" as shown in FIG. 1) and can be used in above pathway have been constructed and are listed in Table N. To construct pET-P1-idi-trGPPS2-P2-ges-ychB-mtipk and pET-P1-idi-trGPPS2-P2-ges-thaipk-mtipk, the gene inserts encoding Idi and trGPPS2 ("tr" means "truncated" as first 84 aa of GPPS2 was truncated to improve the activity) were PCR amplified with idi-f1/idi-r1 and trgpps2-f1/trgpps2-r1 respectively and inserted together into pETDuet-1 cleaved by NeoI through In-Fusion HD Eco-Dry Cloning system to generate pET-P1-idi-trGPPS2. Then, the gene insert encoding GES was PCR amplified with ges-f1/ges-r1 primers and inserted into vector pET-P1-idi-trGPPS2 cleaved by NdeI and KpnI through In-Fusion HD Eco-Dry Cloning system to generate pET-P1-idi-trGPPS2-P2-ges. When constructing pET-P1-idi-trGPPS2-P2-ges-ychB-mtipk, the gene inserts encoding YchB and MtIPK were PCR amplified with ychB-f1/ychB-r1 and mtipk-f1/mtipk-r1 respectively and inserted together into pET-P1-idi-trGPPS2-P2-ges cleaved by XhoI through In-Fusion HD Eco-Dry Cloning system to generate pET-P1-idi-trGPPS2-P2-ges-ychB-mtipk. When constructing pET-P1-idi-trGPPS2-P2-ges-thaipk-mtipk, the gene insert encoding ThaIPK (with V73I, Y141V and K204G mutations) was PCR amplified with thaipk-f1/thaipk-r1 and inserted into pET-P1-idi-trGPPS2-P2-ges cleaved by XhoI through In-Fusion HD Eco-Dry Cloning system to generate pET-P1-idi-trGPPS2-P2-ges-thaipk, and then the gene encoding MtIPK was PCR amplified with mtipk-f2/mtipk-r1 and inserted into pET-P1-idi-trGPPS2-P2-ges-thaipk cleaved by XhoI through In-Fusion HD Eco-Dry Cloning system to generate pET-P1-idi-trGPPS2-P2-ges-thaipk-mtipk. The sequences of required primers can be seen in Table N. The sequences of constructed plasmids were further confirmed by DNA sequencing. Then, the sequence confirmed plasmids were introduced to competent cells of the host strain.

Among above enzymes, in vitro activities of acyl-CoA reductases CbjALD and Maqu_2507 on reduction of 3-methylcrotonyl-CoA and the in vitro activities of alcohol dehydrogenases ChnD, YjgB and YahK on oxidization of prenol have been proven through enzymatic spectrophotometric assay. *E. coli* alcohol dehydrogenases FucO (NP_417279.2), YqhD (NP_417484.1), YiaY (YP_026233.1) were also assayed on prenol, but as mentioned below, they did not show the activity on prenol oxidization.

For the tested enzymes, *E. coli* enzymes were expressed in pCA24N-gene (-gfp) plasmids from the ASKA collection (Kitagawa et al., 2005). Gene encoding Maqu_2507 and ChnD were codon optimized and synthesized by either GeneArt or GenScript. The gene encoding CbjALD was amplified from the genomic DNA of *C. beijerinckii*. The primers required for cloning of these genes are listed in Table O. The cbjALD gene insert was PCR amplified from the genomic DNA of *C. beijerinckii* with cbjALD-f1 and cbjALD-r1 primers and inserted into vector pCDFDuet-1 cleaved by EcoRI through In-Fusion HD Eco-Dry Cloning system to construct pCDF-ntH6-cbjALD. The sequence of the cbjALD gene insert was further confirmed by DNA sequencing. The protein was expressed with an n-terminal 6 His-tag.

The codon-optimized maqu_2507 gene insert was PCR amplified with maqu_2507-f1 and maqu_2507-r1 primers and inserted into vector pCDFDuet-1 (Novagen, Darmstadt, Germany) cleaved by EcoRI through In-Fusion HD Eco-Dry Cloning system to construct pCDF-ntH6-maqu_2507. The sequence of the maqu_2507 gene insert was further confirmed by DNA sequencing. The protein was expressed with an n-terminal 6 His-tag.

The codon-optimized chnD gene insert was PCR amplified with chnD-f1 and chnD-r1 primers and inserted into vector pCDFDuet-1 (Novagen, Darmstadt, Germany) cleaved by EcoRI through In-Fusion HD Eco-Dry Cloning system to construct pCDF-ntH6-chnD. The sequence of the chnD gene insert was further confirmed by DNA sequencing. The protein was expressed with an n-terminal 6 His-tag.

For expression of enzymes, cultures were grown in 25 mL of LB media in 125 mL flasks (Wheaton Industries, Inc., Millville, NJ) at 37° C. A single colony of the desired strain was cultivated overnight (14-16 hrs) in 10 mL of LB medium in baffled flasks (Wheaton Industries, Inc., Millville, NJ) with appropriate antibiotics and used as the inoculum (3%). The cells were induced with 0.1 mM IPTG at an OD550 ~0.6.

After post-induction growth for 4 h for ASKA strains, or 16 for other strains, the cells were collected and washed twice by 9 g/L sodium chloride solution. Cells were then re-suspended in lysis buffer (50 mM $NaH_2PO_4$, 300 mM NaCl, 10 mM imidazole, pH 8.0) to an OD ~40. After re-suspension, the cells were disrupted using glass beads and then centrifuged at 4° C., 13000 g, 10 min in an Optima L-80XP Ultracentrifuge (Beckman-Coulter, Schaumburg, IL). The resultant supernatant is the crude enzyme extract. The His-tagged enzymes were then purified from crude extract by using Ni-NTA spin kit (Qiagen, Valencia, CA). The crude extracts are centrifuged (270 g, 5 min) in spin columns that were equilibrated with lysis buffer and then washed twice by wash buffer (50 mM $NaH_2PO_4$, 300 mM NaCl, 20 mM imidazole, pH 8.0). After washing, the enzyme was eluted twice in elution buffer (50 mM $NaH_2PO_4$, 300 mM NaCl, 500 mM imidazole, pH 8.0). Both washing and elution steps are centrifuged at 890 g for 2 min. The purified enzyme extracts were then further concentrated and dialyzed through Amicon® Ultra 10K Device (Millipore, Billerica, MA). The enzymes were first filtered by centrifugation at 4° C., 14000 g, 10 min, and then washed with 100 mM potassium phosphate, pH 7 buffer under the same centrifugation conditions. Finally, the concentrated and dialyzed enzymes were recovered through 4° C., 1000 g, 2 min centrifugation. The protein concentration was established using the Bradford Reagent (Thermo Scientific, Waltham, MA) using BSA as the protein standard. SDS-PAGE monitor of purified proteins was performed through XCell SureLock™ Mini-cell system (Invitrogen, Carlsbad, CA) with gels (12% acrylamide resolving gel and 4% acrylamide stacking gel) prepared through SureLock™ Mini-cell system (Invitrogen, Carlsbad, CA). The composition of the running buffer for SDS-PAGE was 3 g/L tris base, 14.4 g/L glycine and 1 g/L SDS in water.

Enzymatic reactions were monitored on either a Synergy HT plate reader (BioTek Instruments, Inc., Winooski, VT) or a Biomate 5 Spectrophotometer (Thermo Scientific, Waltham, MA) according to established protocols. Measurement of 3-methylcrotonyl-CoA reduction by acyl-CoA reductases was measured by following the decrease (oxidation of NAD(P)H) in absorbance at 340 nm from a reaction mixture containing 100 mM Tris-HCl (pH 7.5), 5 mM DTT, 0.3 mM NAD(P)H, and 1 or 5 mM 3-methylcrotonyl-CoA. Measurement of alcohol dehydrogenase activity on prenol was measured by following the increase (reduction of NAD (P)+) in absorbance at 340 nm from a reaction mixture containing 100 mM Tris-HCl (pH 8.0), 1 mM NAD(P)+, and 1 mM prenol.

For assays of acyl-CoA reductases, the crude extract of CbjALD did not show the detectable reduction activity on 1 mM 3-methylcrotonyl-CoA, but the activity was detected (0.008 mol/mg/min) when the enzyme was purified and the concentration of 3-methylcrotonyl-CoA was 5 mM. The crude extract of Maqu_2507 showed 0.08±0.01 μmol/mg/min towards 1 mM 3-methylcrotonyl-CoA. These results indicate that CbjALD and Maqu_2507 are suitable for reduction of 3-methylcrotonyl-CoA to prenol. CbjALD uses NADH as cofactor, while Maqu_2507 uses NADPH as cofactor.

Among the assayed alcohol dehydrogenases, YahK, YjgB and ChnD showed the activity on oxidization of prenol to 3-methyl-1-butenal. They should be suitable for catalyzing the required reverse reduction reaction of 3-methyl-1-butenal, which is converted from 3-methylcrotonyl-CoA by CbjALD, to prenol. The results are shown in Table P.

3-methylcrotonyl-CoA, which is then converted to GPP via prenol through the pathway described above, can also be supplied through two different versions of reverse beta-oxidation pathways incorporated with methyl-group transferring mutase. The first pathway starts from non-decarboxylative Claisen condensation between propionyl-CoA, which serves as the primer, and glycolyl-CoA, which serves as the extender unit, catalyzed by thiolase. In this pathway, propionyl-CoA is activated from propionic acid, which is either supplemented or synthesized through overexpressed native pathway of conversion of succinate to propionic acid, while glycolyl-CoA is activated from glycolic acid, which is either supplemented or synthesized through overexpressed native pathway of conversion of glyoxylate, the intermediate of glyoxylate shunt, to glycolic acid. The activations of both propionic acid and glycolic acid are catalyzed by Pct. After three beta-reduction steps catalyzed by hydroxyacyl-CoA dehydrogenase, enoyl-CoA hydratase and enoyl-CoA reductases, 2-hydroxypentanoyl-CoA is generated. Then, mutase moves the methyl group from γ-site to beta-site on 2-hydroxypentanoyl-CoA, generating 2-hydroxy-3-methylbutanoyl-CoA, and 2-hydroxyacyl-CoA dehydratase converts 2-hydroxy-3-methylbutanoyl-CoA to 3-methylcrotonyl-CoA. The second pathway starts from non-decarboxylative Claisen condensation between propionyl-CoA, which serves as the primer, and acetyl-CoA, which serves as the extender unit, catalyzed by thiolase. In the pathway, propionyl-CoA is activated from propionic acid, which is either supplemented or synthesized through overexpressed native pathway of conversion of succinate to propionic acid, catalyzed by Pct. After two beta-reduction steps catalyzed by hydroxyacyl-CoA dehydrogenase and enoyl-CoA hydratase, 3-hydroxypentanoyl-CoA is generated. Then, mutase moves the methyl group from -site to beta-site on 3-hydroxypentanoyl-CoA, generating 3-hydroxy-3-methylbutanoyl-CoA, and enoyl-CoA hydratase converts 3-hydroxy-3-methylbutanoyl-CoA to 3-methylcrotonyl-CoA.

Figure 19:
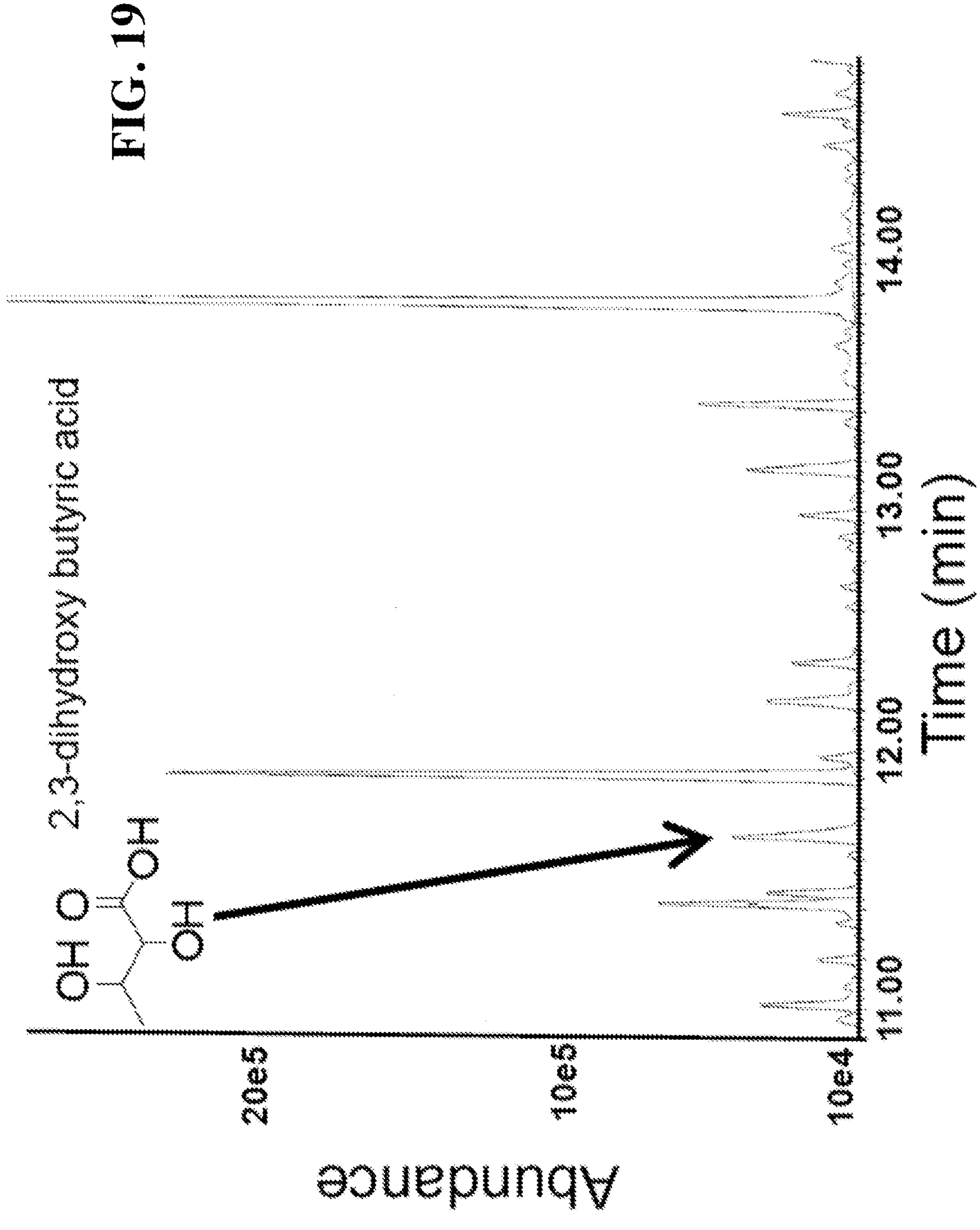
FIG. 19: Total ion GC-MS chromatogram showing peak of synthesized 2,3-dihydroxybutyric acid synthesized by MG1655(DE3) ΔglcD pET-P1-bktB-phaB1-P2-phaJ pCDF-P1-pct-P2-tdter.

The non-decarboxylative Claisen condensation between primer acetyl-CoA, similar to propionyl-CoA required in the above described pathway, and extender unit glycolyl-CoA, and the subsequent beta-reduction by hydroxyacyl-CoA dehydrogenase have been in vivo demonstrated in *E. coli*. MG1655(DE3) ΔglcD (glcD gene encoding a subunit of glycolate oxidase was deleted to block degradation of glycolic acid) strain overexpressing thiolase BktB (AAC38322.1) from *Ralstonia eutropha*, hydroxyacyl-CoA dehydrogenase PhaB1 (P14697.1) from *R. eutropha*, enoyl-CoA hydratase PhaJ (032472.1) from *Aeromonas caviae* and enoyl-CoA reductase TdTer (4GGO_A) from *Treponema denticola* along with activation enzyme Pct, which was supposed to produce 4-hydroxybutyric acid through reverse beta-oxidation pathway starting from non-decarboxylative Claisen condensation between primer glycolyl-CoA and extender unit acetyl-CoA, was also found to produce 2,3-dihydroxybutyric acid detected by GC-MS, after 96 h growth under 30° C. in LB supplemented with glucose and glycolic acid. The GC-MS chromatogram showing the peak of 2,3-dihydroxybutyric acid is shown in FIG. 19. This result indicates that thiolase BktB can accept glycolyl-CoA as extender unit and acetyl-CoA as primer in the condensation, generating 2-hydroxy-3-oxobutanoyl-CoA, and PhaB1 can reduce 2-hydroxy-3-oxobutanoyl-CoA to 2,3-dihydroxybutanoyl-CoA, which is hydrolyzed to 2,3-dihydroxybutyric acid by native *E. coli* enzymes.

In the strain producing 2,3-dihydroxybutyric acid, genes encoding BktB, PhaB1 and PhaJ were overexpressed from pET-P1-bktB-phaB1-P2-phaJ and genes encoding Pct and TdTer were overexpressed from pCDF-P1-pct-P2-tdter, as shown in Table Q, along with primer sequences required for construction of these plasmids. The genes used for 2,3-dihydroxybutyric acid production were codon optimized and synthesized by either GeneArt or GenScript, except bktB and phaB1, which were amplified from the genomic DNA of

*R. eutropha*, and pct, which was amplified from the genomic DNA of *M. elsdenii*. To construct pET-P1-bktB-phaB1-P2-phaJ, the gene insert encoding phaJ was amplified with phaJ-f1/phaJ-r1 and inserted into pETDuet-1 cleaved by NdeI through In-Fusion HD Eco-Dry Cloning system to generate pET-P2-phaJ. Then, the gene insert encoding BktB was PCR amplified with bktB-f1/bktB-r1 and inserted into pET-P2-phaJ cleaved by NcoI and EcoRI through In-Fusion HD Eco-Dry Cloning system to generate pET-P1-bktB-P2-phaJ. Then, the gene insert encoding PhaB1 was PCR amplified with phaB1-f1/phaB1-r1 primers and inserted into vector pET-P1-bktB-P2-phaJ cleaved by EcoRI through In-Fusion HD Eco-Dry Cloning system to generate pET-P1-bktB-phaB1-P2-phaJ. To construct pCDF-P1-pct-P2-tdter, the gene encoding TdTer was was amplified with tdter-f1/tdter-r1 and inserted into pCDFDuet-1 cleaved by NdeI through In-Fusion HD Eco-Dry Cloning system to generate pCDF-P2-tdter. Then, the gene insert encoding pct was PCR amplified with pct-f1/pct-r1 primers and inserted into vector pCDF-P2-tdter cleaved by NcoI and EcoRI through In-Fusion HD Eco-Dry Cloning system to generate pCDF-P1-pct-P2-tdter. The sequences of required primers can be seen in Table Q. The sequences of constructed plasmids were further confirmed by DNA sequencing. Then, the sequence confirmed plasmids were introduced to competent cells of the host strain.

Fermentations for 2,3-dihydroxybutric acid production were conducted in 250 mL Erlenmeyer Flasks filled with 50 mL LB media supplemented with 10 g/L glucose and appropriate antibiotics. A single colony of the desired strain was cultivated overnight (14-16 h) in LB medium with appropriate antibiotics and used as the inoculum (2%). After inoculation, cells were cultivated at 30° C. and 250 rpm in a NBS 124 Benchtop Incubator Shaker (New Brunswick Scientific Co., Inc., Edison, NJ) until an optical density of ~0.8 was reached, at which point IPTG (0.1 mM) and neutralized glycolic acid (40 mM) were added. Flasks were then incubated under the same conditions for 96 hours.

Besides above pathways, there is also a novel pathway of GPP synthesis employing beta-oxidation reversal without usage of methyl-group transferring muase and via 3-methyl-3-butenol (isoprenol) instead of prenol. This pathway starts from non-decarboxylative Claisen condensation between glycolyl-CoA, which serves as the primer, and propionyl-CoA, which serves as the extender unit, catalyzed by thiolase. In this pathway, propionyl-CoA is activated from propionic acid, which is either supplemented or synthesized through overexpressed native pathway of conversion of succinate to propionic acid, while glycolyl-CoA is activated from glycolic acid, which is either supplemented or synthesized through overexpressed native pathway of conversion of glyoxylate, the intermediate of glyoxylate shunt, to glycolic acid. The activations of both propionic acid and glycolic acid are catalyzed by Pct. After three beta-reduction steps catalyzed by hydroxyacyl-CoA dehydrogenase, enoyl-CoA hydratase and enoyl-CoA reductases, 4-hydroxy-2-methylbutanoyl-CoA is generated. 4-hydroxy-2-methylbutanoyl-CoA is converted to 2-methyl-1,4-butanediol by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. Then, an alcohol dehydratase converts 2-methyl-1,4-butanediol to 3-methyl-3-butenol (isoprenol). Isorenol is then converted to IPP by one or two steps of phosphorylation. If phosphorylated by two steps, the first step is catalyzed by *E. coli* alcohol kinase YchB (NP_415726.1) and the second step is catalyzed by *M. thermautotrophicus* phosphate kinase MtIPK (AAB84554.1) or Thermoplasma *acidophilum* phosphate kinase ThaIPK (WP_010900530.1) or *Methanocaldococcus jannaschii* phosphate kinase MjIPK (3K4Y_A). The one step phosphorylation is catalyzed by alcohol diphosphokinase. *E. coli* isopentenyl pyrophosphate isomerase Idi (NP_417365.1) converts DMAPP to IPP. DMAPP and IPP are condensed to GPP catalyzed by *E. coli* GPP synthase IspA (NP_414955.1, S80F) or *A. grandis* GPP synthase GPPS2 (AAN01134.1, N-terminal 84 aa truncation). *Ocimum basilicum* geraniol synthase GES (AR11765.1, N-terminal 65 aa truncation) converts GPP to geraniol, the proxy product for the synthesis pathway. For this pathway, JST06(DE3) serves as the *E. coli* host strain for demonstration. Vector creation, strain creation, growth and analysis of supernatant are conducted as described above.

(Prophetic) GPP Biosynthesis Via 2-Hydroxyisovaleric Acid and Prenol Starting from Decarboxylative Acyloin Condensation Between Two Pyruvates The purpose of this example is to demonstrate the biosynthesis of GPP through a novel pathway that starts from decarboxylative acyloin condensation between two pyruvates 2-hydroxyisovaleric acid and prenol, using *E. coli* as the host organism. This pathway starts from decarboxylative acyloin condensation of two pyruvates to (S)-2-acetolactone by *B. subtilis* acetolactate synthase AlsS (NP_391482.2). *E. coli* acetohydroxy acid isomeroreductase IlvC (NP 418222.1) converts (S)-2-acetolactone to (2R)-2,3-dihydroxy-3-methylbutyric acid. *E. coli* dihydroxy acid dehydratase IlvD (YP_026248.1) dehydrates (2R)-2,3-dihydroxy-3-methylbutanoate to 3-methyl-2-oxobutyric acid (2-oxoisovaleric acid). Then, *L. lactis* 2-hydroxyacid dehydrogenase PanE (AIS03659.1) reduces 2-oxoisovaleric acid to (2R)-3-methyl-2-hydroxybutyric acid (2-hydroxyisovaeleric acid). 2-hydroxyisovaleric acid is then activated to (2R)-3-methyl-2-hydroxybutanoyl-CoA (2-hydroxyisovaleryl-CoA) by acyl-CoA transferase selected from the group consisting *M. elsdenii* Pct (BAU59368.1) and *C. propionicum* Pct540 (CAB77207.1, with V193A mutation to enhance the expression in *E. coli*, Choi et al. 2016). 2-hydroxyisovaleryl-CoA can be directly dehydrated to 3-methyl-2-butenoyl-CoA (3-methylcrotonyl-CoA) by *C. difficile* 2-hydroxyacyl-CoA dehydratase HadBCI (AJP10092.1, AJP10093.1, AJP10091.1 or *C. propionicum* 2-hydroxyacyl-CoA dehydratase LcdABC (G3KIM4.1, G3KIM3.1, G3KIM5.1. HadBCI is originally a 2-hydroxyisocaproyl-CoA dehydratase (Kim et al. 2005). LcdABC is originally a lactonyl-CoA dehydratase. (Hofmeister et al. 1992).

2-hydroxyisovaleryl-CoA can also be converted to 3-methylcrotonyl-CoA by a multi-step pathway. In that pathway, 2-hydroxyisovaleryl-CoA is first reduced to (2R)-3-methyl-1,2-butanediol catalyzed by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. (2R)-3-methyl-1,2-butanediol is dehydrated to 3-methylbutanal by diol dehydratase which is then converted to isovaleryl-CoA by aldehyde-forming acyl-CoA reductase. Isovaleryl-CoA is converted to 3-methylerotonyl-CoA by *P. aeruginosa* acyl-CoA dehydrogenase acyl-CoA dehydrogenase LiuA (APJ52511.1).

3-methylcrotonyl-CoA is converted to prenol by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. Alcohol-forming acyl-CoA reductase is selected from the group consisting *C. acetobutylicum* AdhE2 (YP_009076789.1) and *M. aquaeolei* VT8 Maqu 2507 (YP_959769.1). CbjALD from *C. beijerinckii* aldehyde forming acyl-CoA reductase (AAT66436.1) is selected for conversion of 3-methylcrotonyl-CoA to prenol. Alcohol dehydrogenase is selected from the group consisting *E. coli* YahK (NP_414859.1), *E. coli* YjgB (NP_418690.4) and *Acinetobacter* sp. ChnD (BAC80217.1).

In another route, 2-hydroxyisovaleric acid is dehydrated to 3-methylcrotonic acid by 2-hydroxyacid dehydratase. 3-methylcrotonic acid is either activated to 3-methylcrotonyl-CoA, which is then converted to prenol by alcohol-forming acyl-CoA reductase or aldehyde forming acyl-CoA reductase and alcohol dehydrogenase, or directly converted to prenol by two step reductions by carboxylate reductase and alcohol dehydrogenase. Prenol is then converted to DMAPP by one or two steps of phosphorylation. If phosphorylated by two steps, the first step is catalyzed by *E. coli* alcohol kinase YchB (NP_415726.1) or Thermoplasma *acidophilum* phosphate kinase ThaIPK (WP_010900530.1, V73I, Y141V and K204G mutations to increase specificity on prenol (Liu et al. 2016) and the second is by *M. thermautotrophicus* phosphate kinase MtIPK (AAB84554.1). The one step phosphorylation is catalyzed by alcohol diphosphokinase. *E. coli* isopentenyl pyrophosphate isomerase Idi (NP_417365.1) converts DMAPP to IPP. DMAPP and IPP are condensed to GPP catalyzed by *E. coli* GPP synthase IspA (NP_414955.1, S80F) or *A. grandis* GPP synthase GPPS2 (AAN01134.1, N-terminal 84 aa truncation). *Ocimum basilicum* geraniol synthase GES (AR11765.1, N-terminal 65 aa truncation) converts GPP to geraniol, the proxy product for the synthesis pathway. Because 2-hydroxyacyl-CoA dehydratase is oxygen-sensitive, the strain harboring this pathway is grown under microaerobic or anoxic or anaerobic conditions.

As above, JST06(DE3) serves as the *E. coli* host strain for demonstration of novel pathway. The genes for overexpression are either cloned into appropriate vectors or inserted into chromosome with strong synthetic constitutive promoter M1-93, as described in the previous example. Transformed cells are grown, and supernatant analyzed, also as described in the previous example.

Among above enzymes, as mentioned in the previous example, the in vitro activities of acyl-CoA reductases CbjALD and Maqu_2507 on reduction of 3-methylerotonyl-CoA and the in vitro activities of alcohol dehydrogenases ChnD, YjgB and YahK on oxidization of prenol have been proven through enzymatic spectrophotometric assay. *E. coli* alcohol dehydrogenases FucO (NP_417279.2), YqhD (NP 417484.1), YiaY (YP_026233.1) were also assayed on prenol, but as mentioned above, they did not show the activity on prenol oxidization. The results of assays on alcohol dehydrogenases can be seen in Table P, and the results of assays on acyl-CoA reductases and relevant enzyme preparation and assay methods are described in the previous example.

The in vitro activities of acyl-CoA transferases Pct and Pct540 on activation of 2-hydroxyisovaleric acid to 2-hydroxyisovaleryl-CoA have also been proven through enzymatic spectrophotometric assay.

Genes encoding Pct540 was codon optimized and synthesized by GeneArt. The gene encoding Pct was PCR amplified from the genomic DNA of *M. elsdenii*. The primers required for cloning of these genes are listed in Table R. The pct gene insert was PCR amplified from the genomic DNA of Megasphaera elsdenii with pct-f2 and pct-r2 primers and inserted into vector pUCBB-ctH6-eGFP (Vick et al. 2011) cleaved by BglII and XhoI through In-Fusion HD Eco-Dry Cloning system to construct pUCBB-ctH6-pct. The sequence of the pct gene insert was further confirmed by DNA sequencing. The protein was expressed with a c-terminal 6 His-tag.

The codon-optimized pct540 gene insert was PCR amplified with pct540-f1 and pct540-r1 primers and inserted into vector pTrcHis2A (Invitrogen, Carlsbad, CA) cleaved by NcoI and SalI through In-Fusion HD Eco-Dry Cloning system to construct pTH-ctH6-pct540. The sequence of the pct540 gene insert was further confirmed by DNA sequencing. The protein was expressed with a c-terminal 6 His-tag. The sequence-confirmed plasmids were introduced into BL21(DE3) (Studier et al. 1986).

For expression of enzymes, cultures were grown in 25 mL of LB media in 125 mL flasks (Wheaton Industries, Inc., Millville, NJ) at 37° C. A single colony of the desired strain was cultivated overnight (14-16 hrs) in 10 mL of LB medium in baffled flasks (Wheaton Industries, Inc., Millville, NJ) with appropriate antibiotics and used as the inoculum (3%). Except for the expression of pct, the cells were induced with 0.1 mM IPTG at an OD550 ~0.6, while pct was expressed constitutively.

After post-induction growth for 16 hours, the cells were collected and washed twice by 9 g/L sodium chloride solution. Cells were then re-suspended in lysis buffer (50 mM $NaH_2PO_4$, 300 mM NaCl, 10 mM imidazole, pH 8.0) to an OD ~40. After re-suspension, the cells were disrupted using glass beads and then centrifuged at 4° C., 13000 g, 10 min in an Optima L-80XP Ultracentrifuge (Beckman-Coulter, Schaumburg, IL). The resultant supernatant is the crude enzyme extract. The His-tagged enzymes were then purified from crude extract by using Ni-NTA spin kit (Qiagen, Valencia, CA). The crude extracts are centrifuged (270 g, 5 min) in spin columns that were equilibrated with lysis buffer and then washed twice by wash buffer (50 mM $NaH_2PO_4$, 300 mM NaCl, 20 mM imidazole, pH 8.0). After washing, the enzyme was eluted twice in elution buffer (50 mM $NaH_2PO_4$, 300 mM NaCl, 500 mM imidazole, pH 8.0). Both washing and elution steps are centrifuged at 890 g for 2 min. The purified enzyme extracts were then further concentrated and dialyzed through Amicon® Ultra 10K Device (Millipore, Billerica, MA). The enzymes were first filtered by centrifugation at 4° C., 14000 g, 10 min, and then washed with 100 mM potassium phosphate, pH 7 buffer under the same centrifugation conditions. Finally, the concentrated and dialyzed enzymes were recovered through 4° C., 1000 g, 2 min centrifugation. The protein concentration was established using the Bradford Reagent (Thermo Scientific, Waltham, MA) using BSA as the protein standard. SDS-PAGE monitor of purified proteins was performed through XCell SureLock™ Mini-cell system (Invitrogen, Carlsbad, CA) with gels (12% acrylamide resolving gel and 4% acrylamide stacking gel) prepared through SureLock™ Mini-cell system (Invitrogen, Carlsbad, CA). The composition of the running buffer for SDS-PAGE was 3 g/L tris base, 14.4 g/L glycine and 1 g/L SDS in water.

Enzymatic reactions were monitored on either a Synergy HT plate reader (BioTek Instruments, Inc., Winooski, VT) or a Biomate 5 Spectrophotometer (Thermo Scientific, Waltham, MA) according to established protocols.

Measurement of acyl-CoA transferase activity was conducted in a two-step reaction in which the residual amount of acetyl-CoA after incubation of the enzyme with the substrate of interest was measured. Each assay was carried out in 100 mM Tris-HCL (pH 7.4). First, 0.1 mM acetyl-CoA and 1 or 10 mM of the substrate was incubated with purified enzyme for 15 min at 30° C. After denaturation of the enzyme (90 s at 95° C.), 0.1 mM oxaloacetate, 5 μg citrate synthase and 0.5 mM DTNB were added, and the reaction was further incubated for 15 min at 30° C. The amount of generated CoASH was determined by measuring the absorbance at 412 nm.

Figure 20:
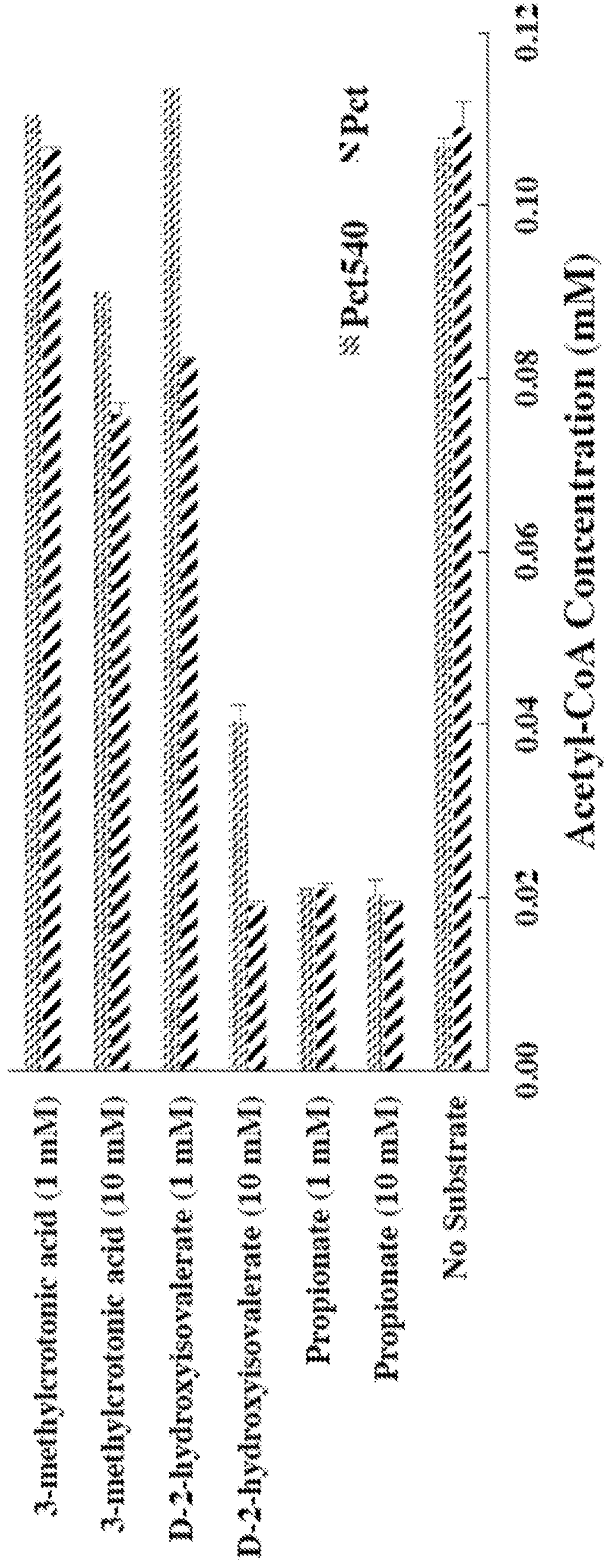
FIG. 20: Results of in vitro enzymatic assays of acyl-CoA transferases Pet and Pct540 on different substrates.

Pet and Pct540 were assayed on CoA transfer from acetyl-CoA to three different substrates: original substrate propionic acid, 2-hydroxyisovaleric acid and 3-methylcrotonic acid, which are required for this novel GPP synthesis pathway. The results of activation of different substrates by Pct and Pct540 are shown in FIG. 20. Pct and Pct540 were shown to have slight activity towards 3-methylcrotonic acid. These enzymes have higher activity towards 2-hydroxyisovaleric acid, and the activity of Pct is higher than that of Pct540, though their activities on 2-hydroxyisovaleric acid are lower than those on original substrate propionic acid. Thus, Pct and Pct540 are suitable acyl-CoA transferases for activation of 2-hydroxyisovaleric acid.

Also, JST06(DE3) strain overexpressing *B. subtilis* acetolactate synthase AlsS, *E. coli* acetohydroxy acid isomeroreductase IlvC, *E. coli* dihydroxy acid dehydratase IlvD and *Lactococcus lactis* 2-hydroxyacid dehydrogenase PanE—the enzymes of first four steps of the pathway—have been grown in shake flasks with 20 mL LB-like MOPS supplemented with 20 g/L glycerol or 32 g/L glucose (55 g/L $CaCO_3$ was also added when glucose was used) for 48 hours under 37° C. with 5 μM IPTG induction. The genes encoding AlsS, IlvC, IlvD and PanE were expressed from the plasmid pET-P1-ilvC-ilvD-P2-alsS-panE. The genes encoding AlsS and PanE were codon optimized and synthesized by either GeneArt or GenScript, while the genes encoding IlvC and IlvD were amplified from genomic DNA of wild type *E. coli* MG1655 strain. The plasmids used for the construction of plasmid are listed in Table R. The codon-optimized alsS and panE gene inserts were PCR amplified with alsS-f1/alsS-r1 and panE-f[1]/panE-r1 primers respectively and inserted together into vector pETDuet-1 cleaved by NdeI through In-Fusion HD Eco-Dry Cloning system, resulting in pET-P2-alsS-panE plasmid. The ilvC and ilvD gene inserts were PCR amplified from the genomic DNA of *E. coli* with ilvC-f[1]/ilvC-r1 and ilvD-f1/ilvD-r1 primers respectively, and inserted together into vector pET-P2-alsS-panE cleaved by NeoI and EcoRI through In-Fusion HD Eco-Dry Cloning system, generating pET-P1-ilvC-ilvD-P2-alsS-panE. The sequences of constructed plasmids are further confirmed by DNA sequencing. The quantification of 2-hydroxyisovaleric acid was performed via ion-exclusion HPLC using a Shimadzu Prominence SIL 20 system (Shimadzu Scientific Instruments, Inc., Columbia, MD) equipped with an HPX-87H organic acid column (Bio-Rad, Hercules, CA) with operating conditions to optimize peak separation (0.3 mL/min flow rate, 30 mM $H_2SO_4$ mobile phase, column temperature 42° C.). Concentration of 2-hydroxyisovaleric acid in fermentation samples was determined through calibration to known 2-hydroxyisovaleric acid standards (5, 1, 0.5, 0.2 and 0.1 g/L).

Figure 21:
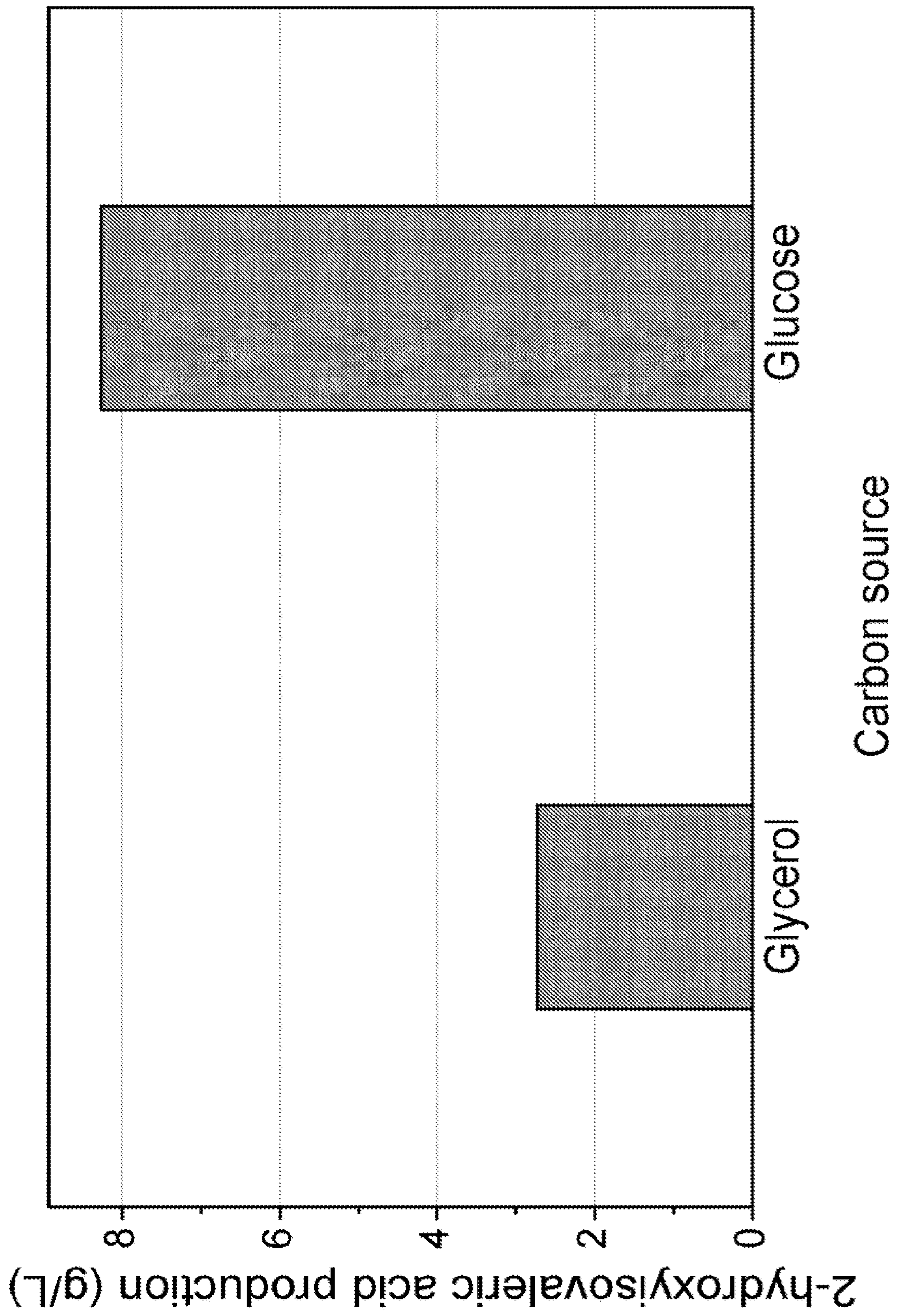
FIG. 21: 2-hydroxyisovaleric acid titer of JST06(DE3) expressing alsS, ilvC, i1vD and panE when grown on various carbon sources.

As shown in FIG. 21, this strain shows high production of 2-hydroxyisovaleric acid, especially when glucose was used as carbon source, in which the titer was 8.27 g/L. This indicates that AlsS, IlvC, IlvD and PanE can supply 2-hydroxyisovaleric acid with high flux, providing sufficient intermediates supply for the subsequent conversion into prenol and GPP.

Plasmids containing the codon optimized gene encoding 6×HIS-tagged Lmo1179 and PddABC were constructed. The resulting construct was transformed into *E. coli* BL21 (DE3) for expression. The resulting strain was cultured in 50 mL of TB media containing appropriate antibiotics in a 250 mL flask. When the culture reached an OD550 of approximately 0.6, expression was induced by the addition of 0.1 mM IPTG, and the cells were harvested by centrifugation after overnight incubation at room temperature.

The HIS-tagged Lmo1179 protein was purified from the cell extract using Talon Metal Affinity Resin (Clontech lab., CA). In short, a 250 μL resin bed was equilibrated twice using 2.5 mL of a buffer containing 50 mM sodium phosphate, 300 mM NaCl, and 10 mM imidazole at pH 7.5 (NPI-10). The cell extract was added to the resin and the mixture shaken gently for 20 minutes on ice. The resin was then washed twice with 2.5 mL buffer NPI-20 (same as NPI-10 but with 20 mM imidazole), shaking gently on ice for 15 minutes each wash. The resin was then transferred to a gravity column and washed once with 1.25 mL NPI-20. Finally, the desired protein was eluted using 1.25 mL of buffer NPI-250 (same as buffer NPI-10 but with 250 mM imidazole), and the eluate collected in 500 μL fractions.

Clarified cell lysates of BL21(DE3) strain overexpressing His-tagged PddABC was prepared by resuspending a saved pellet in 50 mM potassium phosphate buffer pH 7.5 containing 0.2 M ethylene glycol. The resuspened cells were broken by glass beads and supernatant was reserved after centrifugation. Assays were performed by coupling the dehydration of ethylene glycol to acetaldehyde to acyl-CoA reductase Lmo1179 to give acetyl-CoA with the reduction of $NAD^+$ to NADH, which was monitored at 340 nm. The final assay mixture was 250 μL and contained 50 mM potassium phosphate buffer pH 7.5, 5 mM CoASH, 0.5 mM $NAD^+$, 0.2 M ethylene glycol, 7 μL purified Lmo1179, 50 μL cell lysate, and 15 μM coenzyme B12 (the cofactor of PddABC). The relevant controls included were no cell lysates (replaced with 50 μL of buffer) and no coenzyme B12.

Figure 22:
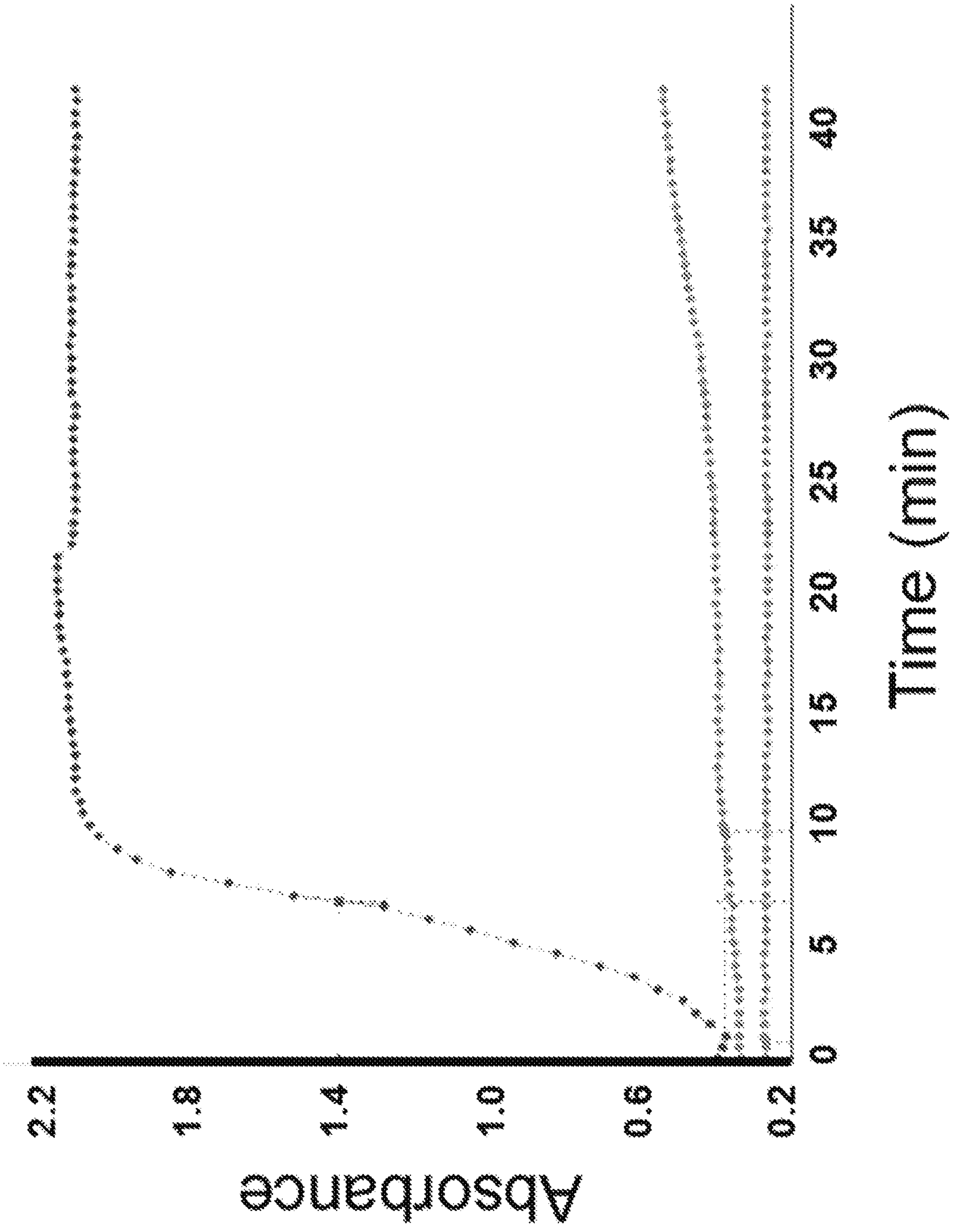
FIG. 22: Absorbance at 340 nm of in vitro assay samples and controls on dehydration of ethylene glycol to acetaldehyde by PddABC, coupled with actaldehyde oxidization to acetyl-CoA by Lmo1179. Red: control without B12 coenzyme; Blue: control without cell lysates; Green: reaction sample with lysate and B12 coenzyme.

The in vitro activity of dehydration of ethylene glycol to acetaldehyde by diol dehydratae PddABC (AFJ04717.1, AFJ04718.1, AFJ04719.1) from *Klebsiella oxytoca* has been proven, as shown in FIG. 22. This assay was coupled with oxidization of resultant acetaldehyde to acetyl-CoA by *Listeria monocytogenes* acyl-CoA reductase (ACR) Lmo1179 (CAC99257.1) and the activity was measured through observation of increased NADH absorbance. Based on these results, PddABC should be a good candidate of diol dehydratase for dehydration of (2R)-3-methyl-1,2-butanediol required for GPP synthesis pathway.

(Prophetic) GPP Biosynthesis Via 2-Hydroxyisovaleric Acid and Prenol Starting from Aldol Condensation Between Acetaldehyde and Pyruvate The purpose of this experiment is to demonstrate the biosynthesis of GPP through a novel pathway that starts from aldol condensation between pyruvate and acetaldehyde via 2-hydroxyisovaleric acid and prenol, using *E. coli* as the host organism. This pathway starts from aldol condensation between pyruvate and acetaldehyde to (S)-4-hydroxy-2-oxopentaonoic acid by *E. coli* aldolase MhpE (NP_414886.1). Acetaldehyde is supplied either through decarboxylation of pyruvate by *Saccharomyces cerevisiae* alpha-keto acid decarboxylase PDC1 (CAA97573.1) or through reduction of acetyl-CoA by *E. coli* aldehyde forming acyl-CoA reductase MhpF (NP_414885.1). Then, a mutase moves the —(C═O)COOH group of (S)-4-hydroxy-2-oxopentaonic acid from C-3 site to C-4 site, forming 3-hydroxy-2-oxo-3-methylbutyric acid. 2-hydroxyacid dehydrogenase converts 3-hydroxy-2-oxo-3-methylbutyric acid to (2R)-2,3-dihydroxy-3-methylbutyric acid. *E. coli* dihydroxy acid dehydratase IlvD (YP_026248.1) dehydrates (2R)-2,3-dihydroxy-3-methylbutanoate to 3-methyl-2-oxobutyric acid (2-oxoisovaleric acid). Then, *L. lactis* 2-hydroxyacid dehydrogenase PanE (AIS03659.1) reduces 2-oxoisovaleric acid to (2R)-3-methyl-2-hydroxybutyric acid (2-hydroxyisovaeleric acid). 2-hydroxyisovaleric acid is then activated to (2R)-3-methyl-2-hydroxybutanoyl-CoA (2-hydroxyisovaleryl-CoA) by acyl-CoA transferase selected from the group consisting *M. elsdenii* Pct (BAU59368.1) and *C. propionicum* Pct540 (CAB77207.1, with V193A mutation to enhance the expression in *E. coli*, Choi et al. 2016). 2-hydroxyisovaleryl-CoA can be directly dehydrated to 3-methyl-2-butenoyl-CoA (3-methylcrotonyl-CoA) by *C. difficile* 2-hydroxyacyl-CoA dehydratase HadBCI (AJP10092.1, AJP10093.1, AJP10091.1. HadBCI is originally a 2-hydroxyisocaproyl-CoA dehydratase, Kim et al. 2005) or *C. propionicum* 2-hydroxyacyl-CoA dehydratase LcdABC (G3KIM4.1, G3KIM3.1, G3KIM5.1. LcdABC is originally a lactonyl-CoA dehydratase, Hofmeister et al. 1992). 2-hydroxyisovaleryl-CoA can also be converted to 3-methylcrotonyl-CoA by a multi-step pathway.

In that pathway, 2-hydroxyisovaleryl-CoA is first reduced to (2R)-3-methyl-1,2-butanediol catalyzed by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. (2R)-3-methyl-1,2-butanediol is dehydrated to 3-methylbutanal by diol dehydratase which is then converted to isovaleryl-CoA by aldehyde-forming acyl-CoA reductase. Isovaleryl-CoA is converted to 3-methylcrotonyl-CoA by *P. aeruginosa* acyl-CoA dehydrogenase acyl-CoA dehydrogenase LiuA (APJ52511.1). 3-methylcrotonyl-CoA is converted to prenol by an alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. Alcohol-forming acyl-CoA reductase is selected from the group consisting *C. acetobutylicum* AdhE2 (YP_009076789.1) and *M. aquaeolei* VT8 Maqu_2507 (YP_959769.1). CbjALD from *C. beijerinckii* aldehyde forming acyl-CoA reductase (AAT66436.1) is selected for conversion of 3-methylcrotonyl-CoA to prenol. Alcohol dehydrogenase is selected from the group consisting *E. coli* YahK (NP_414859.1), *E. coli* YjgB (NP_418690.4) and *Acinetobacter* sp. ChnD (BAC80217.1).

In another route, 2-hydroxyisovaleric acid is dehydrated to 3-methylcrotonic acid by 2-hydroxyacid dehydratase. 3-methylcrotonic acid is either activated to 3-methylcrotonyl-CoA, which is then converted to prenol by alcohol-forming acyl-CoA reductase or aldehyde forming acyl-CoA reductase and alcohol dehydrogenase, or directly converted to prenol by two step reductions by carboxylate reductase and alcohol dehydrogenase. Prenol is then converted to DMAPP by one or two steps of phosphorylation. If phosphorylated by two steps, the first step is catalyzed by *E. coli* alcohol kinase YchB (NP_415726.1) or *Thermoplasma acidophilum* phosphate kinase ThaIPK (WP_010900530.1, V73I, Y141V and K204G mutations to increase specificity on prenol. Liu et al. 2016) and the second is by *M. thermautotrophicus* phosphate kinase MtIPK (AAB84554.1). The one step phosphorylation is catalyzed by alcohol diphosphokinase. *E. coli* isopentenyl pyrophosphate isomerase Idi (NP_417365.1) converts DMAPP to IPP. DMAPP and IPP are condensed to GPP catalyzed by *E. coli* GPP synthase IspA (NP_414955.1, S80F) or *A. grandis* GPP synthase GPPS2 (AAN01134.1, N-terminal 84 aa truncation). *Ocimum basilicum* geraniol stynthase GES (AR11765.1, N-terminal 65 aa truncation) converts GPP to geraniol, the proxy product for the synthesis pathway. Because 2-hydroxyacyl-CoA dehydratase is oxygen-sensitive, the strain harboring this pathway is grown under microaerobic or anoxic or anaerobic conditions.

JST06(DE3) serves as the *E. coli* host strain for demonstration of this novel pathway. Vector creation, strain creation, growth and analysis of supernatant are as described above in previous examples.

Among above enzymes, as mentioned in the previous example, The in vitro activities of acyl-CoA transferases Pct and Pct540 on activation of 2-hydroxyisovaleric acid to 2-hydroxyisovaleryl-CoA, the in vitro activities of acyl-CoA reductases CbjALD and Maqu_2507 on reduction of 3-methylcrotonyl-CoA and the in vitro activities of alcohol dehydrogenases ChnD, YjgB and YahK on oxidization of prenol have been proven through enzymatic spectrophotometric assay. *E. coli* alcohol dehydrogenases FucO (NP_417279.2), YqhD (NP_417484.1), YiaY (YP_026233.1) were also assayed on prenol, but as mentioned above, they did not show the activity on prenol oxidization. The results of assays on alcohol dehydrogenases and acyl-CoA transferases can be seen in Table R and FIG. 20 respectively, and the results of assays on acyl-CoA reductases and relevant enzyme preparation and assay methods are described in the previous example.

The in vitro activity of dehydration of ethylene glycol to acetaldehyde by diol dehydratae PddABC (AFJ04717.1, AFJ04718.1, AFJ04719.1) from *Klebsiella oxytoca* has been proven, as shown in FIG. 22. The assay method is described in the previous examples.

(Prophetic) GPP Biosynthesis Via 2-Hydroxyisovaleryl-Coa and Prenol Starting from Non-Decarboxylative Acyloin Condensation Between Isobutanal and Formyl-Coa The purpose of this experiment is to demonstrate the biosynthesis of GPP through a novel pathway that starts from non-decarboxylative acyloin condensation between formyl-CoA and isobutanal via 2-hydroxyisovaleryl-CoA and prenol, using *E. coli* as the host organism. This pathway starts from non-decarboxylative acyloin condensation between isobutanal and formyl-CoA to (2R)-3-methyl-2-hydroxybutanoyl-CoA (2-hydroxyisovaleryl-CoA) by *Homo sapiens* 2-hydroxyacyl-CoA lyase HACL1 (NP_036392.2). Formyl-CoA is activated from formate, which is a byproduct of conversion of pyruvate to acetyl-CoA by *E. coli* pyruvate-formate lyase PflB (NP_415423.1), catalyzed by activation enzymes selected from the group consisting acyl-CoA synthase, acyl-CoA transferase, carboxylate kinase plus phosphotransacylase. Isobutanal is reduced from isobutyryl-CoA by aldehyde forming acyl-CoA reductase. Isobutyryl-CoA is converted from butyryl-CoA by mutase. Butyryl-CoA can be supplied from butyric acid, either supplemented or intracellularly synthesized through beta-oxidation reversal starting from two acetyl-CoAs composed of ketoacyl-CoA thiolase BktB (AAC38322.1) from *R. eutropha* or thiolase AtoB (NP_416728.1) from *E. coli*, hydroxyacyl-CoA dehydrogenase and enoyl-CoA hydratase multifunctional enzyme FadB from *E. coli* (NP_418288.1) and enoyl-CoA reductase EgTer from *E. gracilis* (Q5EU90.1) or fatty acid biosynthesis pathway starting from acetyl-CoA and malonyl-CoA composed of beta-ketoacyl-ACP synthase FabH (NP_415609.1), beta-ketoacyl-ACP reductase FabG (NP_415611.1), 3-hydroxyacyl-ACP dehydratase FabZ (NP_414722.1) and enoyl-ACP reductase FabI (NP_415804.1), all from *E. coli*, with termination by *E. coli* thioesterase TesA (NP_415027.1, with truncation of 26 aa leader sequence) and activation by *E. coli* acyl-CoA synthetase FadD (NP_416319.1), or directly synthesized through overexpressed beta-oxidation reversal pathway without termination. If malonyl-CoA is used to enhance its supply, *E. coli* acetyl-CoA carboxylase AccABCD (NP_414727.1, NP_417721.1, NP_417722.1, NP_416819.1) is overexpressed.

2-hydroxyisovaleryl-CoA can be directly dehydrated to 3-methyl-2-butenoyl-CoA (3-methylcrotonyl-CoA) by *C. difficile* 2-hydroxyacyl-CoA dehydratase HadBCI (AJP10092.1, AJP10093.1, AJP10091.1. HadBCI is originally a 2-hydroxyisocaproyl-CoA dehydratase. Kim et al. 2005) or *C. propionicum* 2-hydroxyacyl-CoA dehydratase LcdABC (G3KIM4.1, G3KIM3.1, G3KIM5.1. LcdABC is originally a lactonyl-CoA dehydratase. Hofmeister et al. 1992). 2-hydroxyisovaleryl-CoA can also be converted to 3-methylcrotonyl-CoA by a multi-step pathway. In that pathway, 2-hydroxyisovaleryl-CoA is first reduced to (2R)-3-methyl-1,2-butanediol catalyzed by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. (2R)-3-methyl-1,2-butanediol is dehydrated to 3-methylbutanal by diol dehydratase which is then converted to isovaleryl-CoA by aldehyde-forming acyl-CoA reductase. Isovaleryl-CoA is converted to 3-methylcrotonyl-CoA by *P. aeruginosa* acyl-CoA dehydrogenase acyl-CoA dehydrogenase LiuA (APJ52511.1). 3-methylcrotonyl-CoA is converted to prenol by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. Alcohol-forming acyl-CoA reductase is selected from the group consisting *C. acetobutylicum* AdhE2 (YP_009076789.1) and *M. aquaeolei* VT8 Maqu_2507 (YP_959769.1). CbjALD from *C. beijerinckii* aldehyde forming acyl-CoA reductase (AAT66436.1) is selected for conversion of 3-methylcrotonyl-CoA to prenol. Alcohol dehydrogenase is selected from the group consisting *E. coli* YahK (NP_414859.1), *E. coli* YjgB (NP_418690.4) and *Acinetobacter* sp. ChnD (BAC80217.1).

Prenol is then converted to DMAPP by one or two steps of phosphorylation. If phosphorylated by two steps, the first step is catalyzed by *E. coli* alcohol kinase YchB (NP_415726.1) or Thermoplasma *acidophilum* phosphate kinase ThaIPK (WP_010900530.1, V73I, Y141V and K204G mutations to increase specificity on prenol (Liu et al. 2016) and the second is by *M. thermautotrophicus* phosphate kinase MtIPK (AAB84554.1). The one step phosphorylation is catalyzed by alcohol diphosphokinase. *E. coli* isopentenyl pyrophosphate isomerase Idi (NP_417365.1) converts DMAPP to IPP. DMAPP and IPP are condensed to GPP catalyzed by *E. coli* GPP synthase IspA (NP_414955.1, S80F) or *A. grandis* GPP synthase GPPS2 (AAN01134.1, N-terminal 84 aa truncation). *Ocimum basilicum* geraniol stynthase GES (AR11765.1, N-terminal 65 aa truncation) converts GPP to geraniol, the proxy product for the synthesis pathway. Because diol dehydratase is oxygen-sensitive, the strain harboring this pathway is grown under microaerobic or anoxic or anaerobic conditions.

JST06(DE3) serves as the *E. coli* host strain for demonstration of this novel pathway. Vector creation, strain creation, growth and analysis of supernatant are as described above in previous examples.

Figure 23:
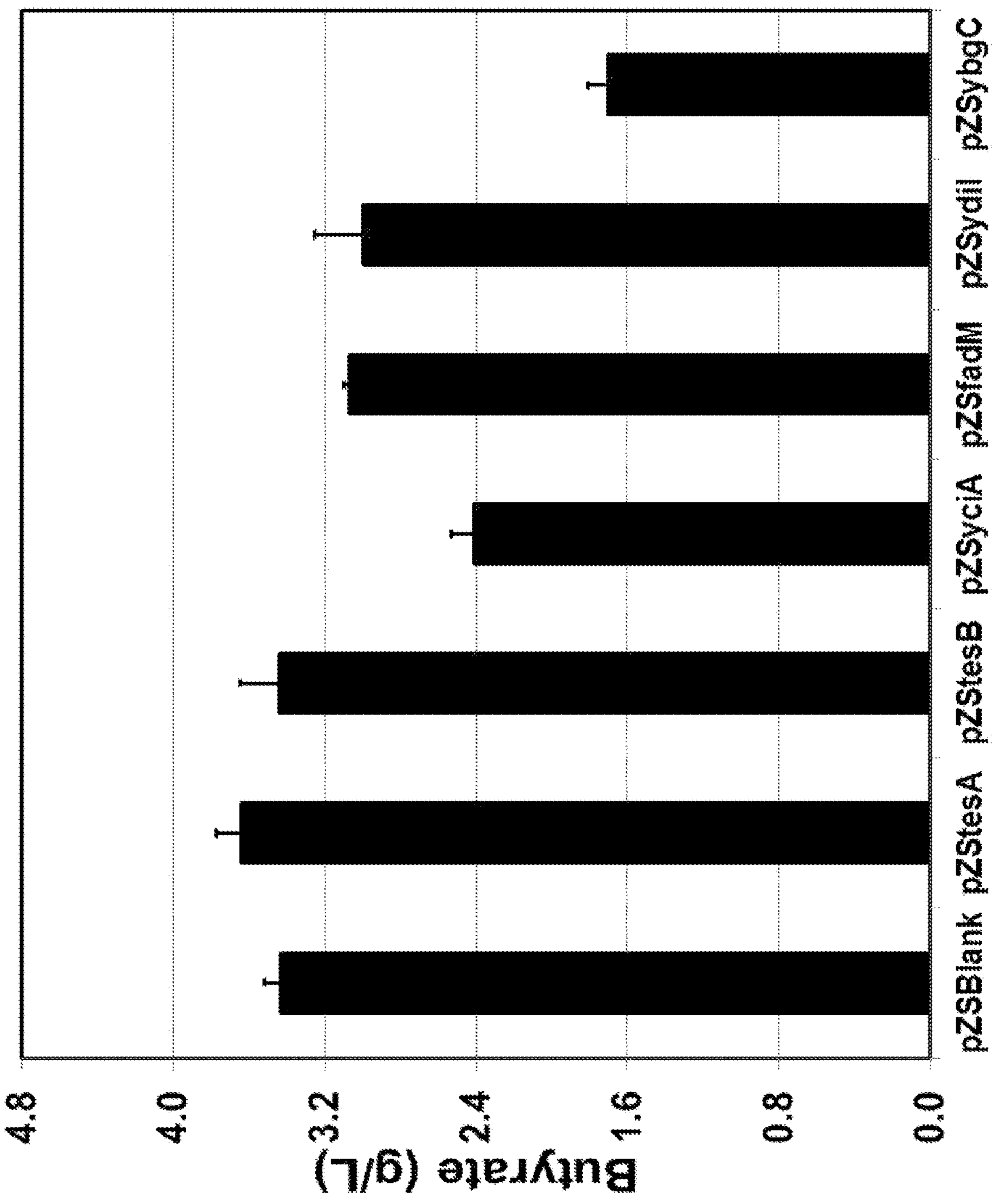
FIG. 23: Butyric acid production of JC01 strain overexpressing AtoB, FadB and EgTer in combination with overexpression of different thioesterase through pZS vector.
Figure 24A:
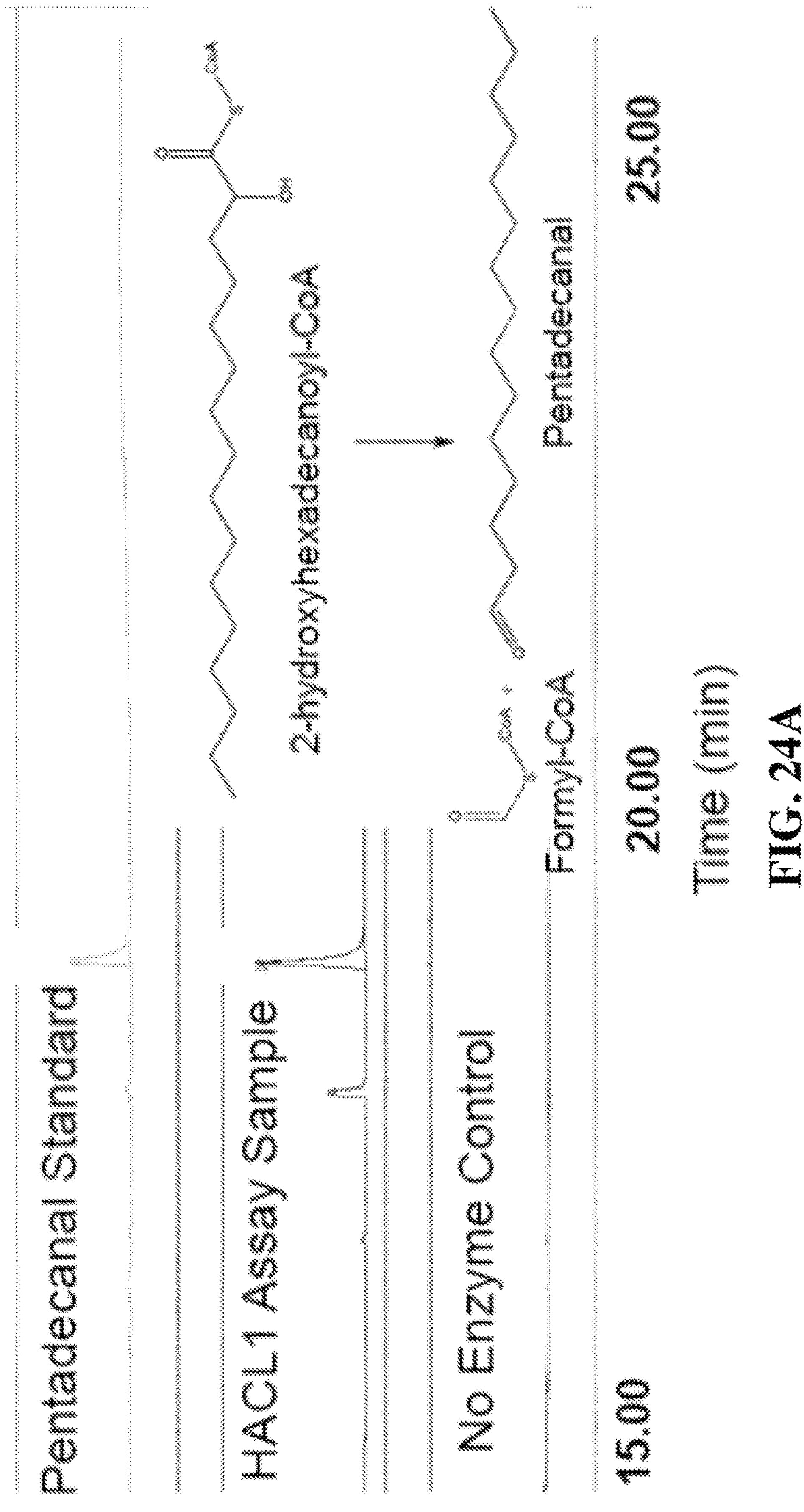
FIG. 24A-D: in vitro characterization of HACL1.
Figure 24B:
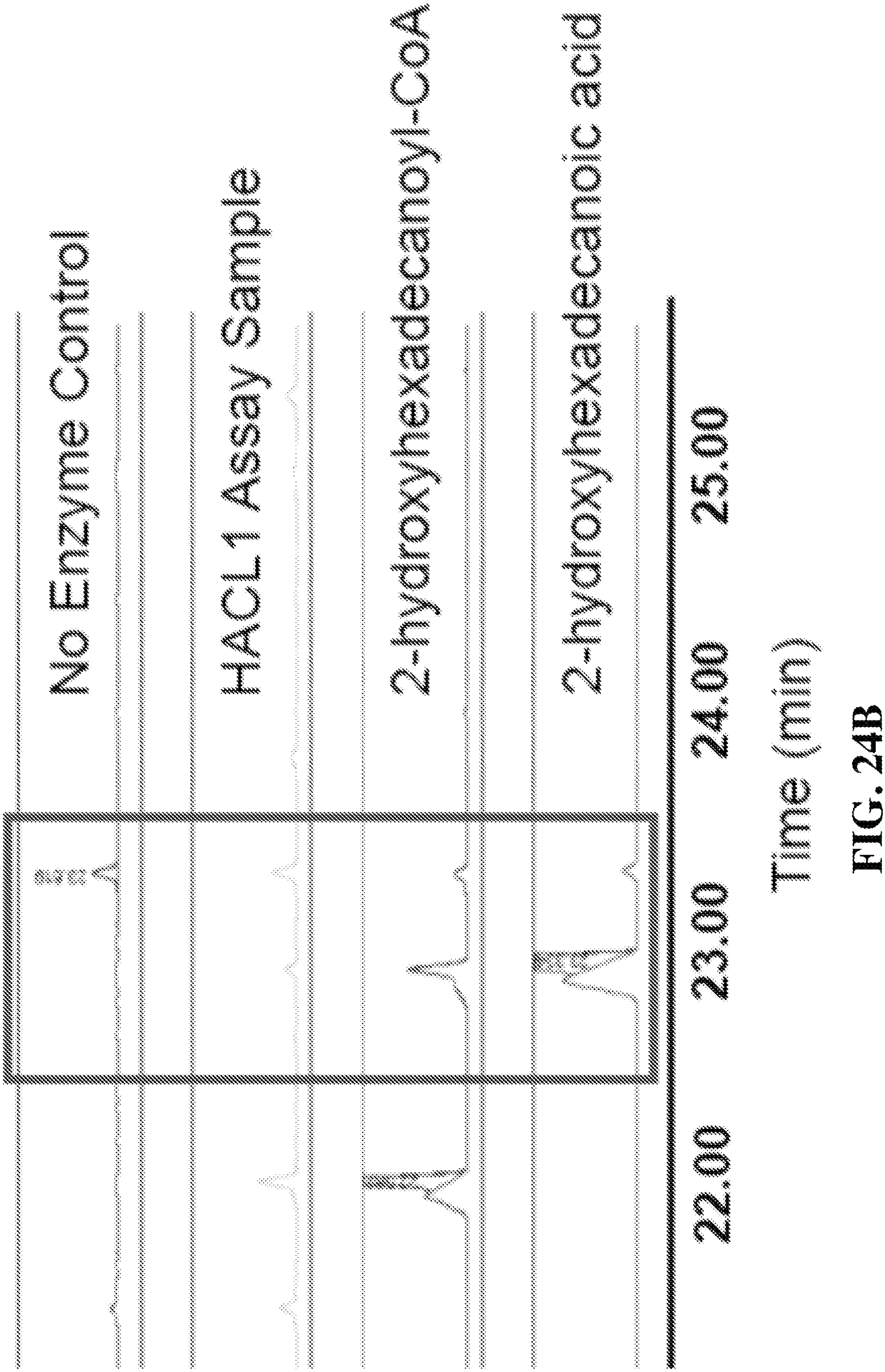
Figure 24C:
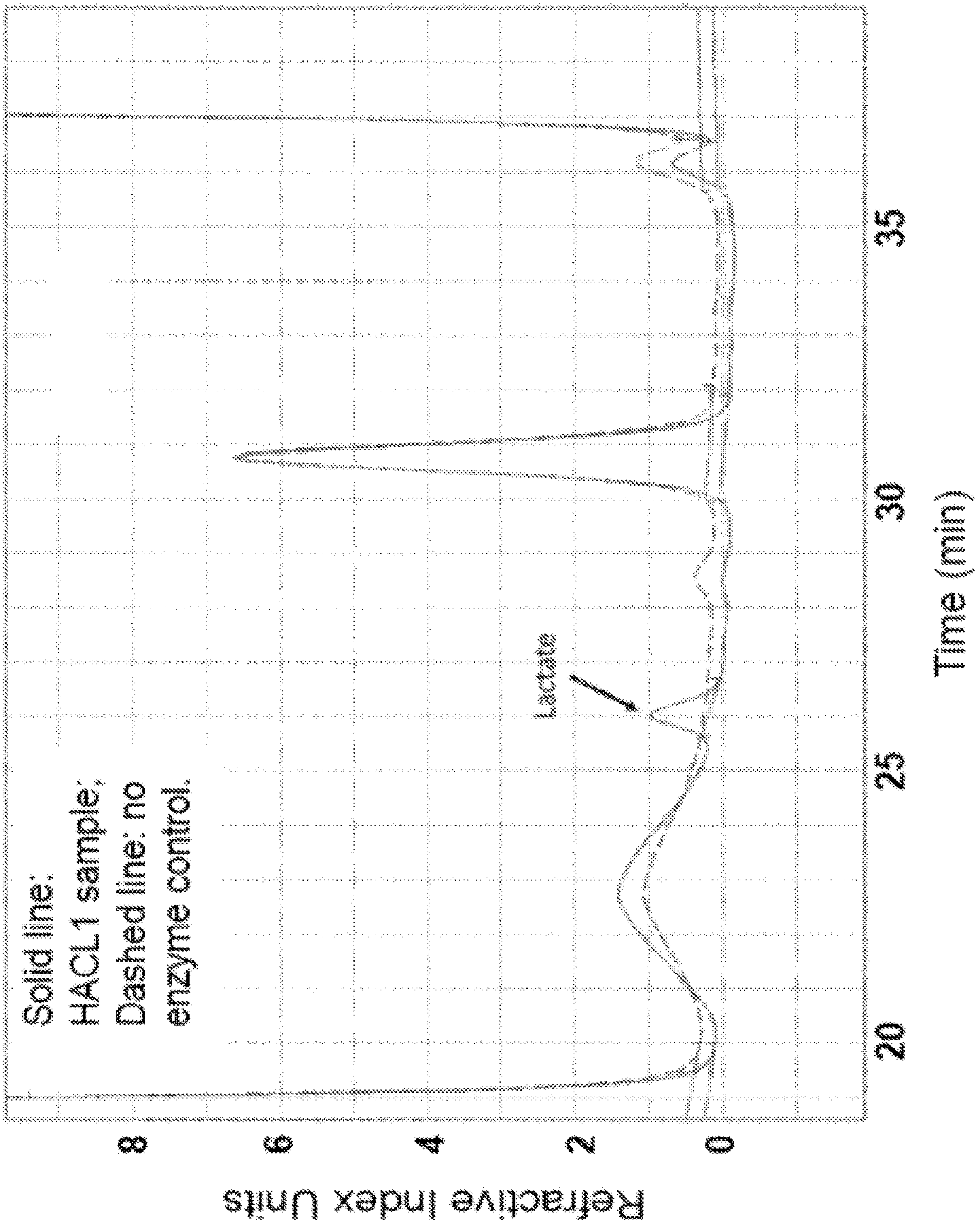
Figure 24D:
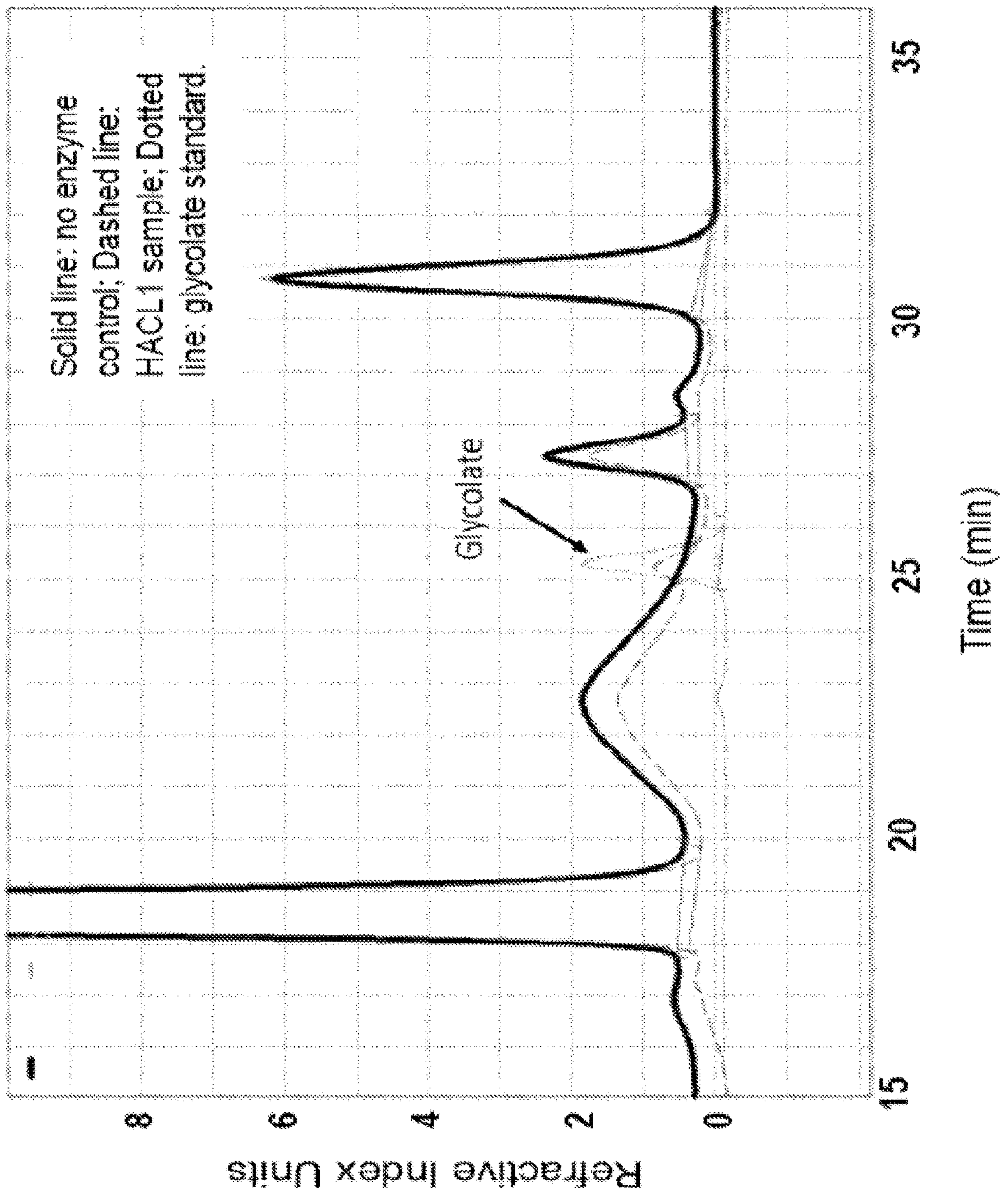

The in vivo butyryl-CoA and butyric acid synthesis through beta-oxidation reversal composed of AtoB, FadB and EgTer has been demonstrated in *E. coli*. JC01 (MG1655 ΔldhA ΔpoxB Δpta ΔadhE ΔfrdA, an *E. coli* strain with removal of mixed-acid fermentation for improved supply of acetyl-CoA), overexpressing AtoB, FadB and EgTer produced 3.3 g/L of butyric acid when grown in LB-like MOPS media with glycerol as carbon source for 48 hours, indicating that beta-oxidation reversal composed of AtoB, FadB and EgTer is functional of supplying butyric acid with acetyl-CoA as primer and extender unit, and native endogenous thioesterases are able to hydrolyze butyryl-CoA to butyric acid. Overexpression of different *E. coli* thoesterases FadM (NP_414977.1), TesA (NP_415027.1), TesB (NP_414986.1), YciA (NP_415769.1), YdiI (NP_416201.1) and YbgC (NP 415264.1) was added, but as seen in FIG. 23, it did not greatly improve butyric acid production. The detailed methods of fermentation conditions and HPLC analysis for butyric acid are described in previous examples.

The vectors and primers used in overexpression of AtoB, FadB, EgTer and thioesterases are listed in Table S. The *E. coli* genes were PCR amplified from genomic DNA of wild type *E. coli* strain, while the gene encoding EgTer was codon-optimized and synthesized by GenScript. For the construction of pTH-atoB-fadB-egter, the atoB gene insert was first PCR amplified with atoB-f1/atoB-r1 primers and inserted into vector pTrcHis2A (Invitrogen, Carlsbad, CA) cleaved by NcoI and EcoRI through In-Fusion HD Eco-Dry Cloning system to construct pTH-atoB. Then, thefadB gene insert was PCR amplified with fadB-f1/fadB-r1 primers and inserted into vector pTH-atoB cleaved by HindIII through In-Fusion HD Eco-Dry Cloning system to generate pTH-atoB-fadB. Finally, the egter gene insert was PCR amplified with egter-f1/egter-r1 primers and inserted into vector pTH-atoB-fadB cleaved by HindIII through In-Fusion HD Eco-Dry Cloning system to generate pTH-atoB-fadB-egter. The thioesterases were overexpressed from pZS vector backbone (Invitrogen, Carlsbad, CA). The genes encoding thioesterases were PCR amplified with relevant primers (fadM-f1/fadM-r1, tesA-f1/tesB-r1, tesA-f1/tesA-r1, ydiI-f1/ydiI-r1, ybgC-f1/ybgC-r1, yciA-f1/yciA-r1) and inserted into pZS cleaved by KpnI and MluI through In-Fusion HD Eco-Dry Cloning system.

The condensations between formyl-CoA and different kinds of aldehyde (pentadecanal, acetaldehyde, formaldehyde) by 2-hydroxyacyl-CoA lyase HACL1 have been proven in vitro, as shown in FIG. 24A-D. HACL1 is a good candidate to also accept required isobutanal as the substrate for acyloin condensation.

2-hydroxyhexadecanoyl-CoA was prepared by the n-hydroxysuccinimide method (Blecher, 1981). In summary, the n-hydroxysuccinimide ester of 2-hydroxyhexadecanoic acid is prepared by reacting n-hydroxysuccinimide with the acid in the presence of dicyclohexylcarbodiimide. The product is filtered and purified by recrystallization from methanol to give pure n-hydroxysuccinimide ester of 2-hydroxyhexadecanoic acid. The ester is reacted with CoA-SH in presence of thioglycolic acid to give 2-hydroxyhexadecanoyl-CoA. The 2-hydroxyhexadecanoyl-CoA is purified precipitation using perchloric acid, filtration, and washing the filtrate with perchloric acid, diethyl ether, and acetone.

Formyl-CoA was prepared by first forming formic ethylcarbonic anhydride as previously described (Parasaran & Tarbell, 1964). Briefly, formic acid (0.4 mmol) and ethyl chloroformate (0.4 mmol) were combined in 4 mL anhydrous diethyl ether and cooled to −20° C. 0.4 mmol triethylamine was added to the mixture and the reaction was allowed to proceed at −20° C. for 30 minutes. The reaction mixture was filtered over glass wool to give a solution containing formic ethylcarbonic anhydride in diethyl ether. To obtain formyl-CoA, 7 μmol CoASH was dissolved in 5 mL 3:2 water:tetrahydrofuran, to which 10 mg of sodium bicarbonate were added. The solution of formic ethylcarbonic anhydride was added dropwise to the CoASH solution with vigorous agitation, after which the organic phase was evaporated under a stream of nitrogen. The mixture was kept at 4° C. for two hours, after which any remaining diethyl ether was evaporated under nitrogen. Solid phase extraction using a Cis column was used to purify formyl-CoA from the reaction mixture. Formyl-CoA was eluted from the $C_{18}$ column in methanol and stored in 2:1 methanol:ammonium acetate pH 5.5.

The resulting cell pellet was resuspended in Bacterial Protein Extraction Reagent (B-PER) (THERMO SCIE., MA) to an OD550 of approximately 40, to which approximately 5000 U of lysozyme and approximately 250 U of Benzonase nuclease (Sigma-Aldrich CO., MO) were added. The cell mixture was left at room temperature until completely clarified to give the cell extract. 1 M stock solution of imidazole was added to provide a final concentration of 10 mM imidazole in the cell extract.

A plasmid containing the codon optimized gene encoding human HIS-tagged HACL1 was constructed as described. The resulting construct, was transformed into *S. cerevisiae* InvSC1 (Life Technologies, Carlsbad, CA). The resulting strain was cultured in 50 mL of SC-URA media containing 2% glucose at 30° C. for 24 hours. The cells were pelleted and the required amount of cells were used to inoculate a 250 mL culture volume of SC-URA media containing 0.2% galactose, 1 mM $MgCl_2$, and 0.1 mM thiamine to 0.4 OD600. After 20 hours of incubation with shaking at 30° C., the cells were pelleted and saved.

When needed, the cell pellets were resuspended to an OD600 of approximately 100 in a buffer containing 50 mM potassium phosphate pH 7.4, 0.1 mM thiamine pyrophosphate, 1 mM $MgCl_2$, 0.5 mM AEBSF, 10 mM imidazole, and 250 units of Benzonase nuclease. To the cell suspension, approximately equal volumes of 425-600 μm glass beads were added. Cells were broken in four cycles of 30 seconds of vortexing at 3000 rpm followed by 30 seconds on ice. The glass beads and cell debris were pelleted by centrifugation and supernatant containing the cell extract was collected. The HIS-tagged HACL1 was purified from the cell extract using Talon Metal Affinity Resin as described above, with the only modification being the resin bed volume and all subsequent washes were halved. The eluate was collected in two 500 μL fractions.

Human HACL1 was cloned, expressed, and purified in *S. cerevisiae* as described above. Purified HACL1 was tested for its native catabolic activity by assessing its ability to cleave 2-hydroxyhexadecanoyl-CoA to pentadecanal and formyl-CoA. Enzyme assays were performed in 50 mM tris-HCl pH 7.5, 0.8 mM $MgCl_2$, 0.02 mM TPP, 6.6 μM BSA, and 0.3 mM 2-hydroxyhexadecanoyl-CoA. The assay mixtures were incubated for one hour at 37° C., after which the presence of pentadecanal was assessed by extraction with hexane and analysis by GC-FID. As shown in FIG. 24A-D, pentadecanal was produced in the sample containing HACL1, but not in the control sample, which did not contain HACL1, indicating that the protein was expressed and purified in an active form.

The ability of purified HACL1 to run in the anabolic direction (reverse from the physiological direction) was also determined. An aldehyde and formyl-CoA were tested for ligation in a buffer comprised of 60 mM potassium phosphate pH 5.4, 2.5 mM MgCl2, 0.1 mM TPP, 6.6 μM BSA, 5 mM aldehyde, 20% DMSO, approximately 1 mM freshly prepared formyl-CoA, and approximately 0.5 mg/mL purified HACL1. The reaction was allowed to take place at room temperature for 16 hours, after which acyl-CoAs were hydrolyzed to their corresponding acids by adjusting to pH >12.0. For situations in which a short carbon chain product was expected, for example lactate production from acetaldehyde, samples were analyzed by HPLC. In the case of longer products, for example the production of 2-hydroxyhexadecanoic acid from pentadecanal, samples were acidified with HCl and extracted with diethyl ether. The extracted diethyl ether was evaporated to dryness under a stream of nitrogen and derivatized by the addition of 1:1 BSTFA: pyridine. After incubation at 70° C. for 30 min, these samples were analyzed by GC-FID.

When the purified enzyme was supplied with pentadecanal and formyl-CoA, as in FIG. 24A-D, HACL1 was shown to catalyze the ligation of these molecules to 2-hydroxyhexadecanoyl-CoA as hypothesized. After hydrolysis of acyl-CoAs, the chromatogram of the sample containing enzyme shows similar peaks to the 2-hydroxyhexadecanoyl-CoA spiked standard, which are absent from the sample containing no enzyme.

The purified HACL1 was further tested for activity on shorter aldehydes, such as the ligation of acetaldehyde or formaldehyde with formyl-CoA to produce lactoyl-CoA or glycolyl-CoA, respectively. After hydrolysis of acyl-CoAs to their acid forms, these samples were analyzed by HPLC. The presence of lactate from elogation of acetaldehyde and formyl-CoA was identified in the sample containing HACL1, but not in the no enzyme control as shown in FIG. 24A-D. Similar results were observed for glycolate from formaldehyde and formyl-CoA as shown in FIG. 24A-D. The presence of lactate in the relevant samples was confirmed by NMR. This demonstrates that HACL1 is capable of catalyzing the ligation of aldehydes with chain lengths ranging at least from C1-C15 with formyl-CoA, making it suitable for acyloin condensation between C5 aldehyde isobutanal with formyl-CoA, required for the GPP synthesis pathway.

Figure 25:
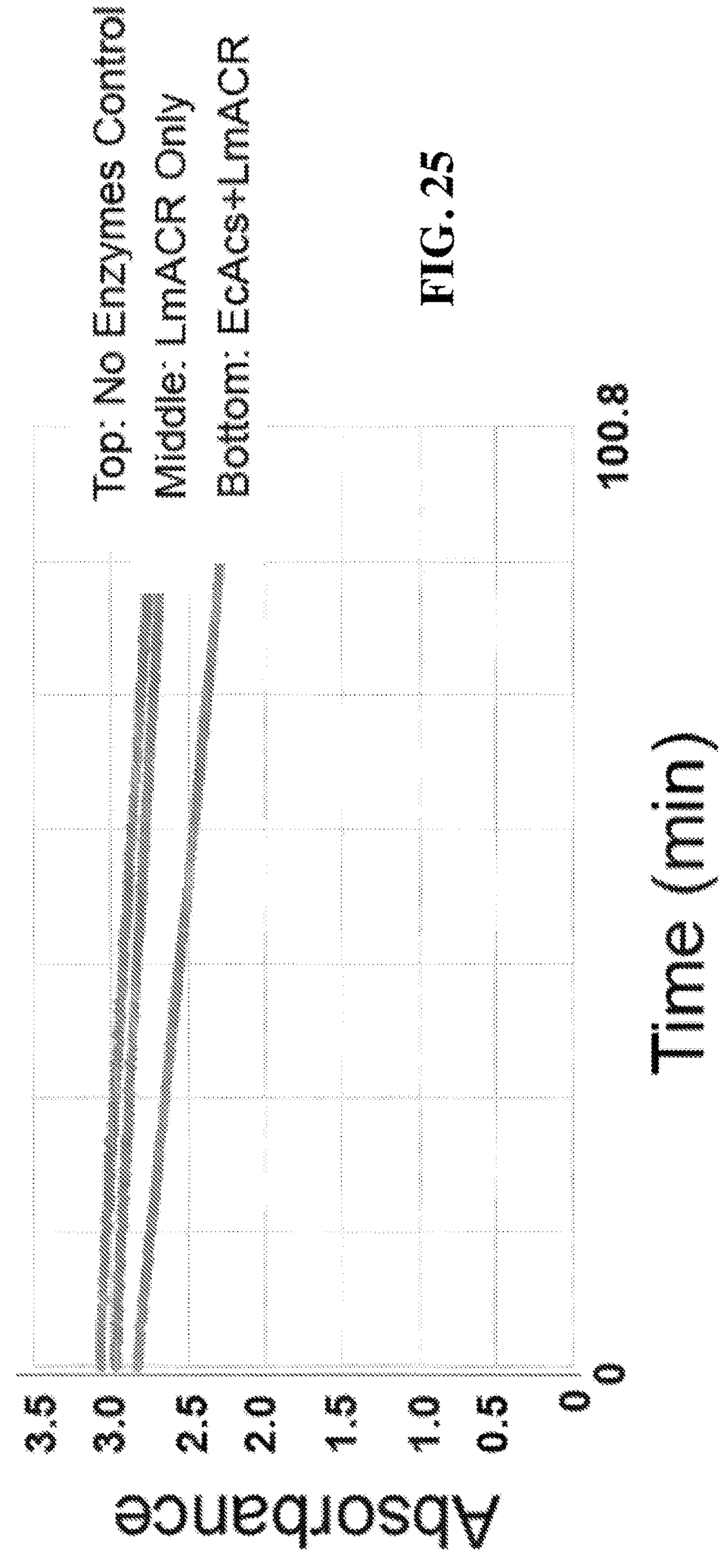
FIG. 25: NADH oxidization of samples and controls of in vitro formate activation assay by *E. coli* acyl-CoA synthase ACS (EcAcs) coupled by *Listeria monocytogenes* acyl-CoA reductase Lmo1179 (LmACR).

Also, the required activity of activation of formate to formyl-CoA by *E. coli* acyl-CoA synthase ACS (NP_418493.1) was also proven in vitro as shown in FIG. 25. This assay was coupled with reduction of resultant formyl-CoA to formaldehyde by *Listeria monocytogenes* acyl-CoA reductase (ACR) Lmo1179 (CAC99257.1) and the activity was measured through observation of NADH oxidization.

A plasmid containing the codon optimized gene encoding 6×HIS-tagged Lmo1179 from *Listeria monocytogenes* was constructed. The resulting construct was transformed into *E. coli* BL21(DE3) for expression. The resulting strain was cultured in 50 mL of TB media containing appropriate antibiotics in a 250 mL flask. When the culture reached an OD550 of approximately 0.6, expression was induced by the addition of 0.1 mM IPTG, and the cells were harvested by centrifugation after overnight incubation at room temperature.

The HIS-tagged Lmo1179 protein was purified from the cell extract using Talon Metal Affinity Resin (Clontech lab., CA). In short, a 250 μL resin bed was equilibrated twice using 2.5 mL of a buffer containing 50 mM sodium phosphate, 300 mM NaCl, and 10 mM imidazole at pH 7.5 (NPI-10). The cell extract was added to the resin and the mixture shaken gently for 20 minutes on ice. The resin was then washed twice with 2.5 mL buffer NPI-20 (same as NPI-10 but with 20 mM imidazole), shaking gently on ice for 15 minutes each wash. The resin was then transferred to a gravity column and washed once with 1.25 mL NPI-20. Finally, the desired protein was eluted using 1.25 mL of buffer NPI-250 (same as buffer NPI-10 but with 250 mM imidazole), and the eluate collected in 500 μL fractions.

*E. coli* ACS was cloned, expressed, and purified in *E. coli* as described above. The purified enzyme was evaluated for its ability to convert formate into the extender unit formate. Enzyme assays were performed in 23 mM potassium phosphate buffer pH 7.0, 1 mM CoASH, 0.5 mM NADH, 5 mM ATP, 2.5 mM $MgCl_2$, 50 mM formate. *E. coli* ACS was added along with *Listeria monocytogenes* Lmo1179, and the reduction of resulting formyl-CoA was monitored by measuring absorbance of NADH at 340 nm. The sample containing ACS resulted in an increased rate of NADH oxidation, indicating that formyl-CoA was produced by ACS.

Among above enzymes, as mentioned in the previous example, the in vitro activities of acyl-CoA reductases CbjALD and Maqu_2507 on reduction of 3-methylcrotonyl-CoA and the in vitro activities of alcohol dehydrogenases ChnD, YjgB and YahK on oxidization of prenol have been proven through enzymatic spectrophotometric assay. *E. coli* alcohol dehydrogenases FucO (NP_417279.2), YqhD (NP_417484.1), YiaY (YP_026233.1) were also assayed on prenol, but as mentioned above, they did not show the activity on prenol oxidization. The results of assays on alcohol dehydrogenases can be seen in Table P, and the results of assays on acyl-CoA reductases and relevant enzyme preparation and assay methods are described in the previous example.

The in vitro activity of dehydration of ethylene glycol to acetaldehyde by diol dehydratae PddABC (AFJ04717.1, AFJ04718.1, AFJ04719.1) from *Klebsiella oxytoca* has been proven, as shown in FIG. 22. The assay method is described in the previous examples.

(Prophetic) GPP Biosynthesis Via 4-Methyl-2-Oxo-4-Pentenoic Acid and Isoprenol Starting Aldol Condensation Between Acetaldehyde and 2-Oxobutyric Acid The purpose of this experiment is to demonstrate the biosynthesis of GPP through a novel pathway that starts from aldol condensation between 2-oxobutyric acid and acetaldehyde via 4-methyl-2-oxo-4-pentenoic acid and isoprenol, using *E. coli* as the host organism. This pathway starts from aldol condensation between pyruvate and acetaldehyde to 4-hydroxy-2-oxo-3-methylpentaonoic acid by *E. coli* aldolase MhpE (NP_414886.1). Acetaldehyde is supplied either through decarboxylation of pyruvate by *Saccharomyces cerevisiae* alpha-keto acid decarboxylase PDC1(CAA97573.1) or through reduction of acetyl-CoA by *E. coli* aldehyde forming acyl-CoA reductase MhpF (NP_414885.1). 2-oxobutyric acid is elongated from pyruvate through alpha-keto acid pathway composed of: citramalate synthase CimA from *Methanocaldococcus jannaschii* (WP_010870909.1) or *Leptospira interrogans* serovar Lai str. 56601 (NP_712531.1); citramalate isomerase LeuCD from *E. coli* (NP_414614.1, NP_414613.1) or *Methanocaldococcus jannaschii* (AAB98487.1, AAB99283.1) or *Leptospira interrogans* serovar Lai str. 56601 (NP_712276.1, NP_712277.1); *Methanocaldococcus jannaschii* 3-methylmalate dehydrogenase MJ0720 (WP_010870225.1) or *Leptospira interrogans* serovar Lai str. 56601 3-methylmalate dehydrogenase LeuB (NP_712333.1).

After the aldol condensation, a mutase transfers the methyl group of 4-hydroxy-2-oxo-3-methylpentaonoic acid from C-3 to C-4 site, generating 4-hydroxy-2-oxo-4-methylpentaonoic acid. Then, *E. coli* 2-oxopent-4-enoate dehydratase MhpD (NP_414884.2) dehydrates 4-hydroxy-2-oxo-4-methylpentaonoic acid into 4-methyl-2-oxo-4-pentenoic acid. 4-methyl-2-oxo-4-pentenoic acid can be converted to 3-methyl-3-butenoyl-CoA by alpha-keto acid dehydrogenase and 3-methyl-3-butenoyl-CoA is converted to isoprenol by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. 4-methyl-2-oxo-4-pentenoic acid can also be converted to isoprenol by two steps of reactions catalyzed by alpha-keto acid decarboxylase and alcohol dehydrogenase. Alcohol-forming acyl-CoA reductase is selected from the group consisting *C. acetobutylicum* AdhE2 (YP_009076789.1) and *M. aquaeolei* VT8 Maqu_2507 (YP_959769.1). CbjALD from *C. beijerinckii* aldehyde forming acyl-CoA reductase (AAT66436.1) is selected for conversion of 3-methyl-3-butenoyl-CoA to isoprenol. Alcohol dehydrogenase is selected from the group consisting *E. coli* YahK (NP_414859.1), *E. coli* YjgB (NP 418690.4) and *Acinetobacter* sp. SE19 ChnD (BAC80217.1).

Isorenol is then converted to IPP by one or two steps of phosphorylation. If phosphorylated by two steps, the first step is catalyzed by *E. coli* alcohol kinase YchB (NP_415726.1) and the second is catalyzed by *M. thermautotrophicus* phosphate kinase MtIPK (AAB84554.1) or *Thermoplasma acidophilum* phosphate kinase ThaIPK (WP_010900530.1) or *Methanocaldococcus jannaschii* phosphate kinase MjIPK (3K4Y_A). The one step phosphorylation is catalyzed by alcohol diphosphokinase. *E. coli* isopentenyl pyrophosphate isomerase Idi (NP_417365.1) converts DMAPP to IPP. DMAPP and IPP are condensed to GPP catalyzed by *E. coli* GPP synthase IspA (NP_414955.1, S80F) or *A. grandis* GPP synthase GPPS2 (AAN01134.1, N-terminal 84 aa truncation). *Ocimum basilicum* geraniol stynthase GES (AR11765.1, N-terminal 65 aa truncation) converts GPP to geraniol, the proxy product for the synthesis pathway.

JST06(DE3) serves as the *E. coli* host strain for demonstration of this novel pathway. Vector creation, strain creation, growth and analysis of supernatant are as described above in previous examples.

(Prophetic) GPP Biosynthesis Via 2-Oxoisovaleric Acid, 2-Oxoisocaproic Acid and Prenol Starting from Decarboxylative Acyloin Condensation Between Two Pyruvates The purpose of this example is to demonstrate the biosynthesis of GPP through a novel pathway via 2-oxoisovaleric acid, 2-oxoisocaproic acid and prenol. *E. coli* serves as the host organism. This pathway starts from decarboxylative acyloin condensation of two pyruvates to (S)-2-acetolactone by *B. subtilis* acetolactate synthase AlsS (NP_391482.2). *E. coli* acetohydroxy acid isomeroreductase IlvC (NP_418222.1) converts (S)-2-acetolactone to (2R)-2,3-dihydroxy-3-methylbutyric acid. *E. coli* dihydroxy acid dehydratase IlvD (YP_026248.1) dehydrates (2R)-2,3-dihydroxy-3-methylbutanoate to 3-methyl-2-oxobutyric acid (2-oxoisovaleric acid). Then, 2-oxoisovaleric acid is elongated into 2-oxoisocaproic acid through alpha-keto acid pathway composed of: *E. coli* isopropylmalate synthase LeuA (NP 414616.1, with a G462D mutation to maximize 2-oxoisocaprate production and minimize 2-oxoisovalerate, Connor et al. 2008) which condenses 2-oxoisovaleric acid and acetyl-CoA to (2S)-2-isopropylmalate; *E. coli* isopropyl isomerase LeuCD (NP_414614.1, NP_414613.1) which converts (2S)-2-isopropylmalate to (2R, 3S)-3-isopropylmalate; *E. coli* isopropylmalate dehydrogenase LeuB (NP_414615.4) which oxidizes and decarboxylates (2R, 3S)-3-isopropylmalate, generating 4-methyl-2-oxopentanoic acid (2-oxoisocaproic acid). Then, *S. avermitilis* alpha-keto acid dehydrogenase complex BkdFGH-LpdA1 (BAC72088.1, BAC72089.1, BAC72090.1, KUN54417.1) converts 2-oxoisocaproic acid into isovaleryl-CoA. Overexpression of heterologous branched alpha-keto acid dehydrogenase complex requires improved lipoylation, which can be realized though supplementation of lipoic acid accompanied with overexpression of *E. coli* lipoate-protein ligase Lp1A (NP 418803.1), or overexpression of *E. coli* endogenous lipoylation pathway consisting lipolate synthase LipA (NP_415161.1) and lipoyl(octanoyl) transferase LipB (NP_415163.2). *P. aeruginosa* acyl-CoA dehydrogenase LiuA (APJ52511.1) converts isovaleryl-CoA to 3-methylcrotonyl-CoA. 3-methylcrotonyl-CoA is converted to prenol by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. Alcohol-forming acyl-CoA reductase is selected from the group consisting *C. acetobutylicum* AdhE2 (YP_009076789.1) and *M. aquaeolei* VT8 Maqu_2507 (YP_959769.1). CbjALD from *C. beijerinckii* aldehyde forming acyl-CoA reductase (AAT66436.1) is selected for conversion of 3-methylcrotonyl-CoA to prenol. Alcohol dehydrogenase is selected from the group consisting of *E. coli* YahK (NP 414859.1), *E. coli* YjgB (NP_418690.4) and *Acinetobacter* sp. SE19 ChnD (BAC80217.1). Prenol is then converted to DMAPP by one or two steps of phosphorylation. If phosphorylated by two steps, the first step is catalyzed by *E. coli* alcohol kinase YchB (NP_415726.1) or Thermoplasma *acidophilum* phosphate kinase ThaIPK (WP_010900530.1, V73I, Y141V and K204G mutations to increase specificity on prenol. Liu et al. 2016) and the second is by *M. thermautotrophicus* phosphate kinase MtIPK (AAB84554.1). The one step phosphorylation is catalyzed by alcohol diphosphokinase. *E. coli* isopentenyl pyrophosphate isomerase Idi (NP 417365.1) converts DMAPP to IPP. Then, DMAPP and IPP are condensed to GPP catalyzed by *E. coli* GPP synthase IspA (NP_414955.1, S80F) or *A. grandis* GPP synthase GPPS2 (AAN01134.1, N-terminal 84 aa truncation). *Ocimum basilicum* geraniol stynthase GES (AR11765.1, with N-terminal 65 aa truncation) converts GPP to geraniol, which serves as a proxy to demonstrate a functioning pathway.

JST06(DE3) serves as the *E. coli* host strain for demonstration of this novel pathway. Vector creation, strain creation, growth and analysis of supernatant is conducted as described in previous examples.

The required plasmids and primers for this example are listed in Table T. The genes encoding *E. coli* enzymes are PCR amplified from the genomic DNA of wild type strain, while genes encoding other enzymes are codon optimized and synthesized by either GeneArt or GenScript. For construction of pET-P1-ilvC-ilvD-P2-alsS-liuA, the codon-optimized alsS and liuA gene inserts were first PCR amplified with alsS-f1/alsS-r2 and liuA-f1/liuA-r1 primers respectively, and inserted together into vector pETDuet-1 cleaved by NdeI and KpnI through In-Fusion HD Eco-Dry Cloning system, resulting in pET-P2-alsS-panE plasmid. The ilvC and ilvD gene inserts were then PCR amplified from the genomic DNA of *E. coli* with ilvC-f1/ilvC-r1 and ilvD-f1/ilvD-r1 primers respectively, and inserted together into vector pET-P2-alsS-liuA cleaved by NcoI and EcoRI through In-Fusion HD Eco-Dry Cloning system, generating pET-P1-ilvC-ilvD-P2-alsS-liuA. For construction of pCDF-P1-bkdF-bkdG-bkdH-P2-lplA-lpdA1, the lplA and lpdA1 gene inserts were first PCR amplified with lplA-f1/lplA-r1 and lpdA1-f1/lpdA1-r1 primers respectively, and inserted together into vector pCDFDuet-1 cleaved by NdeI and KpnI through In-Fusion HD Eco-Dry Cloning system, resulting in pCDF-P2-lplA-lpdA1. The codon-optimized bkdF, bkdG and bkdH gene inserts were then PCR amplified with bkdF-f1/bkdF-r1, bkdG-f1/bkdG-r1, bkdH-f1/bkdH-r1 respectively and inserted together into pCDF-P2-lplA-lpdA1 cleaved by NcoI and EcoRI through In-Fusion HD Eco-Dry Cloning system, generating pCDF-P1-bkdF-bkdG-bkdH-P2-lplA-lpdA1. For construction of pRSF-P1-leuA(G462D)-leuB-P2-leuC-leuD, the leuA and leuB genes were PCR amplified together into two pieces from the genomic DNA of *E. coli* with leuA(G462D)B-f11/leuA(G462D)B-r11 and leuA(G462D)B-f12/leuA(G462D)B-r12 respectively, and attached together through overlap PCR with leuA(G462D)B-f2/leuA(G462D)B-r2 to generate G462D mutation. The overlap PCR product was inserted into pRSF-Duet-1 cleaved by NcoI and EcoRI through In-Fusion HD Eco-Dry Cloning system, generating pRSF-P1-leuA(G462D)-leuB. Then leuC and leuD genes were amplified together from from the genomic DNA of *E. coli* with leuCD-f1/leuCD-r1 and the resulting gene insert was inserted into pRSF-P1-leuA(G462D)-leuB cleaved by KpnI, generating pRSF-P1-leuA(G462D)-leuB-P2-leuC-leuD. Before the introduction to host strain, the sequences of constructed plasmids were confirmed by DNA sequencing.

Among above enzymes, as mentioned in the previous example, the in vitro activities of acyl-CoA reductases CbjALD and Maqu_2507 on reduction of 3-methylcrotonyl-CoA and the in vitro activities of alcohol dehydrogenases ChnD, YjgB and YahK on oxidization of prenol have been proven through enzymatic spectrophotometric assay. *E. coli* alcohol dehydrogenases FucO (NP_417279.2), YqhD (NP_417484.1), YiaY (YP_026233.1) were also assayed on prenol, but as mentioned above, they did not show the activity on prenol oxidization. The results of assays on alcohol dehydrogenases can be seen in Table P, and the results of assays on acyl-CoA reductases and relevant enzyme preparation and assay methods are described in the previous example.

(Prophetic) GPP Biosynthesis Via 2-Oxoisovaleric Acid, 2-Oxoisocaproic Acid and Prenol Starting from Aldol Condensation Between Pyruvate and Acetaldehyde The purpose of this experiment is to demonstrate the biosynthesis of GPP through a novel pathway that starts from aldol condensation between pyruvate and acetaldehyde via 2-oxoisovaleric acid, 2-oxoisocaproic acid and prenol, using *E. coli* as the host organism. This pathway starts from aldol condensation between pyruvate and acetaldehyde to (S)-4-hydroxy-2-oxopentaonoic acid by *E. coli* aldolase MhpE (NP_414886.1). Acetaldehyde is supplied either through decarboxylation of pyruvate by *Saccharomyces cerevisiae* alpha-keto acid decarboxylase PDC1 (CAA97573.1) or through reduction of acetyl-CoA by *E. coli* aldehyde forming acyl-CoA reductase MhpF (NP_414885.1). Then, a mutase moves the —(C═O)COOH group of (S)-4-hydroxy-2-oxopentaonic acid from C-3 site to C-4 site, forming 3-hydroxy-2-oxo-3-methylbutyric acid. 2-hydroxyacid dehydrogenase converts 3-hydroxy-2-oxo-3-methylbutyric acid to (2R)-2,3-dihydroxy-3-methylbutyric acid. *E. coli* dihydroxy acid dehydratase IlvD (YP_026248.1) dehydrates (2R)-2,3-dihydroxy-3-methylbutanoate to 3-methyl-2-oxobutyric acid (2-oxoisovaleric acid). Then, 2-oxoisovaleric acid is elongated into 2-oxoisocaproic acid through alpha-keto acid pathway composed of: *E. coli* isopropylmalate synthase LeuA (NP_414616.1, with a G462D mutation to maximize 2-oxoisocaprate production and minimize 2-oxoisovalerate, Connor et al. 2008) which condenses 2-oxoisovaleric acid and acetyl-CoA to (2S)-2-isopropylmalate; *E. coli* isopropyl isomerase LeuCD (NP_414614.1, NP_414613.1) which converts (2S)-2-isopropylmalate to (2R, 3S)-3-isopropylmalate; *E. coli* isopropylmalate dehydrogenase LeuB (NP 414615.4) which oxidizes and decarboxylates (2R, 3S)-3-isopropylmalate, generating 4-methyl-2-oxopentanoic acid (2-oxoisocaproic acid). Then, *S. avermitilis* alpha-keto acid dehydrogenase complex BkdFGH-LpdA1 (BAC72088.1, BAC72089.1, BAC72090.1, KUN54417.1) converts 2-oxoisocaproic acid into isovaleryl-CoA.

Overexpression of heterologous branched alpha-keto acid dehydrogenase complex requires improved lipoylation, which can be realized though supplementation of lipoic acid accompanied with overexpression of *E. coli* lipoate-protein ligase Lp1A (NP_418803.1), or overexpression of *E. coli* endogenous lipoylation pathway consisting lipolate synthase LipA (NP_415161.1) and lipoyl(octanoyl) transferase LipB (NP 415163.2). *P. aeruginosa* acyl-CoA dehydrogenase LiuA (APJ52511.1) converts isovaleryl-CoA to 3-methylcrotonyl-CoA. 3-methylcrotonyl-CoA is converted to prenol by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. Alcohol-forming acyl-CoA reductase is selected from the group consisting *C. acetobutylicum* AdhE2 (YP_009076789.1) and *M. aquaeolei* VT8 Maqu_2507 (YP_959769.1). CbjALD from *C. beijerinckii* aldehyde forming acyl-CoA reductase (AAT66436.1) is selected for conversion of 3-methylcrotonyl-CoA to prenol. Alcohol dehydrogenase is selected from the group consisting *E. coli* YahK (NP_414859.1), *E. coli* YjgB (NP 418690.4) and *Acinetobacter* sp. SE19 ChnD (BAC80217.1). Prenol is then converted to DMAPP by one or two steps of phosphorylation. If phosphorylated by two steps, the first step is catalyzed by *E. coli* alcohol kinase YchB (NP_415726.1) or Thermoplasma *acidophilum* phosphate kinase ThaIPK (WP 010900530.1, V73I, Y141V and K204G mutations to increase specificity on prenol. Liu et al. 2016) and the second is by *M. thermautotrophicus* phosphate kinase MtIPK (AAB84554.1). The one step phosphorylation is catalyzed by alcohol diphosphokinase. *E. coli* isopentenyl pyrophosphate isomerase Idi (NP 417365.1) converts DMAPP to IPP. Then, DMAPP and IPP are condensed to GPP catalyzed by *E. coli* GPP synthase IspA (NP_414955.1, S80F) or *A. grandis* GPP synthase GPPS2 (AAN01134.1, N-terminal 84 aa truncation). *Ocinum basilicum* geraniol stynthase GES (AR11765.1, with N-terminal 65 aa truncation) converts GPP to geraniol, which serves as a proxy to demonstrate a functioning pathway.

JST06(DE3) serves as the *E. coli* host strain for demonstration of this novel pathway. Vector creation, strain creation, growth and analysis of supernatant are largely as described in previous examples.

The plasmids listed in Table T can be used for required gene expression. The primers required for construction of these plasmids are also listed in Table T and their construction process is described in previous examples.

Among above enzymes, as mentioned in the previous example, the in vitro activities of acyl-CoA reductases CbjALD and Maqu_2507 on reduction of 3-methylerotonyl-CoA and the in vitro activities of alcohol dehydrogenases ChnD, YjgB and YahK on oxidization of prenol have been proven through enzymatic spectrophotometric assay. *E. coli* alcohol dehydrogenases FucO (NP_417279.2), YqhD (NP_417484.1), YiaY (YP_026233.1) were also assayed on prenol, but as mentioned above, they did not show the activity on prenol oxidization. The results of assays on alcohol dehydrogenases can be seen in Table P, and the results of assays on acyl-CoA reductases and relevant enzyme preparation and assay methods are described in the previous example.

GPP Biosynthesis Via 3-Hydroxy-3-Methylglutaryl-Coa (Hmg-Coa) and Prenol Starting from Non-Decarboxylative Claisen Condensation Between Two Acetyl-Coas or Decarboxylative Claisen Condensation Between Acetyl-Coa and Malonyl-Coa The purpose of this example is to demonstrate the biosynthesis of GPP through a novel pathway via HMG-CoA and prenol. *E. coli* serves as the host organism. This pathway starts from non-decarboxylative Claisen condensation between two acetyl-CoAs to acetoacetyl-CoA catalyzed by *E. coli* thiolase AtoB (NP_416728.1) or decarboxylative Claisen condensation between acetyl-CoA and malonyl-CoA by ketoacyl-CoA synthase. Malonyl-CoA is supplied from acetyl-CoA by *E. coli* acetyl-CoA carboxylase AccABCD (NP_414727.1, NP_417721.1, NP_417722.1, NP_416819.1). Then, *S. aureus* 3-hydroxy-3-methylglutaryl-CoA synthase HMGS (BAU36102.1) condenses acetoacetyl-CoA with another acetyl-CoA to generate 3-hydroxy-3-methylglutaryl-CoA (HMG-CoA). HMG-CoA is dehydrated to 3-methylglutaconyl-CoA by *M. xanthus* enoyl-CoA hydratase LiuC (WP_011553770.1). *M. xanthus* glutaconyl-CoA decarboxylase AibAB (WP_011554267.1, WP_011554268.1) decarboxylates 3-methylglutaconyl-CoA to 3-methylcrotonyl-CoA. 3-methylcrotonyl-CoA is converted to prenol by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. Alcohol-forming acyl-CoA reductase is selected from the group consisting *C. acetobutylicum* AdhE2 (YP_009076789.1) and *M. aquaeolei* VT8 Maqu_2507 (YP_959769.1). CbjALD from *C. beijerinckii* aldehyde forming acyl-CoA reductase (AAT66436.1) is selected for conversion of 3-methylcrotonyl-CoA to prenol. Alcohol dehydrogenase is selected from the group consisting *E. coli* YahK (NP_414859.1), *E. coli* YjgB (NP 418690.4) and *Acinetobacter* sp. SE19 ChnD (BAC80217.1). Prenol is then converted to DMAPP by one or two steps of phosphorylation. If phosphorylated by two steps, the first step is catalyzed by *E. coli* alcohol kinase YchB (NP_415726.1) or *Thermoplasma acidophilum* phosphate kinase ThaIPK (WP_010900530.1, V73I, Y141V and K204G mutations to increase specificity on prenol. Liu et al. 2016) and the second is by *M. thermautotrophicus* phosphate kinase MtIPK (AAB84554.1). The one step phosphorylation is catalyzed by alcohol diphosphokinase. *E. coli* isopentenyl pyrophosphate isomerase Idi (NP_417365.1) converts DMAPP to IPP. Then, DMAPP and IPP are condensed to GPP catalyzed by *E. coli* GPP synthase IspA (NP_414955.1, S80F) or *A. grandis* GPP synthase GPPS2 (AAN01134.1, N-terminal 84 aa is truncated). *Ocimum basilicum* geraniol stynthase GES (AR11765.1, N-terminal 65 aa truncation) converts GPP to geraniol, which serves as the proxy for pathway function.

JST06(DE3) atoB$^{CT5}$ ΔfadB serves as the *E. coli* host strain for demonstration of novel pathway. The genotype atoB$^{CT5}$ refers to chromosomal atoB gene, encoding the thiolase that condenses acetyl-CoA to acetoacetyl-CoA, under the p$^{CT5}$ promoter for controlled induction by cumate. To enable the cumate-inducible chromosomal expression of atoB gene in JST06(DE3), *E. coli* atoB gene was first PCR amplified from genomic DNA extracted through Genomic DNA Purification kit (Promega, Fitchburg, WI, USA), digested with BglII and NotI, and ligated by T4 ligase (Invitrogen, Carlsbad, CA) into pUCBB-ntH6-eGFP (Vick et al. 2011) that was previously digested with BglII and NotI to produce pUCBB-P$^{CT5}$-atoB. The resulting ligation products were used to transform *E. coli* DH5alpha (Invitrogen, Carlsbad, CA), and positive clones identified by PCR were confirmed by DNA sequencing. To integrate the cumate-controlled atoB construct into the chromosome of JST06 (DE3), first the cumate repressor (cymR), promoter/operator regions (P$^{CT5}$), and respective ORFs were PCR amplified, as was the kanamycin drug construct via pKD4 (Datsenko and Wanner, 2000). These respective products were linked together via overlap extension PCR to create a final chromosomal targeting construct. Integration of the cumate-controlled constructs was achieved via standard recombineering protocols by using strain HME45 and selection on LB drug plates (Thomason et al. 2001). The primers used in the construction of JST06(DE3) atoB$^{CT5}$ are listed in Table U.

The gene fadB, encoding hydroxyacyl-CoA dehydrogenase and enoyl-CoA hydratase is deleted to minimize the flux of acetoacetyl-CoA entering the competing beta-oxidation reversal pathway. The gene deletion is performed using P1 phage transduction (Yazdani et al. 2008) with single gene knockout mutants from the National BioResource Project (NIG, Japan, Baba et al. 2006) as the specific deletion donor.

The other genes for overexpression are made, put into cells and tested as described above. The quantification of intermediate prenol is also performed via ion-exclusion HPLC using a Shimadzu Prominence SIL 20 system equipped with an HPX-87H organic acid column (Bio-Rad, Hercules, CA) with operating conditions to optimize peak separation (0.3 mL/min flow rate, 30 mM $H_2SO_4$ mobile phase, column temperature 42° C.). Concentration of 2-oxoisovaleric acid in fermentation samples is determined through calibration to known prenol standards (5, 1, 0.5, 0.2 and 0.1 g/L).

The first part of pathway to prenol has demonstrated been in vivo. The plasmids used for demonstration of in vivo prenol production are listed in Table V and the primers required for constructions of these plasmids are listed in Table W. First, the pathway to prenol was expressed in two vectors: the genes encoding acyl-CoA reductases were inserted into pETDuet-1 vector, while other genes were expressed from plasmid pCDF-PI-HMGS-aibA-aibB-P2-liuC. When using CbjALD, endogenous alcohol dehyrogenases without overexpression was used. Except for genes encoding *E. coli* enzymes YjgB and YahK, which were PCR amplified from the genomic DNA of wild type *E. coli* MG1655 strain, and the gene encoding CbjALD, which was PCR amplified from the genomic DNA of *C. beijerinckii*, the genes were codon optimized and synthesized by either GeneArt or GenScript. The adhE2, cbjALD and maqu_2507 gene inserts were PCR amplified with adhE2-f1/adhE2-r1, cbjALD-f2/cbjALD-r2 and maqu_2507-f2/maqu_2507-r2 primers respectively and inserted into vector pETDuet-1 cleaved by NdeI through In-Fusion HD Eco-Dry Cloning system to construct pET-P2-adhE2, pET-P2-cbjALD, pET-P2-maqu_2507 respectively. For construction of pCDF-P1-HMGS-aibA-aibB-P2-liuC, the codon-optimized liuC gene insert was first PCR amplified with liuC-f1/liuC-r1 primers and inserted into vector pCDFDuet-1, cleaved by NdeI through In-Fusion HD Eco-Dry Cloning system to generate pCDF-P2-liuC. Then, the codon-optimized hmgs gene insert was PCR amplified with hmgs-f1/hmgs-r1 primers and inserted into vector pCDF-P2-liuC cleaved with NcoI and EcoRI through In-Fusion HD Eco-Dry Cloning system to generate pCDF-PI-HMGS-P2-liuC. Finally, the codon optimized aibA and aibB gene inserts were PCR amplified with aibA-f1/aibA-r1 and aibB-f1/aibB-r1 primers respectively and inserted into vector pCDF-P2-liuC cleaved with EcoRI and SalI through In-Fusion HD Eco-Dry Cloning system to generate pCDF-PI-HMGS-aibAB-P2-liuC. The sequences of constructed plasmids were further confirmed by DNA sequencing. Then, the sequence confirmed plasmids were introduced to competent cells of host strain JST06(DE3) atoB$^{CT5}$ ΔfadB.

Figure 26:
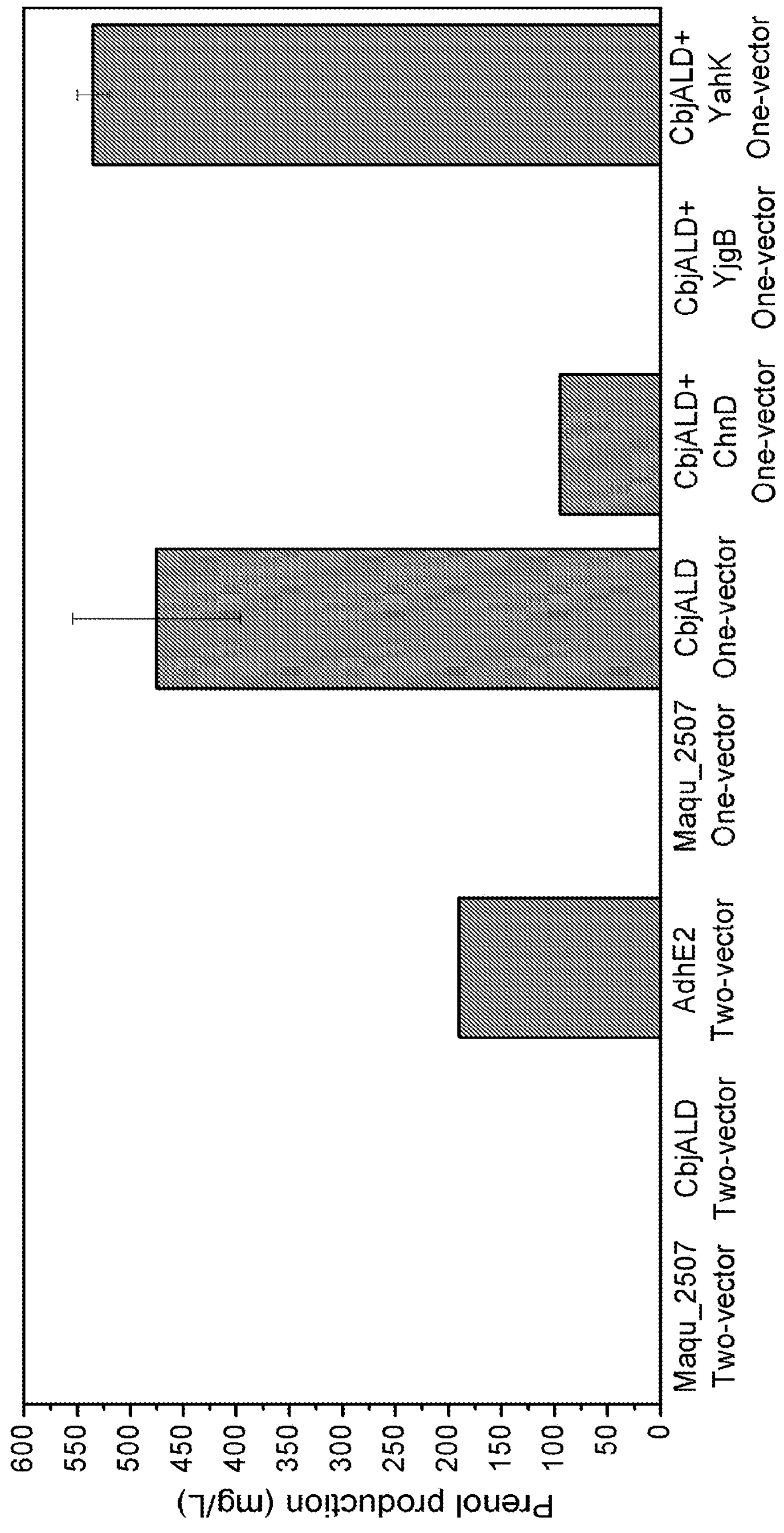
FIG. 26: Prenol production in *E. coli* through the pathway via HMG-CoA with usage of different acyl-CoA reductases and alcohol dehydrogenase and different number of vectors.

As shown in FIG. 26, under the two-vector system, the strain expressing AdhE2 showed 190 mg/L of prenol production when grown under 37° C. for 48 hours in shake flasks with 20 mL LB-like MOPS media supplemented with 20 g/L glycerol, induced under 10 μM IPTG and 100 μM cumate, while prenol production was not detected when expressing CbjALD and Maqu_2507. To test whether the burden caused by multiple vector system led to undetected prenol production when using CbjALD and Maqu 2507, the cbjALD and maqu_2507 gene inserts were PCR amplified with cbjALD-f2/cbjALD-r3 and maqu_2507-f2/maqu_2507-r3 primers respectively and inserted into vector pCDF-P2-HMGS-aibAB-P2-liuC cleaved by NdeI through In-Fusion HD Eco-Dry Cloning system to generate pCDF-P2-HMGS-aibAB-P2-cbjALD-liuC and pCDF-P2-HMGS-aibAB-P2-maqu_2507-liuC respectively, so that whole prenol supplying pathway is expressed through single vector. As a result, while the strain JST06(DE3) atoB$^{CT5}$ ΔfadB pCDF-P2-HMGS-aibAB-P2-maqu_2507-liuC still did not produce detectable prenol, JST06(DE3) atoB$^{CT5}$ ΔfadB pCDF-P2-HMGS-aibAB-P2-cbjALD-liuC produced 475 mg/L of prenol production, higher than the strain with two-vector system using AdhE2, when grown under same conditions as above, possibly due to the added metabolic burden of maintaining two plasmids in the cell.

To test whether co-expression of alcohol dehydrogenases YahK, YjgB and ChnD, which had been proven to be active on oxidizing prenol to 3-methyl-1-butenal through in vitro assay according to the second experiment, can improve prenol production with usage of CbjALD, the chnD, yjgB, yahK gene inserts were PCR amplified with chnD-f2/chnD-r2, yjgB-f1/yjgB-r1 and yahK-f1/yahK-r1 primers respectively and inserted into vector pCDF-P2-HMGS-aibAB-P2-cbjALD-liuC cleaved by BglII and XhoI through In-Fusion HD Eco-Dry Cloning system to generate pCDF-P2-HMGS-aibAB-P2-cbjALD-liuC-chnD, pCDF-P2-HMGS-aibAB- P2-cbjALD-liuC-yjgB and pCDF-P2-HMGS-aibAB-P2-cbjALD-liuC-yahK respectively, and the resultant plasmids were introduced into JST06(DE3) atoB$^{CT5}$ ΔfadB. As a result, the strain overexpressing ChnD and YjgB did not show the detectable prenol production, while the strain overexpressing YahK produced 535 mg/L of prenol, higher than that of JST06(DE3) atoB$^{CT5}$ ΔfadB pCDF-P2-HMGS-aibAB-P2-cbjALD-liuC, which uses endogenous alcohol dehydrogenase without overexpression, when grown under same conditions as above. To summarize, the pathway to prenol is effective in vivo when using acyl-CoA reductases CbjALD and AdhE2, and co-expression of YahK can further improve prenol production when using CbjALD.

After demonstrating the in vivo prenol production, the rest of the pathway, which converts prenol to geraniol, was added. A three-vector system was first used as shown in Table V. The pathway to 3-methylcrotonyl-CoA was expressed through pCDF-PI-HMGS-aibA-aibB-P2-liuC; acyl-CoA reductases AdhE2 or CbjALD were expressed through pRSF-P2-adhE2 or pRSF-P2-cbjALD; the rest of the pathway converting prenol to geraniol was expressed through pET-PI-idi-trGPPS2-P2-ges-ychB-mtipk. For construction of other plasmids, the *E. coli* genes encoding Idi and YchB were PCR amplified from the genomic DNA of wild type *E. coli* MG1655 strain, while the other genes were codon optimized and synthesized by either GeneArt or GenScript. The adhE2 and cbjALD gene inserts were PCR amplified with were PCR amplified with adhE2-f1/adhE2-r1 and cbjALD-f2/cbjALD-r2 primers respectively and inserted into vector pRSFDuet-1 cleaved by NdeI through In-Fusion HD Eco-Dry Cloning system to construct pRSF-P2-adhE2 and pRSF-P2-cbjALD respectively. To construct pET-P1-idi-trGPPS2-P2-ges-ychB-mtipk, the gene inserts encoding Idi and trGPPS2 ("tr" means "truncated" as first 84 aa of GPPS2 was truncated to improve the activity) were PCR amplified with idi-f1/idi-r1 and trgpps2-f1/trgpps2-r1 respectively and inserted together into pETDuet-1 cleaved by NcoI through In-Fusion HD Eco-Dry Cloning system to generate pET-P1-idi-trGPPS2. Then, the gene insert encoding GES was PCR amplified with ges-f1/ges-r1 primers and inserted into vector pET-P1-idi-trGPPS2 cleaved by NdeI and KpnI through In-Fusion HD Eco-Dry Cloning system to generate pET-P1-idi-trGPPS2-P2-ges. Finally, the gene inserts encoding YchB and MtIPK were PCR amplified with ychB-f1/ychB-r1 and mtipk-f1/mtipk-r1 respectively and inserted together into pET-P1-idi-trGPPS2-P2-ges cleaved by XhoI through In-Fusion HD Eco-Dry Cloning system to generate pET-P1-idi-trGPPS2-P2-ges-ychB-mtipk. The sequences of required primers can be seen in Table W. The sequences of constructed plasmids were further confirmed by DNA sequencing. Then, the sequence confirmed plasmids were introduced to competent cells of host strain JST06(DE3) atoB$^{CT5}$ ΔfadB.

Figure 27:
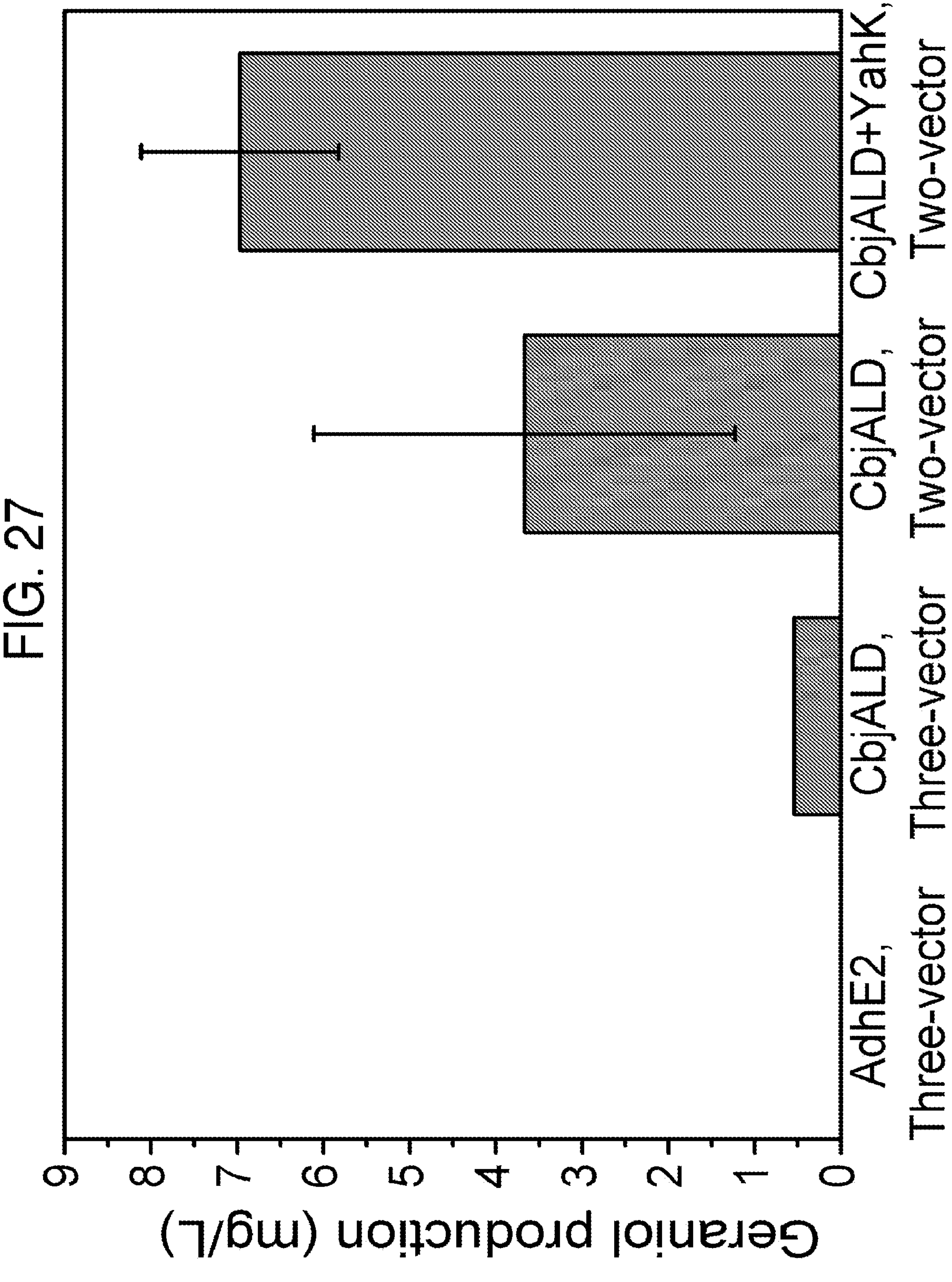
FIG. 27: Geraniol production of *E. coli* strains harboring novel GPP synthesis pathway via HMG-CoA and prenol with usage of acyl-CoA reductases AdhE2 or CbjALD and alcohol dehydrogenase YahK.

As shown in FIG. 27, the resultant strain using AdhE2 did not show detectable geraniol production, while the strain using CbjALD and endogenous alcohol dehydrogenases without overexpression had 0.54 mg/L of geraniol production when grown under 30° C. for 48 hours in shake flasks with 20 mL LB-like MOPS media supplemented with 20 g/L glycerol, induced under 10 μM IPTG and 100 μM cumate. Though the titer was small and further improvement measures, like decreasing the vector number and optimizing fermentation conditions, were required, this result indicates that the claimed novel GPP synthesis pathway via HMG-CoA and prenol is effective in vivo when using acyl-CoA reductase CbjALD.

A two-vector system was also tested for geraniol production with usage of acyl-CoA reductase CbjALD with or without alcohol dehydrogenase YahK. One plasmid was pCDF-P2-HMGS-aibAB-P2-cbjALD-liuC or pCDF-P2-HMGS-aibAB-P2-cbjALD-liuC-yahK that expresses the pathway from acetoacetyl-CoA to prenol (or most of "upper alcohol pathway", as shown in FIG. 1), and the other plasmid was pET-P1-idi-trGPPS2-P2-ges-ychB-mtipk that expresses the pathway converting from prenol to geraniol (or "lower alcohol pathway", as shown in FIG. 1). As shown in FIG. 27, the resultant strain using two-vector system and CbjALD and endogenous alcohol dehydrogenases without overexpression had 3.7 mg/L of geraniol production when grown under 30° C. for 48 hours in shake flasks with 20 mL LB-like MOPS media supplemented with 20 g/L glycerol, induced under 50 μM IPTG and 100 μM cumate, indicating that reduction of expression vector can improve the geraniol production. The addition of YahK overexpression further improved the titer to 7.0 mg/L. When YahK was overexpressed, the strain was grown under 30° C. for 48 hours in shake flasks with 15 mL LB-like MOPS media supplemented with 20 g/L glycerol, induced under 10 μM IPTG and 100 μM cumate.

(Prophetic) GPP Biosynthesis Via 3-Methyl-3-Hydroxybutyryl-Coa and Prenol Starting from Non-Decarboxylative Claisen Condensation Between Two Acetyl-Coas or Decarboxylative Claisen Condensation Between Acetyl-Coa and Malonyl-Coa The purpose of this example is to demonstrate the biosynthesis of GPP through a novel pathway via 3-methyl-3-hydroxybutyryl-CoA and prenol. *E. coli* serves as the host organism. This pathway starts from non-decarboxylative Claisen condensation between two acetyl-CoAs to acetoacetyl-CoA catalyzed by *E. coli* thiolase AtoB (NP_416728.1) or decarboxylative Claisen condensation between acetyl-CoA and malonyl-CoA by ketoacyl-CoA synthase. Malonyl-CoA is supplied from acetyl-CoA by *E. coli* acetyl-CoA carboxylase AccABCD (NP_414727.1, NP_417721.1, NP_417722.1, NP_416819.1). Then, acetoacetyl-CoA is hydrolyzed to acetoacetic acid by enzymes selected from the group consisting thioesterase, acyl-CoA transferase and phosphotransacylase plus carboxylate kinase. Acetoacetate decarboxylase removes the carboxyl group of acetoacetic acid, generating acetone. 3-hydroxy-3-methylglutaryl-CoA (HMG-CoA) synthase then performs a condensation between acetone and another acetyl-CoA, generating 3-methyl-3-hydroxybutyryl-CoA. Enoyl-CoA hydratase dehydrates 3-methyl-3-hydroxybutyryl-CoA to 3-methylcrotonyl-CoA. 3-methylcrotonyl-CoA is converted to prenol by alcohol-forming acyl-CoA reductase or aldehyde forming acyl-CoA reductase and alcohol dehydrogenase or carboxylate reductase and the hydrolysis enzyme selected from the group consisting thioesterase, acyl-CoA synthase, acyl-CoA transferase and carboxylate kinase plus phosphotransacylase. Alcohol-forming acyl-CoA reductase is selected from the group consisting *C. acetobutylicum* AdhE2 (YP_009076789.1) and *M. aquaeolei* VT8 Maqu_2507 (YP_959769.1). CbjALD from *C. beijerinckii* aldehyde forming acyl-CoA reductase (AAT66436.1) is selected for conversion of 3-methylcrotonyl-CoA to prenol. Alcohol dehydrogenase is selected from the group consisting *E. coli* YahK (NP_414859.1), *E. coli* YjgB (NP_418690.4) and *Acinetobacter* sp. SE19 ChnD (BAC80217.1).

Prenol is then converted to DMAPP by one or two steps of phosphorylation. If phosphorylated by two steps, the first step is catalyzed by *E. coli* alcohol kinase YchB (NP_415726.1) or *Thermoplasma acidophilum* phosphate kinase ThaIPK (WP_010900530.1, V73I, Y141V and K204G mutations to increase specificity on prenol, Liu et al. 2016) and the second is by *M. thermautotrophicus* phosphate kinase MtIPK (AAB84554.1). The one step phosphorylation is catalyzed by alcohol diphosphokinase. *E. coli* isopentenyl pyrophosphate isomerase Idi (NP_417365.1) converts DMAPP to IPP, which is condensed with DMAPP to form GPP catalyzed by *E. coli* GPP synthase IspA (NP_414955.1, S80F) or *A. grandis* GPP synthase GPPS2 (AAN01134.1, N-terminal 84 aa truncation). *Ocimum basilicum* geraniol stynthase GES (AR11765.1, N-terminal 65 aa truncation) converts GPP to geraniol, which serves as the proxy product.

JST06(DE3) atoB$^{CT5}$ ΔfadB serves as the *E. coli* host strain for demonstration of novel pathway. The genes for overexpression are made and put into cells, which are gown and the supernatants analyzed as described above.

The quantifications of intermediates prenol and acetone are also performed via ion-exclusion HPLC using a Shimadzu Prominence SIL 20 system equipped with an HPX-87H organic acid column with operating conditions to optimize peak separation (0.3 mL/min flow rate, 30 mM $H_2SO_4$ mobile phase, column temperature 42° C.). Concentration of 2-oxoisovaleric acid in fermentation samples is determined through calibration to known acetone and prenol standards (5, 1, 0.5, 0.2 and 0.1 g/L).

The in vivo production of acetone has been demonstrated in *E. coli*. The JC01 (MG1655 ΔldhA ΔpoxB Δpta ΔadhE ΔfrdA, an *E. coli* strain with removal of mixed-acid fermentation for improved supply of acetyl-CoA) strain overexpressing thiolase AtoB and thioesterase YbgC showed 53 mg/L of acetone production when grown in LB-like MOPS media with glycerol under 37° C. for 48 hours. This result indicates that YbgC can hydrolyze acetoaceetyl-CoA, the product of non-decarboxylative Claisen condensation between two acetyl-CoAs by AtoB, to acetoacetic acid, and aetoacetic acid can be decarboxylated to acetone spontaneously or by endogenous *E. coli* enzymes. These enzymes can be used in this GPP synthesis pathway. The media, fermentation conditions and method of HPLC analysis on acetone are described in previous example. In this fermentation, the atoB gene was expressed from pTH-atoB, while the ybgC gene was expressed from pZS-ybgC. The primers required for construction of these plasmids can be seen in Table S, and the process of construction of these plasmids is described in the previous example.

Among above enzymes, as mentioned in the previous example, the in vitro activities of acyl-CoA reductases CbjALD and Maqu_2507 on reduction of 3-methylcrotonyl-CoA and the in vitro activities of alcohol dehydrogenases ChnD, YjgB and YahK on oxidization of prenol have been proven through enzymatic spectrophotometric assay. *E. coli* alcohol dehydrogenases FucO (NP_417279.2), YqhD (NP_417484.1), YiaY (YP_026233.1) were also assayed on prenol, but as mentioned above, they did not show the activity on prenol oxidization. The results of assays on alcohol dehydrogenases can be seen in Table P, and the results of assays on acyl-CoA reductases and relevant enzyme preparation and assay methods are described in the previous example.

(Prophetic) Synthesis of Isoprenoids

The purpose of this example is to demonstrate the biosynthesis of isoprenoids other than geraniol from isoprenoid precursor GPP or others, which are supplied from claimed novel pathways. *E. coli* serves as the host strain. The possible isoprenoid products are monoterpenes like limonene and pinene, which are derived from GPP, and sesquiterpenes like beta-caryophyllene, valencene, vetispiradiene, amorphadiene and farnesene, which are derived from farnesyl diphosphate (FPP), as shown in FIG. 15. FPP is an isoprenoid precursor with five more carbons than GPP and supplied through condensation between GPP and IPP, which are supplied from above novel claimed pathways, by *E. coli* FPP synthase IspA (NP 414955.1). These mentioned isoprenoids are with great industrial importance and can be used as biofuels and solvents and be used in the fields of cosmetics, pharmaceutics, and perfumery. The conversion of GPP to limonene is caalzyed by *Mentha spicata* limonene synthase LS (AGN90914.1). The conversion of GPP to pinene is catalyzed by *Pinus taeda* pinene synthase Pt30 (AA061228.1). The conversion of FPP to beta-caryophyllene is catalyzed by *Artemisia annua* beta-caryophyllene synthase QHS1 (AAL79181.1). The conversion of FPP to valencene is catalyzed by *Callitropsis nootkatensis* valenecene synthase VALC (AFN21429.1). The conversion of FPP to vetispiradiene is catalyzed by *Hyoscyamus muticus* vetispiradiene synthase VS1 (Q39978.2). The conversion of FPP to amorphadiene is catalyzed by *Artemisia annua* amorphadiene synthase ADS (AAF61439.1). The conversion of FPP to farnesene is catalyzed by *Malus domestica* farnesene synthase FS (NP_001280822.1). The genes encoding enzymes for productions of above isoprenoids are separately cloned into pACYCDuet-1 vector (Novagen, Darmstadt, Germany), and the resultant plasmids can be directly used and introduced to GPP-synthsizing strains as described in previous examples to realized productions of isoprenoids. The resultant vectors are listed in Table X. Except ispA, which is PCR amplified from the genomic DNA of wild type *E. coli*, the genes encoding synthases of isoprenoids are codon-optimized and synthesized by GenScript (Piscataway, NJ) or GeneArt® (Life Technologies, Carlsbad, CA).

In Vivo Synthesis of Olivetolic Acid in *E. coli*

The purpose of this example is to demonstrate in vivo synthesis of olivetolic acid with *E. coli* as host organism. Olivetolic acid is a suitable aromatic acceptor of geranyl group donated from GPP, which is synthesized by claimed novel pathways, MVA, MEP/DXP, or other pathways, the prenylation reaction generating the valuable cannabinoid, cannabigerolic acid (CBGA). Olivetolic acid is synthesized through multiple possible pathways. The first pathway starts from three series of decarboxylative Claisen condensation with hexanoyl-CoA as the initial primer and malonyl-CoA as the extender unit by e.g., *C. sativa* olivetol synthase OLS (BAG14339.1), generating 3,5,7-trioxododecanoyl-CoA. Then, *C. sativa* olivetolic acid cyclase OAC (AFN42527.1, several non-conservative substitutions of residues are performed to improve the activity) cyclizes 3,5,7-trioxododecanoyl-CoA to olivetolic acid.

The second pathway also starts from three series of decarboxylative Claisen condensation with hexanoyl-CoA as the initial primer and malonyl-CoA as the extender unit, but catalyzed by other polyketide synthases selected from e.g., *H. macrophylla* stilbenecarboxylate synthase STCS (AAN76183.1, with a subset of mutations of T135S, T198M and I200C to accept hexanoyl-CoA as the active substrate), a type III polyketide synthase, and type I polyketide synthases AviM from *Streptomyces viridochromogenes* Tue57 (AAK83194.1), ArmB from *Armillaria mellea* (AFL91703.1) and CalO5 from *Micromonospora echinospora* ssp. *Calichensis* (AAM70355.1). These polyketide synthases directly perform the cyclization of 3,5,7-trioxododecanoyl-CoA to olivetolic acid.

The third pathway starts from three series of condensations with hexanoyl-CoA as the initial primer and acetyl-CoA as the extender unit by polyketoacyl-CoA thiolase selected e.g., from the group consisting FadAx (AAK18171.1) and PcaF (AAA85138.1) from *P. putida*, DcaF (CAG68532.1) from *Acinetobacter* sp. ADP1, and ScFadA (AAL10298.1) from *S. collinus*, generating 3,5,7-trioxododecanoyl-CoA, which is then cyclized to olivetolic acid by OAC.

Hexanoyl-CoA can be supplied from hexanoic acid, either supplemented or intracellularly synthesized through beta-oxidation reversal composed of e.g., ketoacyl-CoA thiolase BktB (AAC38322.1) from *R. eutropha,* 3-hydroxyacyl-CoA dehydrogenase and enoyl-CoA hydratase multifunctional enzyme FadB from *E. coli* (NP_418288.1) and enoyl-CoA reductase EgTer from *E. gracilis* (Q5EU90.1) or fatty acid biosynthesis pathway composed of beta-ketoacyl-ACP synthases FabH (NP 415609.1) and FabB (NP_416826.1), acetoacetyl-ACP reductase FabG (NP_415611.1), 3-hydroxyacyl-ACP dehydratase FabZ (NP_414722.1) and enoyl-ACP reductase FabI (NP_415804.1), all from *E. coli*, with termination by *E. coli* thioesterase TesA (NP_415027.1, with truncation of 26 aa leader sequence) and activation by *E. coli* acyl-CoA synthetase FadD (NP_416319.1), or directly synthesized through overexpressed beta-oxidation reversal pathway without termination.

If malonyl-CoA is used as the extender unit, to enhance its supply, e.g., *E. coli* acetyl-CoA carboxylase AccABCD (NP_414727.1, NP_417721.1, NP_417722.1, NP 416819.1) is overexpressed. Also, to improve acetyl-CoA supply, e.g., *E. coli* pyruvate dehydrogenase complex AceEF-Lpd is overexpressed (e.g., NP_414658.1, NP_414656.1, NP_414657.1, A358V mutation in Lpd subunit to increase the activity of pyruvate dehydrogenase by reducing inhibition by NADH, Chen et al. 2014).

JST06(DE3) ΔfadE bktB$^{CT5}$ ΔatoB fadB$^{CT5}$ ΔfadA egter$^{CT5}$, which is able to intracellularly supply hexanoyl-CoA and hexanoic acid through beta-oxidation reversal, can serve as the host strain for the in vivo production of olivetolic acid. JST06(DE3) is described in previous examples and is selected to maximize the flux of beta-oxidation reversal for hexanoyl-CoA supply required for the synthesis of olivetolic acid via polyketoacyl-CoA thiolases. ΔatoB fadB$^{CT5}$ are as described above. BktB, FadB and EgTer are chromosomally expressed under p$^{CT5}$ promoter with control by cumate. To integrate the cumate-controlled bktB construct into the chromosome of the target strain, first the cumate repressor (cymR), promoter/operator regions (P$^{CT5}$), and respective ORFs are PCR amplified using appropriate primers, as is chloramphenicol drug construct via pKD4 (Datsenko and Wanner, 2000). These respective products are linked together via overlap extension PCR to create a final chromosomal targeting construct. The fadA gene was separately deleted via recombineering in the HME45 derivative harboring the cumate-controlled fadBA construct by replacement of the fadA ORF with a zeocin resistance marker amplified from pKDzeo (Magner et al. 2007).

For the creation of the cumate-controlled egTER, the cat gene, cymR repressor gene, hybrid cumate-controlled phage T5 promoter, and egTER gene are PCR amplified from genomic DNA of a strain with egTER seamlessly replacing fadBA at the cumate controlled fadBA locus (See below for details). This product is recombineered into strain HME45 at the end of the fabI locus, selecting on chloramphenicol (12.5 sg/ml) LB plates. Integration is done in a manner to duplicate the last 22 bp of fabI (including stop codon) so as retain an overlapping promoter for the next native downstream gene.

Construction of the strain serving as the PCR template for egTER described above was accomplished by first creating a kan-sacB fusion cassette via overlap extension PCR using pKD4 and genomic DNA, respectively. This kan-sacB cassette was integrated between fadB and fadA of the fadBA$^{CT5}$ strain formerly constructed (Vick et al., 2015) through subsequent recombineering. Seamless replacement of the kan-sacB cassette to create the cat-cymR-P$^{CT5}$-egTER at the fadBA locus was done via recombineering and subsequent sucrose selection with codon optimized egter (Genscript) PCR product. The primers for construction of this strain are listed in Table Y.

The gene fadE, encoding acyl-CoA dehydrogenase is deleted to block the degradation of hexanoyl-CoA through beta-oxidation. The gene deletion is performed using P1 phage transduction (Yazdani et al. 2008) with single gene knockout mutants from the National BioResource Project (NIG, Japan, Baba et al. 2006) as the specific deletion donor.

The constructed vectors for expression of different routes of olivetolic acid synthesis pathways are listed in Table Z. To construct pET-P1-OLS-P2-OAC, the OLS gene insert was first PCR amplified with OLS-BamHI-F/OLS-EcoRI-R primers and inserted into vector pETDuet-1 cleaved by BamHI and EcoRI through Gibson Assembly cloning system, generating pET-P1-OLS. Then, the OAC gene insert was PCR amplified with OAC-NdeI-Up/OAC-XhoI-Dn primers and inserted into pET-P1-OLS cleaved by NdeI and XhoI through Gibson Assembly cloning system, generating pET-P1-OLS-P2-OAC.

Figure 28:
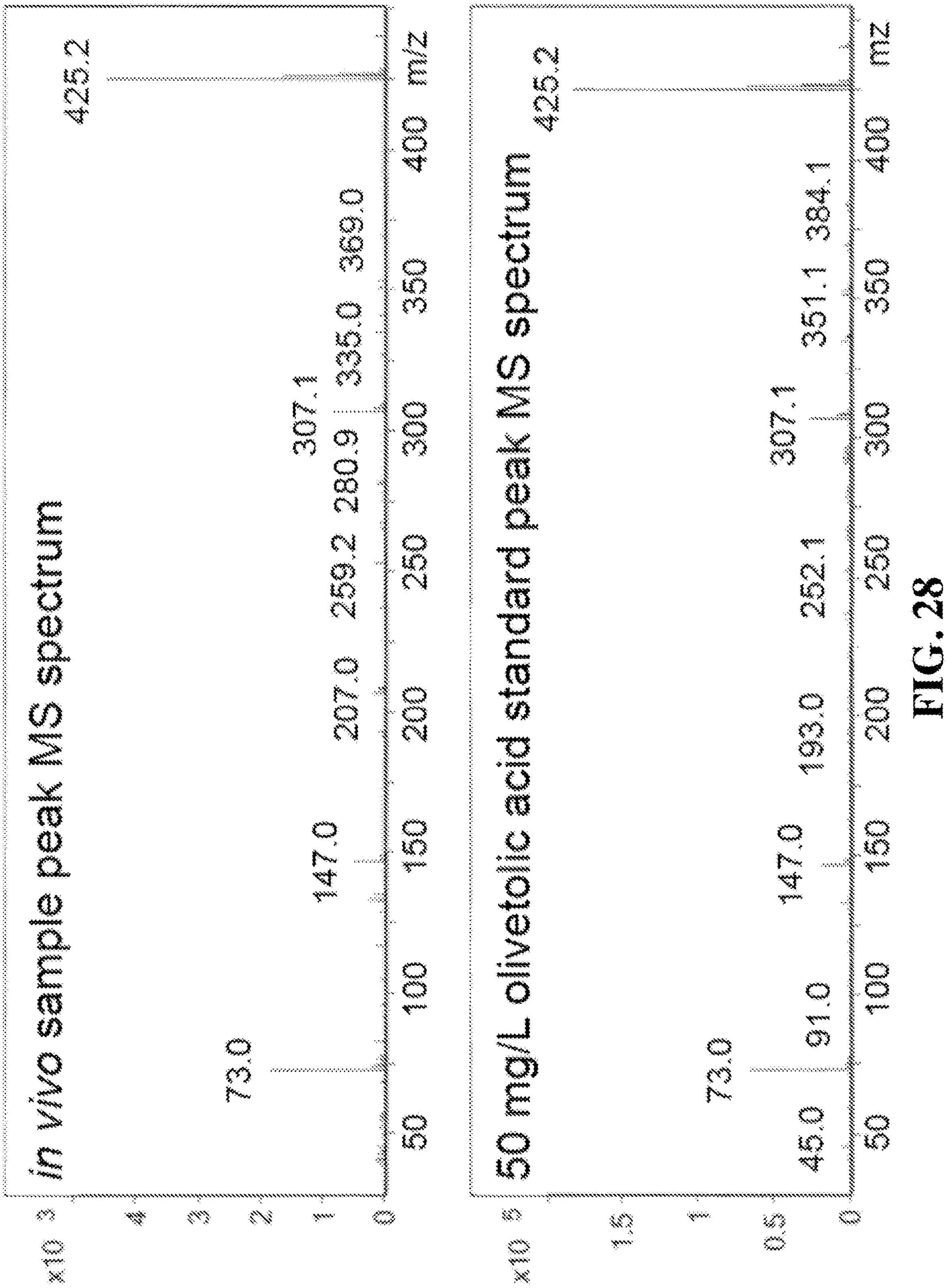
FIG. 28: GC-MS spectra of olivetolic produced in vivo in comparison to olivetolic acid standard.

The in vivo synthesis of olivetolic acid in *E. coli* has been demonstrated by using *C. sativa* olivetol synthase OLS and olivetolic acid cyclase OAC. JST06(DE3) ΔfadE bktB$^{CT5}$ ΔatoBfadB$^{CT5}$ ΔfadA egter$^{CT5}$ @fabI served as the host strain containing plasmid pET-P1-OLS-P2-OAC. The genes encoding OLS and OAC were codon optimized and synthesized by either GeneArt or GenScript. The resultant strain for olivetolic acid production was grown in shake flasks with 15 mL LB-like MOPS media supplemented with 20 g/L glycerol and 55 g/L $CaCO_3$ at 30° C. for 48 hours. Extracellular olivetolic acid was extracted and derivatized following the protocols described in previous examples and the resulting sample analyzed via GC-MS. FIG. 28 shows GC-MS identification of in vivo olivetolic acid synthesis through comparison with an olivetolic acid standard. This result demonstrates that OLS and OAC are effective for in vivo biosynthesis of olivetolic acid which can be used as the acceptor group donated from GPP synthesized through claimed pathways for production of valued compound cannabigerolic acid (CBGA).

(Prophetic) In Vivo Synthesis of Divarinolic Acid in E. *Coli*

The purpose of this example is to demonstrate in vivo synthesis of divarinolic acid with *E. coli* as host organism. Divarinolic acid is a suitable aromatic acceptor of geranyl group donated from GPP, which is synthesized by claimed novel pathways or the known MVA, MEP/DXP pathways, or otherwise, in the prenylation reaction generating cannabinoid cannabigerovarinic acid (CBGVA). Divarinolic acid is synthesized through multiple possible pathways. The first pathway starts from three series of condensation with butyryl-CoA as the initial primer and malonyl-CoA as the extender unit by e.g., *C. sativa* olivetol synthase OLS (BAG14339.1), generating 3,5,7-trioxodecanoyl-CoA. Then, *C. sativa* olivetolic acid cyclase OAC (e.g., AFN42527.1, several non-conservative substitutions of residues are performed to improve the activity) cyclizes 3,5,7-trioxodecanoyl-CoA to divarinolic acid.

The second pathway also starts from three series of condensations with butyryl-CoA as the initial primer and malonyl-CoA as the extender unit, but catalyzed by catalyzed by other polyketide synthases selected from e.g., *H. macrophylla* stilbenecarboxylate synthase STCS (AAN76183.1, with a subset of mutations of T135S, T198M and I200C), a type III polyketide synthase, and type I polyketide synthases AviM from *Streptomyces viridochromogenes* Tue57 (AAK83194.1), ArmB from *Armillaria mellea* (AFL91703.1) and CalO5 from *Micromonospora echinospora* ssp. *Calichensis* (AAM70355.1). These polyketide synthases then directly perform the cyclization of 3,5,7-trioxodecanoyl-CoA to divarinolic acid.

The third pathway starts from three series of condensations with butyryl-CoA as the initial primer and acetyl-CoA as the extender unit by polyketoacyl-CoA thiolase from e.g., FadAx (AAK18171.1) and PcaF (AAA85138.1) from *P. putida*, DcaF (CAG68532.1) from *Acinetobacter* sp. ADP1, and ScFadA (AAL10298.1) from *S. collinus*, generating 3,5,7-trioxodecanoyl-CoA, which is then cyclized to divarinolic acid by OAC.

Butyryl-CoA can be supplied from butyric acid, either supplemented or intracellularly synthesized through beta-oxidation reversal composed of e.g., ketoacyl-CoA thiolase BktB (AAC38322.1) from *R. eutropha* or thiolase AtoB (NP_416728.1) from *E. coli,* 3-hydroxyacyl-CoA dehydrogenase and enoyl-CoA hydratase multifunctional enzyme FadB from *E. coli* (NP_418288.1) and enoyl-CoA reductase EgTer from *E. gracilis* (Q5EU90.1) or fatty acid biosynthesis pathway composed of beta-ketoacyl-ACP synthase FabH (NP_415609.1), beta-ketoacyl-ACP reductase FabG (NP_415611.1), 3-hydroxyacyl-ACP dehydratase FabZ (NP 414722.1) and enoyl-ACP reductase FabI (NP 415804.1), all from *E. coli*, with termination by e.g., *E. coli* thioesterase TesA (NP 415027.1, with truncation of 26 aa leader sequence) and activation by *E. coli* acyl-CoA synthetase FadD (NP_416319.1), or directly synthesized through overexpressed beta-oxidation reversal pathway without termination. If malonyl-CoA is used as the extender unit, to enhance its supply, e.g., *E. coli* acetyl-CoA carboxylase AccABCD is overexpressed. Also, to improve acetyl-CoA supply, e.g., *E. coli* pyruvate dehydrogenase complex AceEF-Lpd is overexpressed.

JST06(DE3) ΔfadE bktB$^{CT5}$ ΔatoBfadB$^{CT5}$ ΔfadA egter$^{CT5}$ @fabI, which is able to intracellularly supply butyryl-CoA through beta-oxidation reversal, can serve as the host strain for the in vivo production of olivetolic acid. Its construction, growth and analysis of products are as described above in previous examples.

The in vivo butyryl-CoA and butyric acid synthesis through beta-oxidation reversal composed of AtoB, FadB and EgTer has been demonstrated in *E. coli*. The results are shown in FIG. 23. Strain and vector constructions, fermentation conditions and analysis method are as described above in previous examples.

(Prophetic) In Vivo Synthesis of Orsellinic Acid in *E. Coli*

The purpose of this example is to demonstrate in vivo synthesis of orsellinic acid with *E. coli* as host organism. Orsellinic acid is a suitable aromatic acceptor of geranyl group donated from GPP, which is synthesized by claimed novel pathways or other pathways, in the prenylation reaction. Orsellinic acid is synthesized through multiple possible pathways. The first pathway starts from three series of decarboxylative Claisen condensations with acetyl-CoA as the initial primer and malonyl-CoA as the extender unit by e.g., *C. sativa* olivetol synthase OLS (BAG14339.1), generating 3,5,7-trioxooctanoyl-CoA. Then, *C. sativa* olivetolic acid cyclase OAC (AFN42527.1) cyclizes 3,5,7-trioxooctanoyl-CoA to orsellinic acid.

The second pathway also starts from three series of decarboxylative Claisen condensations with acetyl-CoA as the initial primer and malonyl-CoA as the extender unit, but catalyzed by other polyketide synthases selected from e.g., *H. macrophylla* stilbenecarboxylate synthase STCS (AAN76183.1, with a subset of mutations of T135S, T198M and I200C), a type III polyketide synthase, and type I polyketide synthases AviM from *Streptomyces viridochromogenes* Tue57 (AAK83194.1), ArmB from *Armillaria mellea* (AFL91703.1) and CalO5 from *Micromonospora echinospora* ssp. *Calichensis* (AAM70355.1). These polyketide synthases then directly perform the cyclization of 3,5,7-trioxooctanoyl-CoA to orsellinic acid.

The third pathway starts from condensation between two acetyl-CoAs to acetoacetyl-CoA catalyzed by *E. coli* thiolase AtoB (NP 416728.1). Then, two series of condensation reactions with acetoacetyl-CoA as the primer and acetyl-CoA as the extender unit by polyketoacyl-CoA thiolase selected from e.g., FadAx (AAK18171.1) and PcaF (AAA85138.1) from *P. putida*, DcaF (CAG68532.1) from *Acinetobacter* sp. ADP1, and ScFadA (AAL10298.1) from *S. collinus*, generates 3,5,7-trioxooctanoyl-CoA, which is then cyclized to orsellinic acid by OAC. If malonyl-CoA is used as the extender unit *E. coli* acetyl-CoA carboxylase AccABCD is preferably overexpressed. Also, to improve acetyl-CoA supply, *E. coli* pyruvate dehydrogenase complex AceEF-Lpd is overexpressed.

JST06(DE3) atoB$^{CT5}$ ΔfadB serves as the *E. coli* host strain for demonstration of the novel pathway. Vector and strain creation, growth and analysis are as described in previous examples.

In Vivo Synthesis of CBGA in *E. coli*

The purpose of this example is to demonstrate in vivo synthesis of cannabigerolic acid (CBGA) with *E. coli* as host organism. In this example, *Streptomyces* sp. strain CL190 prenyltransferase NphB (BAE00106.1), which is soluble and desirable for functional expression and operation in *E. coli*, was used to convert GPP, which was synthesized through mevalonate pathway and GPP synthase in this example, and extracellularly supplemented olivetolic acid, into CBGA. Besides NphB, Lithospermum erythrorhizon PGT-1(Q8W405), Lithospermum erythrorhizon PGT-2 (Q8W404), *E. coli* UbiA (POAGK1), *Arabidopsis thaliana* PPT1 (Q93YP7), *Schizosaccharomyces pombe* Coq2 (Q10252), *Cannabis sativa* CsPT1, *Streptomyces coelicolor* SCO7190 (BAE00107.1), *Streptomyces* sp. CNQ-509 CnqP3 (AKH84817.1) and *Phleum pretense* Phlp4 (ABB78007.1) can be another options of prenyltransferases for transfer of geranyl group from GPP to olivetolic acid forming CBGA.

The mevalonate pathway used herein is composed of 3-hydroxy-3-methylglutaryl-CoA synthase HMGS (BAU36102.1) and 3-hydroxy-3-methylglutaryl-CoA reductase HMGR (OLN67110.1) from *S. aureus*, mevalonate kinase MK (NP_013935.1), phosphomevalonate kinase PMK (NP_013947.1) and phosphomevalonate decarboxylase PMD (NP_014441.1) from *S. cerevisiae* and *E. coli* isopentenyl pyrophosphate isomerase Idi (NP_417365.1). *A. grandis* GPP synthase TrGPPS2 (AAN01134.1, N-terminal 84 aa truncation) was selected for condensation of IPP and DMAPP to GPP.

Except for the gene encoding Idi, which was amplified from the genomic DNA of *E. coli* wild type MG1655 strain, the required genes were codon optimized and synthesized by either GeneArt or GenScript. The genes encoding HMGS, HMGR, MK, PMK and PMD were expressed through pCDF-P1-MK-PMK-PMD-P2-HMGS-HMGR, while the genes encoding Idi, TrGPPS2 and NphB were expressed through pET-P1-idi-trGPPS2-CymR-CT5-NphB. The primers used for constructions of these plasmids are listed in Table AA.

Primers NphB-IF-fwd and NphB-IF-rev were used to PCR amplify NphB gene from the synthesized DNA fragment with usage of Phusion polymerase, and the amplified DNA fragment was assembled with NdeI/KpnI digested pETDuet-1 vector by In-Fusion HD Eco-Dry Cloning system, resulting in plasmid pET-P2-NphB. Primers idi-GB-fwd, idi-GB-rev, trGPPS2-IF-fwd, and GPPS2-GB-rev were utilized to PCR amplify DNA fragments containing idi and trGPPS2 with usage of Phusion polymerase, respectively. These two amplified DNA fragments were assembled with NcoI digested pET-P2-NphB by Gibson assembly cloning system, resulting in plasmid pET-P1-idi-trGPPS2-P2-NphB.

Later, primers CymR-GB-fwd and CymR-GB-rev were used to amplify CymR with CT5 promoters, and NphB-cumate-GB-fwd and NphB-cumate-GB-rev were used to PCR amplify NphB fragment with usage of Phusion polymerase. Two amplified DNA fragments were assembled with NotI/XhoI digested pET-P1-idi-trGPPS2-P2-NphB by Gibson assembly, providing plasmid pET-P1-idi-trGPPS2-CymR-CT5-NphB.

For cloning plasmid pCDF-P1-MK-PMK-PMD-P1-HMGS-HMGR, the synthesized DNA fragments containing HMGS genes and HMGR genes were assembled with NdeI digested pCDFDuet-1 vector by In-Fusion HD Eco-Dry Cloning system, resulting plasmid pCDF-P2-HMGS-HMGR. Primers MK-IF-fwd and MK-IF-rev were used to PCR amplify DNA containing MK gene with usage of Phusion polymerase, and the amplified DNA fragment was assembled with NcoI/EcoRI digested pCDF-P2-HMGS-HMGR by in-fusion cloning, producing plasmid pCDF-P1-MK-P2-HMGS-HMGR.

Similarly, primer PMK-IF-fwd and PMK-IF-rev were used to PCR amplify PMK with usage of Phusion polymerase and the DNA fragment was assembled with EcoRI digested pCDF-P1-MK-P2-HMGS-HMGR by In-fusion cloning, resulting in plasmid pCDF-P1-MK-PMK-P2-HMGS-HMGR.

Finally, primers PMD-IF-fwd and PMD-IF-rev were utilized to PCR amplify PMD gene with usage of Phusion polymerase, and the amplified DNA fragments were assembled with EcorI digested pCDF-P1-MK-PMK-P2-HMGS-HMGR by In-fusion cloning, resulting in the plasmid pCDF-P1-MK-PMK-PMD-P2-HMGS-HMGR.

Host strain JST06(DE3) atoB$^{CT5}$ containing plasmid pCDF-P1-MK-PMK-PMD-P2-HMGS-HMGR and pET-PI-idi-trGPPS2-CymR-CT5-NphB was inoculated into 5 ml LB medium in 25 ml flask with antibiotic and shaking under 37° C. with 200 rpm in NBS 124 Benchtop Incubator Shaker for overnight. The overnight culture was used as the seed culture to start the subculture with appropriate volume of LB-like MOPS medium as described above supplied with 20 g/L glucose in 25 ml flask. After 3 hours shaking under 37° C. at 200 rpm, the culture OD550 reached about 0.5. 20 μM IPTG and 100 μM cumate, and 500 mg/L olivetolic acid were added into the culture to induce enzyme expression and supply the substrate. Then, the flasks were transferred into another same type of shaker to grow under 30° C. After growing for 48 hours, 2 mL of fermentation broths with or without cells were collected for GC-MS identification and GC-FID quantification of CBGA. If without cell, the 5000 g, 5 min centrifuge in an Optima L-80XP Ultracentrifuge (Beckman-Coulter, Schaumburg, IL) was performed to remove the cells.

The fermentation broths of 2 mL were transferred to 5 mL glass vials (Fisher Scientific Co., Pittsburgh, PA). Then, organic solvent (typically hexane) was added at a 1:1 ratio to a fermentation broth sample (e.g. 2 mL for a 2 mL aqueous solution) for extraction. Before extraction, the samples were acidified with sulfuric acid (80 uL per 2 mL sample) and 30% (w/v) NaCl was added (340 uL per 2 mL). Following an appropriate extraction (vortex samples for 15 seconds, spin on a rotator at 60 rpm for 2 hours, and vortex again for 15 seconds), 1 mL of the organic phase was removed and evaporated to dryness under a gentle $N_2$ stream. 100 μL pyridine and 100 μL BSTFA were then added for derivatization, with the reaction allowed to proceed at 70° C. for 60 minutes. After cooling to room temperature, this mixture was used for GC analysis.

GC analysis was conducted on an Agilent 7890B Series Custom Gas Chromatography system equipped with a 5977B Inert Plus Mass Selective Detector Turbo EI Bundle (for identification) or a Flame Ionization Detector (for quantification) and an Agilent HP-5 capillary column (0.25 mm internal diameter, 0.25 μm film thickness, 30 m length). The following temperature profile was used with helium as the carrier gas at a flowrate of 1.2 mL/min: Initial 200° C. (hold 1 min); ramp at 30° C./min to 300° C. (hold 5 min). The injector and detector temperature were 290° C. and 350° C., respectively. 1 μL of sample was injected with a 4:1 split ratio.

Figure 29:
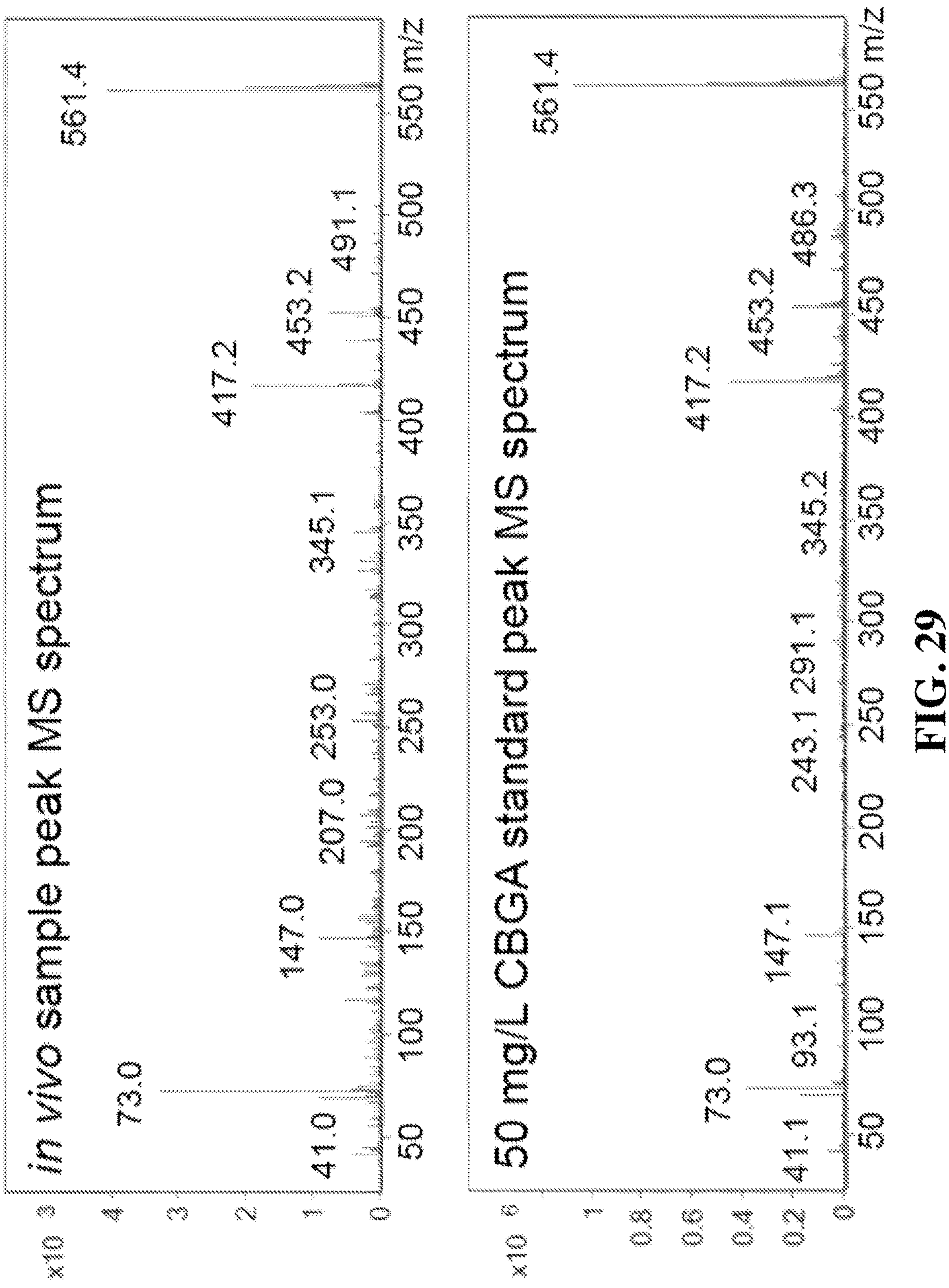
FIG. 29: GC-MS spectra of cannabigerolic acid (CBGA) produced in vivo in comparison to CBGA standard.

Cells grown with 10 mL medium in 25 ml flasks produced 0.2 mg/L CBGA after 48 hours of fermentation, and cells grown with 5 ml medium in 25 ml flasks produced 0.38 mg/L CBGA. FIG. 29 shows GC-MS identification of in vivo CBGA synthesis. This result indicates that prenyltransferase NphB is well expressed and functional on transferring geranyl group from GPP to olivetolic acid to synthesize CBGA in *E. coli.*

Although GPP in this example was supplied through traditional mevalonate pathway, the GPP could also be generated through claimed novel pathways or MEP/DXP pathway or commercially supplied. Alternative to the extracellular supplementation in this example, olivetolic acid can also be intracellularly synthesized through the series of condensations priming from hexanoyl-CoA as described in a previous example. Alternative to NphB used in this example, prenyl transfer can be catalyzed by other suitable enzymes such as those examples listed in Table L. The vectors for expression of some of prenyltransferases have been constructed, which are shown in Table AB.

The following are incorporated by reference herein in its entirety for all purposes:

Atsumi, S. et al. Metabolic engineering of *Escherichia coli* for 1-butanol production. *Metab. Eng.* 10, 305-311 (2008).

Baba, T. et al. Construction of *Escherichia coli* K-12 in-frame, single-gene knockout mutants: the Keio collection. *Mol Syst Biol* 2 (2006).

Blecher, M. (1981). Synthesis of long-chain fatty acyl-CoA thioesters using N-hydroxysuccinimide esters. *Methods in Enzymology,* 72: 404-408.

Chen, J. et al. Activating $C_4$-dicarboxylate transporters DcuB and DcuC for improving succinate production. *Appl. Microbiol. Biotechnol.* 98, 2197-2205 (2014).

Cheong, S., et al. Energy- and carbon-efficient synthesis of functionalized small molecules in bacteria using non-decarboxylative Claisen condensation reactions. *Nat Biotech* 34, 556-561 (2016).

Choi, S. Y. et al. One-step fermentative production of poly(lactate-co-glycolate) from carbohydrates in *Escherichia coli. Nat Biotech* 34, 435-440 (2016).

Clomburg, J. M., et al. A Synthetic Biology Approach to Engineer a Functional Reversal of the beta-Oxidation Cycle. ACS Synthetic Biology 1, 541-554 (2012).

Cracan, V. R., et al. Novel B12-dependent acyl-CoA mutases and their biotechnological potential. Biochemistry 51(31), 6039-6046 (2012).

Dellomonaco, C., et al. Engineered reversal of the beta-oxidation cycle for the synthesis of fuels and chemicals. Nature 476, 355-359 (2011).

Gao, Y., et al. Terpenoid synthase structures: a so far incomplete view of complex catalysis. Natural product reports 29, 1153-1175 (2012).

Haapalainen, A. M., et al. The thiolase superfamily: condensing enzymes with diverse reaction specificities. Trends in Biochemical Sciences 31, 64-71 (2006).

Heath, R. J., et al. The Claisen condensation in biology. Nat. Prod. Rep. 19, 581-596 (2002).

Iijima, Y., et al. Characterization of Geraniol Synthase from the Peltate Glands of Sweet Basil. *Plant Physiol.* 134, 370-379 (2004).

Jiang, C., et al. Divergent evolution of the thiolase superfamily and chalcone synthase family. Molecular Phylogenetics and Evolution 49, 691-701 (2008).

Jiang, Y. et al. Multigene Editing in the *Escherichia coli* Genome via the CRISPR-Cas9 System. *Appl. Environ. Microbiol.* 81, 2506-2514 (2015).

Kim, J., et al. W. 2-Hydroxyisocaproyl-CoA dehydratase and its activator from *Clostridium difficile. Febs J.* 272, 550-561 (2005).

Kitagawa, M. et al. Complete set of ORF clones of *Escherichia coli* ASKA library (A complete Set of *E. coli* K-12 ORF archive): Unique resources for biological research. *DNA Res.* 12, 291-299 (2005).

Kuzuyama, T., et al. Structural basis for the promiscuous biosynthetic prenylation of aromatic natural products. Nature 435, 983-987 (2005).

Liu, Y, et al. Improving the catalytic activity of isopentenyl phosphate kinase through protein coevolution analysis. Scientific Reports 6, 24117 (2016).

Mabanglo, M. F., et al. Mutagenesis of isopentenyl phosphate kinase to enhance geranyl phosphate kinase activity. *ACS Chem. Biol.* 7, 1241-1246 (2012).

Magner, D. B. et al. RecQ promotes toxic recombination in cells lacking recombination intermediate-removal proteins. *Mol. Cell* 26, 273-286 (2007).

Miller, J. H. Experiments in molecular genetics. (Cold Spring Harbor Laboratory, Cold Spring Harbor, N.Y.; 1972).

Neidhardt, F. C. et al. Culture medium for enterobacteria. *J. Bacteriol.* 119, 736-747 (1974).

Parasaran, T, et al. Formic Ethylcarbonic Anhydride. The Journal of *Organic Chemistry,* 29(11): 3422-3423 (1964).

Reiling, K. K. et al. Mono and diterpene production in *Escherichia coli. Biotechnol Bioeng* 87 (2004).

Sambrook, J. et al. Molecular cloning: a laboratory manual Edn. 3rd. (Cold Spring Harbor Laboratory Press., Cold Spring Harbor, N.Y.; 2001).

Schrader, J. et al. Biotechnology of Isoprenoids. Vol. 149. Springer, (2015).

Studier, F. W., et al. Use of bacteriophage T7 RNA polymerase to direct selective high-level expression of cloned genes. *J. Mol. Biol.* 189, 113-130 (1986).

Thomason, L. C., et al. Current Protocols in Molecular Biology (John Wiley & Sons, Inc., 2001).

Vick, J. E. et al. *Escherichia coli* enoyl-acyl carrier protein reductase (FabI) supports efficient operation of a functional reversal of the beta-oxidation cycle. *Appl. Environ. Microbiol.* 81, 1406-1416 (2015).

Vick, J. E. et al. Optimized compatible set of BioBrick™ vectors for metabolic pathway engineering. *Appl. Microbiol. Biotechnol.* 92, 1275-1286 (2011).

Yazdani, S. S. et al. Engineering *Escherichia coli* for the efficient conversion of glycerol to ethanol and co-products. *Metab. Eng.* 10, 340-351 (2008).

US20130316413 WO2012109176 61/440,192, Reverse beta oxidation pathway.

US20140273110 WO2013036812 61/531,911 61/440,192, Functionalized carboxylic acids and alcohols by reverse fatty acid oxidation.

WO2015191972 62/011,474, 62/012,113, 62/011,465, 61/531,911, WO2013036812, US20140273110, Omega-carboxylated carboxylic acids and derivatives.

WO2015191422 62/011,465, 62/012,113, 62/011,474, 61/531,911; WO2013036812, Ser. No. 14/199,528, Omega-hydroxylated carboxylic acids.

WO2016007258 62/011,474, 62/012,113, 62/011,465, 61/531,911, WO2013036812, US20140273110, Omega-aminated carboxylic acids.

WO2017020043, BIOSYNTHESIS OF POLYKETIDES, filed Aug. 1, 2016, and 62/198,764, filed Jul. 30, 2015.

U.S. Ser. No. 62/308,937, filed Mar. 16, 2016.

U.S. Ser. No. 62/198,764, filed Jul. 30, 2015.

TABLE A

Example reactions and enzymes of the Claisen condensation platform for the synthesis of isoprenoid precursors

| Reaction | Illustration | EC Numbers | Enzyme names | Source organism and gene/enzyme name | Protein Accession Numbers |
|---|---|---|---|---|---|
| | | | | *Clostridium acetobutylicum* hbd | AAA95971.1 |
| | | | 3-oxoacyl-[acyl-carrier-protein] reductase | *E. coli* fabG | NP_415611.1 |
| beta-hydroxyacyl-CoA → enoyl-CoA | 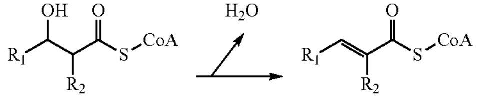 A β-hydroxyacyl-CoA An enoyl-CoA | 4.2.1.17; 4.2.1.119 | enoyl-CoA hydratase | *E. coli* fadB<br>*E. coli* fadJ<br>*E. coli* paaF<br>*P. putida* fadB<br>*P. putida* fadB1x<br>*Acinetobacter* sp. ADP1 dcaE | NP_418288.1<br>NP_416843.1<br>NP_415911.1<br>AAK18167.2<br>AAK18173.1<br>CAG68535.1 |

TABLE A-continued

Example reactions and enzymes of the Claisen condensation platform for the synthesis of isoprenoid precursors

| Reaction | Illustration | EC Numbers | Enzyme names | Source organism and gene/enzyme name | Protein Accession Numbers |
|---|---|---|---|---|---|
| | | | | *Clostridium acetobutylicum* crt | AAA95967.1 |
| | | | | *Aeromonas caviae* phaJ | O32472.1 |
| | | | 3-hydroxyacyl-[acyl-carrier-protein] dehydratase | *E. coli* fabA | NP_415474.1 |
| | | | | *E. coli* fabZ | NP_414722.1 |
| Enoyl-CoA → Acyl-CoA | 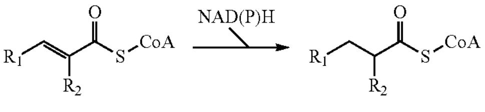 An enoyl-CoA An acyl-CoA | 1.3.1.44 | enoyl-CoA reductase | *Euglena gracilis* TER | Q5EU90.1 |
| | | | | *Treponema denticola* TER | 4GGO_A |
| | | | | *Clostridium acetobutylicum* TER | 4EUH_A |
| | | | enoyl-[acyl-carrier-protein] reductase | *E. coli* fabI | NP_415804.1 |
| | | | | *Enterococcus faecalis* fabK | NP_816503.1 |
| | | | | *Bacillus subtilis* fabL | KFK80655.1 |
| | | | | *Vibrio cholerae* fabV | ABX38717.1 |
| | | | acyl-CoA dehydrogenase | *E. coli* fadE | NP_414756.2 |
| | | | | *E. coli* ydiO | NP_416210.4 |
| Carbon rearrangement (select examples) | 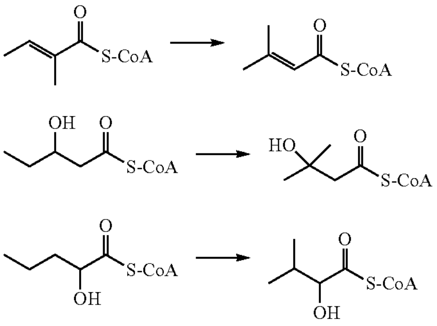 | 5.4.99.- | acyl-CoA mutase | *Streptomyces cinnamonensis* icmAB | AAC08713.1, CAB59633.1 |
| | | | | *Metallosphaera sedula* Msed_0638, Msed_2055 | A4YEG1, A4YIE3 |
| | | | | *Cupriavidus metallidurans* icmF | Q1LRY0 |
| | | | | *Kyrpidia tusciae* rcmAB | D5WTR7, D5WTR8 |
| | | | | *Rhodobacter sphaeroides* meaA | ABA80144.1 |
| | | | | *Clostridium acetobutylicum* hbd | AAA95971.1 |
| | | | 3-oxoacyl-[acyl-carrier-protein] reductase | *E. coli* fabG | NP_415611.1 |

TABLE B

Example termination pathways and enzymes

| Reaction | Illustration | EC Numbers | Enzyme names | Source organism and gene/enzyme name | Protein Accession Numbers |
|---|---|---|---|---|---|
| Acyl-CoA → Carboxylic acid | 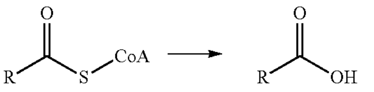 An acyl-CoA A carboxylic acid | 3.1.2.- | Thioesterase | *E. coli* tesA | NP_415027.1 |
| | | | | *E. coli* tesB | NP_414986.1 |
| | | | | *E. coli* yciA | NP_415769.1 |
| | | | | *E. coli* fadM | NP_414977.1 |
| | | | | *E. coli* ydiI | NP_416201.1 |
| | | | | *E. coli* ybgC | NP_415264.1 |
| | | | | *E. coli* paaI | NP_415914.1 |
| | | | | *Mus musculus* acot8 | P58137.1 |
| | | | | *Lycopersicon hirsutum f glabratum* mks2. | ADK38536.1 |
| | | | | *Alcanivorax borkumensis* tesB2 | YP_692749.1 |
| | | | | *Fibrobacter* | YP_005822012.1 |

TABLE B-continued

| Example termination pathways and enzymes | | | | | |
|---|---|---|---|---|---|
| Reaction | Illustration | EC Numbers | Enzyme names | Source organism and gene/enzyme name | Protein Accession Numbers |
| | | | | *succinogenes* Fs2108 | |
| | | | | *Prevotella ruminicola* Pr655 | YP_003574018.1 |
| | | | | *Prevotella ruminicola* Pr1687 | YP_003574982.1 |
| | | 2.8.3.8 | Acyl-CoA:acetyl-CoA transferase | *E. coli* atoD | NP_416725.1 |
| | | | | *Clostridium kluyveri* cat2 | AAA92344.1 |
| | | | | *Clostridium acetobutylicum* ctfAB | NP_149326.1, NP_149327.1 |
| | | | | *E. coli* ydiF | NP_416209.1 |
| | | 2.3.1.-; 2.7.2.1; 2.7.2.15 | Phosphotrans-acylase + Carboxylate kinase | *Clostridium acetobutylicum* ptb | NP_349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| Acyl-CoA → Alcohol | 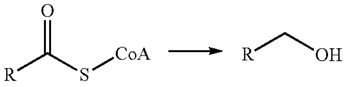 An acyl-CoA An alcohol | 1.2.1.84 | Alcohol-forming CoA reductase | *Clostridium acetobutylicum* adhE2 | YP_009076789.1 |
| | | | | *Arabidopsis thaliana* At3g11980 | AEE75132.1 |
| | | | | *Arabidopsis thaliana* At3g44560 | AEE77915.1 |
| | | | | *Arabidopsis thaliana* At3g56700 | AEE79553.1 |
| | | | | *Arabidopsis thaliana* At5g22500 | AED93034.1 |
| | | | | *Arabidopsis thaliana* CER4 | AEE86278.1 |
| | | | | *Marinobacter aquaeolei* VT8 maqu_2220 | YP_959486.1 |
| | | | | *Marinobacter aquaeolei* VT8 maqu_2507 | YP_959769.1 |
| Acyl-CoA → Aldehyde | 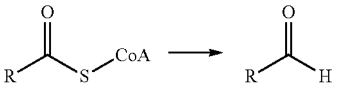 An acyl-CoA An aldehyde | 1.2.1.10 | Aldehyde forming CoA reductase | *Acinetobacter calcoaceticus* acr1 | AAC45217.1 |
| | | | | *Acinetobacter* sp Strain M-1 acrM | BAB85476.1 |
| | | | | *Clostridium beijerinckii* ald | AAT66436.1 |
| | | | | *E. coli* eutE | NP_416950.1 |
| | | | | *Salmonella enterica* eutE | AAA80209.1 |
| | | | | *E. coli* mhpF | NP_414885.1 |
| Carboxylic Acid → Aldehyde | 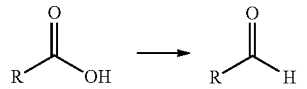 carboxylic acid aldehyde | 1.2.1.- | Carboxylic Acid (Carboxylate) reductase | *E. coli* PaoABC | NP_414820.1, NP_414819.1, NP_414818.1 |
| | | | | *Mycobacterium marinum* Car | WP_012393886.1 |
| | | | | *Nocardia iowensis* Car | AAR91681.1 |
| | | | | *Segniliparus rotundus* Car | WP_013138593.1 |
| Aldehyde → Alcohol | 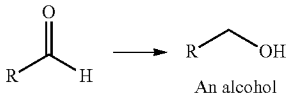 An aldehyde An alcohol | 1.1.1.- | Alcohol dehydrogen-ase | *E. coli* betA | NP_414845.1 |
| | | | | *E. coli* dkgA | NP_417485.4 |
| | | | | *E. coli* eutG | NP_416948.4 |
| | | | | *E. coli* fucO | NP_417279.2 |
| | | | | *E. coli* ucpA | NP_416921.4 |
| | | | | *E. coli* yahK | NP_414859.1 |
| | | | | *E. coli* ybbO | NP_415026.1 |

TABLE B-continued

Example termination pathways and enzymes

| Reaction | Illustration | EC Numbers | Enzyme names | Source organism and gene/enzyme name | Protein Accession Numbers |
|---|---|---|---|---|---|
| | | | | *E. coli* ybdH | NP_415132.1 |
| | | | | *E. coli* yiaY | YP_026233.1 |
| | | | | *E. coli* yjgB | NP_418690.4 |
| | | | | *Acinetobacter* sp. SE19 ChnD | AAG10028.1 |
| | | | | *Marinobacter aquaeolei* VT8 maqu_2507 | YP_959769.1 |
| | | | | *Saccharomyces cerevisiae* ADH6 | Q04894.1 |
| | | | | *Clostridium kluyveri* 4hbD | EDK35022.1 |
| Aldehyde → Alkane | 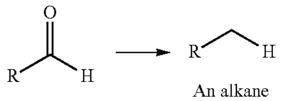<br>An aldehyde An alkane | 4.1.99.5 | Aldehyde decarbonylase | *Synechococcus elongatus* PCC7942 orf1593 | Q54764.1 |
| | | | | *Nostoc punctiforme* PCC73102 npun_R1711 | B2J1M1.1 |
| | | | | *Prochlorococcus marinus* MIT9313 pmt1231 | Q7V6D4.1 |
| Alcohol → Alkenyl | 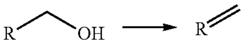 | 4.2.1.- | Dehydratase | *Elizabethkingia meningoseptica* ohyA | GQ144652.1 |
| Alcohol → Phospho | 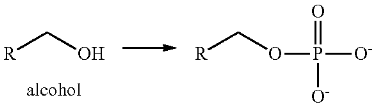<br>alcohol mono-phosphate | 2.7.1.- | Alcohol Kinase/ Phosphotrans-ferase | *Saccharomyces cerevisiae* ERG12 | P07277 |
| | | | | *Saccharomyces cerevisiae* ERG8 | P24521 |
| | | | | *Arabidopsis thaliana* At5g58560 | Q67ZM7 |
| | | | | *Mentha* x *piperita* ipk | P56848 |
| | | | | *Methanocaldococcus jannaschii* mvk | Q58487 |
| | | | | *Arabidopsis thaliana* mvk | AT5G27450.1 |
| | | | | *E. coli* ychB | NP_415726.1 |
| | | | | *E. coli* glpK | P0A6F3 |
| | | | | *Methanothermobacter thermautotrophicus* ipk | AAB84554.1 |
| | | | | *Thermoplasma acidophilum* ipk | WP_010900530.1 |
| | | | | *Methanocaldococcus jannaschii* ipk | 3K4Y_A |
| Phospho → Diphospho | 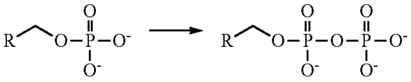<br>mono-phosphate di-phosphate | 2.7.4- | Phosphate Kinase/ Phosphotrans-ferase | *Methanothermobacter thermautotrophicus* ipk | AAB84554.1 |
| | | | | *Thermoplasma acidophilum* ipk | WP_010900530.1 |
| | | | | *Enterococcus faecalis* mvaK2 | Q9FD67 |
| | | | | *Streptococcus pneumoniae* mvaK2 | A0A0I7UH23 |
| | | | | *Staphylococcus aureus* mvaK2 | A0A0E8GDF5 |
| | | | | *Methanocaldococcus jannaschii* ipk | 3K4Y_A |
| Alcohol → Diphospho | 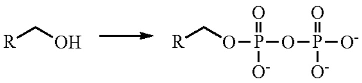 | 2.7.6- | Alcohol diphospho-kinase | *Escherichia coli* Prs | NP_415725.1 |
| | | | | *Mycoplasma pneumoniae* M129 PrsA | NP_109761.1 |
| | | | | *Arabidopsis thaliana* col TPK1 | BAH19964.1 |
| | | | | *Arabidopsis thaliana* col TPK2 | BAH57065.1 |

TABLE B-continued

| Example termination pathways and enzymes | | | | | |
|---|---|---|---|---|---|
| Reaction | Illustration | EC Numbers | Enzyme names | Source organism and gene/enzyme name | Protein Accession Numbers |
| IPP ↔ DMAPP | 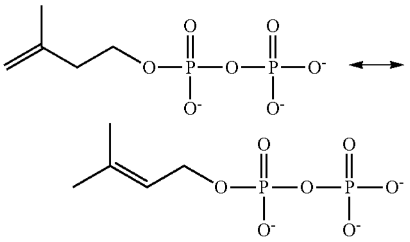 | 5.3.3.2 | isopentenyl diphosphate isomerase | *E. coli* idi | Q46822 |
| 3,5,7-trioxododecanoyl-CoA → olivetolate | 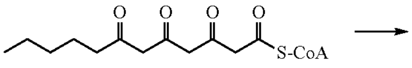 3,5,7-trioxododecanoyl-CoA 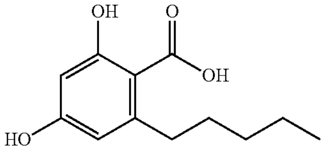 olivetolic acid | 4.4.1.26 | olivetolic acid cyclase | *Cannabis sativa* OAC | I6WU39 |

TABLE C

Example reactions and enzymes of the novel isoprenoid precursor synthesis pathway via 3-hydroxy-3-methylglutaryl-CoA (HMG-CoA) and prenol based on Claisen condensation reactions

| Reaction | Illustration | EC Numbers | Enzyme names | Source organism and gene/enzyme name | Protein Accession Numbers |
|---|---|---|---|---|---|
| 2 acetyl-CoA → acetoacetyl-CoA | 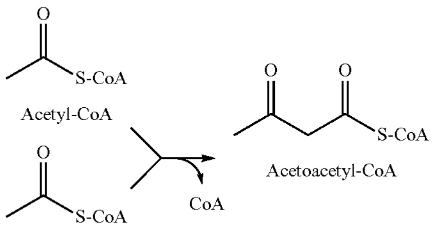 Acetyl-CoA<br>Acetyl-CoA<br>Acetoacetyl-CoA | 2.3.1.- | Thiolase | *E. coli* atoB | NP_416728.1 |
| | | | | *E. coli* yqeF | NP_417321.2 |
| | | | | *E. coli* fadA | YP_026272.1 |
| | | | | *E. coli* fadI | NP_416844.1 |
| | | | | *Ralstonia eutropha* bktB | AAC38322.1 |
| | | | | *Pseudomonas* sp. Strain B13 catF | AAL02407.1 |
| | | | | *E coli* paaJ | NP_415915.1 |
| | | | | *Pseudomonas putida* pcaF | AAA85138.1 |
| | | | | *Rhodococcus opacus* pcaF | YP_002778248.1 |
| | | | | *Streptomyces* sp. pcaF | AAD22035.1 |
| | | | | *Ralstonia eutropha* phaA | AEI80291.1 |
| | | | | *Clostridium acetobutylicum* thIA | AAC26023.1 |
| | | | | *Clostridium acetobutylicum* thIB | AAC26026.1 |
| | | | | *Pseudomonas putida* fadA | AAK18168.1 |
| | | | | *P. putida* fadAx | AAK18171.1 |
| | | | | *Acinetobacter* sp. ADP1 dcaF | CAG68532.1 |
| | | | | *E. coli* paaJ | NP_415915.1 |
| Acetyl-CoA + malonyl-CoA → acetoacetyl-CoA + $CO_2$ | 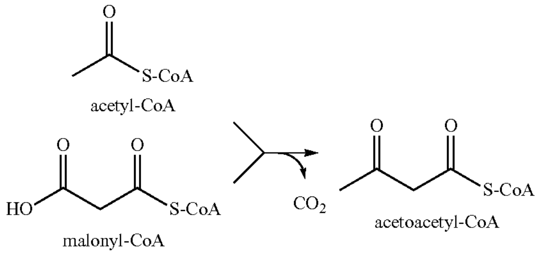 acetyl-CoA<br>malonyl-CoA<br>acetoacetyl-CoA | 2.3.1.- | Ketoacyl-CoA synthase | *Gluconobacter oxydans* GOX0115 | AAW59909.1 |
| | | | | *Pseudomonas aeruginosa* FabH2 | NP_252023.1 |
| | | | | *Streptomyces* sp. MMG1121 PRK09352 | WP_053666104.1 |
| | | | | *Streptomyces tendae* Acs2 | AFS18568.1 |
| | | | | *Streptomyces* sp. strain CL190 NphT7 | BAJ10048.1 |

TABLE C-continued

Example reactions and enzymes of the novel isoprenoid precursor synthesis pathway via 3-hydroxy-3-methylglutaryl-CoA (HMG-CoA) and prenol based on Claisen condensation reactions

| Reaction | Illustration | EC Numbers | Enzyme names | Source organism and gene/enzyme name | Protein Accession Numbers |
|---|---|---|---|---|---|
| | | | | *Physaria fendleri* KCS3 | AAK62348.1 |
| | | | | *Saccharomyces cerevisiae* ELO2 | NP_009963.1 |
| | | | | *Arabidopsis thaliana* col KCS1 | NP_171620.2 |
| | | | | *Arabidopsis thaliana* col FAE1 | NP_195178.1 |
| | | | | *Arabidopsis thaliana* col CER6 | NP_177020.1 |
| Acetoacetyl-CoA + acetyl-CoA → 3-hydroxy-3-methylglutaryl-CoA | 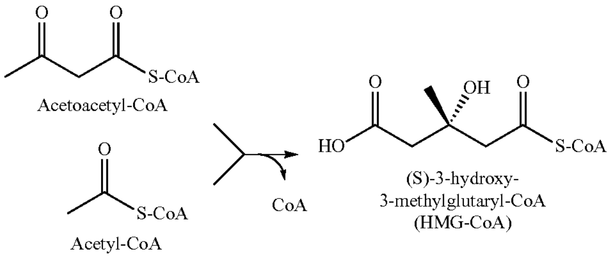  Acetoacetyl-CoA Acetyl-CoA (S)-3-hydroxy-3-methylglutaryl-CoA (HMG-CoA) | 2.3.3.10 | Hydroxymethyl glutaryl-CoA synthase | *Staphylococcus aureus* HMGS | BAU36102.1 |
| | | | | *Saccharomyces cerevisiae* HMGS | NP_013580.1 |
| | | | | *Enterococcus faecalis* mvaS | AAG02438.1 |
| | | | | *Ustilago maydis* hcs1 | KIS66367.1 |
| | | | | *Arabidopsis thaliana* BAP1 | AAD00297.1 |
| | | | | *Homo sapiens* HMGCS1 | NP_001317592.1 |
| | | | | *Homo sapiens* HMGCS2 | NP_001159579. |
| 3-hydroxy-3-methylglutaryl-CoA → 3-methylglutaconyl-CoA | 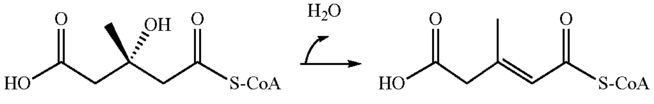  (S)-3-hydroxy-3-methylglutaryl-CoA (HMG-CoA) 3-methylglutaconyl-CoA | 4.2.1.17; 4.2.1.119 | Enoyl-CoA hydratase | *Myxococcus xanthus* liuC | WP_011553770.1 |
| | | | | *E. coli* fadB | NP_418288.1 |
| | | | | *Aeromonas punctata* phaJ | O32472.1 |
| | | | | *E. coli* fadJ | NP_416843.1 |
| | | | | *E. coli* paaF | NP_415911.1 |
| | | | | *P. putida* fadB | AAK18167.2 |
| | | | | *P. putida* fadB1x | AAK18173.1 |
| | | | | *Acinetobacter* sp. ADP1 dcaE | CAG68535.1 |
| | | | | *Clostridium acetobutylicum* crt | AAA95967.1 |
| | | | | *Aeromonas caviae* phaJ | O32472.1 |
| | | | | *E. coli* fabA | NP_415474.1 |
| | | | | *E. coli* fabZ | NP_414722.1 |

TABLE C-continued

Example reactions and enzymes of the novel isoprenoid precursor synthesis pathway via 3-hydroxy-3-methylglutaryl-CoA (HMG-CoA) and prenol based on Claisen condensation reactions

| Reaction | Illustration | EC Numbers | Enzyme names | Source organism and gene/enzyme name | Protein Accession Numbers |
|---|---|---|---|---|---|
| 3-methylglutaconyl-CoA → 3-methyl-2-butenoyl-CoA + $CO_2$ | 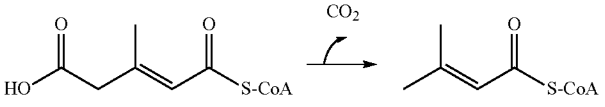 3-methylglutaconyl-CoA; 3-methyl-2-butanoyl-CoA (3-methylcrotonyl-CoA) | 4.1.1.70 | Glutaconyl-CoA decarboxylase | *Myxococcus xanthus* aibAB | WP_011554267.1<br>WP_011554268.1 |
| 3-methyl-2-butenoyl-CoA → 3-methyl-2-butenoate | 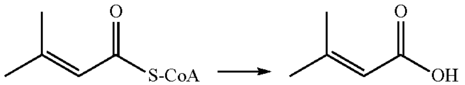 3-methyl-2-butenoyl-CoA; 3-methyl-2-butenoate | 3.1.2.- | Thioesterase | *E. coli* tesA | NP_415027.1 |
| | | | | *E. coli* tesB | NP_414986.1 |
| | | | | *E. coli* yciA | NP_415769.1 |
| | | | | *E. coli* fadM | NP_414977.1 |
| | | | | *E. coli* ydiI | NP_416201.1 |
| | | | | *E. coli* ybgC | NP_415264.1 |
| | | | | *E. coli* paaI | NP_415914.1 |
| | | | | *Mus musculus* acot8 | P58137.1 |
| | | | | *Lycopersicon hirsutum f glabratum* mks2 | ADK38536.1 |
| | | | | *Alcanivorax borkumensis* tesB2 | YP_692749.1 |
| | | | | *Fibrobacter succinogenes* Fs2108 | YP_005822012.1 |
| | | | | *Prevotella ruminicola* Pr655 | YP_003574018.1 |
| | | | | *Prevotella ruminicola* Pr1687 | YP_003574982.1 |
| | | 2.8.3.8 | Acyl-CoA:acetyl-CoA transferase | *E. coli* atoD | NP_416725.1 |
| | | | | *Clostridium kluyveri* cat2 | AAA92344.1 |
| | | | | *Clostridium acetobutylicum* ctfAB | NP_149326.1, NP_149327.1 |
| | | | | *E. coli* ydiF | NP_416209.1 |
| | | 2.3.1.-; 2.7.2.1; 2.7.2.15 | Phosphotransacylase + Carboxylate kinase | *Clostridium acetobutylicum* ptb | NP_349676.1 |
| | | | | *Enterococcus faecalis* ptb | AAD55374.1 |
| | | | | *Salmonella* | AAD39011.1 |

TABLE C-continued

Example reactions and enzymes of the novel isoprenoid precursor synthesis pathway via 3-hydroxy-3-methylglutaryl-CoA (HMG-CoA) and prenol based on Claisen condensation reactions

| Reaction | Illustration | EC Numbers | Enzyme names | Source organism and gene/enzyme name | Protein Accession Numbers |
|---|---|---|---|---|---|
| | | | | *enterica* pduL | |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| 3-methyl-2-butenoate → 3-methyl-2-butenal | 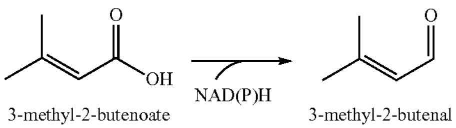 NAD(P)H<br>3-methyl-2-butenoate 3-methyl-2-butenal | 1.2.1.- | Carboxylic Acid (Carboxylate) reductase | *E. coli* PaoABC | NP_414820.1, NP_414819.1, NP_414818.1 |
| | | | | *Mycobacterium marinum* Car | WP_012393886.1 |
| | | | | *Nocardia iowensis* Car | AAR91681.1 |
| | | | | *Segniliparus rotundus* Car | WP_013138593.1 |
| 3-methyl-2-butenoyl-CoA → 3-methyl-2-butenol | 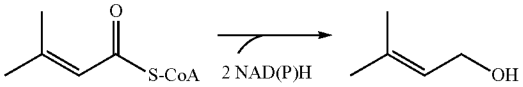 2 NAD(P)H<br>3-methyl-2-butenoyl-CoA 3-methyl-2-butenol (prenol) | 1.2.1.- | Alcohol-forming Acyl-CoA reductase | *Clostridium acetobutylicum* adhE2 | YP_009076789.1 |
| | | | | *Arabidopsis thaliana* At3g11980 | AEE75132.1 |
| | | | | *Arabidopsis thaliana* At3g44560 | AEE77915.1 |
| | | | | *Arabidopsis thaliana* At3g56700 | AEE79553.1 |
| | | | | *Arabidopsis thaliana* At5g22500 | AED93034.1 |
| | | | | *Arabidopsis thaliana* CER4 | AEE86278.1 |
| | | | | *Marinobacter aquaeolei* VT8 maqu_2220 | YP_959486.1 |
| | | | | *Marinobacter aquaeolei* VT8 maqu_2507 | YP_959769.1 |

TABLE C-continued

Example reactions and enzymes of the novel isoprenoid precursor synthesis pathway via 3-hydroxy-3-methylglutaryl-CoA (HMG-CoA) and prenol based on Claisen condensation reactions

| Reaction | Illustration | EC Numbers | Enzyme names | Source organism and gene/enzyme name | Protein Accession Numbers |
|---|---|---|---|---|---|
| 3-methyl-2-butenoyl-CoA → 3-methyl-2-butenol | 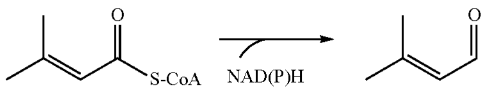 3-methyl-2-butenoyl-CoA 3-methyl-2-butenol | 1.2.1.- | Alcohol-forming Acyl-CoA reductase | *Acinetobacter calcoaceticus* acr1 | AAC45217.1 |
| | | | | *Acinetobacter* sp Strain M-1 acrM | BAB85476.1 |
| | | | | *Clostridium beijerinckii* ald | AAT66436.1 |
| | | | | *E. coli* eutE | NP_416950.1 |
| | | | | *Salmonella enterica* eutE | AAA80209.1 |
| | | | | *E. coli* mhpF | NP_414885.1 |
| 3-methyl-2-butenal → 3-methyl-2-butenol | 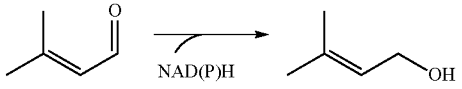 3-methyl-2-butenoyl 3-methyl-2-butenol (prenol) | 1.1.1- | Alcohol dehydro-genase | *E. coli* betA | NP_414845.1 |
| | | | | *E. coli* dkgA | NP_417485.4 |
| | | | | *E. coli* eutG | NP_416948.4 |
| | | | | *E. coli* fucO | NP_417279.2 |
| | | | | *E. coli* ucpA | NP_416921.4 |
| | | | | *E. coli* yahK | NP_414859.1 |
| | | | | *E. coli* ybbO | NP_415026.1 |
| | | | | *E. coli* ybdH | NP_415132.1 |
| | | | | *E. coli* yiaY | YP_026233.1 |
| | | | | *E. coli* yjgB | NP_418690.4 |
| | | | | *Acinetobacter* sp. SE19 ChnD | AAG10028.1 |
| | | | | *Marinobacter aquaeolei* VT8 maqu_2507 | YP_959769.1 |
| | | | | *Saccharomyces cerevisiae* ADH6 | Q04894.1 |
| | | | | *Clostridium kluyveri* 4hbD | EDK35022.1 |
| 3-methyl-2-butenol → dimethyl-allyl phosphate | 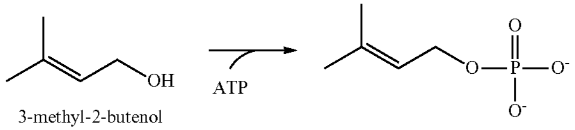 3-methyl-2-butenol (prenol) dimethylallyl phosphate | 2.7.1.- | Alcohol Kinase/ Phospho-trans-ferase | *Saccharomyces cerevisiae* ERG12 | P07277 |
| | | | | *Saccharomyces cerevisiae* ERG8 | P24521 |
| | | | | *Arabidopsis thaliana* | Q67ZM7 |

TABLE C-continued

Example reactions and enzymes of the novel isoprenoid precursor synthesis pathway via 3-hydroxy-3-methylglutaryl-CoA (HMG-CoA) and prenol based on Claisen condensation reactions

| Reaction | Illustration | EC Numbers | Enzyme names | Source organism and gene/enzyme name | Protein Accession Numbers |
|---|---|---|---|---|---|
| | | | | At5g58560 | |
| | | | | *Mentha x piperita* ipk | P56848 |
| | | | | *Methanocaldococcus jannaschii* mvk | Q58487 |
| | | | | *Arabidopsis thaliana* mvk | AT5G27450.1 |
| | | | | *E. coli* ychB | NP_415726.1 |
| | | | | E. coli glpK | P0A6F3 |
| | | | | *Methanothermobacter thermautotrophicus* ipk | AAB84554.1 |
| | | | | *Thermoplasma acidophilum* ipk | WP_010900530.1 |
| | | | | *Methanocaldococcus jannaschii* ipk | 3K4Y_A |
| dimethylallyl phosphate → dimethylallyl pyrophosphate | 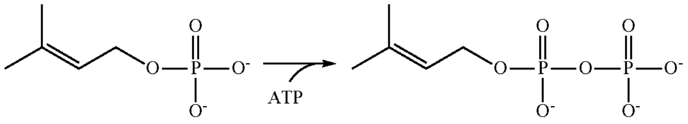 dimethylallyl phosphate dimethylallyl pyrophosphate | 2.7.4- | Phosphate Kinase/ Phosphotransferase | *Methanothermobacter thermautotrophicus* ipk | AAB84554.1 |
| | | | | *Thermoplasma acidophilum* ipk | WP_010900530.1 |
| | | | | *Enterococcus faecalis* mvaK2 | Q9F067 |
| | | | | *Streptococcus pneumoniae* mvaK2 | A0A0I7UH23 |
| | | | | *Staphylococcus aureus* mvaK2 | A0A0E8GDF5 |
| | | | | *Methanocaldococcus jannaschii* ipk | 3K4Y_A |

TABLE C-continued

Example reactions and enzymes of the novel isoprenoid precursor synthesis pathway via 3-hydroxy-3-methylglutaryl-CoA (HMG-CoA) and prenol based on Claisen condensation reactions

| Reaction | Illustration | EC Numbers | Enzyme names | Source organism and gene/enzyme name | Protein Accession Numbers |
|---|---|---|---|---|---|
| 3-methyl-2-butenol → dimethylallyl pyrophos-phate | 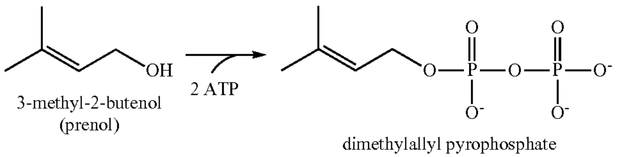 3-methyl-2-butenol (prenol) dimethylallyl pyrophosphate | 2.7.6- | Alcohol diphos-phokinase | *Escherichia coli* Prs<br>*Mycoplasma pneumoniae* M129 PrsA<br>*Arabidopsis thaliana* col TPK1<br>*Arabidopsis thaliana* col TPK2 | NP_415725.1<br>NP_109761.1<br>BAH19964.1<br>BAH57065.1 |
| DMAPP ↔ IPP | 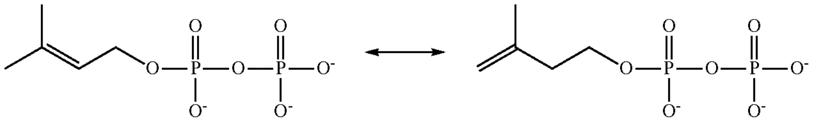 dimethylallyl pyrophosphate Isopentenyl pyrophosphate | 5.3.3.2 | iso-pentenyl diphos-phate isomerase | *E. coli* idi | Q46822 |
| DMAPP + IPP → GPP | 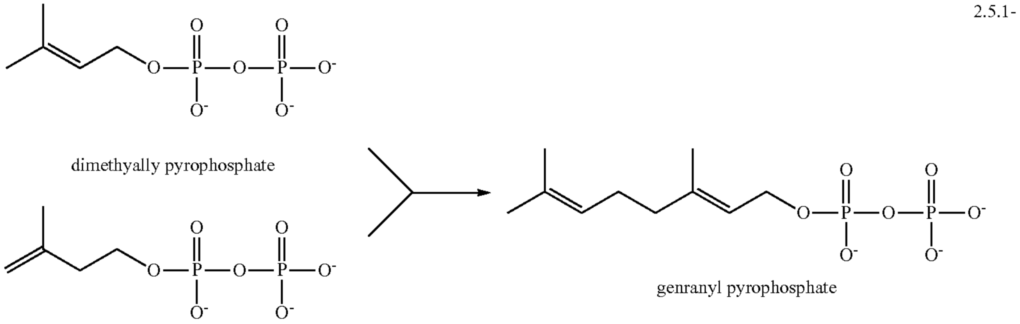 dimethyally pyrophosphate Isopentenyl pyrophosphate genranyl pyrophosphate | 2.5.1- | Geranyl pyrophos-phate synthase | *E. coli* ispA<br>*Abies grandis* GPPS2 | P22939<br>Q8LKJ2 |

TABLE D

Example reactions and enzymes of the novel isoprenoid precursor synthesis pathway via 3-hydroxy-3-methylbutyryl-CoA and prenol based on Claisen condensation reactions

| Reaction | Illustration | EC Numbers | Enzyme names | Source organism and gene/enzyme name | Protein Accession Numbers |
|---|---|---|---|---|---|
| 2 acetyl-CoA → acetoacetyl-CoA | 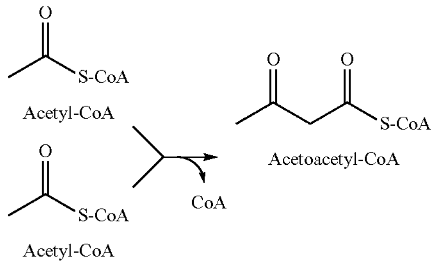 | 2.3.1.- | Thiolase | *E. coli* atoB<br>*E. coli* yqeF<br>*E. coli* fadA<br>*E. coli* fadI<br>*Ralstonia eutropha* bktB<br>*Pseudomonas* sp. Strain B13 catF<br>*E coli* paaJ<br>*Pseudomonas putida* pcaF<br>*Rhodococcus opacus* pcaF<br>*Streptomyces* sp. pcaF<br>*Ralstonia eutropha* phaA<br>*Clostridium acetobutylicum* thlA<br>*Clostridium acetobutylicum* thlB<br>*Pseudomonas putida* fadA<br>*P. putida* fadAx<br>*Acinetobacter* sp. ADP1 dcaF<br>*E. coli* paaJ | NP_416728.1<br>NP_417321.2<br>YP_026272.1<br>NP_416844.1<br>AAC38322.1<br>AAL02407.1<br>NP_415915.1<br>AAA85138.1<br>YP_002778248.1<br>AAD22035.1<br>AEI80291.1<br>AAC26023.1<br>AAC26026.1<br>AAK18168.1<br>AAK18171.1<br>CAG68532.1<br>NP_415915.1 |
| Acetyl-CoA + malonyl-CoA → acetoacetyl-CoA + $CO_2$ | 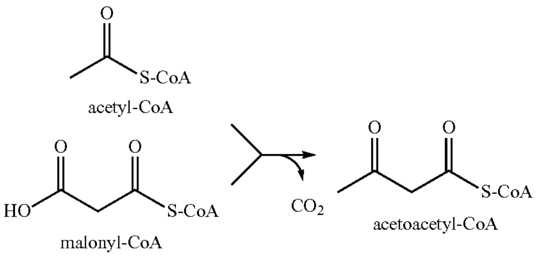 | 2.3.1.- | Ketoacyl-CoA synthase | *Gluconobacter oxydans* GOX0115<br>*Pseudomonas aeruginosa* FabH2<br>*Streptomyces* sp. MMG1121 PRK09352<br>*Streptomyces tendae* Acs2<br>*Streptomyces* sp. strain CL190 | AAW59909.1<br>NP_252023.1<br>WP_053666104.1<br>AFS18568.1<br>BAJ10048.1 |

TABLE D-continued

Example reactions and enzymes of the novel isoprenoid precursor synthesis pathway via 3-hydroxy-3-methylbutyryl-CoA and prenol based on Claisen condensation reactions

| Reaction | Illustration | EC Numbers | Enzyme names | Source organism and gene/enzyme name | Protein Accession Numbers |
|---|---|---|---|---|---|
| | | | | NphT7 | |
| | | | | *Physaria fendleri* KCS3 | AAK62348.1 |
| | | | | *Saccharomyces cerevisiae* ELO2 | NP_009963.1 |
| | | | | *Arabidopsis thaliana* col KCS1 | NP_171620.2 |
| | | | | *Arabidopsis thaliana* col FAE1 | NP_195178.1 |
| | | | | *Arabidopsis thaliana* col CER6 | NP_177020.1 |
| Acetoacetyl-CoA → Acetoacetic acid + CoA | 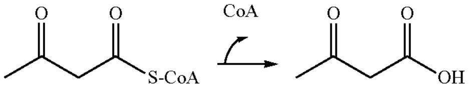 Acetoacetyl-CoA Acetoacetic acid | 3.1.2.- | Thioes-terase | *E. coli* tesA | NP_415027.1 |
| | | | | *E. coli* tesB | NP_414986.1 |
| | | | | *E. coli* yciA | NP_415769.1 |
| | | | | *E. coli* fadM | NP_414977.1 |
| | | | | *E. coli* ydiI | NP_416201.1 |
| | | | | *E. coli* ybgC | NP_415264.1 |
| | | | | *E. coli* paaI | NP_415914.1 |
| 3-methyl-2-butenoyl-CoA → 3-methyl-2-butenoate | 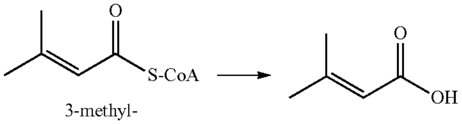 3-methyl-2-butenoyl-CoA 3-methyl-2-butenoate | | | *Mus musculus* acot8 | P58137.1 |
| | | | | *Lycopersicon hirsutum f glabratum* mk52 | ADK38536.1 |
| | | | | *Alcanivorax borkumensis* tesB2 | YP_692749.1 |
| | | | | *Fibrobacter succinogenes* Fs2108 | YP_005822012.1 |
| | | | | *Prevotella ruminicola* Pr655 | YP_003574018.1 |
| | | | | *Prevotella ruminicola* Pr1687 | YP_003574982.1 |
| | | 2.8.3- | CoA trans-ferase | *E. coli* atoD | NP_416725.1 |
| | | | | *E. coli* atoA | NP_416726.1 |
| | | | | *E. coli* scpC | NP_417395.1 |
| | | | | *Clostridium kluyveri* cat1 | AAA92346.1 |
| | | | | *Clostridium kluyveri* cat2 | AAA92344.1 |
| | | | | *Clostridium acetobutylicum* | NP_149326.1, NP_149327.1 |

TABLE D-continued

Example reactions and enzymes of the novel isoprenoid precursor synthesis pathway via 3-hydroxy-3-methylbutyryl-CoA and prenol based on Claisen condensation reactions

| Reaction | Illustration | EC Numbers | Enzyme names | Source organism and gene/enzyme name | Protein Accession Numbers |
|---|---|---|---|---|---|
| | | | | ctfAB | |
| | | | | *Pseudomonas putida* pcaIJ | NP_746081.1<br>NP_746082.1 |
| | | | | *Megasphaera elsdenii* pct | WP_014015705.1 |
| | | | | *Acidaminococcus fermentans* gctAB | CAA57199.1<br>CAA57200.1 |
| | | | | *Acetobacter aceti* aarC | AGG68319.1 |
| | | | | *E. coli* ydiF | NP_416209.1 |
| | | 2.3.1.-;<br>2.7.2.1;<br>2.7.2.15 | Phos-photrans-acylase + Carbox-ylate kinase | *Clostridium acetobutylicum* ptb | NP_349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| Acetoacetic acid → acetone + $CO_2$ | 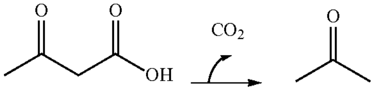<br>Acetoacetic acid Acetone | 4.1.1.56; | Decar-boxylase | *Lycopersicon hirsutum f glabratum* mks1 | ADK38535.1 |
| | | | | *Clostridium acetobutylicum* adc | AAA63761.1 |
| Acetone + acetyl-CoA → 3-hydroxy-3-methylbutyryl-CoA | 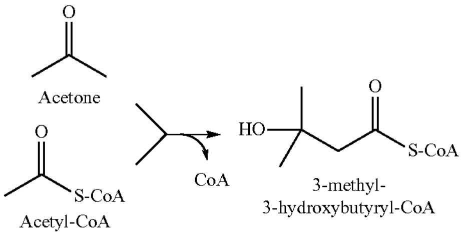<br>Acetone<br>Acetyl-CoA<br>3-methyl-3-hydroxybutyryl-CoA | 2.3.3.- | Hydrox-ymethyl butyryl-CoA synthase | *Staphylococcus aureus* HMGS | BAU36102.1 |
| | | | | *Saccharomyces cerevisiae* HMGS | NP_013580.1 |
| | | | | *Enterococcus aecalis* mvaS | AAG02438.1 |
| | | | | *Ustilago maydis* hcs1 | KIS66367.1 |
| | | | | *Arabidopsis thaliana* BAP1 | AAD00297.1 |
| | | | | *Homo sapiens* HMGCS1 | NP_001317592.1 |
| | | | | *Homo sapiens* HMGCS2 | NP_001159579. |

TABLE D-continued

Example reactions and enzymes of the novel isoprenoid precursor synthesis pathway via 3-hydroxy-3-methylbutyryl-CoA and prenol based on Claisen condensation reactions

| Reaction | Illustration | EC Numbers | Enzyme names | Source organism and gene/enzyme name | Protein Accession Numbers |
|---|---|---|---|---|---|
| 3-hydroxy-3-methylbutyryl-CoA → 3-methyl-2-butenoyl-CoA | 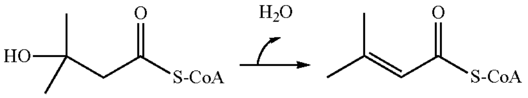 | 4.2.1.17; 4.2.1.119 | Enoyl-CoA hydratase | *Myxococcus xanthus* liuC | WP_011553770.1 |
| | | | | *E. coli* fadB | NP_418288.1 |
| | | | | *Aeromonas punctata* phaJ | O32472.1 |
| | | | | *E. coli* fadJ | NP_416843.1 |
| | | | | *E. coli* paaF | NP_415911.1 |
| | | | | *P. putida* fadB | AAK18167.2 |
| | | | | *P. putida* fadB1x | AAK18173.1 |
| | | | | *Acinetobacter* sp. ADP1 dcaE | CAG68535.1 |
| | | | | *Clostridium acetobutylicum* crt | AAA95967.1 |
| | | | | *Aeromonas caviae* phaJ | O32472.1 |
| | | | | *E. coli* fabA | NP_415474.1 |
| | | | | *E. coli* fabZ | NP_414722.1 |
| 3-methyl-2-butenoate → 3-methyl-2-butenal | 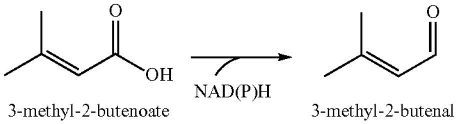 3-methyl-2-butenoate 3-methyl-2-butenal | 1.2.1.- | Carboxylic Acid (Carboxylate) reductase | *E. coli* PaoABC | NP_414820.1, NP_414819.1, NP_414818.1 |
| | | | | *Mycobacterium marinum* Car | WP_012393886.1 |
| | | | | *Nocardia iowensis* Car | AAR91681.1 |
| | | | | *Segniliparus rotundus* Car | WP_013138593.1 |
| 3-methyl-2-butenoyl-CoA → 3-methyl-2-butenol | 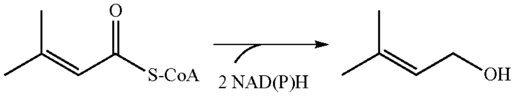 3-methyl-2-butenoyl-CoA 3-methyl-2-butenol (prenol) | 1.2.1.- | Alcohol-forming Acyl-CoA reductase | *Clostridium acetobutylicum* adhE2 | YP_009076789.1 |
| | | | | *Arabidopsis thaliana* At3g11980 | AEE75132.1 |
| | | | | *Arabidopsis thaliana* At3g44560 | AEE77915.1 |
| | | | | *Arabidopsis thaliana* At3g56700 | AEE79553.1 |
| | | | | *Arabidopsis thaliana* At5g22500 | AED93034.1 |
| | | | | *Arabidopsis thaliana* CER4 | AEE86278.1 |
| | | | | *Marinobacter aquaeolei* VT8 maqu_2220 | YP_959486.1 |
| | | | | *Marinobacter aquaeolei* VT8 | YP_959769.1 |

TABLE D-continued

Example reactions and enzymes of the novel isoprenoid precursor synthesis pathway via 3-hydroxy-3-methylbutyryl-CoA and prenol based on Claisen condensation reactions

| Reaction | Illustration | EC Numbers | Enzyme names | Source organism and gene/enzyme name | Protein Accession Numbers |
|---|---|---|---|---|---|
| | | | | maqu_2507 | |
| 3-methyl-2-butenoyl-CoA → 3-methyl-2-butenal | 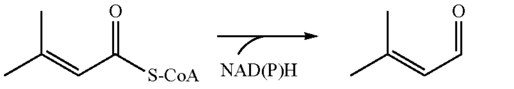 3-methyl-2-butenoyl-CoA; 3-methyl-2-butenal | 1.2.1.- | Aldehyde forming CoA reductase | *Acinetobacter calcoaceticus* acr1 | AAC45217.1 |
| | | | | *Acinetobacter* sp Strain M-1 acrM | BAB85476.1 |
| | | | | *Clostridium beijerinckii* ald | AAT66436.1 |
| | | | | *E. coli* eutE | NP_416950.1 |
| | | | | *Salmonella enterica* eutE | AAA80209.1 |
| | | | | *E. coli* mhpF | NP_414885.1 |
| 3-methyl-2-butenal → 3-methyl-2-butenol | 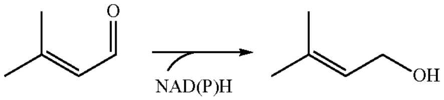 3-methyl-2-butenal; 3-methyl-2-butenol (prenol) | 1.1.1.- | Alcohol dehydrogenase | *E. coli* betA | NP_414845.1 |
| | | | | *E. coli* dkgA | NP_417485.4 |
| | | | | *E. coli* eutG | NP_416948.4 |
| | | | | *E. coli* fucO | NP_417279.2 |
| | | | | *E. coli* ucpA | NP_416921.4 |
| | | | | *E. coli* yahK | NP_414859.1 |
| | | | | *E. coli* ybbO | NP_415026.1 |
| | | | | *E. coli* ybdH | NP_415132.1 |
| | | | | *E. coli* yiaY | YP_026233.1 |
| | | | | *E. coli* yjgB | NP_418690.4 |
| | | | | *Acinetobacter* sp. SE19 ChnD | AAG10028.1 |
| | | | | *Marinobacter aquaeolei* VT8 maqu_2507 | YP_959769.1 |
| | | | | *Saccharomyces cerevisiae* ADH6 | Q04894.1 |
| | | | | *Clostridium kluyveri* 4hbD | EDK35022.1 |
| 3-methyl-2-butenol → dimethylallyl phosphate | 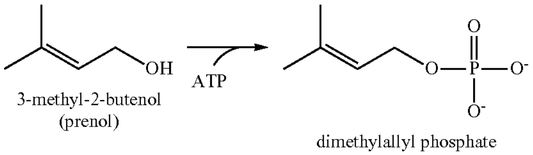 3-methyl-2-butenol (prenol); dimethylallyl phosphate | 2.7.1.- | Alcohol Kinase/Phosphotransferase | *Saccharomyces cerevisiae* ERG12 | P07277 |
| | | | | *Saccharomyces cerevisiae* ERG8 | P24521 |
| | | | | *Arabidopsis thaliana* At5g58560 | Q67ZM7 |
| | | | | *Mentha x piperita* ipk | P56848 |
| | | | | *Methanocaldococcus jannaschii* mvk | Q58487 |
| | | | | *Arabidopsis thaliana* mvk | AT5G27450.1 |

TABLE D-continued

Example reactions and enzymes of the novel isoprenoid precursor synthesis pathway via 3-hydroxy-3-methylbutyryl-CoA and prenol based on Claisen condensation reactions

| Reaction | Illustration | EC Numbers | Enzyme names | Source organism and gene/enzyme name | Protein Accession Numbers |
|---|---|---|---|---|---|
| | | | | *E. coli* ychB<br>*E. coli* glpK<br>*Methanothermobacter thermautotrophicus* ipk<br>*Thermoplasma acidophilum* ipk<br>*Methanocaldococcus jannaschii* ipk | NP_415726.1<br>P0A6F3<br>AAB84554.1<br>WP_010900530.1<br>3K4Y_A |
| dimethylallyl phosphate → dimethylallyl pyrophosphate | 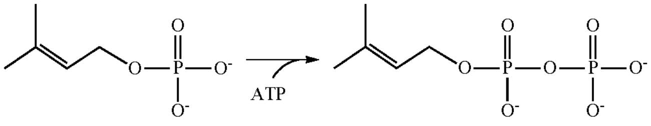 dimethylaoyl phosphate; dimethylallyl pyrophosphate | 2.7.4- | Phosphate Kinase/ Phosphotransferase | *Methanothermobacter thermautotrophicus* ipk<br>*Thermoplasma acidophilum* ipk<br>*Enterococcus faecalis* mvaK2<br>*Streptococcus pneumoniae* mvaK2<br>*Staphylococcus aureus* mvaK2<br>*Methanocaldococcus jannaschii* ipk | AAB84554.1<br>WP_010900530.1<br>Q9F067<br>A0A0I7UH23<br>A0A0E8GDF5<br>3K4Y_A |
| 3-methyl-2-butenol → dimethylallyl pyrophosphate | 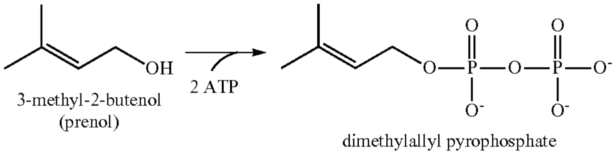 3-methyl-2-butenol (prenol); dimethylallyl pyrophosphate | 2.7.6- | Alcohol diphosphokinase | *Escherichia coli* Prs<br>*Mycoplasma pneumoniae* M129 PrsA<br>*Arabidopsis thaliana* col TPK1<br>*Arabidopsis thaliana* col TPK2 | NP_415725.1<br>NP_109761.1<br>BAH19964.1<br>BAH57065.1 |
| DMAPP ↔ IPP | 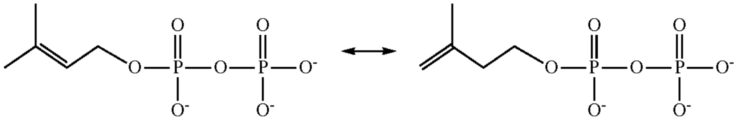 dimethylallyl pyrophosphate; isopentenyl pyrophosphate | 5.3.3.2 | isopentenyl diphosphate isomerase | *E. coli* idi | Q46822 |

TABLE D-continued

Example reactions and enzymes of the novel isoprenoid precursor synthesis pathway via 3-hydroxy-3-methylbutyryl-CoA and prenol based on Claisen condensation reactions

| Reaction | Illustration | EC Numbers | Enzyme names | Source organism and gene/enzyme name | Protein Accession Numbers |
| --- | --- | --- | --- | --- | --- |
| DMAPP + IPP → GPP | 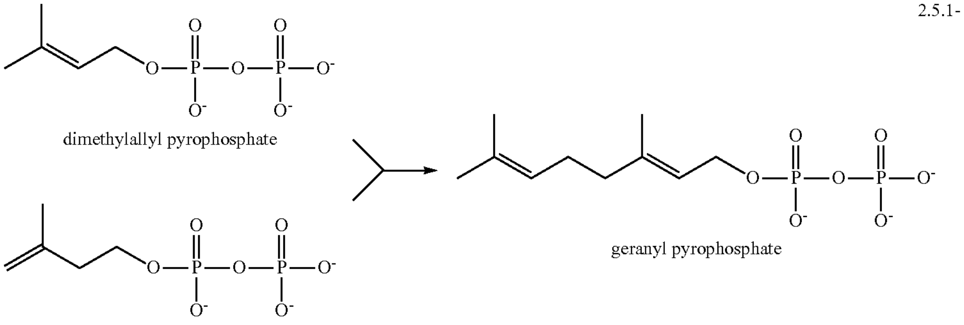 dimethylallyl pyrophosphate; isopentenyl pyrophosphate; geranyl pyrophosphate | 2.5.1- | Geranyl pyrophos-phate synthase | *E. coli* ispA<br>*Abies grandis* GPPS2 | P22939<br>Q8LKJ2 |

TABLE E

Example reactions and enzymes of the pathway for isoprenoid precursor synthesis based on acyloin condensation via 2-hydroxyisovaleric acid and prenol through utilization of 2-hydroxyacid/2-hydroxyacyl-CoA dehydratase

| Reaction | Illustration | EC Numbers | Enzyme names | Source organism and gene/enzyme name | Protein Accession Numbers |
|---|---|---|---|---|---|
| 2 pyruvate → acetolactate | 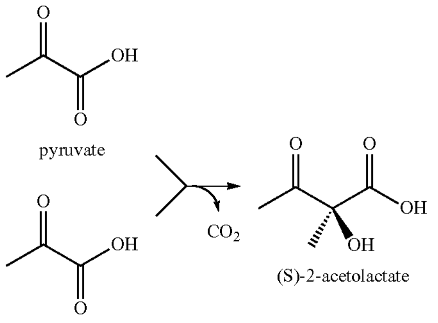 pyruvate, pyruvate, (S)-2-acetolactate | 2.2.1.6 | Aceto-lactate synthase | *E. coli* ilvBN<br>*E. coli* ilvH<br>*B. subtilis* alsS | P08142, P0ADF8<br>P00893, P00894<br>Q04789 |
| aceto-lactate → 2,3-dihydroxy-3-meth-ylbutanoate | 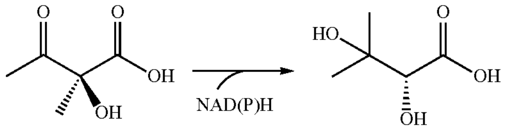 (S)-2-acetolactate, (2R)-2,3-dihydroxy-3-methylbutanoate | 1.1.1.86 | Acetohy-droxy acid isomerore-ductase | *E. coli* ilvC | P05793 |
| 2,3-dihydroxy-3-methylbu-tanoate → 3-methyl-2-oxobu-tanoate | 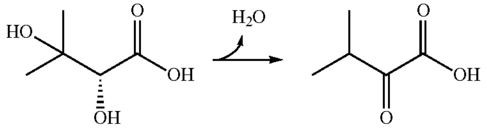 (2R)-2,3-dihydroxy-3-methylbutanoate, 3-methyl-2-oxobutanoate | 4.2.1.9 | Dihydrox-yacid dehy-dratase | *E. coli* ilvD | P05791 |

TABLE E-continued

Example reactions and enzymes of the pathway for isoprenoid precursor synthesis based on acyloin condensation via 2-hydroxyisovaleric acid and prenol through utilization of 2-hydroxyacid/2-hydroxyacyl-CoA dehydratase

| Reaction | Illustration | EC Numbers | Enzyme names | Source organism and gene/enzyme name | Protein Accession Numbers |
|---|---|---|---|---|---|
| 3-methyl-2-oxobutanoate → 3-methyl-2-hydroxybutanoate | 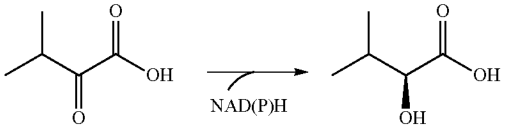 3-methyl-2-oxobutanoate 3-methyl-2-hydroxybutanoate | 1.1.1.- | 2-hydroxyacid dehydrogenase | *Acidaminococcus fermentans* hgdH<br>*Methanocaldococcus jannaschii* mdh<br>*M. jannaschii* comC<br>*E. coli* mdh<br>*E. coli* serA<br>*E. coli* ldhA<br>*Haloferax mediterranei* ddh<br>*Lactococcus lactis* panE | D2RMS7<br>Q60176<br>Q58820<br>P61889<br>P0A9T0<br>P52643<br>Q2VEQ7<br>A0A089XK51 |
| 3-methyl-2-hydroxybutanoate → 3-methyl-2-butenoate | 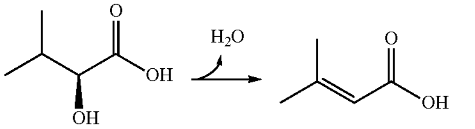 3-methyl-2-hydroxybutanoate 3-methyl-2-butenoate | 4.2.1.- | 2-hydroxyacid dehydratase | *E. coli* fumA<br>*E. coli* fumB<br>*E. coli* fumC | P0AC33<br>P14407<br>P05042 |
| | | 4.2.1- | 2-hydroxyacyl-CoA dehydratase | *Acidaminococcus fermentans* hgdCAB<br>*Clostridium symbiosum* hgdCAB<br>*Fusobacterium nucleatum* hgdCAB<br>*Peptoclostridium difficile* hadIBC<br>*Clostridium propionicum* lcdCAB | P11568, P11569, P11570,<br>Q9X5B6, Q9X5B7, Q9X5B8,<br>A5TT16, A5TT17, A5TT18,<br>AAV40818.1, AAV40819.1, AAV40820.1<br>G3KIM3, G3KIM4, G3KIM5 |

TABLE E-continued

Example reactions and enzymes of the pathway for isoprenoid precursor synthesis based on acyloin condensation via 2-hydroxyisovaleric acid and prenol through utilization of 2-hydroxyacid/2-hydroxyacyl-CoA dehydratase

| Reaction | Illustration | EC Numbers | Enzyme names | Source organism and gene/enzyme name | Protein Accession Numbers |
|---|---|---|---|---|---|
| 3-methyl-2-hydroxybutanoate → 3-methyl-2-hydroxybutanoyl-CoA | 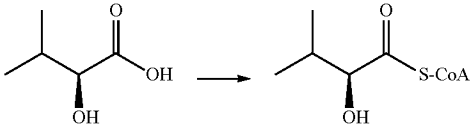 3-methyl-2-hydroxybutanoate 3-methyl-2-hydroxybutanoyl-CoA | 6.2.1.- | Acyl-CoA synthetase | *E. coli* paaK | NP_415916.1 |
| | | | | *E. coli* sucCD | NP_415256.1 NP_415257.1 |
| | | | | *E. coli* fadK | NP_416216.4 |
| | | | | *E. coli* fadD | NP_416319.1 |
| | | | | *E. coli* prpE | NP_414869.1 |
| | | | | *E. coli* menE | NP_416763.1 |
| | | | | *Penicillium chrysogenum* phl | CAJ15517.1 |
| | | | | *Salmonella typhimurium* LT2 prpE | AAL19325.1 |
| 3-methyl-2-butenoate → 3-methyl-2-butenoyl-CoA | 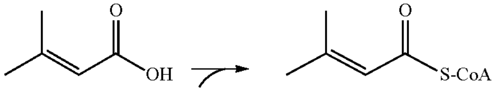 3-methyl-2-butanoate (3-methylcrotonate) CoA 3-methyl-2-butenoyl-CoA | | | *Bacillus subtilis* bioW | AAC00261.1 |
| | | | | *Cupriavidus basilensis* hmfD | ADE20402.1 |
| | | | | *Rhodopseudo-monas palustris* badA | CAJ18317.1 |
| | | | | *R. palustris* hbaA | CAE26113.1 |
| | | | | *Pseudomonas aeruginosa* PAO1 pqsA | NP_249687.1 |
| | | | | *Arabidopsis thaliana* 4cl | Q42524.1 |
| | | 2.8.3- | CoA transferase | *E. coli* atoD | NP_416725.1 |
| | | | | *E. coli* atoA | NP_416726.1 |
| | | | | *E. coli* scpC | NP_417395.1 |
| | | | | *Clostridium kluyveri* cat1 | AAA92346.1 |
| | | | | *Clostridium kluyveri* cat2 | AAA92344.1 |
| | | | | *Clostridium acetobutylicum* ctfAB | NP_149326.1, NP_149327.1 |
| | | | | *Pseudomonas putida* pcaIJ | NP_746081.1 NP_746082.1 |
| | | | | *Megasphaera elsdenii* pct | WP_014015705.1 |
| | | | | *Acidaminococcus fermentans* gctAB | CAA57199.1 CAA57200.1 |
| | | | | *Acetobacter aceti* aarC | AGG68319.1 |
| | | | | *E. coli* ydiF | NP_416209.1 |

TABLE E-continued

Example reactions and enzymes of the pathway for isoprenoid precursor synthesis based on acyloin condensation via 2-hydroxyisovaleric acid and prenol through utilization of 2-hydroxyacid/2-hydroxyacyl-CoA dehydratase

| Reaction | Illustration | EC Numbers | Enzyme names | Source organism and gene/enzyme name | Protein Accession Numbers |
|---|---|---|---|---|---|
| | | | | *Clostridium propionicum* Pct540 | CAB77207.1 |
| | | 2.3.1.-; 2.7.2.- | Carboxylate kinase + Phosphotrans-acylase | *Clostridium acetobutylicum* ptb | NP_349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| 3-methyl-2-hydroxybutanoyl-CoA → 3-methyl-2-butenoyl-CoA | 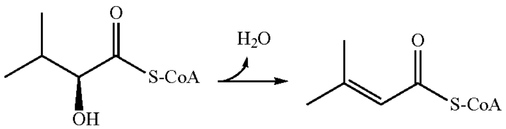 3-methyl-2-hydroxybutanoyl-CoA 3-methyl-2-butenoyl-CoA | 4.2.1- | 2-hydroxyacyl-CoA dehydratase | *Acidaminococcus fermentans* hgdCAB | P11568, P11569, P11570, |
| | | | | *Clostridium symbiosum* hgdCAB | Q9X5B6, Q9X5B7, Q9X5B8, |
| | | | | *Fusobacterium nucleatum* hgdCAB | A5TT16, A5TT17, A5TT18, |
| | | | | *Peptoclostridium difficile* hadIBC | AAV40818.1, AAV40819.1, AAV40820.1 |
| | | | | *Clostridium propionicum* lcdCAB | G3KIM3, G3KIM4, G3KIM5 |

TABLE E-continued

Example reactions and enzymes of the pathway for isoprenoid precursor synthesis based on acyloin condensation via 2-hydroxyisovaleric acid and prenol through utilization of 2-hydroxyacid/2-hydroxyacyl-CoA dehydratase

| Reaction | Illustration | EC Numbers | Enzyme names | Source organism and gene/enzyme name | Protein Accession Numbers |
|---|---|---|---|---|---|
| 3-methyl-2-butenoyl-CoA → 3-methyl-2-butenoate | 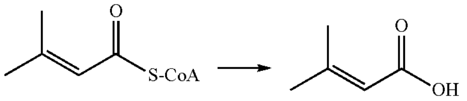 3-methyl-2-butenoyl-CoA 3-methyl-2-butenoate | 3.1.2.- | Thioesterase | *E. coli* tesA | NP_415027.1 |
| | | | | *E. coli* tesB | NP_414986.1 |
| | | | | *E. coli* yciA | NP_415769.1 |
| | | | | *E. coli* fadM | NP_414977.1 |
| | | | | *E. coli* ydiI | NP_416201.1 |
| | | | | *E. coli* ybgC | NP_415264.1 |
| | | | | *E. coli* paaI | NP_415914.1 |
| 3-methyl-2-hydroxybutanoyl-CoA → 3-methyl-2-hydroxybutanoate | 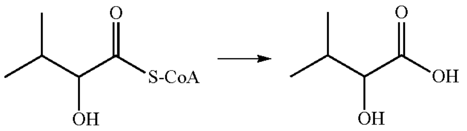 3-methyl-2-hydroxybutanoyl-CoA 3-methyl-2-hydroxybutanoate | | | *Mus musculus* acot8 | P58137.1 |
| | | | | *Lycopersicon hirsutum f glabratum* mks2 | ADK38536.1 |
| | | | | *Alcanivorax borkumensis* tesB2 | YP_692749.1 |
| | | | | *Fibrobacter succinogenes* Fs2108 | YP_005822012.1 |
| | | | | *Prevotella ruminicola* Pr655 | YP_003574018.1 |
| | | | | *Prevotella ruminicola* Pr1687 | YP_003574982.1 |
| | | 2.8.3.8 | Acyl-CoA:acyl-CoA transferase | *E. coli* atoD | NP_416725.1 |
| | | | | *Clostridium kluyveri* cat2 | AAA92344.1 |
| | | | | *Clostridium acetobutylicum* ctfAB | NP_149326.1, NP_149327.1 |
| | | | | *E. coli* ydiF | NP_416209.1 |
| | | 2.3.1.-; 2.7.2.1; 2.7.2.15 | Phosphotransacylase + Carboxylate kinase | *Clostridium acetobutylicum* ptb | NP_349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |

TABLE E-continued

Example reactions and enzymes of the pathway for isoprenoid precursor synthesis based on acyloin condensation via 2-hydroxyisovaleric acid and prenol through utilization of 2-hydroxyacid/2-hydroxyacyl-CoA dehydratase

| Reaction | Illustration | EC Numbers | Enzyme names | Source organism and gene/enzyme name | Protein Accession Numbers |
|---|---|---|---|---|---|
| | | | | *Enterococcus faecalis* buk<br>*Salmonella enterica* pduW | AAD55375.1<br>AAD39021.1 |
| 3-methyl-2-butenoate → 3-methyl-2-butenal | 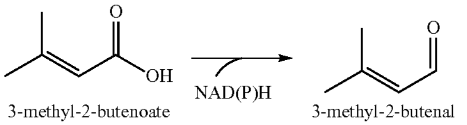 3-methyl-2-butenoate 3-methyl-2-butenal | 1.2.1.- | Carbox-ylic Acid (Carbox-ylate) reductase | *E. coli* PaoABC<br>*Mycobacterium marinum* Car<br>*Nocardia iowensis* Car<br>*Segniliparus rotundus* Car | NP_414820.1, NP_414819.1, NP_414818.1<br>WP_012393886.1<br>AAR91681.1<br>WP_013138593.1 |
| 3-methyl-2-hydrox-ybu-tanoate → 3-methyl-2-hydrox-ybutanal | 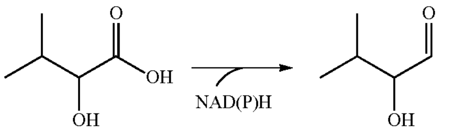 3-methyl-2-hydroxybutanoate 3-methyl-2-hydroxybutanal | | | | |
| 3-methyl-2-butenoyl-CoA → 3-methyl-2-butenol | 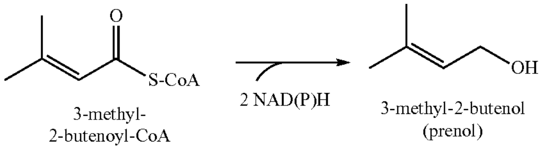 3-methyl-2-butenoyl-CoA 3-methyl-2-butenol (prenol) | 1.2.1.- | Alcohol-forming Acyl-CoA reductase | *Clostridium acetobutylicum* adhE2<br>*Arabidopsis thaliana* At3g11980<br>*Arabidopsis thaliana* At3g44560<br>*Arabidopsis thaliana* At3g56700<br>*Arabidopsis thaliana* At5g22500<br>*Arabidopsis thaliana* CER4<br>*Marinobacter aquaeolei* VT8 maqu_2220<br>*Marinobacter aquaeolei* VT8 maqu_2507 | YP_009076789.1<br>AEE75132.1<br>AEE77915.1<br>AEE79553.1<br>AE093034.1<br>AEE86278.1<br>YP_959486.1<br>YP_959769.1 |
| 3-methyl-2-hydrox-ybutanoyl-CoA → 3-methyl-1,2-butandiol | 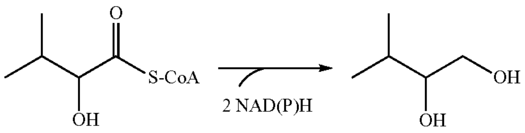 3-methyl-2-hydroxybutanoyl-CoA 3-methyl-1,2-butanediol | | | | |

TABLE E-continued

Example reactions and enzymes of the pathway for isoprenoid precursor synthesis based on acyloin condensation via 2-hydroxyisovaleric acid and prenol through utilization of 2-hydroxyacid/2-hydroxyacyl-CoA dehydratase

| Reaction | Illustration | EC Numbers | Enzyme names | Source organism and gene/enzyme name | Protein Accession Numbers |
|---|---|---|---|---|---|
| 3-methyl-2-butenoyl-CoA → 3-methyl-2-butenal | 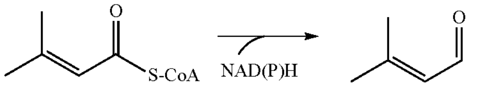  3-methyl-2-butenoyl-CoA; 3-methyl-2-butenal | 1.2.1.- | Aldehyde forming CoA reductase | *Acinetobacter calcoaceticus* acr1 | AAC45217.1 |
| | | | | *Acinetobacter* sp Strain M-1 acrM | BAB85476.1 |
| | | | | *Clostridium beijerinckii* ald | AAT66436.1 |
| | | | | *E. coli* eutE | NP_416950.1 |
| 3-methyl-2-hydroxy-butanoyl-CoA → 3-methyl-2-hydroxybutanal | 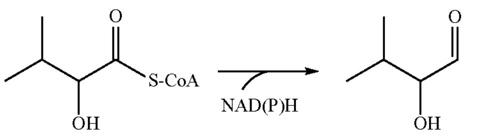  3-methyl-2-hydroxybutanoyl-CoA; 3-methyl-2-hydroxybutanal | | | *Salmonella enterica* | AAA80209.1 |
| | | | | eutE | NP_414885.1 |
| | | | | *E. coli* mhpF | |
| 3-methylbutanal → isovaleryl-CoA | 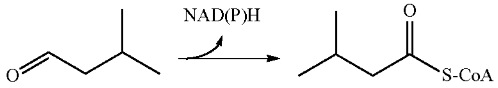  3-methylbutanal; isovaleryl-CoA | | | | |
| 3-methyl-2-butenal → 3-methyl-2-butenol | 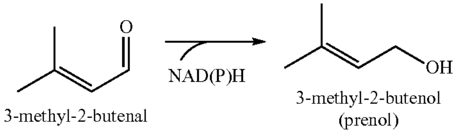  3-methyl-2-butenal; 3-methyl-2-butenol (prenol) | 1.1.1.- | Alcohol dehydrogenase | *E. coli* betA | NP_414845.1 |
| | | | | *E. coli* dkgA | NP_417485.4 |
| | | | | *E. coli* eutG | NP_416948.4 |
| | | | | *E. coli* fucO | NP_417279.2 |
| | | | | *E. coli* ucpA | NP_416921.4 |
| | | | | *E. coli* yahK | NP_414859.1 |
| | | | | *E. coli* ybbO | NP_415026.1 |
| 3-methyl-2-hydroxybutanal → 3-methyl-1,2-butandiol | 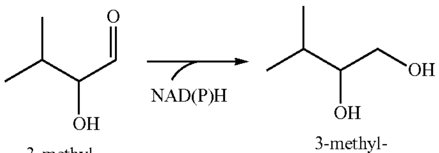  3-methyl-2-hydroxybutanal; 3-methyl-1,2-butanediol | | | *E. coli* ybdH | NP_415132.1 |
| | | | | *E. coli* yiaY | YP_026233.1 |
| | | | | *E. coli* yjgB | NP_418690.4 |
| | | | | *Acinetobacter* sp. SE19 ChnD | AAG10028.1 |
| | | | | *Marinobacter aquaeolei* VT8 maqu_2507 | YP_959769.1 |
| | | | | *Saccharomyces cerevisiae* ADH6 | Q04894.1 |
| | | | | *Clostridium kluyveri* 4hbD | E0K35022.1 |

TABLE E-continued

Example reactions and enzymes of the pathway for isoprenoid precursor synthesis based on acyloin condensation via 2-hydroxyisovaleric acid and prenol through utilization of 2-hydroxyacid/2-hydroxyacyl-CoA dehydratase

| Reaction | Illustration | EC Numbers | Enzyme names | Source organism and gene/enzyme name | Protein Accession Numbers |
|---|---|---|---|---|---|
| 3-methyl-1,2-butandiol → 3-methylbutanal | 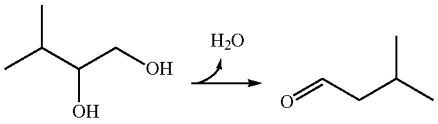 3-methyl-1,2-butanediol; 3-methylbutanal | 4.2.1.- | Diol dehydratase | *Klebsiella ocytoca* pddABC | Q59470, Q59471, Q59472 |
| | | | | *E. coli* pduCDE | CAS09680, CAS09681, CAS09682 |
| | | | | *S. enterica* pduCDE | NP_456590, NP_456591, NP_456592 |
| isovaleryl-CoA → 3-methyl-2-butenoyl-CoA | 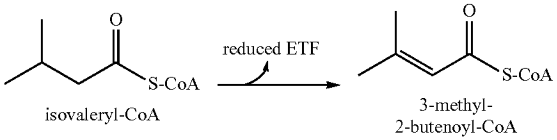 isovaleryl-CoA; 3-methyl-2-butenoyl-CoA | 1.3.8.4 | Acyl-CoA dehydrogenase | *Pseudomonas aeruginosa* liuA | APJ52511.1 |
| | | | | *E. coli* aidB | NP_418608.6 |
| | | | | *E. coli* fadE | NP_414756.2 |
| | | | | *Streptomyces avermitilis* acdH | AAD44196.1 |
| 3-methyl-2-butenol → dimethylallyl phosphate | 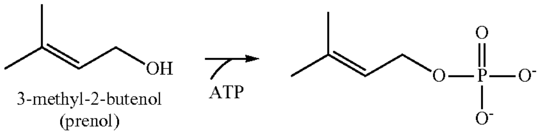 3-methyl-2-butenol (prenol); dimethylallyl phosphate | 2.7.1.- | Alcohol Kinase/Phosphotransferase | *Saccharomyces cerevisiae* ERG12 | P07277 |
| | | | | *Saccharomyces cerevisiae* ERG8 | P24521 |
| | | | | *Arabidopsis thaliana* At5g58560 | Q67ZM7 |
| | | | | *Mentha x piperita* ipk | P56848 |
| | | | | *Methanocaldococcus jannaschii* mvk | Q58487 |
| | | | | *Arabidopsis thaliana* mvk | AT5G27450.1 |
| | | | | *E. coli* ychB | NP_415726.1 |
| | | | | *E. coli* glpK | P0A6F3 |
| | | | | *Methanothermobacter thermautotrophicus* ipk | AAB84554.1 |
| | | | | *Thermoplasma acidophilum* ipk | WP_010900530.1 |
| | | | | *Methanocaldococcus jannaschii* ipk | 3K4Y_A |

TABLE E-continued

Example reactions and enzymes of the pathway for isoprenoid precursor synthesis based on acyloin condensation via 2-hydroxyisovaleric acid and prenol through utilization of 2-hydroxyacid/2-hydroxyacyl-CoA dehydratase

| Reaction | Illustration | EC Numbers | Enzyme names | Source organism and gene/enzyme name | Protein Accession Numbers |
|---|---|---|---|---|---|
| dimethylallyl phosphate → dimethylallyl pyrophosphate | 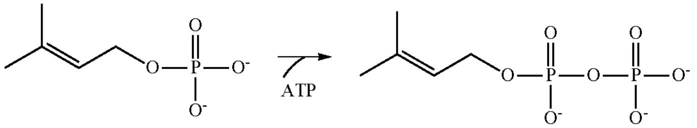 dimethylallyl phosphate; dimethylallyl pyrophosphate | 2.7.4- | Phosphate Kinase/Phosphotransferase | *Methanothermobacter thermautotrophicus* ipk | AAB84554.1 |
| | | | | *Thermoplasma acidophilum* ipk | WP_010900530.1 |
| | | | | *Enterococcus* | Q9FD67 |
| | | | | *faecalis* mvaK2 | |
| | | | | *Streptococcus pneumoniae* mvaK2 | A0A0I7UH23 |
| | | | | *Staphylococcus aureus* mvaK2 | A0A0E8GDF5 |
| | | | | *Methanocaldococcus jannaschii* ipk | 3K4Y_A |
| 3-methyl-2-butenol → dimethylallyl pyrophosphate | 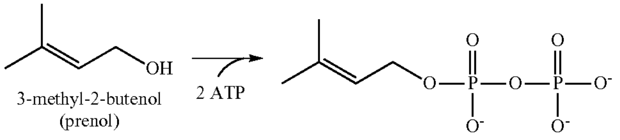 3-methyl-2-butenol (prenol); dimethylallyl pyrophosphate | 2.7.6- | Alcohol diphosphokinase | *Escherichia coli* Prs | NP_415725.1 |
| | | | | *Mycoplasma pneumoniae* M129 PrsA | NP_109761.1 |
| | | | | *Arabidopsis thaliana* col TPK1 | BAH19964.1 |
| | | | | *Arabidopsis thaliana* col TPK2 | BAH57065.1 |
| DMAPP ↔ IPP | 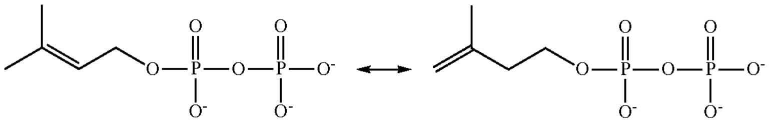 dimethylallyl pyrophosphate; isopentenyl pyrophosphate | 5.3.3.2 | isopentenyl diphosphate isomerase | *E. coli* idi | Q46822 |

TABLE E-continued

Example reactions and enzymes of the pathway for isoprenoid precursor synthesis based on acyloin condensation via 2-hydroxyisovaleric acid and prenol through utilization of 2-hydroxyacid/2-hydroxyacyl-CoA dehydratase

| Reaction | Illustration | EC Numbers | Enzyme names | Source organism and gene/enzyme name | Protein Accession Numbers |
|---|---|---|---|---|---|
| DMAPP + IPP → GPP | 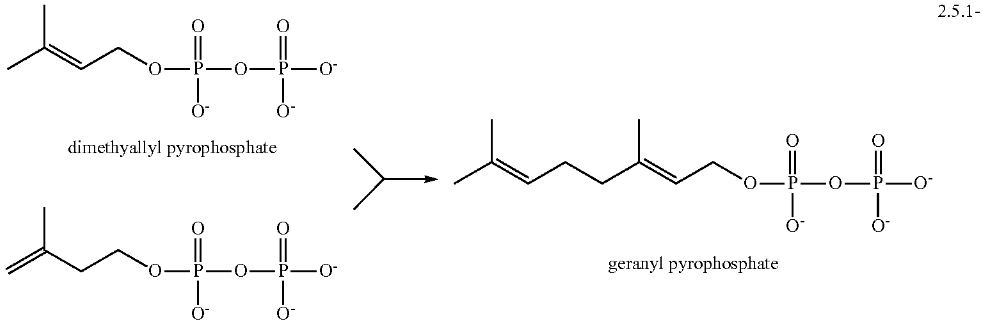 dimethyallyl pyrophosphate; Isopentenyl pyrophosphate; geranyl pyrophosphate | 2.5.1- | Geranyl pyrophos-phate synthase | *E. coli* ispA<br>*Abies grandis* GPPS2 | P22939<br>Q8LKJ2 |

TABLE F

Example reactions and enzymes of the pathway for isoprenoid precursor synthesis based on acyloin condensation via 2-oxoisovaleric acid, 2-oxoisocaproic acid and prenol through alpha-keto acid pathway and branched alpha-keto acid dehydrogenase

| Reaction | Illustration | EC Numbers | Enzyme names | Source organism and gene/enzyme name | Protein Accession Numbers |
|---|---|---|---|---|---|
| 2 pyruvate → acetolactate | 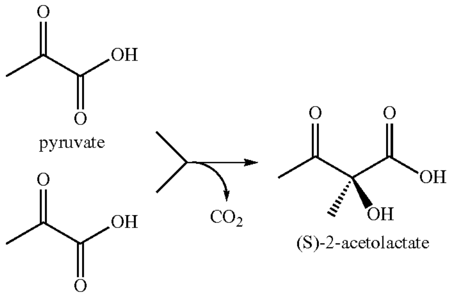 pyruvate; pyruvate; (S)-2-acetolactate | 2.2.1.6 | Acetolactate synthase | *E. coli* ilvBN<br>*E. coli* ilvIH<br>*B. subtilis* alsS | P08142, P0ADF8<br>P00893, P00894<br>Q04789 |
| acetolactate → 2,3-dihydroxy-3-methylbutanoate | 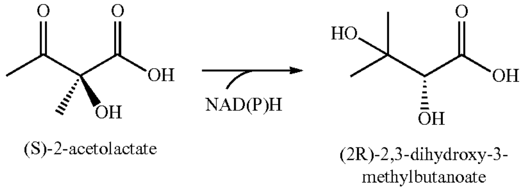 (S)-2-acetolactate; (2R)-2,3-dihydroxy-3-methylbutanoate | 1.1.1.86 | Acetohydroxy acid isomeroreductase | *E. coli* ilvC | P05793 |
| 2,3-dihydroxy-3-methylbutanoate → 3-methyl-2-oxobutanoate | 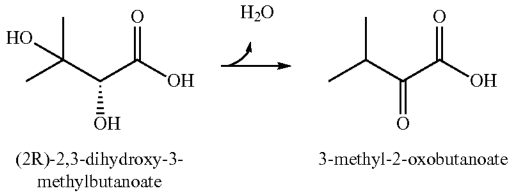 (2R)-2,3-dihydroxy-3-methylbutanoate; 3-methyl-2-oxobutanoate | 4.2.1.9 | Dihydroxy acid dehydratase | *E. coli* ilvD | P05791 |

TABLE F-continued

Example reactions and enzymes of the pathway for isoprenoid precursor synthesis based on acyloin condensation via 2-oxoisovaleric acid, 2-oxoisocaproic acid and prenol through alpha-keto acid pathway and branched alpha-keto acid dehydrogenase

| Reaction | Illustration | EC Numbers | Enzyme names | Source organism and gene/enzyme name | Protein Accession Numbers |
|---|---|---|---|---|---|
| 3-methyl-2-oxobutanoate + acetyl-CoA → 2-isopropylmalate + CoA | 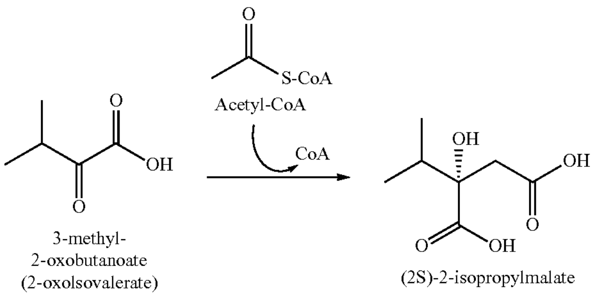3-methyl-2-oxobutanoate (2-oxolsovalerate)<br>(2S)-2-isopropylmalate | 2.3.3.13 | Isopropylmalate synthase | *E. coli* leuA | NP_414616.1 |
| 2-isopropylmalate → 3-isopropylmalate | 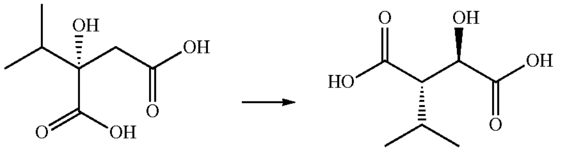(2S)-2-isopropylmalate<br>(2R,3S)-3-isopropylmalate | 4.2.1.33 | Isopropylmalate isomerase | *E. coli* leuCD | NP_414614.1<br>NP_414613.1 |
| 3-isopropylmalate → 4-methyl-2-oxopentanoate + $CO_2$ | 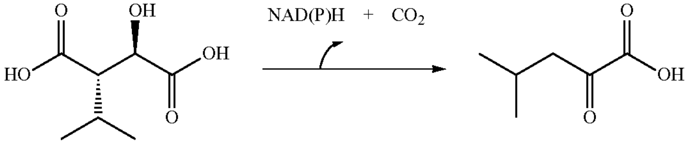(2R,3S)-3-isopropylmalate<br>4-methyl-2-oxopentanoate (2-oxoisocaproate) | 1.1.1.85 | Isopropylmalate dehydrogenase | *E. coli* leuB | NP_414615.4 |
| 4-methyl-2-oxopentanoate + CoA → isovaleryl-CoA + $CO_2$ | 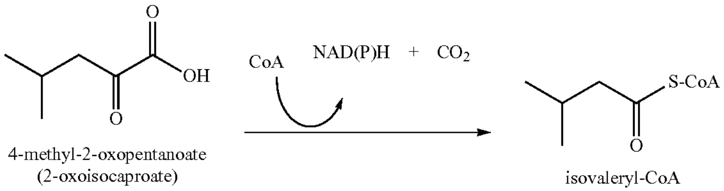4-methyl-2-oxopentanoate (2-oxoisocaproate)<br>isovaleryl-CoA | 1.2.1.- | alpha-keto acid dehydrogenase complex | *Streptomyces avermitilis* bkdFGH-lpdA1<br><br>*Homo sapiens* BKDHAB-DBT-DLD<br><br>*Bacillus subtilis* bfmBAA-bfmBAB- | BAC72088.1<br>BAC72089.1<br>BAC72090.1<br>KUN54417.1<br>NP_000700.1<br>NP_000047.1<br>NP_001909.3<br>NP_000099.2<br>WP_004398565.1<br>WP_004398638.1 |

TABLE F-continued

Example reactions and enzymes of the pathway for isoprenoid precursor synthesis based on acyloin condensation via 2-oxoisovaleric acid, 2-oxoisocaproic acid and prenol through alpha-keto acid pathway and branched alpha-keto acid dehydrogenase

| Reaction | Illustration | EC Numbers | Enzyme names | Source organism and gene/enzyme name | Protein Accession Numbers |
|---|---|---|---|---|---|
| | | | | bfmBB-pdhD | WP_003230323.1 WP_003232309.1 |
| | | | | *E. coli* lpdA-aceEF | NP_414657.1 NP_414658.1 NP_414656.1 |
| Isovaleryl-CoA → 3-methyl-2-butenoyl-CoA | 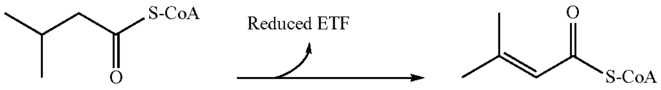 isovaleryl-CoA; 3-methyl-2-butenoyl-CoA (3-methylcrotonyl-CoA) | 1.3.8.4 | Acyl-CoA dehydrogenase | *Pseudomonas aeruginosa* liuA | APJ52511.1 |
| | | | | *E. coli* aidB | NP_418608.6 |
| | | | | *E. coli* fadE | NP_414756.2 |
| | | | | *Streptomyces avermitilis* acdH | AAD44196.1 |
| 3-methyl-2-butenoyl-CoA → 3-methyl-2-butanoate | 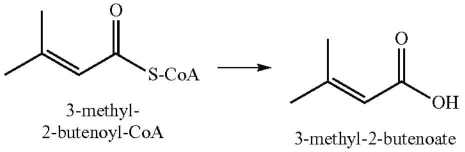 3-methyl-2-butenoyl-CoA; 3-methyl-2-butenoate | 3.1.2.- | Thioesterase | *E. coli* tesA | NP_415027.1 |
| | | | | *E. coli* tesB | NP_414986.1 |
| | | | | *E. coli* yciA | NP_415769.1 |
| | | | | *E. coli* fadM | NP_414977.1 |
| | | | | *E. coli* ydiI | NP_416201.1 |
| | | | | *E. coli* ybgC | NP_415264.1 |
| | | | | *E. coli* paaI | NP_415914.1 |
| | | | | *Mus musculus* acot8 | P58137.1 |
| | | | | *Lycopersicon hirsutum f glabratum* mks2 | ADK38536.1 |
| | | | | *Alcanivorax borkumensis* tesB2 | YP_692749.1 |
| | | | | *Fibrobacter succinogenes* Fs2108 | YP_005822012.1 |
| | | | | *Prevotella ruminicola* Pr655 | YP_003574018.1 |
| | | | | *Prevotella ruminicola* Pr1687 | YP_003574982.1 |
| | | 2.8.3.8 | Acyl-CoA:acetyl-CoA transferase | *E. coli* atoD | NP_416725.1 |
| | | | | *Clostridium kluyveri* cat2 | AAA92344.1 |
| | | | | *Clostridium acetobutylicum* ctfAB | NP_149326.1, NP_149327.1 |
| | | | | *E. coli* ydiF | NP_416209.1 |
| | | 2.3.1.-; 2.7.2.1; | Phosphotrans- | *Clostridium acetobutylicum* ptb | NP_349676.1 |

TABLE F-continued

Example reactions and enzymes of the pathway for isoprenoid precursor synthesis based on acyloin condensation via 2-oxoisovaleric acid, 2-oxoisocaproic acid and prenol through alpha-keto acid pathway and branched alpha-keto acid dehydrogenase

| Reaction | Illustration | EC Numbers | Enzyme names | Source organism and gene/enzyme name | Protein Accession Numbers |
|---|---|---|---|---|---|
| | | 2.7.2.15 | acylase + Carboxylate kinase | *Enterococcus faecalis* ptb | AAD55374.1 |
| | | | | *Salmonella enterica* pduL | AA039011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| 3-methyl-2-butenoate → 3-methyl-2-butenal | 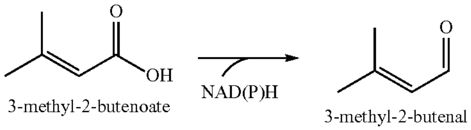 3-methyl-2-butenoate; 3-methyl-2-butenal | 1.2.1.- | Carboxylic Acid (Carboxylate) reductase | *E. coli* PaoABC | NP_414820.1, NP_414819.1, NP_414818.1 |
| | | | | *Mycobacterium marinum* Car | WP_012393886.1 |
| | | | | *Nocardia iowensis* Car | AAR91681.1 |
| | | | | *Segniliparus rotundus* Car | WP_013138593.1 |
| 3-methyl-2-butenoyl-CoA → 3-methyl-2-butenol | 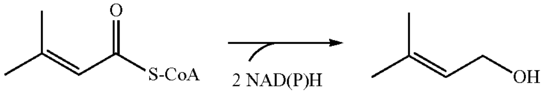 3-methyl-2-butenoyl-CoA; 3-methyl-2-butenol (prenol) | 1.2.1.- | Alcohol-forming Acyl-CoA reductase | *Clostridium acetobutylicum* adhE2 | YP_009076789.1 |
| | | | | *Arabidopsis thaliana* At3g11980 | AEE75132.1 |
| | | | | *Arabidopsis thaliana* At3g44560 | AEE77915.1 |
| | | | | *Arabidopsis thaliana* At3g56700 | AEE79553.1 |
| | | | | *Arabidopsis thaliana* At5g22500 | AED93034.1 |
| | | | | *Arabidopsis thaliana* CER4 | AEE86278.1 |
| | | | | *Marinobacter aquaeolei* VT8 maqu_2220 | YP_959486.1 |
| | | | | *Marinobacter aquaeolei* VT8 maqu_2507 | YP_959769.1 |

TABLE F-continued

Example reactions and enzymes of the pathway for isoprenoid precursor synthesis based on acyloin condensation via 2-oxoisovaleric acid, 2-oxoisocaproic acid and prenol through alpha-keto acid pathway and branched alpha-keto acid dehydrogenase

| Reaction | Illustration | EC Numbers | Enzyme names | Source organism and gene/enzyme name | Protein Accession Numbers |
|---|---|---|---|---|---|
| 3-methyl-2-butenoyl-CoA → 3-methyl-2-butenal | 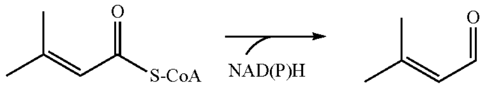 3-methyl-2-butenoyl-CoA 3-methyl-2-butenal | 1.2.1.- | Aldehyde forming CoA reductase | *Acinetobacter calcoaceticus* acr1 | AAC45217.1 |
| | | | | *Acinetobacter* sp Strain M-1 acrM | BAB85476.1 |
| | | | | *Clostridium beijerinckii* ald | AAT66436.1 |
| | | | | *E. coli* eut E | NP_416950.1 |
| | | | | *Salmonella enterica* eutE | AAA80209.1 |
| | | | | *E. coli* mhpF | NP_414885.1 |
| 3-methyl-2-butenal → 3-methyl-2-butenol | 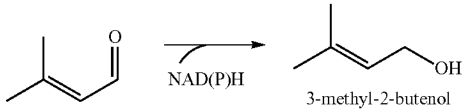 3-methyl-2-butenal 3-methyl-2-butenol (prenol) | 1.1.1.- | Alcohol dehy-drogenase | *E. coli* betA | NP_414845.1 |
| | | | | *E. coli* dkgA | NP_417485.4 |
| | | | | *E. coli* eutG | NP_416948.4 |
| | | | | *E. coli* fucO | NP_417279.2 |
| | | | | *E. coli* ucpA | NP_416921.4 |
| | | | | *E. coli* yahK | NP_414859.1 |
| | | | | *E. coli* ybbO | NP_415026.1 |
| | | | | *E. coli* ybdH | NP_415132.1 |
| | | | | *E. coli* yiaY | YP_026233.1 |
| | | | | *E. coli* yjgB | NP_418690.4 |
| | | | | *Acinetobacter* sp. SE19 ChnD | AAG10028.1 |
| | | | | *Marinobacter aquaeolei* VT8 maqu_2507 | YP_959769.1 |
| | | | | *Saccharomyces cerevisiae* ADH6 | Q04894.1 |
| | | | | *Clostridium kluyveri* 4hbD | EDK35022.1 |
| 3-methyl-2-butenol → dimethylallyl phosphate | 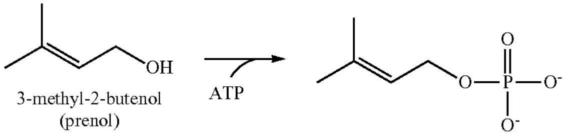 3-methyl-2-butenol (prenol) dimethylallyl phosphate | 2.7.1.- | Alcohol Kinase/ Phos-photrans-ferase | *Saccharomyces cerevisiae* ERG12 | P07277 |
| | | | | *Saccharomyces cerevisiae* ERG8 | P24521 |
| | | | | *Arabidopsis thaliana* At5g58560 | Q67ZM7 |
| | | | | *Mentha x piperita* | P56848 |
| | | | | ipk | |
| | | | | *Methanocaldo-coccus jannaschii* mvk | Q58487 |
| | | | | *Arabidopsis thaliana* mvk | AT5G27450.1 |

TABLE F-continued

Example reactions and enzymes of the pathway for isoprenoid precursor synthesis based on acyloin condensation via 2-oxoisovaleric acid, 2-oxoisocaproic acid and prenol through alpha-keto acid pathway and branched alpha-keto acid dehydrogenase

| Reaction | Illustration | EC Numbers | Enzyme names | Source organism and gene/enzyme name | Protein Accession Numbers |
|---|---|---|---|---|---|
| | | | | *E. coli* ispE<br>*E. coli* glpK<br>*E. coli* ychB<br>*Thermoplasma acidophilum* IPK | P62615<br>P0A6F3<br>NP_415726.1<br>WP_010900530.1 |
| dimethylallyl phosphate → dimethylallyl pyrophosphate | 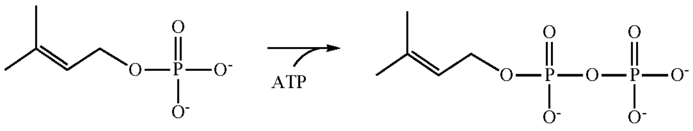 dimethylallyl phosphate; dimethylallyl pyrophosphate | 2.7.4- | Phosphate Kinase/ Phosphotransferase | *Methanothermobacter thermautotrophicus* ipk<br>*Thermoplasma acidophilum* ipk<br>*Enterococcus faecalis* mvaK2<br>*Streptococcus pneumoniae* mvaK2<br>*Staphylococcus aureus* mvaK2<br>*Methanocaldococcus jannaschii* ipk | AAB84554.1<br>WP_010900530.1<br>Q9FD67<br>A0A0I7UH23<br>A0A0E8GDF5<br>3K4Y_A |
| 3-methyl-2-butenol → dimethylallyl pyrophosphate | 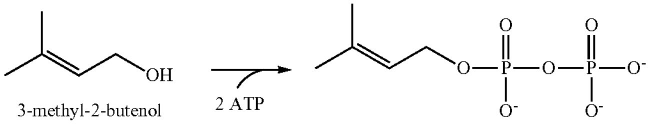 3-methyl-2-butenol (prenol); dimethylallyl pyrophosphate | 2.7.6- | Alcohol diphosphokinase | *Escherichia coli* Prs<br>*Mycoplasma pneumoniae* M129 PrsA<br>*Arabidopsis thaliana* col TPK1<br>*Arabidopsis thaliana* col TPK2 | NP_415725.1<br>NP_109761.1<br>BAH19964.1<br>BAH57065.1 |
| DMAPP ↔ IPP | 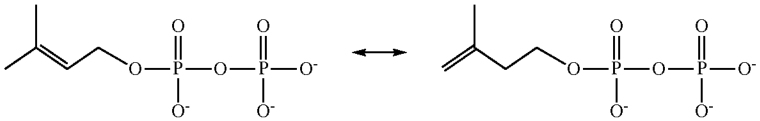 dimethylallyl pyrophosphate; isopentenyl pyrophosphate | 5.3.3.2 | isopentenyl diphosphate isomerase | *E. coli* idi | Q46822 |

TABLE F-continued

Example reactions and enzymes of the pathway for isoprenoid precursor synthesis based on acyloin condensation via 2-oxoisovaleric acid, 2-oxoisocaproic acid and prenol through alpha-keto acid pathway and branched alpha-keto acid dehydrogenase

| Reaction | Illustration | EC Numbers | Enzyme names | Source organism and gene/enzyme name | Protein Accession Numbers |
|---|---|---|---|---|---|
| DMAPP + IPP → GPP | 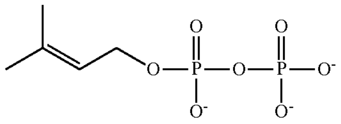 dimethyallyl pyrophosphate 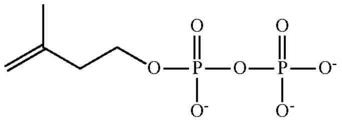 Isopentenyl pyrophosphate 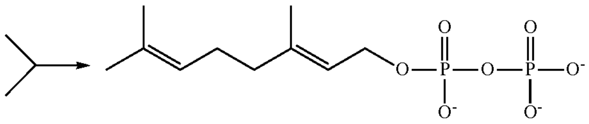 geranyl pyrophosphate | 2.5.1- | Geranyl pyro-phosphate synthase | *E. coli* ispA<br>*Abies grandis* GPPS2 | P22939<br>Q8LKJ2 |

TABLE G

Example reactions and enzymes of the novel isoprenoid precursor synthesis pathway via 2-hydroxyisovaleric acid and prenol starting from non-decarboxylative acyloin condensation between isobutanal and formyl-CoA

| Reaction | Illustration | EC Numbers | Enzyme names | Source organism and gene/enzyme name | Protein Accession Numbers |
|---|---|---|---|---|---|
| pyruvate → formate + acetyl-CoA | 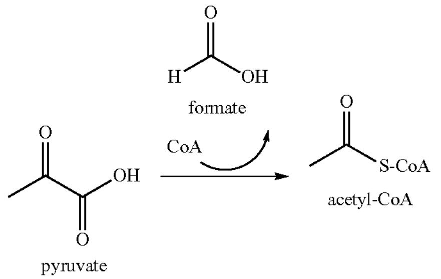 formate; pyruvate; acetyl-CoA | 2.3.1.54 | Pruvate formate lyase | *E. coli* pflB | NP_415423.1 |
| | | | | *E. coli* tdcE | YP_026205.1 |
| | | | | *Chlamydomonas reinhardtii* pfl1 | CAF04129.1 |
| | | | | *Streptococcus mutans* pfl | WP_002262619.1 |
| formate + CoA → formyl-CoA | 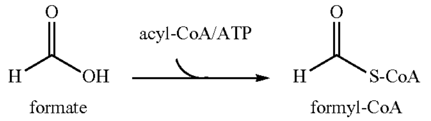 formate; formyl-CoA | 6.2.1.- | Acyl-CoA synthetase | *E. coli* paaK | NP_415916.1 |
| | | | | *E. coli* sucCD | NP_415256.1<br>NP_415257.1 |
| | | | | *E. coli* fadK | NP_416216.4 |
| | | | | *E. coli* fadD | NP_416319.1 |
| | | | | *E. coli* prpE | NP_414869.1 |
| | | | | *E. coli* menE | NP_416763.1 |
| | | | | *Penicillium chrysogenum* phl | CAJ15517.1 |
| | | | | *E. coli* acs | NP_418493.1 |
| | | | | *Salmonella typhimurium* LT2 prpE | AAL19325.1 |
| | | | | *Bacillus subtilis* bioW | AAC00261.1 |
| | | | | *Cupriavidus basilensis* hmfD | ADE20402.1 |
| | | | | *Rhodopseudomonas palustris* badA | CAJ18317.1 |
| | | | | *R. palustris* hbaA | CAE26113.1 |
| | | | | *Pseudomonas aeruginosa* PAO1 pqsA | NP_249687.1 |
| | | | | *Arabidopsis thaliana* 4cl | Q42524.1 |
| | | 2.8.3- | CoA transferase | *E. coli* atoD | NP_416725.1 |
| | | | | *E. coli* atoA | NP_416726.1 |
| | | | | *E. coli* scpC | NP_417395.1 |

TABLE G-continued

Example reactions and enzymes of the novel isoprenoid precursor synthesis pathway via 2-hydroxyisovaleric acid and prenol starting from non-decarboxylative acyloin condensation between isobutanal and formyl-CoA

| Reaction | Illustration | EC Numbers | Enzyme names | Source organism and gene/enzyme name | Protein Accession Numbers |
|---|---|---|---|---|---|
| | | | | *Clostridium kluyveri* cat1 | AAA92346.1 |
| | | | | *Clostridium kluyveri* cat2 | AAA92344.1 |
| | | | | *Clostridium acetobutylicum* ctfAB | NP_149326.1, NP_149327.1 |
| | | | | *Pseudomonas putida* pcalJ | NP_746081.1 NP_746082.1 |
| | | | | *Megasphaera elsdenii* pct | WP_014015705.1 |
| | | | | *Acidaminococcus fermentans* gctAB | CAA57199.1 CAA57200.1 |
| | | | | *Acetobacter aceti* aarC | AGG68319.1 |
| | | | | *E. coli* ydiF | NP_416209.1 |
| | | | | *Clostridium propionicum* *Pct*540 | CAB77207.1 |
| | | 2.3.1.-; 2.7.2.- | Carboxylate kinase + Phosphotrans-acylase | *Clostridium acetobutylicum* ptb | NP-349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| acetyl-CoA + $CO_2$ → malonyl-CoA | 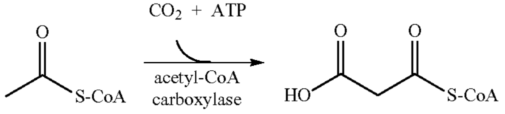 acetyl-CoA malonyl-CoA | 6.4.1.2 | Acetyl-CoA carboxylase | *E. coli* accABCD | NP_414727.1 NP_417721.1 NP_417722.1 NP_416819.1 |
| | | | | *Saccharomyces cerevisiae* HFA1 | P32874.2 |
| | | | | *Homo sapiens* ACC2 | NP_001084.3 |
| | | | | *Acidianus brierleyi* accBC + pccB | BAC55868.1 BAC55867.1 BAC55869.1 |
| | | | | *Mycobacterium tuberculosis* H37Rv | WP_003900487.1 |

TABLE G-continued

Example reactions and enzymes of the novel isoprenoid precursor synthesis pathway via 2-hydroxyisovaleric acid and prenol starting from non-decarboxylative acyloin condensation between isobutanal and formyl-CoA

| Reaction | Illustration | EC Numbers | Enzyme names | Source organism and gene/enzyme name | Protein Accession Numbers |
|---|---|---|---|---|---|
| | | | | accD6 | |
| | | | | *Streptomyces venezuelae* ATCC 10712 jadJ | AAD37851.1 |
| 2 acetyl-CoA → aceoacetyl-CoA | 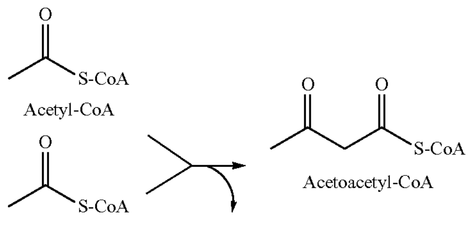 Acetyl-CoA, Acetyl-CoA, CoA, Acetoacetyl-CoA | 2.3.1.- | Thiolase | *E. coli* atoB | NP_416728.1 |
| | | | | *E. coli* yqeF | NP_417321.2 |
| | | | | *E. coli* fadA | YP_026272.1 |
| | | | | *E. coli* fadI | NP_416844.1 |
| | | | | *Ralstonia eutropha* bktB | AAC38322.1 |
| | | | | *Pseudomonas* sp. Strain B13 catF | AAL02407.1 |
| | | | | *E coli* paaJ | NP_415915.1 |
| | | | | *Pseudomonas putida* pcaF | AAA85138.1 |
| | | | | *Rhodococcus opacus* pcaF | YP_002778248.1 |
| | | | | *Streptomyces* sp. pcaF | AAD22035.1 |
| | | | | *Ralstonia eutropha* phaA | AEI80291.1 |
| | | | | *Clostridium acetobutylicum* thlA | AAC26023.1 |
| | | | | *Clostridium acetobutylicum* thlB | AAC26026.1 |
| | | | | *Pseudomonas putida* fadA | AAK18168.1 |
| | | | | *P. putida* fadAx | AAK18171.1 |
| | | | | *Acinetobacter* sp. ADP1 dcaF | CAG68532.1 |
| | | | | *E. coli* paaJ | NP_415915.1 |
| acetyl-CoA + malonyl-CoA → acetoacetyl-CoA + $CO_2$ | 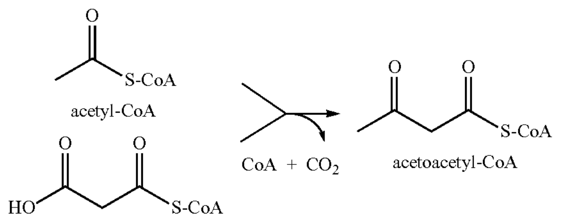 acetyl-CoA, malonyl-CoA, CoA + $CO_2$, acetoacetyl-CoA | 2.3.1.- | ketoacyl-CoA synthase | *Gluconobacter oxydans* GOX0115 | AAW59909.1 |
| | | | | *Pseudomonas aeruginosa* FabH2 | NP_252023.1 |
| | | | | *Streptomyces* sp. MMG1121 PRK09352 | WP_053666104.1 |
| | | | | *Streptomyces tendae* Acs2 | AFS18568.1 |
| | | | | *Streptomyces* sp. CL190 nphT7 | BAJ10048.1 |

TABLE G-continued

Example reactions and enzymes of the novel isoprenoid precursor synthesis pathway via 2-hydroxyisovaleric acid and prenol starting from non-decarboxylative acyloin condensation between isobutanal and formyl-CoA

| Reaction | Illustration | EC Numbers | Enzyme names | Source organism and gene/enzyme name | Protein Accession Numbers |
|---|---|---|---|---|---|
| | | | | *Physaria fendleri* KCS3 | AAK62348.1 |
| | | | | *Saccharomyces cerevisiae* ELO2 | NP_009963.1 |
| | | | | *Arabidopsis thaliana* col KCS1 | NP_171620.2 |
| | | | | *Arabidopsis thaliana* col FAE1 | NP_195178.1 |
| | | | | *Arabidopsis thaliana* col CER6 | NP_177020.1 |
| Acetoacetyl-CoA → 3-hydroxy-butyryl-CoA | 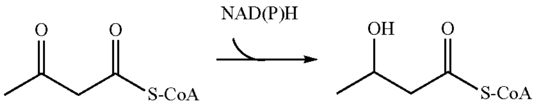 acetoacetyl-CoA 3-hydroxybutyryl-CoA | 1.1.1.35; 1..1.1.36 | Hydroxy-acyl-CoA dehydro-genase | *E. coli* fadB | NP_418288.1 |
| | | | | *E. coli* fadJ | NP_416843.1 |
| | | | | *E. coli* paaH | NP_415913.1 |
| | | | | *P. putida* fadB | AAK18167.2 |
| | | | | *P. putida* fadB2x | AAK18170.1 |
| | | | | *Acinetobacter* sp. ADP1 dcaH | CAG68533.1 |
| | | | | *Ralstonia eutrophus* phaB | P14697.1 |
| | | | | *Clostridium acetobutylicum* hbd | AAA95971.1 |
| | | | 3-oxoacyl-[acyl-carrier-protein] reductase | *E. coli* fabG | NP_415611.1 |
| 3-hydroxy-butyryl-CoA → crotonyl-CoA | 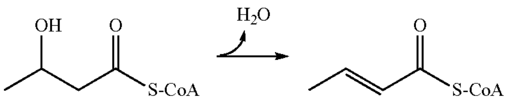 3-hydroxybutyryl-CoA crotonyl-CoA | 4.2.1.17; 4.2.1.119 | enoyl-CoA hydratase | *E. coli* fadB | NP_418288.1 |
| | | | | *E. coli* fadJ | NP_416843.1 |
| | | | | *E. coli* paaF | NP_415911.1 |
| | | | | *P. putida* fadB | AAK18167.2 |
| | | | | *P. putida* fadB1x | AAK18173.1 |
| | | | | *Acinetobacter* sp. ADP1 dcaE | CAG68535.1 |
| | | | | *Clostridium acetobutylicum* crt | AAA95967.1 |
| | | | | *Aeromonas caviae* phaJ | O32472.1 |
| | | | 3-hydroxyacyl-[acyl-carrier-protein] dehydratase | *E. coli* fabA | NP_415474.1 |
| | | | | *E. coli* fabZ | NP_414722.1 |

TABLE G-continued

Example reactions and enzymes of the novel isoprenoid precursor synthesis pathway via 2-hydroxyisovaleric acid and prenol starting from non-decarboxylative acyloin condensation between isobutanal and formyl-CoA

| Reaction | Illustration | EC Numbers | Enzyme names | Source organism and gene/enzyme name | Protein Accession Numbers |
|---|---|---|---|---|---|
| Crotonyl-CoA → butyryl-CoA | 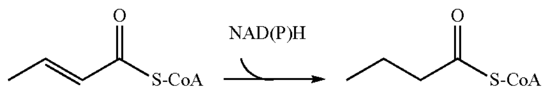 crotonyl-CoA butanoyl-CoA | 1.3.1.44 | enoyl-CoA reductase | *Euglena gracilis* TER | Q5EU90.1 |
| | | | | *Treponema denticola* TER | 4GGO_A |
| | | | | *Clostridium acetobutylicum* TER | 4EUH_A |
| | | | enoyl-[acyl-carrier-protein] reductase | *E. coli* fabI | NP_415804.1 |
| | | | | *Enterococcus faecalis* fabK | NP_816503.1 |
| | | | | *Bacillus subtilis* fabL | KFK80655.1 |
| | | | | *Vibrio cholerae* fabV | ABX38717.1 |
| | | | acyl-CoA dehydrogenase | *E. coli* fadE | NP-414756.2 |
| | | | | *E. coli* ydiO | NP_416210.4 |
| Butyryl-CoA → isobutyryl-CoA | 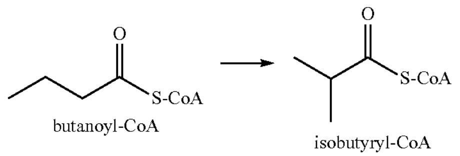 butanoyl-CoA isobutyryl-CoA | 5.4.99.- | mutase | *Aquincola tertiaricarbonis* ibmF | 4R3U_A |
| Isobutanal + formyl-CoA → 3-methyl-2-hydroxy-butanoyl-CoA | 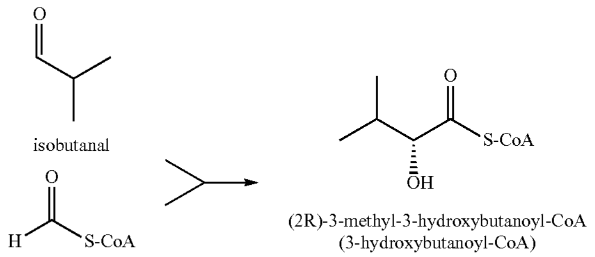 isobutanal formyl-CoA (2R)-3-methyl-3-hydroxybutanoyl-CoA (3-hydroxybutanoyl-CoA) | 4.1.-.- | 2-hydroxy-acyl-CoA lyase | *Homo sapiens* hacl1 | Q9UJ83 |
| | | | | *Rattus norvegicus* hacl1 | Q8CHM7 |
| | | | | *Dictyostelium discoidcum* hacl1 | Q54DA9 |
| | | | | *Mus musculus* hacl1 | Q9QXE0 |

TABLE G-continued

Example reactions and enzymes of the novel isoprenoid precursor synthesis pathway via 2-hydroxyisovaleric acid and prenol starting from non-decarboxylative acyloin condensation between isobutanal and formyl-CoA

| Reaction | Illustration | EC Numbers | Enzyme names | Source organism and gene/enzyme name | Protein Accession Numbers |
|---|---|---|---|---|---|
| 3-methyl-2-hydroxy-butanoyl-CoA → 3-methyl-2-butenoyl-CoA | 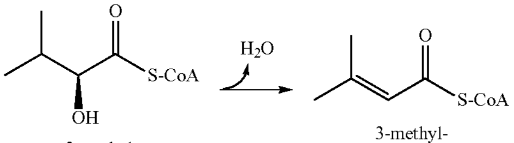 3-methyl-2-hydroxybutanoyl-CoA; 3-methyl-2-butanoyl-CoA | 4.2.1- | 2-hydroxy-acyl-CoA dehydratase | *Acidaminococcus fermentans* hgdCAB | P11568, P11569, P11570, |
| | | | | *Clostridium symbiosum* hgdCAB | Q9X5B6, Q9X5B7, Q9X5B8, |
| | | | | *Fusobacterium nucleatum* hgdCAB | A5TT16, A5TT17, A5TT18, |
| | | | | *Peptoclostridium difficile* hadIBC | AAV40818.1, AAV40819.1, AAV40820.1 |
| | | | | *Clostridium propionicum* lcdCAB | G3KIM3, G3KIM4, G3KIM5 |
| 3-methyl-2-butenoyl-CoA → 3-methyl-2-butenoate | 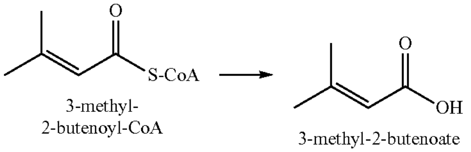 3-methyl-2-butenoyl-CoA; 3-methyl-2-butenoate | 3.1.2.- | Thioesterase | *E. coli* tesA | NP_415027.1 |
| | | | | *E. coli* tesB | NP_414986.1 |
| | | | | *E. coli* yciA | NP_415769.1 |
| | | | | *E. coli* fadM | NP_414977.1 |
| | | | | *E. coli* ydiI | NP_416201.1 |
| | | | | *E. coli* ybgC | NP_415264.1 |
| 3-methyl-2-hydroxy-butanoyl-CoA → 3-methyl-2-hydroxy-butanoate | 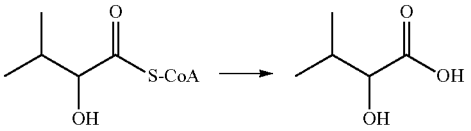 3-methyl-2-hydroxybutanoyl-CoA; 3-methyl-2-hydroxybutanoate | | | *E. coli* paaI | NP_415914.1 |
| | | | | *Mus musculus* acot8 | P58137.1 |
| | | | | *Lycopersicon hirsutum f glabratum* mks2 | ADK38536.1 |
| | | | | *Alcanivorax borkumensis* tesB2 | YP_692749.1 |
| | | | | *Fibrobacter succinogenes* Fs2108 | YP_005822012.1 |
| | | | | *Prevotella ruminicola* Pr655 | YP_003574018.1 |
| | | | | *Prevotella ruminicola* Pr1687 | YP_003574982.1 |
| | | 2.8.3- | CoA transferase | *E. coli* atoD | NP_416725.1 |
| | | | | *E. coli* atoA | NP_416726.1 |
| | | | | *E. coli* scpC | NP_417395.1 |
| | | | | *Clostridium kluyveri* cat1 | AAA92346.1 |
| | | | | *Clostridium kluyveri* | AAA92344.1 |

TABLE G-continued

Example reactions and enzymes of the novel isoprenoid precursor synthesis pathway via 2-hydroxyisovaleric acid and prenol starting from non-decarboxylative acyloin condensation between isobutanal and formyl-CoA

| Reaction | Illustration | EC Numbers | Enzyme names | Source organism and gene/enzyme name | Protein Accession Numbers |
|---|---|---|---|---|---|
| | | | | cat2 | |
| | | | | *Clostridium acetobutylicum* ctfAB | NP_149326.1, NP_149327.1 |
| | | | | *Pseudomonas putida* pcalJ | NP_746081.1 NP_746082.1 |
| | | | | *Megasphaera elsdenii* pct | WP_014015705.1 |
| | | | | *Acidaminococcus fermentans* gctAB | CAA57199.1 CAA57200.1 |
| | | | | *Acetobacter aceti* aarC | AGG68319.1 |
| | | | | *E. coli* ydiF | NP_416209.1 |
| | | 2.3.1.-; 2.7.2.1; 2.7.2.15 | Phospho-transacylase + Carboxylate kinase | *Clostridium acetobutylicum* ptb | NP_349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| 3-methyl-2-butenoate → 3-methyl-2-butenal | 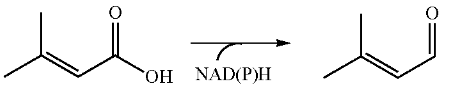 3-methyl-2-butenoate (3-methylcrotonate) 3-methyl-2-butenal | 1.2.1.- | Carboxylic Acid (Carboxylate) reductase | *E. coli* PaoABC | NP_414820.1, NP_414819.1, NP_414818.1 |
| | | | | *Mycobacterium marinum* Car | WP_012393886.1 |
| | | | | *Nocardia iowensis* Car | AAR91681.1 |
| | | | | *Segniliparus rotundus* Car | WP_013138593.1 |

TABLE G-continued

Example reactions and enzymes of the novel isoprenoid precursor synthesis pathway via 2-hydroxyisovaleric acid and prenol starting from non-decarboxylative acyloin condensation between isobutanal and formyl-CoA

| Reaction | Illustration | EC Numbers | Enzyme names | Source organism and gene/enzyme name | Protein Accession Numbers |
|---|---|---|---|---|---|
| 3-methyl-2-butenoyl-CoA → 3-methyl-2-butenal | 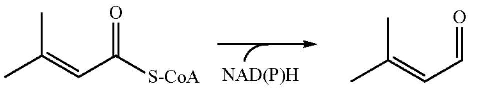  3-methyl-2-butenoyl-CoA 3-methyl-2-butenal | 1.2.1.- | Aldehyde forming CoA reductase | *Acinetobacter calcoaceticus* acr1<br>*Acinetobacter* sp *Strain* M-1 acrM<br>*Clostridium beijerinckii* ald<br>*E. coli* eut E<br>*Salmonella enterica* eutE<br>*E. coli* mhpF | AAC45217.1<br>BAB85476.1<br>AAT66436.1<br>NP_416950.1<br>AAA80209.1<br>NP_414885.1 |
| Isobutyryl-CoA → isobutanal | 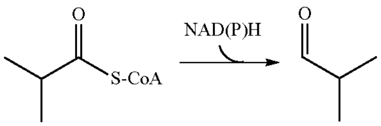  isobutyryl-CoA isobutanal | | | | |
| 3-methyl-butanal → isovaleryl-CoA | 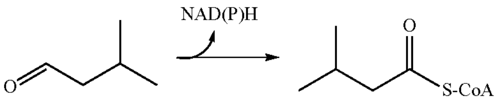  3-methylbutanal isovaleryl-CoA | | | | |
| 3-methyl-2-butanal → 3-methyl-2-butenol | 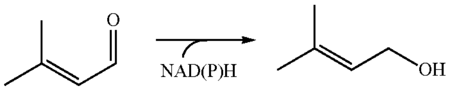  3-methyl-2-butenal 3-methyl-2-butenol (prenol) | 1.1.1.- | Alcohol dehydro-genase | *E. coli* betA<br>*E. coli* dkgA<br>*E. coli* eutG<br>*E. coli* fucO<br>*E. coli* ucpA<br>*E. coli* yahK<br>*E. coli* ybbO<br>*E. coli* ybdH<br>*E. coli* yiaY<br>*E. coli* yjgB<br>*Acinetobacter* sp. *SE*19 ChnD<br>*Marinobacter aquaeolei* VT8 maqu_2507<br>*Saccharomyces cerevisiae*<br>*Clostridium kluyveri* 4hbD | NP_414845.1<br>NP_417485.4<br>NP_416948.4<br>NP_417279.2<br>NP_416921.4<br>NP_414859.1<br>NP_415026.1<br>NP_415132.1<br>YP_026233.1<br>NP_418690.4<br>AAG10028.1<br>YP_959769.1<br>Q04894.1<br>EDK35022.1 |
| 3-methyl-2-hydroxy-butanal → 3-methyl-2-butandiol | 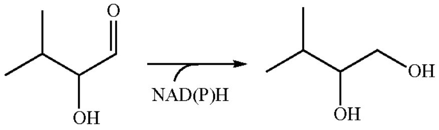  3-methyl-2-hydroxybutanal 3-methyl-1,2-butanediol | | | | |

TABLE G-continued

Example reactions and enzymes of the novel isoprenoid precursor synthesis pathway via 2-hydroxyisovaleric acid and prenol starting from non-decarboxylative acyloin condensation between isobutanal and formyl-CoA

| Reaction | Illustration | EC Numbers | Enzyme names | Source organism and gene/enzyme name | Protein Accession Numbers |
|---|---|---|---|---|---|
| 3-methyl-2-butenoyl-CoA → 3-methyl-2-butenol | 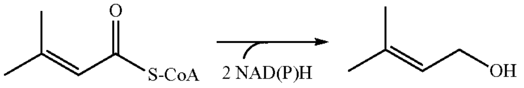<br><br>3-methyl-2-butenoyl-CoA 3-methyl-2-butenol (prenol) | 1.2.1.- | Alcohol-forming Acyl-CoA reductase | *Salmonella enterica* pduW<br>*Arabidopsis thaliana* At3g11980<br>*Arabidopsis thaliana* At3g44560<br>*Arabidopsis thaliana* At3g56700<br>*Arabidopsis thaliana* At5g22500<br>*Arabidopsis thaliana* CER4<br>*Marinobacter aquaeolei* VT8 maqu_2220<br>*Marinobacter aquaeolei* VT8 maqu_2507 | AAD39021.1<br>AEE75132.1<br>AEE77915.1<br>AEE79553.1<br>AED93034.1<br>AEE86278.1<br>YP_959486.1<br>YP_959769.1 |
| 3-methyl-2-hydroxy-butanoyl-CoA → 3-methyl-1,2-butandiol | 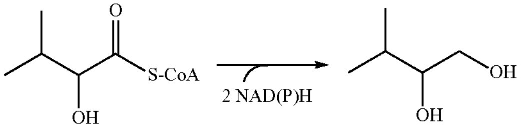<br><br>3-methyl-2-hydroxybutanoyl-CoA 3-methyl-1,2-butanediol | | | | |
| 3-methyl-1,2-butandiol → 3-methyl-butanal | 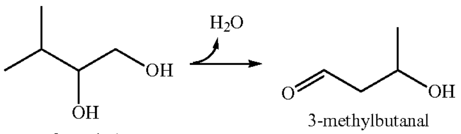<br><br>3-methyl-1,2-butanediol 3-methylbutanal | 4.2.1- | Diol dehydratase | *Klebsiella ocytoca* pddABC<br>*E. coli* pduCDE<br>*S. enterica* pduCDE | Q59470, Q59471, Q59472<br>CAS09680, CAS09681, CAS09682<br>NP_456590, NP_456591, NP_456592 |
| isovaleryl-CoA → 3-methyl-2-butenoyl-CoA | 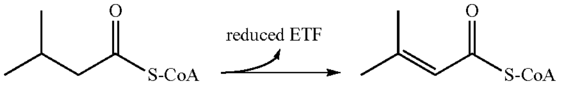<br><br>isovaleryl-CoA 3-methyl-2-butenoyl-CoA | 1.3.8.4 | Acyl-CoA dehydro-genase | *Pseudomonas aeruginosa* liuA<br>*E. coli* aidB<br>*E. coli* fadE<br>*Streptomyces avermitilis* acdH | APJ52511.1<br>NP_418608.6<br>NP_414756.2<br>AAD44196.1 |
| 3-methyl-2-butenol → dimethylallyl phosphate | 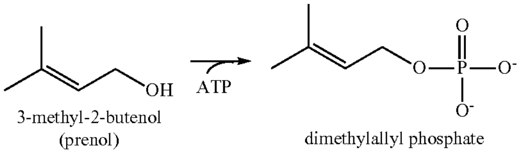<br><br>3-methyl-2-butenol (prenol) dimethylallyl phosphate | 2.7.1- | Alcohol Kinase/ Phospho-transferase | *Saccharomyces cerevisiae* ERG12<br>*Saccharomyces cerevisiae* ERG8<br>*Arabidopsis thaliana* At5g58560<br>*Mentha x piperita* ipk<br>*Arabidopsis* | P07277<br>P24521<br>Q67ZM7<br>P56848<br>AT5G27450.1 |

TABLE G-continued

Example reactions and enzymes of the novel isoprenoid precursor synthesis pathway via 2-hydroxyisovaleric acid and prenol starting from non-decarboxylative acyloin condensation between isobutanal and formyl-CoA

| Reaction | Illustration | EC Numbers | Enzyme names | Source organism and gene/enzyme name | Protein Accession Numbers |
|---|---|---|---|---|---|
| | | | | *thaliana* mvk | |
| | | | | *E. coli* ychB | NP_415726.1 |
| | | | | *E. coli* glpK | P0A6F3 |
| | | | | *Methanothermobacter thermautotrophicus* ipk | AAB84554.1 |
| | | | | *Thermoplasma acidophilum* ipk | WP_010900530.1 |
| | | | | *Methanocaldo-coccus jannaschii* ipk | 3K4Y_A |
| dimethylallyl phosphate → dimethylallyl pyrophosphate | 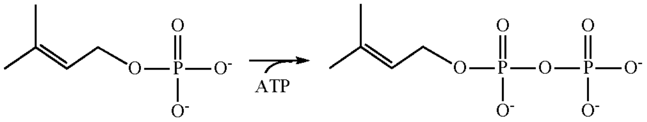 dimethylallyl phosphate; dimethylallyl pyrophosphate | 2.7.4- | Phosphate Kinase/ Phospho-transferase | *Methanothermobacter thermautotrophicus* ipk | AAB84554.1 |
| | | | | *Thermoplasma acidophilum* ipk | WP_010900530.1 |
| | | | | *Enterococcus faecalis* mvaK2 | Q9FD67 |
| | | | | *Streptococcus pneumoniae* mvaK2 | A0A0I7UH23 |
| | | | | *Staphylococcus aureus* mvaK2 | A0A0E8GDF5 |
| | | | | *Methanocaldococcus jannaschii* ink | 3K4Y_A |
| 3-methyl-2-butenol → dimethylallyl pyrophosphate | 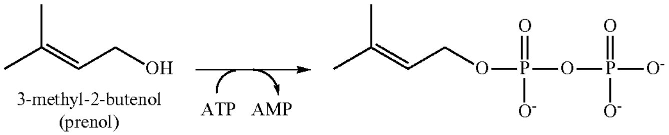 3-methyl-2-butenol (prenol); dimethylallyl pyrophosphate | 2.7.6.- | Alcohol diphospho-kinase | *E. coli* prs | NP_415725.1 |
| | | | | *Mycoplasma pneumoniae* M129 prsA | NP_109761.1 |
| | | | | *Arabidopsis thaliana* col TPK1 | BAH19964.1 |
| | | | | *Arabidopsis thaliana* col TPK2 | BAH57065.1 |
| DMAPP ↔ IPP | 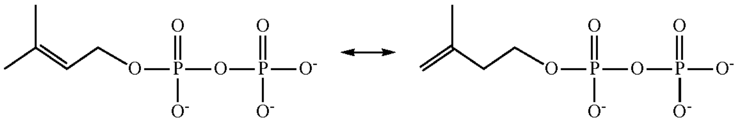 dimethylallyl pyrophosphate; isopentenyl pyrophosphate | 5.3.3.2 | isopentenyl diphosphate isomerase | *E. coli* idi | NP_417365.1 |

TABLE G-continued

Example reactions and enzymes of the novel isoprenoid precursor synthesis pathway via 2-hydroxyisovaleric acid and prenol starting from non-decarboxylative acyloin condensation between isobutanal and formyl-CoA

| Reaction | Illustration | EC Numbers | Enzyme names | Source organism and gene/enzyme name | Protein Accession Numbers |
|---|---|---|---|---|---|
| DMAPP + IPP → GPP | 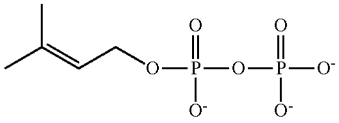 dimethyallyl pyrophosphate 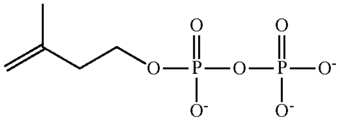 Isopentenyl pyrophosphate 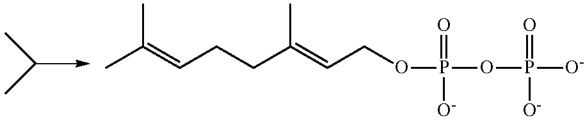 geranyl pyrophosphate | 2.5.1- | Geranyl pyro-phosphate synthase | *E. coli* ispA<br>*Abies grandis* GPPS2 | NP_414955.1<br>AAN01134.1 |

TABLE H

Example reactions and enzymes of the pathway for isoprenoid precursor synthesis via 2-hydroxyisovaleric acid and prenol starting from aldol condensation between acetaldehyde and pyruvate

| Reaction | Illustration | EC Numbers | Enzyme names | Source organism and gene/enzyme name | Protein Accession Numbers |
|---|---|---|---|---|---|
| pyruvate → acetaldehyde | 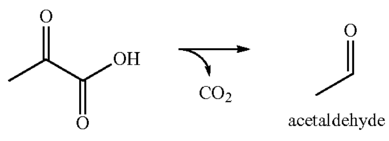  pyruvate acetaldehyde | 4.1.1.1 | alpha-ketoacid decarboxylase | *Saccharomyces cerevisiae PDC*1 | NP_013145.1 |
| | | | | *Saccharomyces cerevisiae* PDC5 | NP_013235.1 |
| | | | | *Saccharomyces cerevisiae* PDC6 | NP_011601.3 |
| | | | | *Pisum sativum* PDC1 | CAA91444.1 |
| | | | | *Saccharomyces cerevisiae* ARO10 | NP_010668.3 |
| | | | | *Saccharomyces cerevisiae* THI3 | NP_010203.1 |
| | | | | *Lactococcus lactis* kivd | CAG34226.1 |
| | | | | *Pantoea agglomerans* idpC | WP_003848906.1 |
| | | | | *Enterobacter cloacae* idpC | WP_073396207.1 |
| pyruvate + acetaldehyde → 4-hydroxy-2-oxopentanoate | 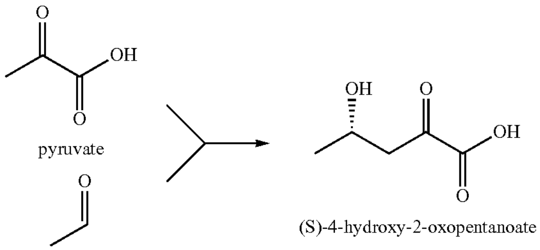 pyruvate acetaldehyde (S)-4-hydroxy-2-oxopentanoate | 4.1.3.39 | aldolase | *E. coli* mhpE | NP_414886.1 |
| | | | | *Pseudomonas putida* xylK | WP_011005904.1 |
| | | | | *Pseudomonas* sp. CF600 dmpG | WP_017849278.1 |
| 4-hydroxy-2-oxopentanoate → 3-hydroxy-2-oxo-3-methylbutanoate | 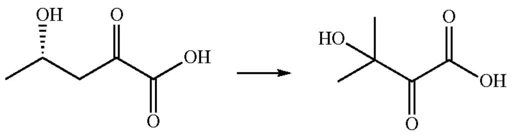 (S)-4-hydroxy-2-oxopentanoate 3-hydroxy-2-oxo-3-methylbutanoate | 5.4.99.- | mutase | *Streptomyces cinnamonensis* icmAB | AAC08713.1. CAB59633.1 |
| | | | | *Metallosphaera sedula* Msed_0638, Msed_2055 | A4YEG1, A4YIE3 |
| | | | | *Cupriavidus metallidurans* icmF | Q1LRY0 |
| | | | | *Kyrpidia tusciae* rcmAB | D5WTR7, D5WTR8 |

TABLE H-continued

Example reactions and enzymes of the pathway for isoprenoid precursor synthesis via 2-hydroxyisovaleric acid and prenol starting from aldol condensation between acetaldehyde and pyruvate

| Reaction | Illustration | EC Numbers | Enzyme names | Source organism and gene/enzyme name | Protein Accession Numbers |
|---|---|---|---|---|---|
| | | | | *Rhodobacter sphaeroides* meaA | ABA80144.1 |
| 2,3-dihydroxy-3-methyl-butanoate → 3-methyl-2-oxo-butanoate | 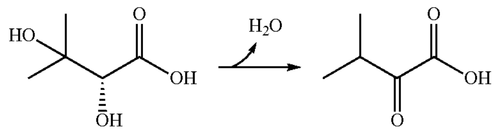 (2R)-2,3-dihydroxy-3-methylbutanoate; 3-methyl-2-oxobutanoate | 4.2.1.9 | Dihydroxyacid dehydratase | *E. coli* ilvD | P05791 |
| 3-hydroxy-2-oxo-3-methyl-butanoate → 2,3-dihydroxy-3-methyl-butanoate | 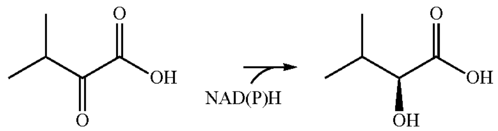 3-methyl-2-oxobutanoate; 3-methyl-2-hydroxybutanoate | 1.1.1.- | 2-hydroxyacid dehydrogenase | *Acidaminococcus fermentans* hgdH<br>*Methanocaldococcus jannaschii* mdh | D2RMS7<br>Q60176 |
| 3-methyl-2-oxo-butanoate → 3-methyl-2-hydroxy-butanoate | 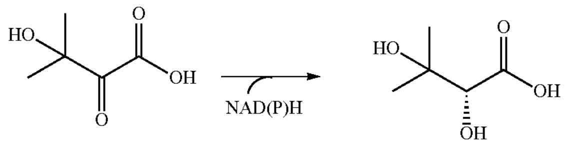 3-hydroxy-2-oxo-3-methylbutanoate; (2R)-2,3-dihydroxy-3-methylbutanoate | | | *M. jannaschii* comC<br>*E. coli* mdh<br>*E. coli* serA<br>*E. coli* ldhA<br>*Haloferax mediterranei* ddh<br>*Lactococcus lactis* panE | Q58820<br>P61889<br>P0A9T0<br>P52643<br>Q2VEQ7<br>A0A089XK51 |
| 3-methyl-2-hydroxy-butanoate → 3-methyl-2-butenoate | 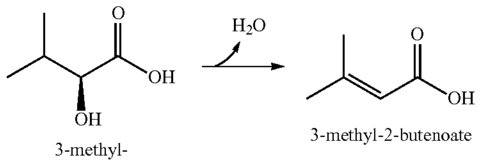 3-methyl-2-hydroxybutanoate; 3-methyl-2-butenoate | 4.2.1.-<br>4.2.1- | 2-hydroxy acid dehydratase<br>2-hydroxy-acyl-CoA dehydratase | *E. coli* fumA<br>*E. coli* fumB<br>*E. coli* fumC<br>*Acidaminococcus fermentans* hgdCAB<br>*Clostridium symbiosum* hgdCAB<br>*Fusobacterium nucleatum* hgdCAB<br>*Peptoclostridium* | P0AC33<br>P14407<br>P05042<br>P11568, P11569, P11570, Q9X5B6, Q9X5B7, Q9X5B8, A5TT16, A5TT17, A5TT18, AAV40818.1, |

TABLE H-continued

Example reactions and enzymes of the pathway for isoprenoid precursor synthesis via 2-hydroxyisovaleric acid and prenol starting from aldol condensation between acetaldehyde and pyruvate

| Reaction | Illustration | EC Numbers | Enzyme names | Source organism and gene/enzyme name | Protein Accession Numbers |
|---|---|---|---|---|---|
| | | | | *difficile* hadIBC | AAV40819.1, AAV40820.1 |
| | | | | *Clostridium propionicum* lcdCAB | G3KIM3, G3KIM4, G3KIM5 |
| 3-methyl-2-hydroxy-butanoate → 3-methyl-2-hydroxy-butanoyl-CoA | 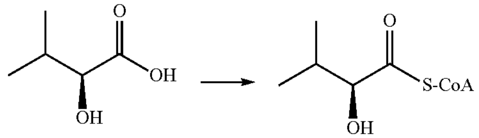 3-methyl-2-hydroxybutanoate; 3-methyl-2-hydroxybulanoyl-CoA | 6.2.1.- | Acyl-CoA synthetase | *E. coli* paaK | NP_415916.1 |
| | | | | *E. coli* sucCD | NP_415256.1 NP_415257.1 |
| | | | | *E. coli* fadK | NP_416216.4 |
| | | | | *E. coli* fadD | NP_416319.1 |
| | | | | *E. coli* prpE | NP_414869.1 |
| | | | | *E. coli* menE | NP_416763.1 |
| | | | | *Penicillium chrysogenum* phl | CAJ15517.1 |
| 3-methyl-2-butanoate → 3-methyl-2-butenoyl-CoA | 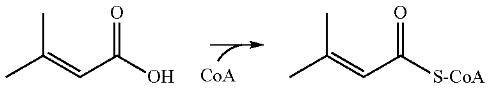 3-methyl-2-butenoate (3-methylcrotonate); 3-methyl-2-butenoyl-CoA | | | *Salmonella typhimurium* LT2 prpE | AAL19325.1 |
| | | | | *Bacillus subtilis* bioW | AAC00261.1 |
| | | | | *Cupriavidus basilensis* hmfD | ADE20402.1 |
| | | | | *Rhodopseudomonas palustris* badA | CAJ18317.1 |
| | | | | *R. palustris* hbaA | CAE26113.1 |
| | | | | *Pseudomonas aeruginosa* PAO1 pqsA | NP_249687.1 |
| | | | | *Arabidopsis thaliana* 4cl | Q42524.1 |
| | | 2.8.3- | CoA transferase | *E. coli* atoD | NP_416725.1 |
| | | | | *E. coli* atoA | NP_416726.1 |
| | | | | *E. coli* scpC | NP_417395.1 |
| | | | | *Clostridium kluyveri* cat1 | AAA92346.1 |
| | | | | *Clostridium kluyveri* cat2 | AAA92344.1 |
| | | | | *Clostridium acetobutylicum* ctfAB | NP_149326.1, NP_149327.1 |
| | | | | *Pseudomonas putida* pcaIJ | NP_746081.1 NP_746082.1 |
| | | | | *Megasphaera elsdenii* pct | WP_014015705.1 |

TABLE H-continued

Example reactions and enzymes of the pathway for isoprenoid precursor synthesis via 2-hydroxyisovaleric acid and prenol starting from aldol condensation between acetaldehyde and pyruvate

| Reaction | Illustration | EC Numbers | Enzyme names | Source organism and gene/enzyme name | Protein Accession Numbers |
|---|---|---|---|---|---|
| | | | | *Acidaminococcus fermentans* gctAB | CAA57199.1 CAA57200.1 |
| | | | | *Acetobacter aceti* aarC | AGG68319.1 |
| | | | | *E. coli* ydiF | NP_416209.1 |
| | | | | *Clostridium propionicum* Pct540 | CAB77207.1 |
| | | 2.3.1.-; 2.7.2.- | Carboxylate kinase + Phospho-transacylase | *Clostridium acetobutylicum* ptb | NP_349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| 3-methyl-2-hydroxy-butanoyl-CoA → 3-methyl-2-butenoyl-CoA | 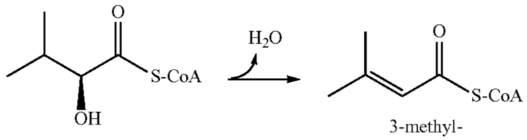 3-methyl-2-hydroxybutanoyl-CoA 3-methyl-2-butenoyl-CoA | 4.2.1- | 2-hydroxyacyl-CoA dehydratase | *Acidaminococcus fermentans* hgdCAB | P11568, P11569, P11570, |
| | | | | *Clostridium symbiosum* hgdCAB | Q9X5B6, Q9X5B7, Q9X5B8, |
| | | | | *Fusobacterium nucleatum* hgdCAB | A5TT16, A5TT17, A5TT18, |
| | | | | *Peptoclostridium difficile* hadIBC | AAV40818.1, AAV40819.1, AAV40820.1 |
| | | | | *Clostridium propionicum* lcdCAB | G3KIM3, G3KIM4, G3KIM5 |

TABLE H-continued

Example reactions and enzymes of the pathway for isoprenoid precursor synthesis via 2-hydroxyisovaleric acid and prenol starting from aldol condensation between acetaldehyde and pyruvate

| Reaction | Illustration | EC Numbers | Enzyme names | Source organism and gene/enzyme name | Protein Accession Numbers |
|---|---|---|---|---|---|
| 3-methyl-2-butanoyl-CoA → 3-methyl-2-butenoate | 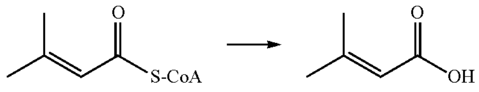 3-methyl-2-butenoyl-CoA; 3-methyl-2-butenoate | 3.1.2.- | Thioesterase | *E. coli* tesA | NP_415027.1 |
| | | | | *E. coli* tesB | NP_414986.1 |
| | | | | *E. coli* yciA | NP_415769.1 |
| | | | | *E. coli* fadM | NP_414977.1 |
| | | | | *E. coli* ydiI | NP_416201.1 |
| | | | | *E. coli* ybgC | NP_415264.1 |
| | | | | *E. coli* paaI | NP_415914.1 |
| | | | | *Mus musculus* acot8 | P58137.1 |
| 3-methyl-2-hydroxy-butanoyl-CoA → 3-methyl-2-hydroxy-butanoate | 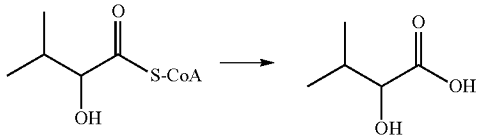 3-methyl-2-hydroxybutanoyl-CoA; 3-methyl-2-hydroxybutanoate | | | *Lycopersicon hirsutum f glabratum* mks2 | ADK38536.1 |
| | | | | *Alcanivorax borkumensis* tesB2 | YP_692749.1 |
| | | | | *Fibrobacter succinogenes* Fs2108 | YP_005822012.1 |
| | | | | *Prevotella ruminicola* Pr655 | YP_003574018.1 |
| | | | | *Prevotella ruminicola* Pr1687 | YP_003574982.1 |
| | | 2.8.3.8 | Acyl-CoA: acetyl-CoA transferase | *E. coli* atoD | NP_416725.1 |
| | | | | *Clostridium kluyveri* cat2 | AAA92344.1 |
| | | | | *Clostridium acetobutylicum* ctfAB | NP_149326.1, NP_149327.1 |
| | | | | *E. coli* ydiF | NP_416209.1 |
| | | 2.3.1-; 2.7.2.1; 2.7.2.15 | Phospho-transacylase + Carboxylate kinase | *Clostndium acetobutylicum* ptb | NP_349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |

TABLE H-continued

Example reactions and enzymes of the pathway for isoprenoid precursor synthesis via 2-hydroxyisovaleric acid and prenol starting from aldol condensation between acetaldehyde and pyruvate

| Reaction | Illustration | EC Numbers | Enzyme names | Source organism and gene/enzyme name | Protein Accession Numbers |
|---|---|---|---|---|---|
| 3-methyl-2-butenoate → 3-methyl-2-butenal | 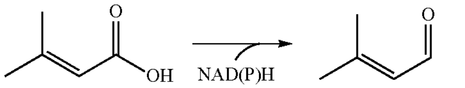 3-methyl-2-butenoate 3-methyl-2-butenal | 1.2.1.- | Carboxylic Acid (Carboxylate) reductase | *E. coli* PaoABC | NP_414820.1, NP_414819.1, NP_414818.1 |
| | | | | *Mycobacterium marinum* Car | WP_012393886.1 |
| | | | | *Nocardia iowensis* Car | AAR91681.1 |
| | | | | *Segniliparus rotundus* Car | WP_013138593.1 |
| 3-methyl-2-hydroxy-butanoate → 3-methyl-2-hydroxy-butanal | 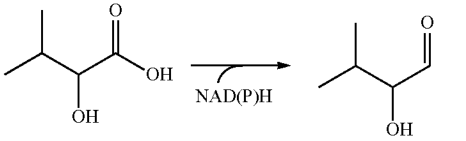 3-methyl-2-hydroxybutanoate 3-methyl-2-hydroxybutanal | | | | |
| 3-methyl-2-butenoyl-CoA → 3-methyl-2-butenol | 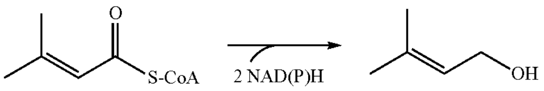 3-methyl-2-butenoyl-CoA 3-methyl-2-butenol (prenol) | 1.2.1- | Alcohol-forming Acyl-CoA reductase | *Clostridium acetobutylicum adhE2* | YP_009076789.1 |
| | | | | *Arabidopsis thaliana* At3g11980 | AEE75132.1 |
| | | | | *Arabidopsis thaliana* At3g44560 | AEE77915.1 |
| | | | | *Arabidopsis thaliana* At3g56700 | AEE79553.1 |
| 3-methyl-2-hydroxy-butanoyl-CoA → 3-methyl-1,2-butandiol | 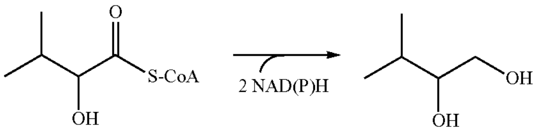 3-methyl-2-hydroxybutanoyl-CoA 3-methyl-1,2-butanediol | | | *Arabidopsis thaliana* At5g22500 | AED93034.1 |
| | | | | *Arabidopsis thaliana* CER4 | AEE86278.1 |
| | | | | *Marinobacter aquaeolei* VT8 maqu_2220 | YP_959486.1 |
| | | | | *Marinobacter aquaeolei* VT8 maqu_2507 | YP_959769.1 |
| acetyl-CoA → acetaldehyde | 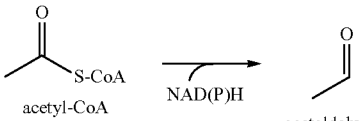 acetyl-CoA acetaldehyde | 1.2.1.- | Aldehyde forming CoA reductase | *Acinetobacter calcoaceticus* acr1 | AAC45217.1 |
| | | | | *Acinetobacter* sp Strain M-1 acrM | BAB85476.1 |
| | | | | *Clostridium* beijerinckii ald | AAT66436.1 |

TABLE H-continued

Example reactions and enzymes of the pathway for isoprenoid precursor synthesis via 2-hydroxyisovaleric acid and prenol starting from aldol condensation between acetaldehyde and pyruvate

| Reaction | Illustration | EC Numbers | Enzyme names | Source organism and gene/enzyme name | Protein Accession Numbers |
|---|---|---|---|---|---|
| 3-methyl-2-butenoyl-CoA → 3-methyl-2-butenal | 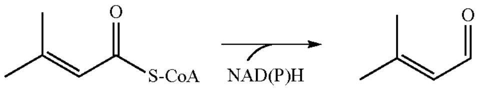<br><br>3-methyl-2-butenoyl-CoA 3-methyl-2-butenal | | | *E. coli* eutE<br>*Salmonella enterica* eutE<br>*E. coli* mhpF | NP_416950.1<br>AAA80209.1<br>NP_414885.1 |
| 3-methyl-2-hydroxy-butanoyl-CoA → 3-methyl-2-hydroxy-butanal | 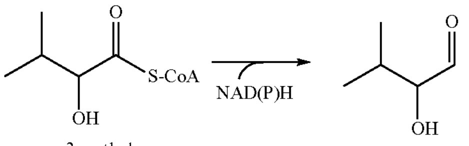<br><br>3-methyl-2-hydroxybutanoyl-CoA 3-methyl-2-hydroxybutanal | | | | |
| 3-methyl-butanal → isovaleryl-CoA | 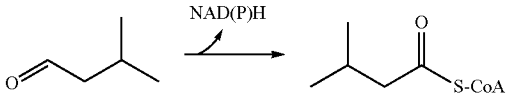<br><br>3-methylbutanal isovaleryl-CoA | | | | |
| 3-methyl-2-butenal → 3-methyl-2-butenol | 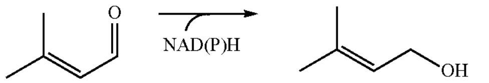<br><br>3-methyl-2-butenal 3-methyl-2-butenol(prenol) | 1.1.1.- | Alcohol dehydrogenase | *E. coli* betA<br>*E. coli* dkgA<br>*E. coli* eutG<br>*E. coli* fucO<br>*E. coli* ucpA<br>*E. coli* yahK<br>*E. coli* ybbO<br>*E. coli* ybdH<br>*E. coli* yiaY<br>*E. coli* yjgB<br>*Acinetobacter* sp. SE19 ChnD<br>*Marinobacter aquaeolei VT*8 maqu_2507<br>*Saccharomyces cerevisiae* ADH6<br>*Clostridium kluyveri* 4hbD | NP_414845.1<br>NP_417485.4<br>NP_416948.4<br>NP_417279.2<br>NP_416921.4<br>NP_414859.1<br>NP_415026.1<br>NP_415132.1<br>YP_026233.1<br>NP_418690.4<br>AAG10028.1<br><br>YP_959769.1<br><br>Q04894.1<br><br>EDK35022.1 |
| 3-methyl-2-hydroxy-butanal → 3-methyl-1,2-butandiol | 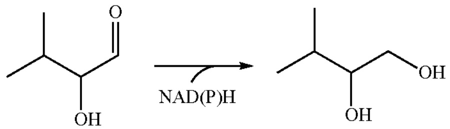<br><br>3-methyl-2-hydroxybutanal 3-methyl-1,2-butanediol | | | | |

TABLE H-continued

Example reactions and enzymes of the pathway for isoprenoid precursor synthesis via 2-hydroxyisovaleric acid and prenol starting from aldol condensation between acetaldehyde and pyruvate

| Reaction | Illustration | EC Numbers | Enzyme names | Source organism and gene/enzyme name | Protein Accession Numbers |
|---|---|---|---|---|---|
| 3-methyl-1,2-butandiol → 3-methyl-butanal | 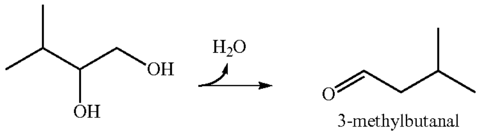  3-methyl-1,2-butanediol 3-methylbutanal | 4.2.1.- | Diol dehydratase | *Klebsiella ocytoca* pddABC | Q59470, Q59471, Q59472 |
| | | | | *E. coli* pduCDE | CAS09680, CAS09681, CAS09682 |
| | | | | *S. enterica* pduCDE | NP_456590, NP_456591, NP_456592 |
| isovaleryl-CoA → 3-methyl-2 butenoyl-CoA | 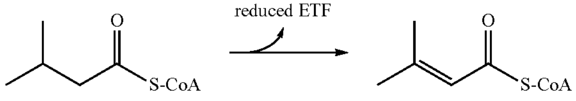  isovaleryl-CoA 3-methyl-2-butenoyl-CoA | 1.3.8.4 | Acyl-CoA dehydrogenase | *Pseudomonas aeruginosa* liuA | APJ52511.1 |
| | | | | *E. coli* aidB | NP_418608.6 |
| | | | | *E. coli* fadE | NP_414756.2 |
| | | | | *Streptomyces avermitilis* acdH | AAD44196.1 |
| 3-methyl-2-butenol → dimethyallyl phosphate | 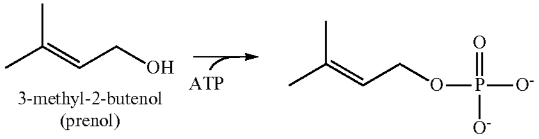  3-methyl-2-butenol (prenol) dimethylallyl phosphate | 2.7.1.- | Alcohol Kinase/ Phosphotrans-ferase | *Saccharomyces cerevisiae* ERG12 | P07277 |
| | | | | *Saccharomyces cerevisiae* ERG8 | P24521 |
| | | | | *Arabidopsis thaliana* At5g58560 | Q67ZM7 |
| | | | | *Mentha x piperita* ipk | P56848 |
| | | | | *Methanocaldococcus jannaschii* mvk | Q58487 |
| | | | | *Arabidopsis thaliana* mvk | AT5G27450.1 |
| | | | | *E. coli* ychB | NP_415726.1 |
| | | | | *E. coli* glpK | P0A6F3 |
| | | | | *Methanothermobacter thermautotrophicus* ipk | AAB84554.1 |
| | | | | *Thermoplasma acidophilum* ipk | WP_010900530.1 |
| | | | | *Methanocaldococcus jannaschii* ipk | 3K4Y_A |

TABLE H-continued

Example reactions and enzymes of the pathway for isoprenoid precursor synthesis via 2-hydroxyisovaleric acid and prenol starting from aldol condensation between acetaldehyde and pyruvate

| Reaction | Illustration | EC Numbers | Enzyme names | Source organism and gene/enzyme name | Protein Accession Numbers |
|---|---|---|---|---|---|
| dimethyallyl phosphate → dimethyallyl pyrophos-phate | 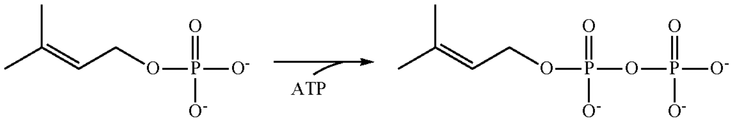 dimethylallyl phosphate; dimethylallyl pyrophosphate | 2.7.4- | Phosphate Kinase/ Phosphotrans-ferase | *Methanothermobacter thermautotrophicus* ipk | AAB84554.1 |
| | | | | *Thermoplasma acidophilum* ipk | WP_010900530.1 |
| | | | | *Enterococcus faecalis* mvaK2 | Q9FD67 |
| | | | | *Streptococcus pneumoniae* mvaK2 | A0A0I7UH23 |
| | | | | *Staphylococcus aureus* mvaK2 | A0A0E8GDF5 |
| | | | | *Methanocaldococcus jannaschii* ipk | 3K4Y_A |
| 3-methyl-2-butenol → dimethylallyl pyrophosphate | 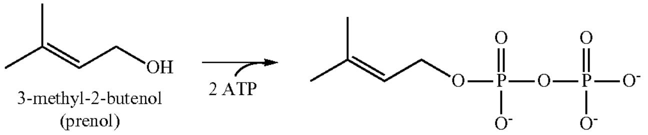 3-methyl-2-butenol (prenol); dimethylallyl pyrophosphate | 2.7.6- | Alcohol dis-phosphokinase | *Escherichia coli* Prs | NP_415725.1 |
| | | | | *Mycoplasma pneumoniae* M129 PrsA | NP_109761.1 |
| | | | | *Arabidopsis thaliana* col TPK1 | BAH19964.1 |
| | | | | *Arabidopsis thaliana* col TPK2 | BAH57065.1 |
| DMAPP ↔ IPP | 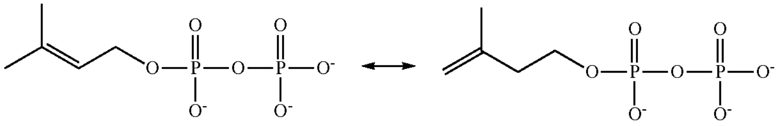 dimethylallyl pyrophosphate; Isopentenyl pyrophosphate | 5.3.3.2 | isopentenyl diphosphate isomerase | *E. coli* idi | Q46822 |

TABLE H-continued

Example reactions and enzymes of the pathway for isoprenoid precursor synthesis via 2-hydroxyisovaleric acid and prenol starting from aldol condensation between acetaldehyde and pyruvate

| Reaction | Illustration | EC Numbers | Enzyme names | Source organism and gene/enzyme name | Protein Accession Numbers |
|---|---|---|---|---|---|
| DMAPP + IPP → GPP | 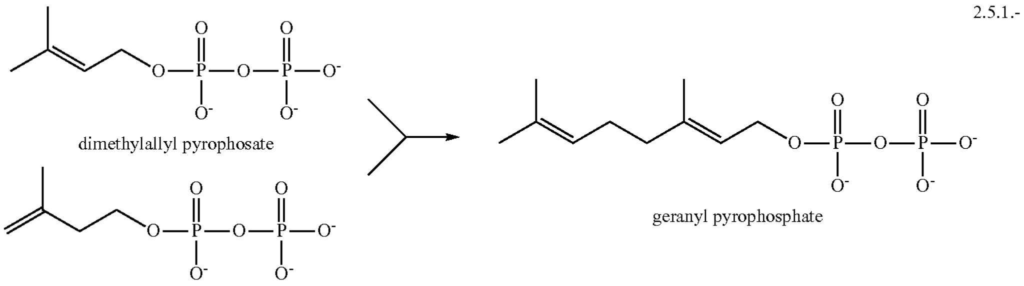 dimethylallyl pyrophosate; Isopentenyl pyrophosate; geranyl pyrophosphate | 2.5.1.- | Geranyl pyrophosphate synthase | *E. coli* ispA<br>*Abies grandis* GPPS2 | P22939<br>Q8LKJ2 |

TABLE I

Example reactions and enzymes of the pathway for isoprenoid precursor synthesis via 2-oxoisovaleric acid, 2-oxoisocaproic acid and prenol starting from aldol condensation between pyruvate and acetaldehyde

| Reaction | Illustration | EC Numbers | Enzyme names | Source organism and gene/enzyme name | Protein Accession Numbers |
|---|---|---|---|---|---|
| pyruvate → acetaldehyde | 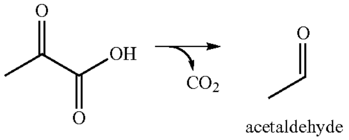 pyruvate; $CO_2$; acetaldehyde | 4.1.1.1 | alpha-ketoacid decarboxylase | *Saccharomyces cerevisiae* PDC1<br>*Saccharomyces cerevisiae* PDC5<br>*Saccharomyces cerevisiae* PDC6<br>*Pisum sativum* PDC1<br>*Saccharomyces cerevisiae* ARO10<br>*Saccharomyces cerevisiae* THI3<br>*Lactococcus lactis* kivd<br>*Pantoea agglomerans* idpC<br>*Enterobacter cloacae* idpC | NP_013145.1<br>NP_013235.1<br>NP_011601.3<br>CAA91444.1<br>NP_010668.3<br>NP_010203.1<br>CAG34226.1<br>WP_003848906.1<br>WP_073396207.1 |
| 4-methyl-2-oxo-pentanoate → 3-methlbutanal + $CO_2$ | 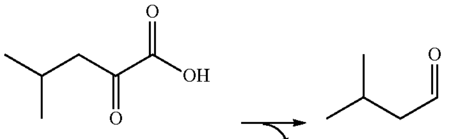 4-methyl-2-oxopentanoate (2-oxoisocaproate); $CO_2$; 3-methylbutanal | | | | |
| pyruvate + acetalde-hyde → 4-hydroxy-2-oxopentan-oate | 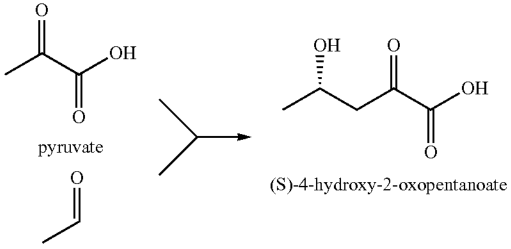 pyruvate; acetaldehyde; (S)-4-hydroxy-2-oxopentanoate | 4.1.3.39 | aldolase | *E. coli* mhpE<br>*Pseudomonas putida* xylK<br>*Pseudomonas* sp. CF600 dmpG | NP_414886.1<br>WP_011005904.1<br>WP_017849278.1 |

TABLE I-continued

| Example reactions and enzymes of the pathway for isoprenoid precursor synthesis via 2-oxoisovaleric acid, 2-oxoisocaproic acid and prenol starting from aldol condensation between pyruvate and acetaldehyde | | | | | |
|---|---|---|---|---|---|
| Reaction | Illustration | EC Numbers | Enzyme names | Source organism and gene/enzyme name | Protein Accession Numbers |
| 4-hydroxy-2-oxopentanoate → 3-hydroxy-2-oxo-3-methyl-butanoate | 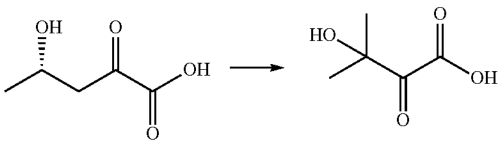 (S)-4-hydroxy-2-oxopentanoate; 3-hydroxy-2-oxo-3-methylbutanoate | 5.4.99.- | mutase | *Streptomyces cinnamonensis* icmAB<br>*Metallosphaera sedula* Msed_0638, Msed_2055<br>*Cupriavidus metallidurans* icmF<br>*Kyrpidia tusciae* rcmAB<br>*Rhodobacter sphaeroides* meaA | AAC08713.1. CAB59633.1<br>A4YEG1, A4YIE3<br>Q1LRY0<br>D5WTR7, D5WTR8<br>ABA80144.1 |
| 3-hydroxy-2-oxo-3-methyl-butanoate → 2,3-dihydroxy-3-methyl- | 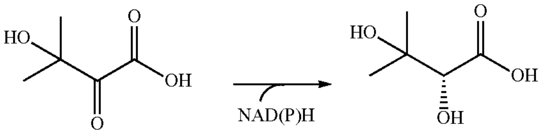 3-hydroxy-2-oxo-3-methylbutanoate; (2R)-2,3-dihydroxy-3-methylbutanoate | 1.1.1.- | 2-hydroxyacid dehydrogenase | *Acidammococcus fermentans* hgdH<br>*Methanocaldococcus jannaschii* mdh<br>*M. jannaschii* comC<br>*E. coli* mdh<br>*E. coli* serA<br>*E. coli* ldhA<br>*Haloferax mediterranei* ddh<br>*Lactococcus lactis* panE | D2RMS7<br>Q60176<br>Q58820<br>NP_417703.1<br>NP_417388.1<br>NP_415898.1<br>Q2VEQ7<br>A0A089XK51 |
| 2,3-dihydroxy-3-methyl-butanoate → 3-methyl-2-oxo-butanoate | 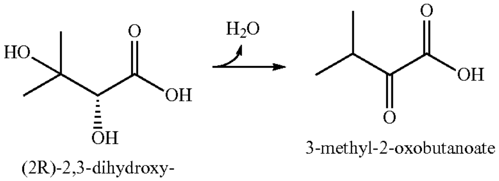 (2R)-2,3-dihydroxy-3-methylbutanoate; 3-methyl-2-oxobutanoate | 4.2.1.9 | Dihydroxyacid dehydratase | *E. coli* ilvD | P05791 |

TABLE I-continued

Example reactions and enzymes of the pathway for isoprenoid precursor synthesis via 2-oxoisovaleric acid, 2-oxoisocaproic acid and prenol starting from aldol condensation between pyruvate and acetaldehyde

| Reaction | Illustration | EC Numbers | Enzyme names | Source organism and gene/enzyme name | Protein Accession Numbers |
|---|---|---|---|---|---|
| 3-methyl-2-oxo-butanoate + acetyl-CoA → 2-isopropyl-malate + CoA | 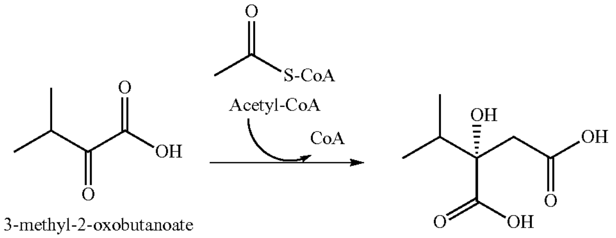 3-methyl-2-oxobutanoate (2-oxoisovalerate) (2S)-2-isopropylmalate | 2.3.3.13 | Isopropylmalate synthase | *E. coli* leuA | NP_414616.1 |
| 2-isopropyl-malate → 3-isopropyl-malate | 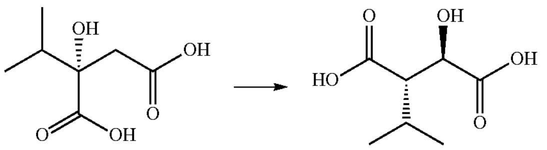 (2S)-2-isopropylmalate (2R, 3S)-3-isopropylmalate | 4.2.1.33 | Isopropylmalate isomerase | *E. coli* leuCD | NP_414614.1<br>NP_414613.1 |
| 3-isopropyl-malate → 4-methyl-2-oxopentanoate + $CO_2$ | 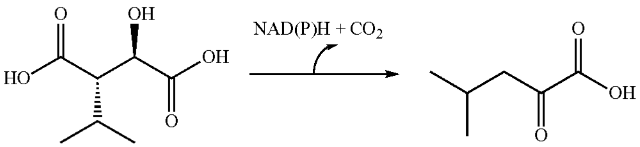 (2R, 3S)-3-isopropylmalate 4-methyl-2-oxopentanoate (2-oxoisocaproate) | 1.1.1.85 | Isopropylmalate dehydrogenase | *E. coli* leuB | NP_414615.4 |
| 4-methyl-2-oxopentanoate + CoA → isovaleryl-CoA + $CO_2$ | 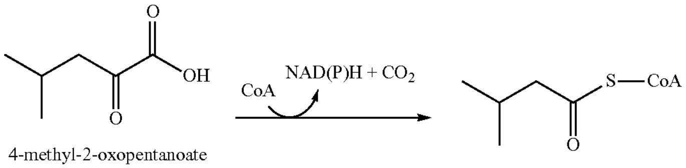 4-methyl-2-oxopentanoate (2-oxoisocaproate) Isovaleryl-CoA | 1.2.1.- | alpha-keto acid dehydrogenase complex | *Streptomyces avermitilis* bkdFGH-lpdA1<br><br>*Homo sapiens* BKDHAB-DBT-DLD<br>*Bacillus subtilis*<br><br>bfmBAA-bfmBAB-bfmBB-pdhD | BAC72088.1<br>BAC72089.1<br>BAC72090.1<br>KUN54417.1<br>NP_000700.1<br>NP_000047.1<br>NP_001909.3<br>NP_000099.2<br>WP_004398565.1<br>WP_004398638.1<br>WP_003230323.1<br>WP_003232309.1 |

TABLE I-continued

Example reactions and enzymes of the pathway for isoprenoid precursor synthesis via 2-oxoisovaleric acid, 2-oxoisocaproic acid and prenol starting from aldol condensation between pyruvate and acetaldehyde

| Reaction | Illustration | EC Numbers | Enzyme names | Source organism and gene/enzyme name | Protein Accession Numbers |
|---|---|---|---|---|---|
| | | | | *E. coli* lpdA-aceEF | NP_414657.1<br>NP_414658.1<br>NP_414656.1 |
| Isovaleryl-CoA → 3-methyl-2-butenoyl-CoA | 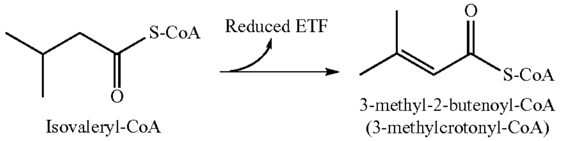<br>Isovaleryl-CoA<br>3-methyl-2-butenoyl-CoA (3-methylcrotonyl-CoA) | 1.3.8.4 | Acyl-CoA dehydrogenase | *Pseudomonas aeruginosa* liuA | APJ52511.1 |
| | | | | *E. coli* aidB | NP_418608.6 |
| | | | | *E. coli* fadE | NP_414756.2 |
| | | | | *Streptomyces avermitilis* acdH | AAD44196.1 |
| 3-methyl-2-butanoyl-CoA → 3-methyl-2-butenoate | 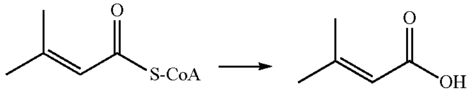<br>3-methyl-2-butenoyl-CoA<br>3-methyl-2-butenoate | 3.1.2.- | Thioesterase | *E. coli* tesA | NP_415027.1 |
| | | | | *E. coli* tesB | NP_414986.1 |
| | | | | *E. coli* yciA | NP_415769.1 |
| | | | | *E. coli* fadM | NP_414977.1 |
| | | | | *E. coli* ydiI | NP_416201.1 |
| | | | | *E. coli* ybgC | NP_415264.1 |
| | | | | *E. coli* paaI | NP_415914.1 |
| | | | | *Mus musculus* acot8 | P58137.1 |
| | | | | *Lycopersicon hirsutum f glabratum* mks2 | ADK38536.1 |
| | | | | *Alcanivorax borkumensis* tesB2 | YP_692749.1 |
| | | | | *Fibrobacter succinogenes* Fs2108 | YP_005822012.1 |
| | | | | *Prevotella ruminicola* Pr655 | YP_003574018.1 |
| | | | | *Prevotella ruminicola Pr*1687 | YP_003574982.1 |
| | | 2.8.3.8 | Acyl-CoA: acetyl-CoA transferase | *E. coli* atoD | NP_416725.1 |
| | | | | *Clostridium kluyveri* cat2 | AAA92344.1 |
| | | | | *Clostridium acetobutylicum* ctfAB | NP_149326.1, NP_149327.1 |
| | | | | *E. coli* ydiF | NP_416209.1 |
| | | 2.3.1.-; 2.7.2.1; 2.7.2.15 | Phospho-transacylase + Carboxylate kinase | *Clostridium acetobutylicum* ptb | NP_349676.1 |
| | | | | *Enterococcus faecalis* ptb | AAD55374.1 |
| | | | | *Salmonella enterica* pduL | AAD39011.1 |

TABLE I-continued

Example reactions and enzymes of the pathway for isoprenoid precursor synthesis via 2-oxoisovaleric acid, 2-oxoisocaproic acid and prenol starting from aldol condensation between pyruvate and acetaldehyde

| Reaction | Illustration | EC Numbers | Enzyme names | Source organism and gene/enzyme name | Protein Accession Numbers |
|---|---|---|---|---|---|
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| 3-methyl-2-butenoate → 3-methyl-2-butenal | 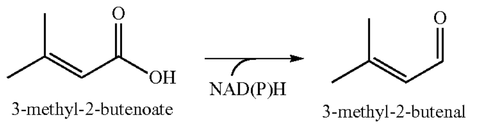 3-methyl-2-butenoate 3-methyl-2-butenal | 1.2.1- | Carboxylic Acid (Carboxylate) reductase | *E. coli* PaoABC | NP_414820.1, NP_414819.1, NP_414818.1 |
| | | | | *Mycobacterium marinum* Car | WP_012393886.1 |
| | | | | *Nocardia iowensis* Car | AAR91681.1 |
| | | | | *Segniliparus rotundus* Car | WP_013138593.1 |
| 3-methyl-2-butenoyl-CoA → 3-methyl-2-butenol | 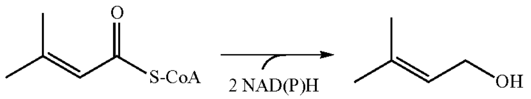 3-methyl-2-butenoyl-CoA 3-methyl-2-butenol (prenol) | 1.2.1- | Alcohol-forming Acyl-CoA reductase | *Clostridium acetobutylicum* adhE2 | YP_009076789.1 |
| | | | | *Arabidopsis thaliana* At3g11980 | AEE75132.1 |
| | | | | *Arabidopsis thaliana* At3g44560 | AEE77915.1 |
| | | | | *Arabidopsis thaliana* At3g56700 | AEE79553.1 |
| | | | | *Arabidopsis thaliana* At5g22500 | AED93034.1 |
| | | | | *Arabidopsis thaliana* CER4 | AEE86278.1 |
| | | | | *Marinobacter aquaeolei* VT8 maqu_2220 | YP_959486.1 |
| | | | | *Marinobacter aquaeolei* VT8 maqu_2507 | YP_959769.1 |

TABLE I-continued

Example reactions and enzymes of the pathway for isoprenoid precursor synthesis via 2-oxoisovaleric acid, 2-oxoisocaproic acid and prenol starting from aldol condensation between pyruvate and acetaldehyde

| Reaction | Illustration | EC Numbers | Enzyme names | Source organism and gene/enzyme name | Protein Accession Numbers |
|---|---|---|---|---|---|
| 3-methyl-2-butenoyl-CoA → 3-methyl-2-butenal | 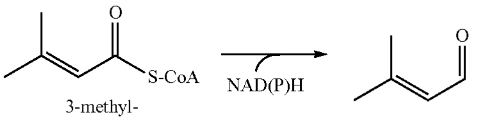 3-methyl-2-butenoyl-CoA; 3-methyl-2-butenal | 1.2.1- | Aldehyde forming CoA reductase | *Acinetobacter calcoaceticus* acr1 | AAC45217.1 |
| | | | | *Acinetobacter* sp Strain M-1 acrM | BAB85476.1 |
| | | | | *Clostridium beijerinckii* ald | AAT66436.1 |
| | | | | *E. coli* eutE | NP_416950.1 |
| acetyl-Coa → acetaldehyde | 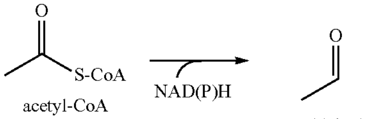 acetyl-CoA; acetaldehyde | | | *Salmonella enterica* eutE | AAA80209.1 |
| | | | | *E. coli* mhpF | NP_414885.1 |
| 3-methyl-2-butenal → 3-methyl-2-butenol | 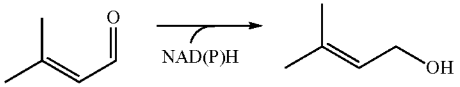 3-methyl-2-butenal; 3-methyl-2-butenol (prenol) | 1.1.1.- | Alcohol dehydrogenase | *E. coli* betA | NP_414845.1 |
| | | | | *E. coli* dkgA | NP_417485.4 |
| | | | | *E. coli* eutG | NP_416948.4 |
| | | | | *E. coli* fucO | NP_417279.2 |
| | | | | *E. coli* ucpA | NP_416921.4 |
| | | | | *E. coli* yahK | NP_414859.1 |
| | | | | *E. coli* ybbO | NP_415026.1 |
| | | | | *E. coli* ybdH | NP_415132.1 |
| | | | | *E. coli* yiaY | YP_026233.1 |
| | | | | *E. coli* yjgB | NP_418690.4 |
| | | | | *Acinetobacter* sp. SE19 ChnD | AAG10028.1 |
| | | | | *Marinobacter aquaeolei* VT8 maqu_2507 | YP_959769.1 |
| | | | | *Saccharomyces cerevisiae* ADH6 | Q04894.1 |
| | | | | *Clostridium kluyveri* 4hbD | EDK35022.1 |
| 3-methyl-2-butenol → dimethylallyl phosphate | 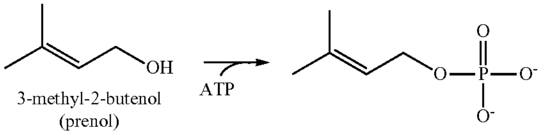 3-methyl-2-butenol (prenol); dimethylallyl phosphate | 2.7.1.- | Alcohol Kinase/ Phospho-transferase | *Saccharomyces cerevisiae* ERG12 | P07277 |
| | | | | *Saccharomyces cerevisiae* ERG8 | P24521 |
| | | | | *Arabidopsis thaliana* At5g58560 | Q67ZM7 |
| | | | | *Mentha x piperita* ipk | P56848 |
| | | | | *Methanocaldococcus jannaschii* mvk | Q58487 |
| | | | | *Arabidopsis* | AT5G27450.1 |

TABLE I-continued

Example reactions and enzymes of the pathway for isoprenoid precursor synthesis via 2-oxoisovaleric acid, 2-oxoisocaproic acid and prenol starting from aldol condensation between pyruvate and acetaldehyde

| Reaction | Illustration | EC Numbers | Enzyme names | Source organism and gene/enzyme name | Protein Accession Numbers |
|---|---|---|---|---|---|
| | | | | *thaliana* mvk | |
| | | | | *E. coli* ispE | P62615 |
| | | | | *E. coli* glpK | P0A6F3 |
| | | | | *E. coli* ychB | NP_415726.1 |
| | | | | *Thermoplasma acidophilum* IPK | WP_010900530.1 |
| dimethylallyl phosphate → dimethylallyl pyrophosphate | 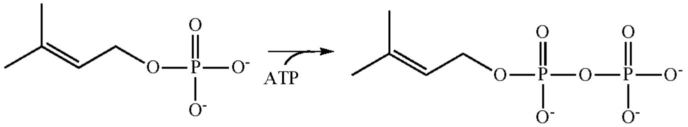  dimethylallyl phosphate; dimethyallyl pyrophosphate | 2.7.4- | Phosphate Kinase/ Phospho-transferase | *Methanothermobacter thermautotrophicus* ipk | AAB84554.1 |
| | | | | *Thermoplasma acidophilum* ipk | WP_010900530.1 |
| | | | | *Enterococcus faecalis* mvaK2 | Q9FD67 |
| | | | | *Streptococcus pneumoniae* mvaK2 | A0A0I7UH23 |
| | | | | *Staphylococcus aureus* mvaK2 | A0A0E8GDF5 |
| | | | | *Methanocaldococcus jannaschii* ipk | 3K4Y_A |
| 3-methyl-2-butenol → dimethylallyl pyrophosphate | 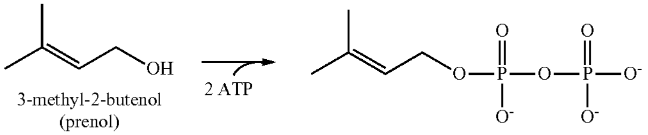  3-methyl-2-butenol (prenol); dimethylallyl pyrophosphate | 2.7.6- | Alcohol diphospho-kinase | *Escherichia coli* Prs | NP_415725.1 |
| | | | | *Mycoplasma pneumoniae* M129 PrsA | NP_109761.1 |
| | | | | *Arabidopsis thaliana* col TPK1 | BAH19964.1 |
| | | | | *Arabidopsis thaliana* col TPK2 | BAH57065.1 |
| DMAPP ↔ IPP | 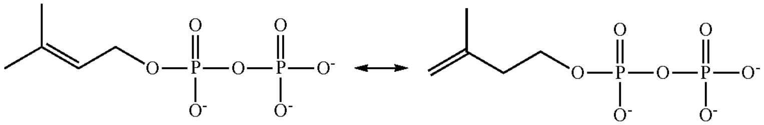 dimethylallyl pyrophosphate; Isopentenyl pyrophosphate | 5.3.3.2 | isopentenyl diphosphate isomerase | *E. coli* idi | Q46822 |

TABLE I-continued

Example reactions and enzymes of the pathway for isoprenoid precursor synthesis via 2-oxoisovaleric acid, 2-oxoisocaproic acid and prenol starting from aldol condensation between pyruvate and acetaldehyde

| Reaction | Illustration | EC Numbers | Enzyme names | Source organism and gene/enzyme name | Protein Accession Numbers |
|---|---|---|---|---|---|
| DMAPP + IPP → GPP | 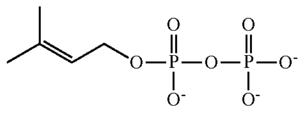 dimethylallyl pyrophosphate 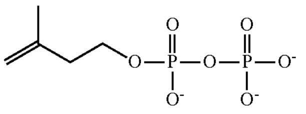 Isopentenyl pyrophosphate 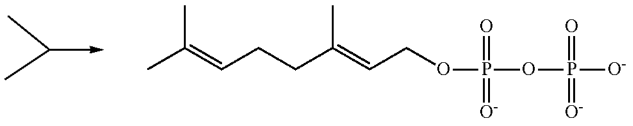 garenyl pyrophosphate | 2.5.1- | Geranyl pyrophosphate synthase | *E. coli* ispA<br>*Abies grandis* GPPS2 | P22939<br>Q8LKJ2 |

TABLE J

Reactions of the isoprenoid precursor synthesis pathway via 4-methyl-2-oxopent-4-enoic acid and isoprenol starting from aldol condensation between acetaldehyde and 2-oxobutyric acid

| Reaction | Illustration | EC Numbers | Enzyme names | Source organism and gene/enzyme name | Protein Accession Numbers |
|---|---|---|---|---|---|
| acetyl-Coa → acetaldehyde | 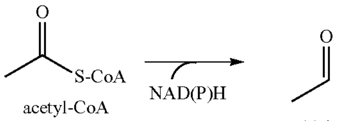 acetyl-CoA acetaldehyde | 1.2.1.- | Aldehyde forming CoA reductase | *Acinetobacter calcoaceticus* acr1 | AAC45217.1 |
| | | | | *Acinetobacter* sp Strain M-1 acrM | BAB85476.1 |
| | | | | *Clostridium beijerinckii* ald | AAT66436.1 |
| | | | | *E. coli* eutE | NP_416950.1 |
| 3-methyl-2-butenoyl-CoA → 3-methyl-2-butenal | 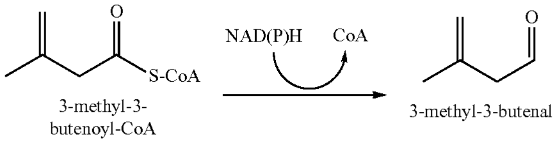 3-methyl-3-butenoyl-CoA 3-methyl-3-butenal | | | *Salmonella enterica* eutE | AAA80209.1 |
| | | | | *E. coli* mhpF | NP_414885.1 |
| pyruvate → acetaldehyde | 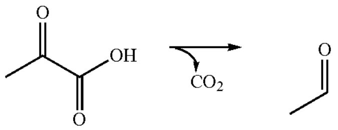 pyruvate acetaldehyde | 4.1.1.1 | alpha-ketoacid decarboxylase | *Saccharomyces cerevisiae* PDC1 | NP_013145.1 |
| | | | | *Saccharomyces cerevisiae* PDC5 | NP_013235.1 |
| | | | | *Saccharomyces cerevisiae* PDC6 | NP_011601.3 |
| | | | | *Pisum sativum* PDC1 | CAA91444.1 |
| 4-methyl-2-oxopent-4-enoate → 3-methyl-3-butenal | 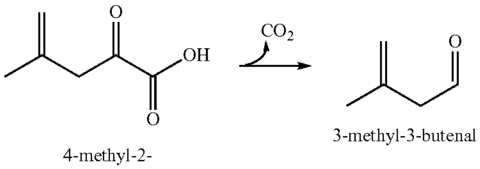 4-methyl-2-oxopent-4-enoate 3-methyl-3-butenal | | | *Saccharomyces cerevisiae* ARO10 | NP_010668.3 |
| | | | | *Saccharomyces cerevisiae* THI3 | NP_010203.1 |
| | | | | *Lactococcus lactis* kivd | CAG34226.1 |
| | | | | *Pantoea agglomerans* idpC | WP_003848906.1 |
| | | | | *Enterobacter cloacae* idpC | WP_073396207.1 |

TABLE J-continued

Reactions of the isoprenoid precursor synthesis pathway via 4-methyl-2-oxopent-4-enoic acid and isoprenol starting from aldol condensation between acetaldehyde and 2-oxobutyric acid

| Reaction | Illustration | EC Numbers | Enzyme names | Source organism and gene/enzyme name | Protein Accession Numbers |
|---|---|---|---|---|---|
| Pyruvate + acetyl-CoA → citramalate | 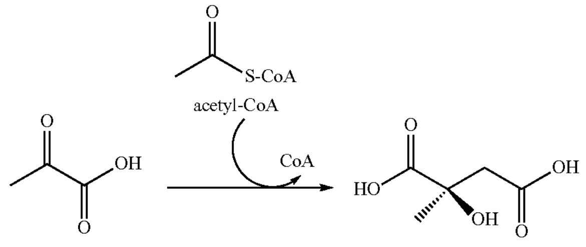 acetyl-CoA; pyruvate; (R)-citramalate | 2.3.1.182 | Citramalate synthase | *Methanocaldococcus jannaschii* cimA<br>*Leptospira interrogans serovar Lai* str. 56601 cimA | WP_10870909.1<br>NP_712531.1 |
| Citramalate → 3-methyl-malate | 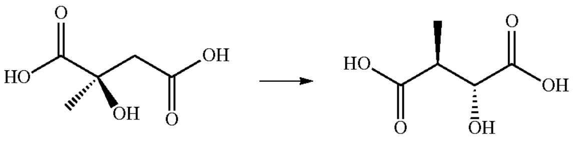 (R)-citramalate; (2R,3S)-3-methylmalate | 4.2.1.35 | Citramalate isomerase | *E. coli* leuCD<br>*Methanocaldococcus jannaschii* leuCD<br>*Leptospira interrogans serovar Lai* str. 56601 leuCD | NP_414614.1<br>NP_414613.1<br>AAB98487.1<br>AAB99283.1<br>NP_712276.1<br>NP_712277.1 |
| 3-methyl-malate →2-oxobutyric acid + $CO_2$ | 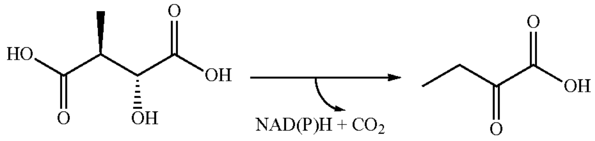 (2R,3S)-3-methylmalate; 2-oxobutanoate | 1.2.1- | 3-methylmalate dehydrogenase | *Methanocaldococcus jannaschii* MJ0270<br>*Leptospira interrogans serovar Lai* str. 56601 leuB | WP_010870225.1<br>NP_712333.1 |

TABLE J-continued

Reactions of the isoprenoid precursor synthesis pathway via 4-methyl-2-oxopent-4-enoic acid and isoprenol starting from aldol condensation between acetaldehyde and 2-oxobutyric acid

| Reaction | Illustration | EC Numbers | Enzyme names | Source organism and gene/enzyme name | Protein Accession Numbers |
|---|---|---|---|---|---|
| 2-oxobutyric acid + acetaldehyde → 4-hydroxy-2-oxo-3-methyl-pentanoate | 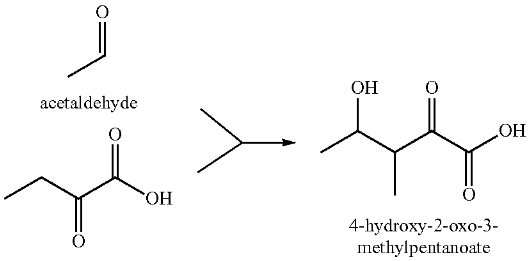 acetaldehyde; 2-oxobutanoate; 4-hydroxy-2-oxo-3-methylpentanoate | 4.1.3.- | aldolase | *E. coli* mhpE<br>*Pseudomonas putida* xylK<br>*Pseudomonas* sp. CF600 dmpG | NP_414886.1<br>WP_011005904.1<br>WP_017849278.1 |
| 4-hydroxy-2-oxo-3-methyl-pentanoate → 4-methyl-pentanoate | 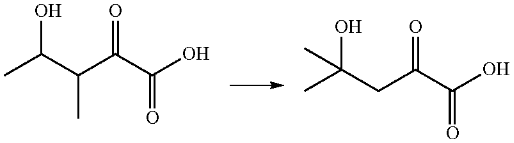 4-hydroxy-2-oxo-3-methylpentanoate; 4-hydroxy-2-oxo-4-methylpentanoate | 5.4.99.- | mutase | *Streptomyces cinnamonensis* icmAB<br>*Metallosphaera sedula* Msed_0638, Msed_2055<br>*Cupriavidus metallidurans* icmF<br>*Kyrpidia tusciae* rcmAB<br>*Rhodobacter sphaeroides* meaA | AAC08713.1. CAB59633.1<br>A4YEG1, A4YIE3<br>Q1LRY0<br>D5WTR7, D5WTR8<br>ABA80144.1 |
| 4-hydroxy-2-oxo-4-methyl-pentanoate → 4-methyl-2-oxopent-4-enoate | 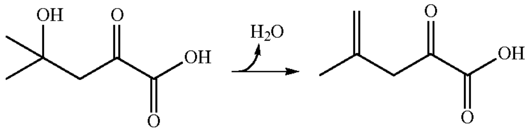 4-hydroxy-2-oxo-4-methylpentanoate; 4-methyl-2-oxopent-4-enoate | 4.2.1.- | 2-oxopent-4-enoate hydratase | *E. coli* mhpD<br>*Comamonas testosteroni* CNB-1 cnbE<br>*Pseudomonas putida* xylJ | NP_414884.2<br>WP_012478201.1<br>WP_011005906.1 |

TABLE J-continued

Reactions of the isoprenoid precursor synthesis pathway via 4-methyl-2-oxopent-4-enoic acid and isoprenol starting from aldol condensation between acetaldehyde and 2-oxobutyric acid

| Reaction | Illustration | EC Numbers | Enzyme names | Source organism and gene/enzyme name | Protein Accession Numbers |
|---|---|---|---|---|---|
| 4-methyl-2-oxopent-4-enoate → 3-methyl-3-butenoyl-CoA | 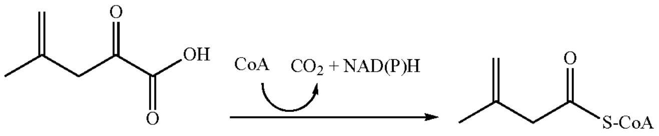<br>4-methyl-2-oxopent-4-enoate<br>3-methyl-3-butenoyl-CoA | 1.2.1.,- | alpha-keto acid dehydrogenase | *Streptomyces avermitilis* bkdFGH-lpdA1 | BAC72088.1<br>BAC72089.1<br>BAC72090.1<br>KUN54417.1 |
| | | | | *Homo sapiens* BKDHAB-DBT-DLD | NP_000700.1<br>NP_000047.1<br>NP_001909.3<br>NP_000099.2 |
| | | | | *Bacillus subtilis* bfmBAA-bfmBAB-bfmBB-pdhD | WP_004398565.1<br>WP_004398638.1<br>WP_003230323.1<br>WP_003232309.1 |
| | | | | *E. coli* lpdA-aceEF | NP_414657.1<br>NP_414658.1<br>NP_414656.1 |
| 3-methyl-3-butenoyl-CoA →3-methyl-3-butenoate | 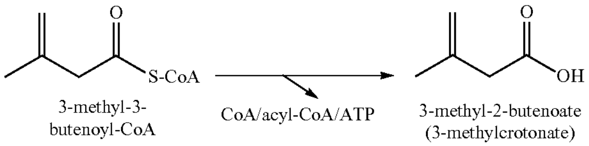<br>3-methyl-3-butenoyl-CoA<br>3-methyl-2-butenoate (3-methylcrotonate) | 3.1.2.- | Thioesterase | *E. coli* tesA<br>*E. coli* tesB<br>*E. coli* yciA<br>*E. coli* fadM<br>*E. coli* ydiI<br>*E. coli* ybgC | NP_415027.1<br>NP_414986.1<br>NP_415769.1<br>NP_414977.1<br>NP_416201.1<br>NP_415264.1 |
| | | | | *E. coli* paaI | NP_415914.1 |
| | | | | *Mus musculus* acot8 | P58137.1 |
| | | | | *Lycopersicon hirsutum f glabratum* mks2 | ADK38536.1 |
| | | | | *Alcanivorax borkumensis* tesB2 | YP_692749.1 |
| | | | | *Fibrobacter succinogenes* Fs2108 | YP_005822012.1 |
| | | | | *Prevotella ruminicola* Pr655 | YP_003574018.1 |
| | | | | *Prevotella ruminicola* Pr1687 | YP_003574982.1 |
| | | 2.8.3- | CoA transferase | *E. coli* atoD<br>*E. coli* atoA<br>*E. coli* scpC | NP_416725.1<br>NP_416726.1<br>NP_417395.1 |
| | | | | *Clostridium kluyveri* cat1 | AAA92346.1 |
| | | | | *Clostridium kluyveri* cat2 | AAA92344.1 |

TABLE J-continued

Reactions of the isoprenoid precursor synthesis pathway via 4-methyl-2-oxopent-4-enoic acid and isoprenol starting from aldol condensation between acetaldehyde and 2-oxobutyric acid

| Reaction | Illustration | EC Numbers | Enzyme names | Source organism and gene/enzyme name | Protein Accession Numbers |
|---|---|---|---|---|---|
| | | | | *Clostridium acetobutylicum* ctfAB | NP_149326.1, NP_149327.1 |
| | | | | *Pseudomonas putida* pcalJ | NP_746081.1 NP_746082.1 |
| | | | | *Megasphaera elsdenii* pct | WP_014015705.1 |
| | | | | *Acidaminococcus fermentans* gctAB | CAA57199.1 CAA57200.1 |
| | | | | *Acetobacter aceti* aarC | AGG68319.1 |
| | | | | *E. coli* ydiF | NP_416209.1 |
| | | 2.3.1.-; 2.7.2.1; 2.7.2.15 | Phosphotrans-acylase + Carboxylate kinase | *Clostndium acetobutylicum* ptb | NP_349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| 3-methyl-3-butenoate → 3-methyl-butenal | 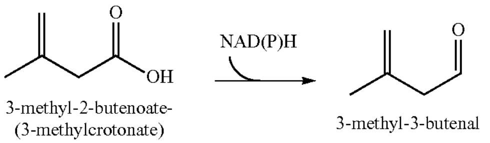 3-methyl-2-butenoate-(3-methylcrotonate) NAD(P)H 3-methyl-3-butenal | 1.2.99.6 | Carboxylic Acid (Carboxylate) reductase | *E. coli* PaoABC | NP_414820.1, NP_414819.1, NP_414818.1 |
| | | | | *Mycobacterium marinum* Car | WP_012393886.1 |
| | | | | *Nocardia iowensis* Car | AAR91681.1 |
| | | | | *Segniliparus rotundus* Car | WP_013138593.1 |
| 3-methyl-3-butenal → 3-methyl-3 butenol | 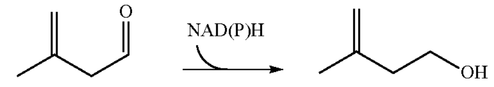 3-methyl-3-butenal NAD(P)H 3-methyl-3-butenol (isoprenol) | 1.1.1.- | Alcohol dehydrogenase | *E. coli* betA | NP_414845.1 |
| | | | | *E. coli* dkgA | NP_417485.4 |
| | | | | *E. coli* eutG | NP_416948.4 |
| | | | | *E. coli* fucO | NP_417279.2 |
| | | | | *E. coli* ucpA | NP_416921.4 |
| | | | | *E. coli* yahK | NP_414859.1 |
| | | | | *E. coli* ybbO | NP_415026.1 |
| | | | | *E. coli* ybdH | NP_415132.1 |
| | | | | *E. coli* yiaY | YP_026233.1 |
| | | | | *E. coli* yjgB | NP_418690.4 |

TABLE J-continued

Reactions of the isoprenoid precursor synthesis pathway via 4-methyl-2-oxopent-4-enoic acid and isoprenol starting from aldol condensation between acetaldehyde and 2-oxobutyric acid

| Reaction | Illustration | EC Numbers | Enzyme names | Source organism and gene/enzyme name | Protein Accession Numbers |
|---|---|---|---|---|---|
| | | | | *Acinetobacter* sp. SE19 ChnD | AAG10028.1 |
| | | | | *Marinobacter aquaeolei* VT8 maqu_2507 | YP_959769.1 |
| | | | | *Saccharomyces cerevisiae* ADH6 | Q04894.1 |
| | | | | *Clostridium kluyveri* 4hbD | EDK35022.1 |
| 3-methyl-3-butenoyl-CoA → 3-methyl-butenol | 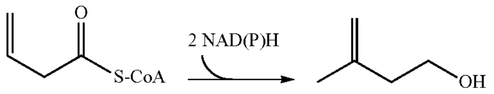  3-methyl-3-butenoyl-CoA; 3-methyl-3-butenol (isoprenol) | 1.2.1- | Alcohol-forming Acyl-CoA reductase | *Salmonella enterica* pduW | AAD39021.1 |
| | | | | *Arabidopsis thaliana* At3g11980 | AEE75132.1 |
| | | | | *Arabidopsis thaliana* At3g44560 | AEE77915.1 |
| | | | | *Arabidopsis thaliana* At3g56700 | AEE79553.1 |
| | | | | *Arabidopsis thaliana* At5g22500 | AED93034.1 |
| | | | | *Arabidopsis thaliana* CER4 | AEE86278.1 |
| | | | | *Marinobacter aquaeolei* VT8 maqu_2220 | YP_959486.1 |
| | | | | *Marinobacter aquaeolei* VT8 maqu_2507 | YP_959769.1 |
| 3-methyl-3-butenol → Isopentenyl phosphate | 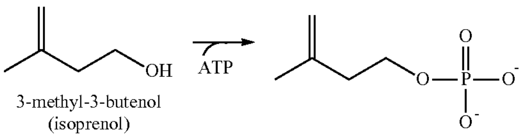  3-methyl-3-butenol (isoprenol); isopentenyl phosphate | 2.7.1.- | Alcohol Kinase/ Phospho-transferase | *Saccharomyces cerevisiae* ERG12 | P07277 |
| | | | | *Saccharomyces cerevisiae* ERG8 | P24521 |
| | | | | *Arabidopsis thaliana* At5g58560 | Q67ZM7 |
| | | | | *Mentha x piperita* ipk | P56848 |
| | | | | *Arabidopsis thaliana* mvk | AT5G27450.1 |
| | | | | *E. coli* ychB | NP_415726.1 |
| | | | | *E. coli* glpK | P0A6F3 |

TABLE J-continued

Reactions of the isoprenoid precursor synthesis pathway via 4-methyl-2-oxopent-4-enoic acid and isoprenol starting from aldol condensation between acetaldehyde and 2-oxobutyric acid

| Reaction | Illustration | EC Numbers | Enzyme names | Source organism and gene/enzyme name | Protein Accession Numbers |
|---|---|---|---|---|---|
| | | | | *Methanothermobacter thermautotrophicus* ipk | AAB84554.1 |
| | | | | *Thermoplasma acidophilum* ipk | WP_010900530.1 |
| | | | | *Methanocaldococcus jannaschii* ipk | 3K4Y_A |
| isopentenyl phosphate → isopentenyl pyrophosphate | 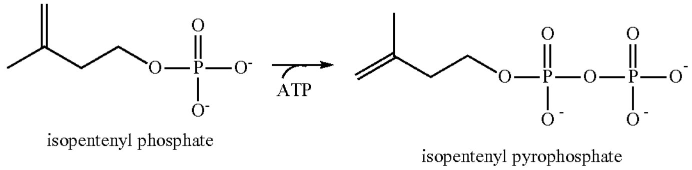 isopentenyl phosphate; isopentenyl pyrophosphate | 2.7.4- | Phosphate Kinase/ Phospho-transferase | *Methanothermobacter thermautotrophicus* ipk | AAB84554.1 |
| | | | | *Thermoplasma acidophilum* ipk | WP_010900530.1 |
| | | | | *Enterococcus faecalis* mvaK2 | Q9FD67 |
| | | | | *Streptococcus pneumoniae* mvaK2 | A0A0I7UH23 |
| | | | | *Staphylococcus aureus* mvaK2 | A0A0E8GDF5 |
| | | | | *Methanocaldococcus jannaschii* ipk | 3K4Y_A |
| 3-methyl-3-butenol → Isopentenyl pyrophosphate | 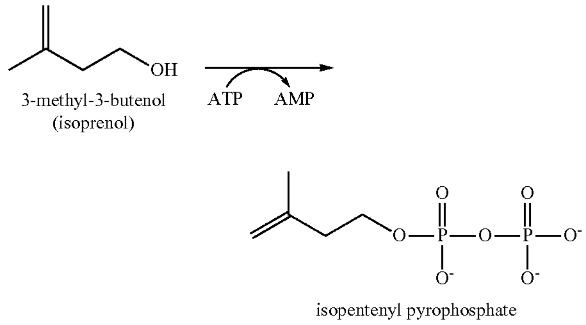 3-methyl-3-butenol (isoprenol); isopentenyl pyrophosphate | 2.7.6- | Alcohol diphosphokinase | *E. coli* prs | NP_415725.1 |
| | | | | *Mycoplasma pneumoniae* M129 prsA | NP_109761.1 |
| | | | | *Arabidopsis thaliana* col TPK1 | BAH19964.1 |
| | | | | *Arabidopsis thaliana* col TPK2 | BAH57065.1 |

TABLE J-continued

Reactions of the isoprenoid precursor synthesis pathway via 4-methyl-2-oxopent-4-enoic acid and isoprenol starting from aldol condensation between acetaldehyde and 2-oxobutyric acid

| Reaction | Illustration | EC Numbers | Enzyme names | Source organism and gene/enzyme name | Protein Accession Numbers |
|---|---|---|---|---|---|
| IPP ↔ DMAPP | 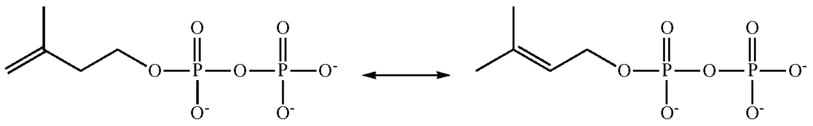 isopentenyl pyrophosphate; dimethylallyl pyrophosphate | 5.3.3.2 | isopentenyl diphosphate isomerase | *E. coli* idi | NP_417365.1 |
| DMAPP + IPP → GPP | 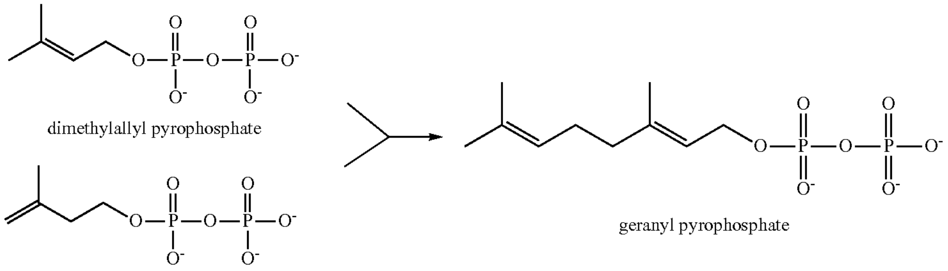 dimethylallyl pyrophosphate; Isopentenyl pyrophosphate; geranyl pyrophosphate | 2.5.1- | Geranyl pyrophosphate synthase | *E. coli* ispA<br>*Abies grandis* GPPS2 | NP_414955.1<br>AAN01134.1 |

TABLE K

| Example reactions and enzymes for the synthesis of isoprenoids | | | | | |
|---|---|---|---|---|---|
| Reaction | Illustration | EC Numbers | Enzyme names | Source organism and gene name | Protein Accession Numbers |
| GPP → limonene | 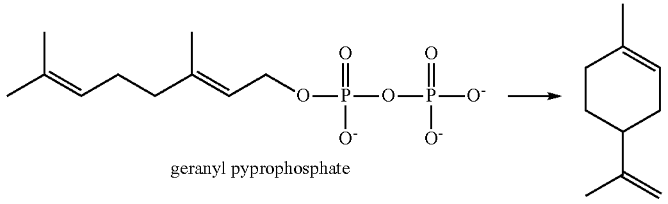 geranyl pyprophosphate limonene | 4.2.3.16 | limonene synthase | *Mentha spitaca* LS<br>*Ocimum basilicum* FES<br>*Abies grandis* g-lim1<br>*Abies grandis* g-pin2<br>*Arabidopsis thaliana* col TPS 10<br>*Picea abies* TPS-car<br>*Picea abies* TPS-lim | AGN90914.1<br>AAV63790.1<br>AAB70907.1<br>AAF61455.1<br>NP_179998.1<br>AAO73863.1<br>AAS47694.1 |
| GPP → pinene | 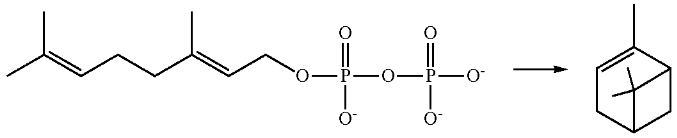 geranyl pyrophosphate pinene | 4.2.3.119<br>4.2.3.120<br>4.2.3.121<br>4.2.3.122 | pinene synthase | *Pinus taeda* pt30<br>*Abies grandis* g-pin1<br>*Abies grandis* g-lim1<br>*Abies grandis* g-pin2<br>*Picea abies* TPS-car<br>*Picea abies* TPS-lim<br>*Ocimum basilicum* FES | AAQ61228.1<br>AAB71085.1<br>AAB70907.1<br>AAF61455.1<br>AAO73863.1<br>AAS47694.1<br>AAV63790.1 |

TABLE K-continued

| Example reactions and enzymes for the synthesis of isoprenoids | | | | | |
|---|---|---|---|---|---|
| Reaction | Illustration | EC Numbers | Enzyme names | Source organism and gene name | Protein Accession Numbers |
| GPP + IPP → FPP | 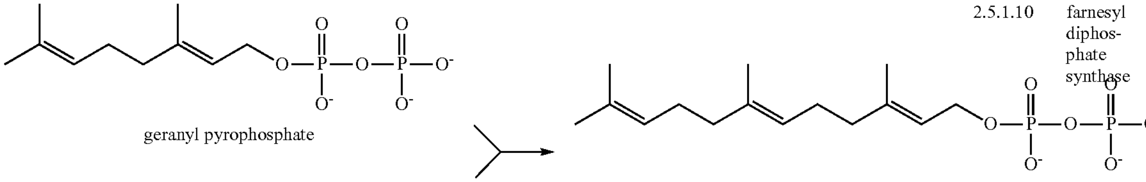<br>geranyl pyrophosphate<br>isopentenyl pyrophosphate<br>farnesyl pyrophosphate | 2.5.1.10 | farnesyl diphos-phate synthase | *E. coli* ispA<br>*Saccharomyces cerevisiae* FPP1<br>*Solanum lycopersicum* lefps1<br>*Arabidopsis thaliana* col FPS1<br>*Capsicum annuum* GGPPS<br>*Ginkgo biloba* FPS<br>*Hevea brasiliensis* hbgg<br>*Homo sapiens* FDPS<br>*Methanother-mobacter marburgensis Marburg* idsA<br>*Mycobacterium tuberculosis* H37Rv rv3398c | NP_414955.1<br>NP_012368.1<br>NP_001234068.1<br>NP_199588.1<br>XP_016568624.1<br>AAR27053.1<br>BAB60678.1<br>NP_001129293.1<br>WP_013295358.1<br>WP_003417957.1 |
| FPP → beta-caryophyllene | 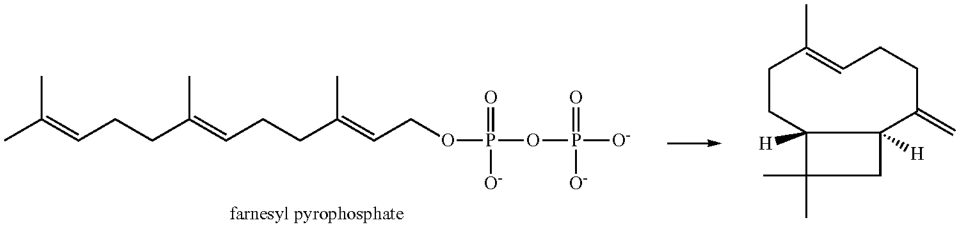<br>farnesyl pyrophosphate<br>β-caryophyllene | 4.2.3.57 | beta-caryo-phyllene synthase | *Artemisia annua* QHS1<br>*Arabidopsis thaliana* col AT5G23960<br>*Cucumis sativus* bcp<br>*Oryza sativa* osTPS3<br>*Zingiber zerumbet* zss1 | AAL79181.1<br>NP_197784.2<br>NP_001292628.1<br>XP_015648213.1<br>BAG12020.1 |

TABLE K-continued

Example reactions and enzymes for the synthesis of isoprenoids

| Reaction | Illustration | EC Numbers | Enzyme names | Source organism and gene name | Protein Accession Numbers |
|---|---|---|---|---|---|
| FPP → valencene | 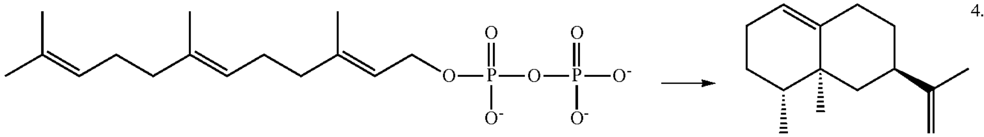 farnesyl pyrophosphate; valencene | 4.2.3.73 | valencene synthase | *Callitropsis nootkatensis* VALC<br>*Citrus sinensis* tps1<br>*Vitis vinifera* valcs | AFN21429.1<br>AAQ04608.1<br>AAS66358.1 |
| FPP → vetispiradiene | 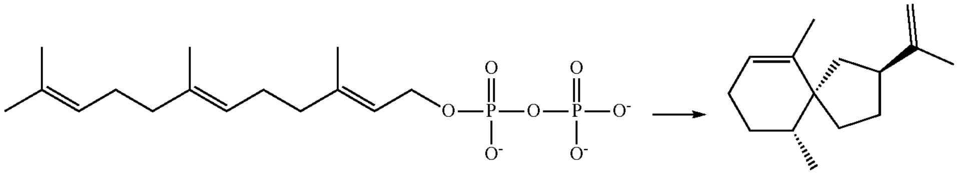 farnesyl pyrophosphate; vetispiradiene | 4.2.3.21 | vetispir-adiene synthase | *Hyoscyamus muticus* VS1 | Q39978.2 |
| FPP → amorphadiene | 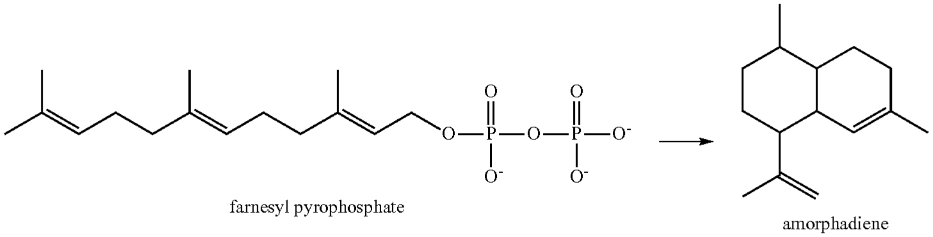 farnesyl pyrophosphate; amorphadiene | 4.2.3.24 | amor-phadiene synthase | *Artemisia annua* ads | AAF61439.1 |
| FPP → farnesene | 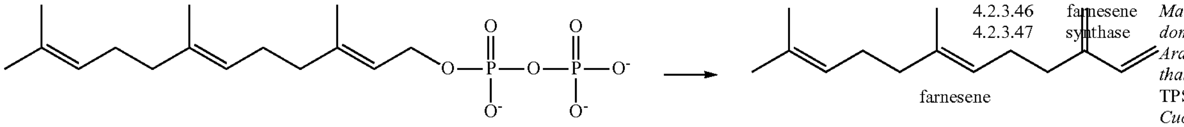 farnesyl pyrophosphate; farnesene | 4.2.3.46<br>4.2.3.47 | farnesene synthase | *Malus domestica* FS<br>*Arabidopsis thaliana* col TPS03<br>*Cucumis sativus* afs<br>*Picea abies* TPS-far<br>*Arabidopsis thaliana* col AT5G44630<br>*Artemisia annua* FS | NP_001280822.1<br>NP_567511.3<br>NP_001267674.1<br>AAS47697.1<br>NP_199276.1<br>CAC12731.1 |

TABLE K-continued

Example reactions and enzymes for the synthesis of isoprenoids

| Reaction | Illustration | EC Numbers | Enzyme names | Source organism and gene name | Protein Accession Numbers |
|---|---|---|---|---|---|
| | | | | *Citrus junos* CJFS | AAK54279.1 |
| | | | | *Mentha x piperita* tspa 11 | AAB95209.1 |
| | | | | *Picea abies* TPS-lon | AAS47695.1 |
| | | | | *Zea mays* TPS10 | NP_001105850.2 |
| | | | | *Zea mays* TPS1 | NP_001105097.1 |

TABLE L

Example reactions for the production of prenylated aromatic compounds and example enzymes

| Reaction | Illustration | EC Numbers | Enzyme names | Source organism and gene/enzyme name | Protein Accession Numbers |
|---|---|---|---|---|---|
| Olivetolic acid + GPP → cannabigerolic acid | 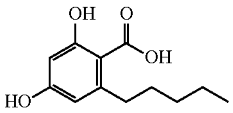 olivetolic acid 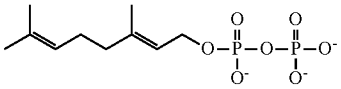 geranyl pyrophosate 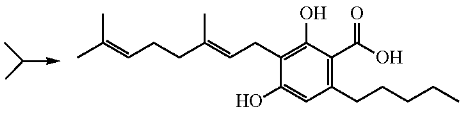 cannabigerolic acid | 2.5.1.- | geranyl-pyrophosphate:olivetolate geranyltransferase | *Lithospermum erythrorhizon* PGT-1 | Q8W405 |
| | | | | *Lithospermum erythrorhizon* PGT-2 | Q8W404 |
| | | | | *E. coli* ubiA | P0AGK1 |
| | | | | *Arabidopsis thaliana* PPT1 | Q93YP7 |
| | | | | *Schizosaccharomyces pombe* coq2 | Q10252 |
| | | | | *Cannabis sativa* CsPT1 | |
| | | | | *Streptomyces* sp. strain CL190 nphB | BAE00106.1 |
| | | | | *Streptomyces Coelicolor* SCO7190 | BAE00107.1 |
| | | | | *Streptomyces* sp. CNQ-509 cnqp3 | AKH84817.1 |
| | | | | *Phleum pretense* phl p4 | ABB78007.1 |

TABLE M

Plasmids and primers used for in vivo tiglic acid production

Plasmids
pCDF-P1-pct-fadAx
pET-P1-fadB2x-fadB1x
pET-P1-fadB2x-fadB1x-P2-ydil
Primers

| Name | SEQ ID NO: | Sequence |
|---|---|---|
| pct-f1 | 1 | 5'-AGGAGATATACCATGAGAAAAGTAGAA ATCATTAC-3' |
| pct-r1 | 2 | 5'-CGCCGAGCTCGAATTCTTATTTTTTCA GTCCCATGGGAC-3' |
| fadAx-f1 | 3 | 5'-GAAAAAATAAGAATTTAAGGAGGAATA AACC ATGACCCTGGCAAATGATCC-3' |
| fadAx-r1 | 4 | 5'-CGCCGAGCTCGAATTCTTAATACAGAC ATTCAACTGCC-3' |
| fadB2x-f1 | 5 | 5'-AGGAGATATACCATGCATATCGCCAAC AAACAC-3' |
| fadB2x-r1 | 6 | 5'-CGCCGAGCTCGAATTCTTATTTTGCTG CCATGCGCAG-3' |
| fadB1x-f1 | 7 | 5'-AGCAAAATAAGAATTTAAGGAGGAATA AACC ATGGCCTTTGAAACCATTCTG-3' |
| fadB1x-r1 | 8 | 5'-CGCCGAGCTCGAATTCTTAGCGATCTT TAAACTGTGC-3' |
| ydil-f1 | 9 | 5'-AAGGAGATATACATATGATATGGAAAC GGAAAATCAC-3' |
| ydil-r1 | 10 | 5'-TTGAGATCTGCCATATGTCACAAAATG GCGGTCGTC-3' |

TABLE N plasmids and primers used for conversion of prenol to GPP and geraniol

Plasmids
pET-P1-idi-trGPPS2-P2-ges-ychB-mtipk
pET-P1-idi-trGPPS2-P2-ges-thaipk-mtipk
Primers

| Name | SEQ ID NO: | Sequence |
|---|---|---|
| idi-f1 | 11 | AGGAGATATACCATGCAAACGGAACACGTCAT TT |
| idi-r1 | 12 | TGCGCTATATGCCATGGTTTATTCCTCCTTAA ATTATTTAAGCTGGGTAAATGCAGATA |
| trgpps2-f1 | 13 | ATGGCATATAGCGCAATGGC |
| trgpps2-r1 | 14 | GTGATGGCTGCTGCCTTAGTTCTGACGAAATG CAACAT |
| ges-f1 | 15 | AAGGAGATATACATAATGGAAGAAAGCAGCAG CAAA |
| ges-r1 | 16 | TTACCAGACTCGAGGTTACTGGGTAAAAAACA GGGC |
| ychB-f1 | 17 | ACCCAGTAACCTCGAAAGGAGGAATAAGGC A TGCGGACACAGTGGCCCT |

TABLE N-continued plasmids and primers used for conversion of prenol to GPP and geraniol Plasmids
pET-P1-idi-trGPPS2-P2-ges-ychB-mtipk
pET-P1-idi-trGPPS2-P2-ges-thaipk-mtipk
Primers

| Name | SEQ ID NO: | Sequence |
|---|---|---|
| ychB-r1 | 18 | TTTCAGGATGATCATTTGTTATTCCTCCTTAA GGTCTTAAAGCATGGCTCTGTGCAA |
| mtipk-f1 | 19 | ATGATCATCCTGAAACTGGGT |
| mtipk-r1 | 20 | CTTTACCAGACTCGAGTTAGTGTTTACCTGTA ATACGTG |
| mtipk-f2 | 21 | GATCCGCTAACTCGATAAGGAGGAATAACAA ATGATCATCCTGAAACTGGGT |
| taipk-f1 | 22 | ACCCAGTAACCTCGAAAGGAGGAATAAGGCAT GATGATCCTGAAAATTGGTG |
| taipk-r1 | 23 | CTTTACCAGACTCGAGTTAGCGGATCACGGTG CCA |

TABLE O

List of primers

| Name | SEQ ID NO: | Sequence | Description |
|---|---|---|---|
| maqu_2507-f1 | 24 | GCCAGGATCCGAATTCGAACT ACTTTCTGACCGGTGG | maqu_2507 forward |
| maqu_2507-r1 | 25 | CGCCGAGCTCGAATTCTTACC AGTAAATGCCACGCA | maqu_2507 reverse |
| cbjALD-f1 | 26 | GCCAGGATCCGAATTCGAATA AAGACACACTAATACCTAC | cbjALD forward |
| cbjALD-r1 | 27 | CGCCGAGCTCGAATTCTTAGC CGGCAAGTACACATC | cbjALD reverse |
| chnD-f1 | 28 | GCCAGGATCCGAATTCGCACT GCTATTGTGTTACCCAC | chnD forward |
| chnD-r1 | 29 | CGCCGAGCTCGAATTCTCAAT TTTCGTGCATCAGAAC | chnD reverse |

TABLE P

Measured activities of different alcohol dehydrogenases on oxidization of prenol.

| Enzyme (cofactor) | Specific activity (μmol/mg/min) |
|---|---|
| FucO ($NAD^+$) | N.D. |
| YqhD ($NADP^+$) | N.D. |
| YjgB ($NADP^+$) | 0.30 ± 0.03 |
| YahK ($NADP^+$) | 0.167 ± 0.005 |
| YiaY ($NAD^+$) | N.D. |
| ChnD ($NAD^+$) | 0.123 ± 0.007 |

TABLE Q plasmids and primers used for in vivo 2,3-dihydroxybutyric acid production Plasmids
pET-P1-bktB-phaB1-P2-phaJ
pCDF-P1-pct-P2-tdter Primers

| Name | SEQ ID NO: | Sequence |
|---|---|---|
| tdTer-f1 | 30 | 5'-AAGGAGATATACATATGATTGTTAAG CCGATGGTCC-3' |
| tdTer-r1 | 31 | 5'-TTGAGATCTGCCATATGTTAGATGCG GTCAAAACGTTCA-3' |
| pct-f1 | 32 | 5'-AGGAGATATACCATGAGAAAAGTAGA AATCATTAC-3' |
| pct-r1 | 33 | 5'-CGCCGAGCTCGAATTCTTATTTTTTC AGTCCCATGGGAC-3' |
| bktB-f1 | 34 | 5'-AGGAGATATACCATGATGACGCGTGA AGTGGTAGT-3' |
| bktB-r1 | 35 | 5'-CGCCGAGCTCGAATTCTCAGATACGC TCGAAGATGG-3' |
| phaB1-f1 | 36 | 5'-GCGTATCTGAGAATTAGGAGGCTCTC TATGACTCAGCGCATTGCGTA |
| phaB1-r1 | 37 | 5'-CGCCGAGCTCGAATTCTCAGCCCATG TGCAGGCC-3' |
| phaJ-f1 | 38 | 5'-AAGGAGATATACATATGTCGGCACAA AGCCTG-3' |
| phaJ-r1 | 39 | 5'-TTGAGATCTGCCATATGTTACGGCAG TTTCACCACC-3' |

TABLE R

List of primers used in example of GPP BIOSYNTHESIS VIA 2-HYDROXYISOVALERIC ACID AND PRENOL STARTING FROM DECARBOXYLATIVE ACYLOIN CONDENSATION BETWEEN TWO PYRUVATES

| Name | SEQ ID NO: | Sequence | Description |
|---|---|---|---|
| pct540-f1 | 40 | GAGGAATAAACCATGCGTAAAGTGCCGATTATTA | pct540 forward |
| pct540-r1 | 41 | GATGATGATGGTCGACGCTTTTCATTTCTTTCAGGCC | pct540 reverse |
| pct-f2 | 42 | TAGAAGGAGGAGATCTATGAGAAAAGTAGAAATCATTACAG | pct forward |
| pct-r2 | 43 | GGGGGACCAGCTCGAGTTTTTTCAGTCCCATGGGACC | pct reverse |
| alsS-f1 | 44 | AAGGAGATATACATATGACCAAAGCAACCAAAGAA | alsS forward |
| alsS-r1 | 45 | AATGGTAATACGCATGTTAATTTCCTCCTAGAATTACAGGG CTTTGGTTTTCAT | alsS reverse |
| panE-f1 | 46 | ATGCGTATTACCATTGCCGG | panE forward |
| panE-r1 | 47 | TTGAGATCTGCCATATTATTTGGCTTTCAGCAGTTCTT | panE reverse |
| ilvC-f1 | 48 | AGGAGATATACCATGGCTAACTACTTCAATAC | ilvC forward |
| ilvC-r1 | 49 | ACGGTACTTAGGCATGGTTTATTCCTCCTTAAACTCTTAAC CCGCAACAGCAATAC | ilvC reverse |
| ilvD-f1 | 50 | ATGCCTAAGTACCGTTCCG | ilvD forward |
| ilvD-r1 | 51 | CGCCGAGCTCGAATTCTTAACCCCCCAGTTTCGATTT | ilvD reverse |

TABLE S plasmids and primers used for in vivo butyric acid production through beta-oxidation reversal Plasmids
pTH-atoB-fadB-egter
pZS-fadM
pZS-tesA
pZS-tesB
pZS-yciA
pZS-ybgC
pZS-ydil
pCDF-P1-pct-P2-tdter Primers

| Name | SEQ ID NO: | Sequence |
|---|---|---|
| fadM-f1 | 129 | 5'-TTAAAGAGGAGAAAGGTACCATGCAAACACAAATCAAAGT-3' |
| fadM-r1 | 52 | 5'-TGCCTCTAGCACGCGTCGTTTACTTAACCATCTGCTCCA-3' |
| tesA-f1 | 53 | 5'-TTAAAGAGGAGAAAGGTACCATGATGAACTTCAACAATGTTTTC-3' |
| tesA-r1 | 54 | 5'-TGCCTCTAGCACGCGTTCCGTTGCTTTATGAGTCATG-3 |
| tesB-f1 | 55 | 5'-TTAAAGAGGAGAAAGGTACCATGAGTCAGGCGCTAAAAAA-3' |
| tesB-r1 | 56 | 5'-TGCCTCTAGCACGCGTAACAGCCGGACGGTTTTC-3 |
| ybgC-f1 | 57 | 5'-TTAAAGAGGAGAAAGGTACCGTGAATACAACGCTGTTTCGAT-3' |
| ybgC-r1 | 58 | 5'-TGCCTCTAGCACGCGTTCACTGCTTAAACTCCGCGA-3' |
| yciA-f1 | 59 | 5'-TTAAAGAGGAGAAAGGTACCATGTCTACAACACATAACGTCCC-3' |
| yciA-r1 | 60 | 5'-TGCCTCTAGCACGCGTTTCAGTAAGCAGAAAGTCAAAAGC-3' |
| ydil-f1 | 61 | 5'-TTAAAGAGGAGAAAGGTACCATGATATGGAAACGGAAAATCA-3' |
| ydil-r1 | 62 | 5'-TGCCTCTAGCACGCGTGGTGACAACGTCACAAAATGG-3' |
| atoB-f1 | 63 | 5'-GAGGAATAAACCATGAAAAATTGTGTCATCGTCA-3' |
| atoB-r1 | 64 | 5'-CCCAAGCTTCGAATTCTTAATTCAACCGTTCAATCAC-3' |
| fadB-f1 | 65 | 5'-TAAGAATTCGAAGCTGCGGATTCAGGAGACTGACA-3' |
| fadB-r1 | 66 | 5'-GTTCGGGCCCAAGCTTTAAGCCGTTTTCAGGTCGC-3' |
| egter-f1 | 67 | 5'-AAACGGCTTAAAGCTAATAAGGAGGAATAAACCATGGCAATGTTTACCACGAC-3' |
| egter-r1 | 68 | 5'- GTTCGGGCCCAAGCTTGCGGCCGCTTATTGCTGTGCTGCGGAC -3' |

TABLE T plasmids and primers required for GPP biosynthesis via 2-oxoisovaleric acid, 2-oxoisocaproic acid and prenol starting from decarboxylative acyloin condensation between two pyruvates Plasmids
pET-P1-ilvC-ilvD-P2-alsS-liuA
pCDF-P1-bkdF-bkdG-bkdH-P2-IpIA-IpdA1
pRSF-P1-leuA(G462D)-leuB-P2-leuC-leuD Primers

| Name | SEQ ID NO: | Sequence |
|---|---|---|
| alsS-f1 | 44 | AAGGAGATATACATATGACCAAAGCAACCAAAGAA |
| alsS-r2 | 69 | GCTCGGATAGGTCATGTGATATTCCTCCTAGCTATGTTACAGGGCTTTGGTTTTCATC |
| ilvC-f1 | 48 | AGGAGATATACCATGGCTAACTACTTCAATAC |
| ilvC-r1 | 49 | ACGGTACTTAGGCATGGTTTATTCCTCCTTAAACTCTTAACCCGCAACAGCAATAC |
| ilvD-f1 | 50 | ATGCCTAAGTACCGTTCCG |
| ilvD-r1 | 51 | CGCCGAGCTCGAATTCTTAACCCCCCAGTTTCGATTT |
| liuA-f1 | 70 | ATGACCTATCCGAGCCTGAA |
| liuA-r1 | 71 | TTACCAGACTCGAGGGTACCTTAGCGGGTTTCATTAAACAGT |
| bkdF-f1 | 72 | AGGAGATATACCATGACCGTTGAAAGCACCGC |
| bkdF-r1 | 73 | CATTTTTTCTGCCATGAGTTATTCCTCCTACAACTCTTAATTACCACCTTGACCGG |
| bkdG-f1 | 74 | ATGGCAGAAAAAATGGCAATCG |
| bkdG-r1 | 75 | GCTTGCTTCGGTCATGCTTTATTCCTCCTTTAATTGTTAATATGCCAGGCTACGATC |
| bkdH-f1 | 76 | ATGACCGAAGCAAGCGTTCG |
| bkdH-r1 | 77 | TTACCAGACTCGAGGGTACCTTAGCGGGTTTCATTAAACAGT |
| IpIA-f1 | 78 | AAGGAGATATACATATGTCCACATTACGCCTGCT |
| IpIA-r1 | 79 | TGCATCATTTGCCATCCATTATTCCTCCTTGGGTAACTACCTTACAGCCC |
| IpdA1-f1 | 80 | ATGGCAAATGATGCAAGCAC |
| IpdA1-r1 | 81 | TTACCAGACTCGAGGGTACCTTAATCATGGCTATGCAGCGG |
| leuA(G462D)B-f11 | 82 | AGGAGATATACCatgAGCCAGCAAGTCAT |
| leuA(G462D)B-r11 | 83 | CACCTGgtCaAGCGCATCTTTACCGTGGC |

TABLE T-continued plasmids and primers required for GPP biosynthesis via 2-oxoisovaleric acid, 2-oxoisocaproic acid and prenol starting from decarboxylative acyloin condensation between two pyruvates Plasmids
pET-P1-ilvC-ilvD-P2-alsS-liuA
pCDF-P1-bkdF-bkdG-bkdH-P2-IpIA-IpdA1
pRSF-P1-leuA(G462D)-leuB-P2-leuC-leuD Primers

| Name | SEQ ID NO: | Sequence |
|---|---|---|
| leuA(G462D)B-f12 | 84 | AAGATGCGCTtGacCAGGTG GATATCGTCGCTAA |
| leuA(G462D)B-r12 | 85 | CGCCGAGCTCGAATTCTTACACCCCTTCTGCTACATA |
| leuA(G462D)B-f2 | 86 | AGGAGATATACCatgAGCCAG |
| leuA(G462D)B-r2 | 87 | CGCCGAGCTCGAATTCTTAC |
| leuCD-f1 | 88 | CGATCGCTGACGTCGatgGCTAAGACGTTATACGAAAA |
| leuCD-r1 | 89 | TTACCAGACTCGAGGGTACCttaATTCATAAACGCAGGTTGTT |

TABLE U

List of primers used in the construction of strain JST06(DE3) atoB$^{CT5}$

| Name | SEQ ID NO: | Sequence |
|---|---|---|
| kan-homatoE-L | 90 | TTGGTTTAACGCTGTTCTGACGGCACCCCTACAAACAGAAGGAATATAAACATATGAATATCCTCCTTA |
| kan-ovcymatoB-R | 91 | TCTGAAATTCTGCCTCGTGAGTGTAGGCTGGAGCTGCTTCG |
| cym-pCTC-atoB-ovkan-L | 92 | CGAAGCAGCTCCAGCCTACACTCACGAGGCAGAATTTCAGA |
| atoBintrecomb-R | 93 | GCCAGCCCGCTTTTTAAC |

TABLE V

Strains and plasmids

| Host strain | Plasmid 1 | Plasmid 2 | Plasmid 3 | Product |
|---|---|---|---|---|
| JST06(DE3) atoB$^{CT5}$ ΔfadB | pCDF-P1-HMGS-aibAB-P2-liuC | pET-P2-maqu_2507 | | Prenol |
| JST06(DE3) atoB$^{CT5}$ ΔfadB | pCDF-P1-HMGS-aibAB-P2-liuC | pET-P2-adhE2 | | Prenol |
| JST06(DE3) atoB$^{CT5}$ ΔfadB | pCDF-P1-HMGS-aibAB-P2-liuC | pET-P2-cbjALD | | Prenol |
| JST06(DE3) atoB$^{CT5}$ ΔfadB | pCDF-P1-HMGS-aibAB-P2-cbjALD-liuC | | | Prenol |
| JST06(DE3) atoB$^{CT5}$ ΔfadB | pCDF-P1-HMGS-aibAB-P2-maqu_2507-liuC | | | Prenol |
| JST06(DE3) atoB$^{CT5}$ ΔfadB | pCDF-P1-HMGS-aibAB-P2-cbjALD-liuC-chnD | | | Prenol |
| JST06(DE3) atoB$^{CT5}$ ΔfadB | pCDF-P1-HMGS-aibAB-P2-cbjALD-liuC-yjgB | | | Prenol |
| JST06(DE3) atoB$^{CT5}$ ΔfadB | pCDF-P1-HMGS-aibAB-P2-cbjALD-liuC-yahK | | | Prenol |
| JST06(DE3) atoB$^{CT5}$ ΔfadB | pCDF-P1-HMGS-aibAB-P2-liuC | pRSF-P2-adhE2 | pET-P1-idi-trGPPS2-P2-ges-ychB-mtipk | Geraniol |
| JST06(DE3) atoB$^{CT5}$ ΔfadB | pCDF-P1-HMGS-aibAB-P2-liuC | pRSF-P2-cbjALD | pET-P1-idi-trGPPS2-P2-ges-ychB-mtipk | Geraniol |
| JST06(DE3) atoB$^{CT5}$ | pCDF-P1-HMGS- | pET-P1-idi-trGPPS2- | | Geraniol |

TABLE V-continued

| Strains and plasmids | | | | |
|---|---|---|---|---|
| Host strain | Plasmid 1 | Plasmid 2 | Plasmid 3 | Product |
| ΔfadB | aibAB-P2-cbjALD-liuC | P2-ges-ychB-mtipk | | |
| JST06(DE3) atoB$^{CT5}$ ΔfadB | pCDF-P1-HMGS-aibAB-P2-cbjALD-liuC-yahK | pET-P1-idi-trGPPS2-P2-ges-ychB-mtipk | | Geraniol |

TABLE W

| Primers used | | | |
|---|---|---|---|
| Name | SEQ ID NO: | Sequence | Description |
| maqu_2507-f2 | 94 | AAGGAGATATACATATGAACTACTTTCTGACCGGT | maqu_2507 forward |
| maqu_2507-r2 | 95 | TTGAGATCTGCCATATGTTACCAGTAAATGCCACGCAT | maqu_2507 reverse |
| maqu_2507-r3 | 96 | TTAAATTCCGGCATAATTACTCCTTCACTGCCATATTACCAGTAAATGCCACGCAT | maqu_2507 reverse |
| cbjALD-f2 | 97 | AAGGAGATATACATATGAATAAAGACACACTAATACCTA | cbjALD forward |
| cbjALD-r2 | 98 | TTGAGATCTGCCATATGTTAGCCGGCAAGTACACATC | cbjALD reverse |
| cbjALD-r3 | 99 | TTAAATTCCGGCATAATTACTCCTTCACTGCCATATTAGCCGGCAAGTACACATC | cbjALD reverse |
| adhE2-f1 | 100 | AAGGAGATATACATATGAAAGTTACAAATCAAAAAGAAC | adhE2 forward |
| adhE2-r1 | 101 | TTGAGATCTGCCATATGTTAAAATGATTTTATATAGATATCCTTAAG | adhE2 reverse |
| hmgs-f1 | 102 | AGGAGATATACCATGACCATCGGCATCGATAAG | hmgs forward |
| hmgs-r1 | 103 | CGCCGAGCTCGAATTCTTATTCCGGACGATGATATTCG | hmgs reverse |
| aibA-f1 | 104 | TCCGGAATAAGAATTGTAGGAGGAATACTACATGAAAACCGCACGTTGGTG | aibA forward |
| aibA-r1 | 105 | CAGGGTTGCGCTCATGGTTTATTCCTCCTTAAAATCTTATGCTGCACGACGGGTCA | aibA reverse |
| aibB-f1 | 106 | ATGAGCGCAACCCTGGATAT | aibB forward |
| aibB-r1 | 107 | CCTGCAGGCGCGCCGAGCTCTTATGCACCAACCAGTGCAT | aibB reverse |
| liuC-f1 | 108 | AAGGAGATATACATATGCCGGAATTTAAAGTTGATG | liuC forward |
| liuC-r1 | 109 | TTGAGATCTGCCATATTAACGACCTTTATAAACCGGT | liuC reverse |
| chnD-f2 | 110 | TTAATATGGCAGATCAGGAGGAATAGCTGATGCACTGCTATTGTGTTACC | chnD forward |
| chnD-r2 | 111 | CTTTACCAGACTCGAGTCAATTTTCGTGCATCAGAAC | chnD reverse |
| yjgB-f1 | 112 | TTAATATGGCAGATCAGGAGGAATAGCTGATGTCGATGATAAAAAGCTATG | yjgB forward |

TABLE W-continued

| Primers used | | | |
|---|---|---|---|
| Name | SEQ ID NO: | Sequence | Description |
| yjgB-r1 | 113 | CTTTACCAGACTCGAGTCAAAAATCGGCTTTCAACAC | yjgB reverse |
| yahK-f1 | 114 | TTAATATGGCAGATCAGGAGGAATAGCTGATGAAGATCAAAGCTGTTGGTG | yahK forward |
| yahK-r1 | 115 | CTTTACCAGACTCGAGTCAGTCTGTTAGTGTGCGATT | yahK reverse |

TABLE X

| Plasmids for the synthesis of isoprenoids Name |
|---|
| pACYC-P1-ls |
| pACYC-P1-pt30 |
| pACYC-P1-qhs1-P2-ispA |
| pACYC-P1-valc-P2-ispA |
| pACYC-P1-vs1-P2-ispA |
| pACYC-P1-fs-P2-ispA |

TABLE Y

List of primers used in the construction of strain JST06(DE3) ΔfadE bktB$^{CT5}$ ΔatoB fadB$^{CT5}$ ΔfadA egter$^{CT5}$

| Construct/PCR Product | SEQ ID NO: | Sequences |
|---|---|---|
| kan-cymR-P$^{CT5}$-atoB-(cat-sacB) cat-sacB cassette with atoB homology | 130, 116 | F-GATGTTCAAGAAAACACCCGATAACTTTCGCTATCGGGTGTTTTTATTGAATCAAAGGGAAAACTGTCCATAT<br>R-GCATTGGCGGCGGTCAGGGAATTGCGATGGTGATTGAACGGTTGAATTAAAAAATGAGACGTTGATCGGC |
| kan-cymR-P$^{CT5}$-bktB ΔatoB bktB for replacement of atoB-cat-sacB cassette | 117, 118 | F-CAACAAACAGACAATCTGGTCTGTTTGTATTATGAACGAAGGAGAGATCTATGACGCGTGAAGTGGTAGT<br>R-GATGTTCAAGAAAACACCCGATAACTTTCGCTATCGGGTGTTTTTATTGATCAGATACGCTCGAAGATGG |
| cat-cymR-P$^{CT5}$-egTER @ fabl cat-cymR-PCT5-egTER with fabl homology | 119, 120 | F-TTGACGGCGGTTTCAGCATTGCTGCAATGAACGAACTCGAACTGAAATAAGTGTAGGCTGGAGCTGCTTCG<br>R-AACAGAGATAACGGGCGGCAGAACGCCGCCCATCTTTACCAACAGAACGATTATTTCAGTTCGAGTTCGTTTTATTGCTGTGCTGCGGAC |
| cat-cymR-P$^{CT5}$-egTER @ fadBA ΔfadBA egTER for replacement of fadB-(kansacB)-fadA cassette | 121, 122 | F-CAACAAACAGACAATCTGGTCTGTTTGTATTATGAACGAAGGAGAGATCTATGGCAATGTTTACCACGAC<br>R-TTAAACCCGCTCAAACACCGTCGCAATACCCTGACCCAGACCGATACACATTATTGCTGTGCTGCGGAC |

TABLE Y-continued

List of primers used in the construction of strain JST06(DE3) ΔfadE bktB$^{CT5}$ ΔatoB fadB$^{CT5}$ ΔfadA egter$^{CT5}$

| Construct/PCR Product | SEQ ID NO: | Sequences |
|---|---|---|
| cat-cymR-P$^{CT5}$--fadB-(kan-sacB)-fadA @ fadBA Overlap extension of kan and sacB with fadBA junction homology | 123, 124, 125, 126 | F1-ATCCTCCGGTTGAGCCAGCCCGTCCGGTTGGCGACCTGAAAACGGCTTAAATGATTGAACAAGATGGATTGC<br>R1-TAAGGGGTGACGCCAAAGTATCAGAAGAACTCGTCAAGAAGG<br>F2-CCTTCTTGACGAGTTCTTCTGATACTTTGGCGTCACCCCTTA<br>R2-ATCGGGGTGCGAATTGCATCGACAATGACAACCTGTTCCATTGTGACTCCATCAAAGGGAAAACTGTCCATAT |
| fadA deletion | 127, 128 | F-TTGAGCCAGCCCGTCCGGTTGGCGACCTGAAAACGGCTTAAGGAGTCACAATGGCCAAGTTGACCAGTG<br>R-TTAAACCCGCTCAAACACCGTCGCAATACCCTGACCCAGACCGATACACATCAGTCCTGCTCCTCTGC |

TABLE Z

| Plasmids for expression of olivetolic acid synthesis pathways | |
|---|---|
| Name | Synthesis pathway |
| pRSF-P1-OLS-P2-OAC | Olivetol synthase with olivetolic acid cyclase |
| pCDF-P1-OLS-P2-OAC | Olivetol synthase with olivetolic acid cyclase |
| pET-P1-OLS-P2-OAC | Olivetol synthase with olivetolic acid cyclase |
| pET-P1-OLS-P2-OAC(Y27F) | Olivetol synthase with olivetolic acid cyclase |
| pRSF-P1-STC | Polyketide synthase without cyclase |
| pET-P1-STCS | Polyketide synthase without cyclase |
| pET-P1-STCS (T135S) | Polyketide synthase without cyclase |
| pET-P1-STCS (T198M) | Polyketide synthase without cyclase |
| pET-P1-STCS (I200C) | Polyketide synthase without cyclase |
| pET-P1-STCS (T135S T198M) | Polyketide synthase without cyclase |
| pET-P1-STCS (T135S I200C) | Polyketide synthase without cyclase |
| pET-P1-STCS (T198M I200C) | Polyketide synthase without cyclase |
| pET-P1-STCS (T135S T198M I200C) | Polyketide synthase without cyclase |

TABLE Z-continued

| Plasmids for expression of olivetolic acid synthesis pathways | |
|---|---|
| Name | Synthesis pathway |
| pET-P1-dcaF-P2-OAC | Polyketoacyl-CoA thiolase with olivetol cyclase |
| pET-P1-fadAx-P2-OAC | Polyketoacyl-CoA thiolase with olivetol cyclase |
| pET-P1-ScfadA-P2-OAC | Polyketoacyl-CoA thiolase with olivetol cyclase |
| pET-P1-dcaF-P2-OAC | Polyketoacyl-CoA thiolase with olivetol cyclase |
| pET-P1-bktB-P2-OAC | Polyketoacyl-CoA thiolase with olivetol cyclase |

TABLE AA

Primers for constructions of plasmids used for demonstration of in vivo production of CBGA in *E. coli*.

| Name | SEQ ID NO: | Sequence |
|---|---|---|
| MK-IF-fwd | 131 | AGGAGATATACCATGAGCCTGCCGTTTCTG |
| MK-IF-rev | 132 | CGCCGAGCTCGAATTCTTAGCTGGTCCACGGCAG |
| PMK-IF-fwd | 133 | GACCAGCTAAGAATTTAGGAGGAATAACTCATGAGCG |
| PMK-IF-rev | 134 | CGCCGAGCTCGAATTCATTCCTCCTTTAATTGTTATTTGTC |
| PMD-IF-fwd | 135 | AAGGAGGAATGAATTATGACCGTTTATACCGCAAG |
| PMD-IF-rev | 136 | CGCCGAGCTCGAATTCTTATTCTTTCGGCAGACC |
| idi-GB-fwd | 137 | GTTTAACTTTAAGAAGGAGATATACatgCAAACGGAACACGTC |
| idi-GB-rev | 138 | ATGGTTTATTCCTCCTTAAAttaTTTAAGCTGGGTAAATGCAG |

TABLE AA-continued

Primers for constructions of plasmids used for demonstration of in vivo production of CBGA in *E. coli*.

| Name | SEQ ID NO: | Sequence |
|---|---|---|
| trGPPS2-IF-fwd | 139 | TTTAAGGAGGAATAAACCATGGTGGAATTTGACTTTAACAAATATAT |
| GPPS2-GB-rev | 140 | GTGATGGCTGCTGCCTTAGTTCTGACGAAATGCAAC |
| CymR-GB-fwd | 141 | CTGCAGGTCGACAAGCTTGCAGGCGTATCACGAGGCAG |
| CymR-GB-rev | 142 | CATCTGCTGCTTCGCTCATATGAGATCTCTCCTTCGTTCATAATACAAAC |
| NphB-cumate-GB-fwd | 143 | TCTCATATGAGCGAAGCAGCAGATG |
| NphB-cumate-GB-rev | 144 | AGCAGCGGTTTCTTTACCAGACTCGAGGTCAATCTTCCAGGCTATCAA |
| NphB-IF-fwd | 145 | AAGGAGATATACATAATGAGCGAAGCAGCAGAT |
| NphB-IF-rev | 146 | TTACCAGACTCGAGGTCAATCTTCCAGGCTATCAA |

TABLE AB

| Plasmids for expression of prenyltransferase and CBGA in vivo synthesis in *E. coli* Name |
|---|
| pET-P1-idi-trGPPS2-P2-NphB |
| pET-P1-idi-trGPPS2-CT5-NphB |
| pET-P1-idi-trGPPS2-CT5-CnqP3 |
| pET-P1-idi-trGPPS2-CT5-CphB |
| pET-P1-idi-trGPPS2-CT5-SCO7190 |
| pET-P1-idi-trGPPS2-CT5-SCO7190(R65S) |
| pET-P1-idi-trGPPS2-CT5-SCO7190(E278G) |

The invention claimed is:

1. A recombinant bacteria for synthesizing an isoprenoid, the recombinant bacteria comprising the following overexpressed enzymes:

a) a thiolase capable of condensing two acetyl-CoAs to form acetoacetyl CoA;

b) an overexpressed 3-hydroxy-3-methylglutaryl-CoA synthase capable of condensing said acetoacetyl-CoA with acetyl-CoA to form 3-hydroxy-3-methylglutaryl-CoA (HMG-CoA);

c) an enoyl-CoA hydratase capable of dehydrating said HMG-CoA to 3-methylglutaconylCoA;

d) a glutaconyl-CoA decarboxylase capable of decarboxylating said 3-methylglutaconyl-CoA to 3-methylcrotonyl-CoA (aka 3-methyl-2-butenoyl-CoA);

e) one or more enzyme(s) catalyzing conversion of said 3-methylcrotonyl-CoA to prenol (aka 3-methyl, 2-butenol), wherein said enzyme(s) are selected from:

i) an alcohol-forming acyl-CoA reductase;

ii) an aldehyde forming acyl-CoA reductase plus an alcohol dehydrogenase; or iii) a carboxylate reductase plus an alcohol dehydrogenase plus an enzyme(s) selected from an acyl-CoA synthase, an acyl-CoA transferase, a thioesterase, or a carboxylate kinase plus a phosphotransacylase;

f) one or more enzyme(s) to convert said prenol to dimethylallyl pyrophosphate (DMAPP) and isopentenyl pyrophosphate (IPP), said enzyme(s) selected from:

i) an alcohol kinase (EC 2.7.1.-) plus a phosphate kinase (EC 2.7.4.-); or ii) an alcohol diphosphokinase (EC 2.7.6.-) plus an IPP isomerase (5.3.3.2);

g) a GPP synthase capable of catalyzing condensation of said DMAPP and IPP to form geranyl diphosphate (GPP); and h) a terpene synthase (EC 4.2.3.-) capable of converting said GPP to an isoprenoid.

2. The recombinant bacteria of claim 1, comprising: a) AtoB, b) HMGS, c) LiuC, d) AibAB, e) cbjALD plus YahK, f) YchB or *T. acidophilum* IPK plus *M. thermautotrophicus* IPK, and idi, g) geranyl diphosphate synthase (GPPS2) and h) GES.

3. The recombinant bacteria of claim 2, comprising the genes atoB, HMGS, liuC, aibA, aibB, cbjALD, yahK, *T. acidophilum* IPK, *M. thermautotrophicus* IPK, idi, GPPS2 and GES.

4. The recombinant bacteria of claim 2, comprising the genes atoB, HMGS, liuC, aibA, aibB, cbjALD, yahK, ychB, *M. thermautotrophicus* IPK, idi, GPPS2 and GES.

5. A method of making an isoprenoid, said method comprising growing the bacteria of claim 1 in a nutrient broth under conditions to allow the overexpression of said enzymes and production of said isoprenoid.

6. A method of making an isoprenoid, said method comprising growing the bacteria of claim 2 in a nutrient broth under conditions to allow the overexpression of said enzymes and production of said isoprenoid.

7. A method of making an isoprenoid, said method comprising growing the bacteria of claim 3 in a nutrient broth under conditions to allow the expression of said genes and production of said isoprenoid.

8. A method of making an isoprenoid, said method comprising growing the bacteria of claim 4 in a nutrient broth under conditions to allow the expression of said genes and production of said isoprenoid.

* * * * *

SEQUENCE LISTING

```
Sequence total quantity: 146
SEQ ID NO: 1            moltype = DNA  length = 35
FEATURE                 Location/Qualifiers
misc_feature            1..35
                        note = Synthetic: pct-f1
source                  1..35
                        mol_type = other DNA
                        organism = synthetic construct
SEQUENCE: 1
aggagatata ccatgagaaa agtagaaatc attac                        35

SEQ ID NO: 2            moltype = DNA  length = 39
FEATURE                 Location/Qualifiers
misc_feature            1..39
                        note = Synthetic: pct-r1
source                  1..39
                        mol_type = other DNA
                        organism = synthetic construct
SEQUENCE: 2
cgccgagctc gaattcttat tttttcagtc ccatgggac                    39

SEQ ID NO: 3            moltype = DNA  length = 51
```

-continued

```
FEATURE                Location/Qualifiers
misc_feature           1..51
                       note = Synthetic: fadAx-f1
source                 1..51
                       mol_type = other DNA
                       organism = synthetic construct
SEQUENCE: 3
gaaaaaataa gaatttaagg aggaataaac catgaccctg gcaaatgatc c           51

SEQ ID NO: 4           moltype = DNA  length = 38
FEATURE                Location/Qualifiers
misc_feature           1..38
                       note = Synthetic: fadAx-r1
source                 1..38
                       mol_type = other DNA
                       organism = synthetic construct
SEQUENCE: 4
cgccgagctc gaattcttaa tacagacatt caactgcc                          38

SEQ ID NO: 5           moltype = DNA  length = 33
FEATURE                Location/Qualifiers
misc_feature           1..33
                       note = Synthetic: fadB2x-f1
source                 1..33
                       mol_type = other DNA
                       organism = synthetic construct
SEQUENCE: 5
aggagatata ccatgcatat cgccaacaaa cac                               33

SEQ ID NO: 6           moltype = DNA  length = 37
FEATURE                Location/Qualifiers
misc_feature           1..37
                       note = Synthetic: fadB2x-r1
source                 1..37
                       mol_type = other DNA
                       organism = synthetic construct
SEQUENCE: 6
cgccgagctc gaattcttat tttgctgcca tgcgcag                           37

SEQ ID NO: 7           moltype = DNA  length = 52
FEATURE                Location/Qualifiers
misc_feature           1..52
                       note = Synthetic: fadB1x-f1
source                 1..52
                       mol_type = other DNA
                       organism = synthetic construct
SEQUENCE: 7
agcaaaataa gaatttaagg aggaataaac catggccttt gaaaccattc tg          52

SEQ ID NO: 8           moltype = DNA  length = 37
FEATURE                Location/Qualifiers
misc_feature           1..37
                       note = Synthetic: fadB1x-r1
source                 1..37
                       mol_type = other DNA
                       organism = synthetic construct
SEQUENCE: 8
cgccgagctc gaattcttag cgatctttaa actgtgc                           37

SEQ ID NO: 9           moltype = DNA  length = 37
FEATURE                Location/Qualifiers
misc_feature           1..37
                       note = Synthetic: ydiI-f1
source                 1..37
                       mol_type = other DNA
                       organism = synthetic construct
SEQUENCE: 9
aaggagatat acatatgata tggaaacgga aaatcac                           37

SEQ ID NO: 10          moltype = DNA  length = 36
FEATURE                Location/Qualifiers
misc_feature           1..36
                       note = Synthetic: ydiI-r1
source                 1..36
                       mol_type = other DNA
                       organism = synthetic construct
SEQUENCE: 10
ttgagatctg ccatatgtca caaaatggcg gtcgtc                            36
```

-continued

```
SEQ ID NO: 11           moltype = DNA  length = 34
FEATURE                 Location/Qualifiers
misc_feature            1..34
                        note = Synthetic: idi-f1
source                  1..34
                        mol_type = other DNA
                        organism = synthetic construct
SEQUENCE: 11
aggagatata ccatgcaaac ggaacacgtc attt                              34

SEQ ID NO: 12           moltype = DNA  length = 59
FEATURE                 Location/Qualifiers
misc_feature            1..59
                        note = Synthetic: idi-r1
source                  1..59
                        mol_type = other DNA
                        organism = synthetic construct
SEQUENCE: 12
tgcgctatat gccatggttt attcctcctt aaattattta agctgggtaa atgcagata   59

SEQ ID NO: 13           moltype = DNA  length = 20
FEATURE                 Location/Qualifiers
misc_feature            1..20
                        note = Synthetic: trgpps2-f1
source                  1..20
                        mol_type = other DNA
                        organism = synthetic construct
SEQUENCE: 13
atggcatata gcgcaatggc                                              20

SEQ ID NO: 14           moltype = DNA  length = 38
FEATURE                 Location/Qualifiers
misc_feature            1..38
                        note = Synthetic: trgpps2-r1
source                  1..38
                        mol_type = other DNA
                        organism = synthetic construct
SEQUENCE: 14
gtgatggctg ctgccttagt tctgacgaaa tgcaacat                          38

SEQ ID NO: 15           moltype = DNA  length = 36
FEATURE                 Location/Qualifiers
misc_feature            1..36
                        note = Synthetic: ges-f1
source                  1..36
                        mol_type = other DNA
                        organism = synthetic construct
SEQUENCE: 15
aaggagatat acataatgga agaaagcagc agcaaa                            36

SEQ ID NO: 16           moltype = DNA  length = 36
FEATURE                 Location/Qualifiers
misc_feature            1..36
                        note = Synthetic: ges-r1
source                  1..36
                        mol_type = other DNA
                        organism = synthetic construct
SEQUENCE: 16
ttaccagact cgaggttact gggtaaaaaa cagggc                            36

SEQ ID NO: 17           moltype = DNA  length = 49
FEATURE                 Location/Qualifiers
misc_feature            1..49
                        note = Synthetic: ychB-f1
source                  1..49
                        mol_type = other DNA
                        organism = synthetic construct
SEQUENCE: 17
acccagtaac ctcgaaagga ggaataaggc atgcggacac agtggccct              49

SEQ ID NO: 18           moltype = DNA  length = 57
FEATURE                 Location/Qualifiers
misc_feature            1..57
                        note = Synthetic: ychB-r1
source                  1..57
                        mol_type = other DNA
                        organism = synthetic construct
SEQUENCE: 18
tttcaggatg atcatttgtt attcctcctt aaggtcttaa agcatggctc tgtgcaa     57
```

-continued

```
SEQ ID NO: 19           moltype = DNA  length = 21
FEATURE                 Location/Qualifiers
misc_feature            1..21
                        note = Synthetic: mtipk-f1
source                  1..21
                        mol_type = other DNA
                        organism = synthetic construct
SEQUENCE: 19
atgatcatcc tgaaactggg t                                            21

SEQ ID NO: 20           moltype = DNA  length = 39
FEATURE                 Location/Qualifiers
misc_feature            1..39
                        note = Synthetic: mtipk-r1
source                  1..39
                        mol_type = other DNA
                        organism = synthetic construct
SEQUENCE: 20
ctttaccaga ctcgagttag tgtttacctg taatacgtg                         39

SEQ ID NO: 21           moltype = DNA  length = 52
FEATURE                 Location/Qualifiers
misc_feature            1..52
                        note = Synthetic: mtipk-f2
source                  1..52
                        mol_type = other DNA
                        organism = synthetic construct
SEQUENCE: 21
gatccgctaa ctcgataagg aggaataaca aatgatcatc ctgaaactgg gt          52

SEQ ID NO: 22           moltype = DNA  length = 52
FEATURE                 Location/Qualifiers
misc_feature            1..52
                        note = Synthetic: taipk-f1
source                  1..52
                        mol_type = other DNA
                        organism = synthetic construct
SEQUENCE: 22
acccagtaac ctcgaaagga ggaataaggc atgatgatcc tgaaaattgg tg          52

SEQ ID NO: 23           moltype = DNA  length = 35
FEATURE                 Location/Qualifiers
misc_feature            1..35
                        note = Synthetic: taipk-r1
source                  1..35
                        mol_type = other DNA
                        organism = synthetic construct
SEQUENCE: 23
ctttaccaga ctcgagttag cggatcacgg tgcca                             35

SEQ ID NO: 24           moltype = DNA  length = 37
FEATURE                 Location/Qualifiers
misc_feature            1..37
                        note = Synthetic: maqu_2507- f1
source                  1..37
                        mol_type = other DNA
                        organism = synthetic construct
SEQUENCE: 24
gccaggatcc gaattcgaac tactttctga ccggtgg                           37

SEQ ID NO: 25           moltype = DNA  length = 36
FEATURE                 Location/Qualifiers
misc_feature            1..36
                        note = Synthetic: maqu_2507- r1
source                  1..36
                        mol_type = other DNA
                        organism = synthetic construct
SEQUENCE: 25
cgccgagctc gaattcttac cagtaaatgc cacgca                            36

SEQ ID NO: 26           moltype = DNA  length = 40
FEATURE                 Location/Qualifiers
misc_feature            1..40
                        note = Synthetic: cbjALD-f1
source                  1..40
                        mol_type = other DNA
                        organism = synthetic construct
SEQUENCE: 26
```

-continued

```
gccaggatcc gaattcgaat aaagacacac taatacctac                        40

SEQ ID NO: 27           moltype = DNA  length = 36
FEATURE                 Location/Qualifiers
misc_feature            1..36
                        note = Synthetic: cbjALD-r1
source                  1..36
                        mol_type = other DNA
                        organism = synthetic construct
SEQUENCE: 27
cgccgagctc gaattcttag ccggcaagta cacatc                            36

SEQ ID NO: 28           moltype = DNA  length = 38
FEATURE                 Location/Qualifiers
misc_feature            1..38
                        note = Synthetic: chnD-f1
source                  1..38
                        mol_type = other DNA
                        organism = synthetic construct
SEQUENCE: 28
gccaggatcc gaattcgcac tgctattgtg ttacccac                          38

SEQ ID NO: 29           moltype = DNA  length = 37
FEATURE                 Location/Qualifiers
misc_feature            1..37
                        note = Synthetic: chnD-r1
source                  1..37
                        mol_type = other DNA
                        organism = synthetic construct
SEQUENCE: 29
cgccgagctc gaattctcaa ttttcgtgca tcagaac                           37

SEQ ID NO: 30           moltype = DNA  length = 36
FEATURE                 Location/Qualifiers
misc_feature            1..36
                        note = Synthetic: tdTer-f1
source                  1..36
                        mol_type = other DNA
                        organism = synthetic construct
SEQUENCE: 30
aaggagatat acatatgatt gttaagccga tggtcc                            36

SEQ ID NO: 31           moltype = DNA  length = 39
FEATURE                 Location/Qualifiers
misc_feature            1..39
                        note = Synthetic: tdTer-r1
source                  1..39
                        mol_type = other DNA
                        organism = synthetic construct
SEQUENCE: 31
ttgagatctg ccatatgtta gatgcggtca aaacgttca                         39

SEQ ID NO: 32           moltype = DNA  length = 35
FEATURE                 Location/Qualifiers
misc_feature            1..35
                        note = Synthetic: pct-f1
source                  1..35
                        mol_type = other DNA
                        organism = synthetic construct
SEQUENCE: 32
aggagatata ccatgagaaa agtagaaatc attac                             35

SEQ ID NO: 33           moltype = DNA  length = 39
FEATURE                 Location/Qualifiers
misc_feature            1..39
                        note = Synthetic: pct-r1
source                  1..39
                        mol_type = other DNA
                        organism = synthetic construct
SEQUENCE: 33
cgccgagctc gaattcttat tttttcagtc ccatgggac                         39

SEQ ID NO: 34           moltype = DNA  length = 35
FEATURE                 Location/Qualifiers
misc_feature            1..35
                        note = Synthetic: bktB-f1
source                  1..35
                        mol_type = other DNA
                        organism = synthetic construct
```

```
SEQUENCE: 34
aggagatata ccatgatgac gcgtgaagtg gtagt                          35

SEQ ID NO: 35          moltype = DNA  length = 36
FEATURE                Location/Qualifiers
misc_feature           1..36
                       note = Synthetic: bktB-r1
source                 1..36
                       mol_type = other DNA
                       organism = synthetic construct
SEQUENCE: 35
cgccgagctc gaattctcag atacgctcga agatgg                         36

SEQ ID NO: 36          moltype = DNA  length = 47
FEATURE                Location/Qualifiers
misc_feature           1..47
                       note = Synthetic: phaB1-f1
source                 1..47
                       mol_type = other DNA
                       organism = synthetic construct
SEQUENCE: 36
gcgtatctga gaattaggag gctctctatg actcagcgca ttgcgta             47

SEQ ID NO: 37          moltype = DNA  length = 34
FEATURE                Location/Qualifiers
misc_feature           1..34
                       note = Synthetic: phaB1-r1
source                 1..34
                       mol_type = other DNA
                       organism = synthetic construct
SEQUENCE: 37
cgccgagctc gaattctcag cccatgtgca ggcc                           34

SEQ ID NO: 38          moltype = DNA  length = 32
FEATURE                Location/Qualifiers
misc_feature           1..32
                       note = Synthetic: phaJ-f1
source                 1..32
                       mol_type = other DNA
                       organism = synthetic construct
SEQUENCE: 38
aaggagatat acatatgtcg gcacaaagcc tg                             32

SEQ ID NO: 39          moltype = DNA  length = 36
FEATURE                Location/Qualifiers
misc_feature           1..36
                       note = Synthetic: phaJ-r1
source                 1..36
                       mol_type = other DNA
                       organism = synthetic construct
SEQUENCE: 39
ttgagatctg ccatatgtta cggcagtttc accacc                         36

SEQ ID NO: 40          moltype = DNA  length = 34
FEATURE                Location/Qualifiers
misc_feature           1..34
                       note = Synthetic: pct540- f1
source                 1..34
                       mol_type = other DNA
                       organism = synthetic construct
SEQUENCE: 40
gaggaataaa ccatgcgtaa agtgccgatt atta                           34

SEQ ID NO: 41          moltype = DNA  length = 37
FEATURE                Location/Qualifiers
misc_feature           1..37
                       note = Synthetic: pct540- r1
source                 1..37
                       mol_type = other DNA
                       organism = synthetic construct
SEQUENCE: 41
gatgatgatg gtcgacgctt ttcatttctt tcaggcc                        37

SEQ ID NO: 42          moltype = DNA  length = 41
FEATURE                Location/Qualifiers
misc_feature           1..41
                       note = Synthetic: pct-f2
source                 1..41
                       mol_type = other DNA
```

```
                          organism = synthetic construct
SEQUENCE: 42
tagaaggagg agatctatga gaaaagtaga aatcattaca g                        41

SEQ ID NO: 43             moltype = DNA  length = 37
FEATURE                   Location/Qualifiers
misc_feature              1..37
                          note = Synthetic: pct-r2
source                    1..37
                          mol_type = other DNA
                          organism = synthetic construct
SEQUENCE: 43
gggggaccag ctcgagtttt ttcagtccca tgggacc                             37

SEQ ID NO: 44             moltype = DNA  length = 35
FEATURE                   Location/Qualifiers
misc_feature              1..35
                          note = Synthetic: alsS-f1
source                    1..35
                          mol_type = other DNA
                          organism = synthetic construct
SEQUENCE: 44
aaggagatat acatatgacc aaagcaacca aagaa                               35

SEQ ID NO: 45             moltype = DNA  length = 54
FEATURE                   Location/Qualifiers
misc_feature              1..54
                          note = Synthetic: alsS-r1
source                    1..54
                          mol_type = other DNA
                          organism = synthetic construct
SEQUENCE: 45
aatggtaata cgcatgttaa tttcctccta gaattacagg gctttggttt tcat          54

SEQ ID NO: 46             moltype = DNA  length = 20
FEATURE                   Location/Qualifiers
misc_feature              1..20
                          note = Synthetic: panE-f1
source                    1..20
                          mol_type = other DNA
                          organism = synthetic construct
SEQUENCE: 46
atgcgtatta ccattgccgg                                                20

SEQ ID NO: 47             moltype = DNA  length = 38
FEATURE                   Location/Qualifiers
misc_feature              1..38
                          note = Synthetic: panE-r1
source                    1..38
                          mol_type = other DNA
                          organism = synthetic construct
SEQUENCE: 47
ttgagatctg ccatattatt tggctttcag cagttctt                            38

SEQ ID NO: 48             moltype = DNA  length = 32
FEATURE                   Location/Qualifiers
misc_feature              1..32
                          note = Synthetic: ilvC-f1
source                    1..32
                          mol_type = other DNA
                          organism = synthetic construct
SEQUENCE: 48
aggagatata ccatggctaa ctacttcaat ac                                  32

SEQ ID NO: 49             moltype = DNA  length = 56
FEATURE                   Location/Qualifiers
misc_feature              1..56
                          note = Synthetic: ilvC-r1
source                    1..56
                          mol_type = other DNA
                          organism = synthetic construct
SEQUENCE: 49
acggtactta ggcatggttt attcctcctt aaactcttaa cccgcaacag caatac        56

SEQ ID NO: 50             moltype = DNA  length = 19
FEATURE                   Location/Qualifiers
misc_feature              1..19
                          note = Synthetic: ilvD-f1
source                    1..19
```

```
                        mol_type = other DNA
                        organism = synthetic construct
SEQUENCE: 50
atgcctaagt accgttccg                                              19

SEQ ID NO: 51           moltype = DNA  length = 37
FEATURE                 Location/Qualifiers
misc_feature            1..37
                        note = Synthetic: ilvD-r1
source                  1..37
                        mol_type = other DNA
                        organism = synthetic construct
SEQUENCE: 51
cgccgagctc gaattcttaa ccccccagtt tcgattt                          37

SEQ ID NO: 52           moltype = DNA  length = 39
FEATURE                 Location/Qualifiers
misc_feature            1..39
                        note = Synthetic: fadM-r1
source                  1..39
                        mol_type = other DNA
                        organism = synthetic construct
SEQUENCE: 52
tgcctctagc acgcgtcgtt tacttaacca tctgctcca                        39

SEQ ID NO: 53           moltype = DNA  length = 44
FEATURE                 Location/Qualifiers
misc_feature            1..44
                        note = Synthetic: tesA-f1
source                  1..44
                        mol_type = other DNA
                        organism = synthetic construct
SEQUENCE: 53
ttaaagagga gaaaggtacc atgatgaact tcaacaatgt tttc                  44

SEQ ID NO: 54           moltype = DNA  length = 37
FEATURE                 Location/Qualifiers
misc_feature            1..37
                        note = Synthetic: tesA-r1
source                  1..37
                        mol_type = other DNA
                        organism = synthetic construct
SEQUENCE: 54
tgcctctagc acgcgttccg ttgctttatg agtcatg                          37

SEQ ID NO: 55           moltype = DNA  length = 40
FEATURE                 Location/Qualifiers
misc_feature            1..40
                        note = Synthetic: tesB-f1
source                  1..40
                        mol_type = other DNA
                        organism = synthetic construct
SEQUENCE: 55
ttaaagagga gaaaggtacc atgagtcagg cgctaaaaaa                       40

SEQ ID NO: 56           moltype = DNA  length = 34
FEATURE                 Location/Qualifiers
misc_feature            1..34
                        note = Synthetic: tesB-r1
source                  1..34
                        mol_type = other DNA
                        organism = synthetic construct
SEQUENCE: 56
tgcctctagc acgcgtaaca gccggacggt tttc                             34

SEQ ID NO: 57           moltype = DNA  length = 42
FEATURE                 Location/Qualifiers
misc_feature            1..42
                        note = Synthetic: ybgC-f1
source                  1..42
                        mol_type = other DNA
                        organism = synthetic construct
SEQUENCE: 57
ttaaagagga gaaaggtacc gtgaatacaa cgctgtttcg at                    42

SEQ ID NO: 58           moltype = DNA  length = 36
FEATURE                 Location/Qualifiers
misc_feature            1..36
                        note = Synthetic: ybgC-r1
```

```
source                  1..36
                        mol_type = other DNA
                        organism = synthetic construct
SEQUENCE: 58
tgcctctagc acgcgttcac tgcttaaact ccgcga                        36

SEQ ID NO: 59           moltype = DNA  length = 43
FEATURE                 Location/Qualifiers
misc_feature            1..43
                        note = Synthetic: yciA-f1
source                  1..43
                        mol_type = other DNA
                        organism = synthetic construct
SEQUENCE: 59
ttaaagagga gaaaggtacc atgtctacaa cacataacgt ccc                43

SEQ ID NO: 60           moltype = DNA  length = 40
FEATURE                 Location/Qualifiers
misc_feature            1..40
                        note = Synthetic: yciA-r1
source                  1..40
                        mol_type = other DNA
                        organism = synthetic construct
SEQUENCE: 60
tgcctctagc acgcgtttca gtaagcagaa agtcaaaagc                    40

SEQ ID NO: 61           moltype = DNA  length = 42
FEATURE                 Location/Qualifiers
misc_feature            1..42
                        note = Synthetic: ydiI-f1
source                  1..42
                        mol_type = other DNA
                        organism = synthetic construct
SEQUENCE: 61
ttaaagagga gaaaggtacc atgatatgga aacggaaaat ca                 42

SEQ ID NO: 62           moltype = DNA  length = 37
FEATURE                 Location/Qualifiers
misc_feature            1..37
                        note = Synthetic: ydiI-r1
source                  1..37
                        mol_type = other DNA
                        organism = synthetic construct
SEQUENCE: 62
tgcctctagc acgcgtggtg acaacgtcac aaaatgg                       37

SEQ ID NO: 63           moltype = DNA  length = 34
FEATURE                 Location/Qualifiers
misc_feature            1..34
                        note = Synthetic: atoB-f1
source                  1..34
                        mol_type = other DNA
                        organism = synthetic construct
SEQUENCE: 63
gaggaataaa ccatgaaaaa ttgtgtcatc gtca                          34

SEQ ID NO: 64           moltype = DNA  length = 37
FEATURE                 Location/Qualifiers
misc_feature            1..37
                        note = Synthetic: atoB-r1
source                  1..37
                        mol_type = other DNA
                        organism = synthetic construct
SEQUENCE: 64
cccaagcttc gaattcttaa ttcaaccgtt caatcac                       37

SEQ ID NO: 65           moltype = DNA  length = 35
FEATURE                 Location/Qualifiers
misc_feature            1..35
                        note = Synthetic: fadB-f1
source                  1..35
                        mol_type = other DNA
                        organism = synthetic construct
SEQUENCE: 65
taagaattcg aagctgcgga ttcaggagac tgaca                         35

SEQ ID NO: 66           moltype = DNA  length = 35
FEATURE                 Location/Qualifiers
misc_feature            1..35
```

-continued

```
                       note = Synthetic: fadB-r1
source                 1..35
                       mol_type = other DNA
                       organism = synthetic construct
SEQUENCE: 66
gttcgggccc aagctttaag ccgttttcag gtcgc                             35

SEQ ID NO: 67          moltype = DNA  length = 53
FEATURE                Location/Qualifiers
misc_feature           1..53
                       note = Synthetic: egter-f1
source                 1..53
                       mol_type = other DNA
                       organism = synthetic construct
SEQUENCE: 67
aaacggctta aagctaataa ggaggaataa accatggcaa tgtttaccac gac         53

SEQ ID NO: 68          moltype = DNA  length = 43
FEATURE                Location/Qualifiers
misc_feature           1..43
                       note = Synthetic: egter-r1
source                 1..43
                       mol_type = other DNA
                       organism = synthetic construct
SEQUENCE: 68
gttcgggccc aagcttgcgg ccgcttattg ctgtgctgcg gac                    43

SEQ ID NO: 69          moltype = DNA  length = 58
FEATURE                Location/Qualifiers
misc_feature           1..58
                       note = Synthetic: alsS-r2
source                 1..58
                       mol_type = other DNA
                       organism = synthetic construct
SEQUENCE: 69
gctcggatag gtcatgtgat attcctccta gctatgttac agggctttgg ttttcatc    58

SEQ ID NO: 70          moltype = DNA  length = 20
FEATURE                Location/Qualifiers
misc_feature           1..20
                       note = Synthetic: liuA-f1
source                 1..20
                       mol_type = other DNA
                       organism = synthetic construct
SEQUENCE: 70
atgacctatc cgagcctgaa                                              20

SEQ ID NO: 71          moltype = DNA  length = 42
FEATURE                Location/Qualifiers
misc_feature           1..42
                       note = Synthetic: liuA-r1
source                 1..42
                       mol_type = other DNA
                       organism = synthetic construct
SEQUENCE: 71
ttaccagact cgagggtacc ttagcgggtt tcattaaaca gt                     42

SEQ ID NO: 72          moltype = DNA  length = 32
FEATURE                Location/Qualifiers
misc_feature           1..32
                       note = Synthetic: bkdF-f1
source                 1..32
                       mol_type = other DNA
                       organism = synthetic construct
SEQUENCE: 72
aggagatata ccatgaccgt tgaaagcacc gc                                32

SEQ ID NO: 73          moltype = DNA  length = 56
FEATURE                Location/Qualifiers
misc_feature           1..56
                       note = Synthetic: bkdF-r1
source                 1..56
                       mol_type = other DNA
                       organism = synthetic construct
SEQUENCE: 73
catttttct gccatgagtt attcctccta caactcttaa ttaccacctt gaccgg      56

SEQ ID NO: 74          moltype = DNA  length = 22
FEATURE                Location/Qualifiers
```

```
misc_feature            1..22
                        note = Synthetic: bkdG-f1
source                  1..22
                        mol_type = other DNA
                        organism = synthetic construct
SEQUENCE: 74
atggcagaaa aaatggcaat cg                                                    22

SEQ ID NO: 75           moltype = DNA  length = 57
FEATURE                 Location/Qualifiers
misc_feature            1..57
                        note = Synthetic: bkdG-r1
source                  1..57
                        mol_type = other DNA
                        organism = synthetic construct
SEQUENCE: 75
gcttgcttcg gtcatgcttt attcctcctt taattgttaa tatgccaggc tacgatc              57

SEQ ID NO: 76           moltype = DNA  length = 20
FEATURE                 Location/Qualifiers
misc_feature            1..20
                        note = Synthetic: bkdH-f1
source                  1..20
                        mol_type = other DNA
                        organism = synthetic construct
SEQUENCE: 76
atgaccgaag caagcgttcg                                                       20

SEQ ID NO: 77           moltype = DNA  length = 42
FEATURE                 Location/Qualifiers
misc_feature            1..42
                        note = Synthetic: bkdH-r1
source                  1..42
                        mol_type = other DNA
                        organism = synthetic construct
SEQUENCE: 77
ttaccagact cgagggtacc ttagcgggtt tcattaaaca gt                              42

SEQ ID NO: 78           moltype = DNA  length = 34
FEATURE                 Location/Qualifiers
misc_feature            1..34
                        note = Synthetic: lplA-f1
source                  1..34
                        mol_type = other DNA
                        organism = synthetic construct
SEQUENCE: 78
aaggagatat acatatgtcc acattacgcc tgct                                       34

SEQ ID NO: 79           moltype = DNA  length = 50
FEATURE                 Location/Qualifiers
misc_feature            1..50
                        note = Synthetic: lplA-r1
source                  1..50
                        mol_type = other DNA
                        organism = synthetic construct
SEQUENCE: 79
tgcatcattt gccatccatt attcctcctt gggtaactac cttacagccc                      50

SEQ ID NO: 80           moltype = DNA  length = 20
FEATURE                 Location/Qualifiers
misc_feature            1..20
                        note = Synthetic: lpdA1-f1
source                  1..20
                        mol_type = other DNA
                        organism = synthetic construct
SEQUENCE: 80
atggcaaatg atgcaagcac                                                       20

SEQ ID NO: 81           moltype = DNA  length = 41
FEATURE                 Location/Qualifiers
misc_feature            1..41
                        note = Synthetic: lpdA1-r1
source                  1..41
                        mol_type = other DNA
                        organism = synthetic construct
SEQUENCE: 81
ttaccagact cgagggtacc ttaatcatgg ctatgcagcg g                               41

SEQ ID NO: 82           moltype = DNA  length = 29
```

```
FEATURE                 Location/Qualifiers
misc_feature            1..29
                        note = Synthetic: leuA(G462 D)B-f11
source                  1..29
                        mol_type = other DNA
                        organism = synthetic construct
SEQUENCE: 82
aggagatata ccatgagcca gcaagtcat                                   29

SEQ ID NO: 83           moltype = DNA  length = 29
FEATURE                 Location/Qualifiers
misc_feature            1..29
                        note = Synthetic: leuA(G462 D)B-r11
source                  1..29
                        mol_type = other DNA
                        organism = synthetic construct
SEQUENCE: 83
cacctggtca agcgcatctt taccgtggc                                   29

SEQ ID NO: 84           moltype = DNA  length = 34
FEATURE                 Location/Qualifiers
misc_feature            1..34
                        note = Synthetic: leuA(G462 D)B-f12
source                  1..34
                        mol_type = other DNA
                        organism = synthetic construct
SEQUENCE: 84
aagatgcgct tgaccaggtg gatatcgtcg ctaa                             34

SEQ ID NO: 85           moltype = DNA  length = 37
FEATURE                 Location/Qualifiers
misc_feature            1..37
                        note = Synthetic: leuA(G462 D)B-r12
source                  1..37
                        mol_type = other DNA
                        organism = synthetic construct
SEQUENCE: 85
cgccgagctc gaattcttac accccttctg ctacata                          37

SEQ ID NO: 86           moltype = DNA  length = 21
FEATURE                 Location/Qualifiers
misc_feature            1..21
                        note = Synthetic: leuA(G462 D)B-f2
source                  1..21
                        mol_type = other DNA
                        organism = synthetic construct
SEQUENCE: 86
aggagatata ccatgagcca g                                           21

SEQ ID NO: 87           moltype = DNA  length = 20
FEATURE                 Location/Qualifiers
misc_feature            1..20
                        note = Synthetic: leuA(G462 D)B-r2
source                  1..20
                        mol_type = other DNA
                        organism = synthetic construct
SEQUENCE: 87
cgccgagctc gaattcttac                                             20

SEQ ID NO: 88           moltype = DNA  length = 38
FEATURE                 Location/Qualifiers
misc_feature            1..38
                        note = Synthetic: leuCD-f1
source                  1..38
                        mol_type = other DNA
                        organism = synthetic construct
SEQUENCE: 88
cgatcgctga cgtcgatggc taagacgtta tacgaaaa                         38

SEQ ID NO: 89           moltype = DNA  length = 43
FEATURE                 Location/Qualifiers
misc_feature            1..43
                        note = Synthetic: leuCD-r1
source                  1..43
                        mol_type = other DNA
                        organism = synthetic construct
SEQUENCE: 89
ttaccagact cgagggtacc ttaattcata aacgcaggtt gtt                   43
```

-continued

```
SEQ ID NO: 90          moltype = DNA  length = 69
FEATURE                Location/Qualifiers
misc_feature           1..69
                       note = Synthetic: kan-homatoE-L
source                 1..69
                       mol_type = other DNA
                       organism = synthetic construct
SEQUENCE: 90
ttggtttaac gctgttctga cggcacccct acaaacagaa ggaatataaa catatgaata  60
tcctcctta                                                          69

SEQ ID NO: 91          moltype = DNA  length = 41
FEATURE                Location/Qualifiers
misc_feature           1..41
                       note = Synthetic: kan-ovcymatoB- R
source                 1..41
                       mol_type = other DNA
                       organism = synthetic construct
SEQUENCE: 91
tctgaaattc tgcctcgtga gtgtaggctg gagctgcttc g                      41

SEQ ID NO: 92          moltype = DNA  length = 41
FEATURE                Location/Qualifiers
misc_feature           1..41
                       note = Synthetic: cym-pCTC- atoB-ovkan-L
source                 1..41
                       mol_type = other DNA
                       organism = synthetic construct
SEQUENCE: 92
cgaagcagct ccagcctaca ctcacgaggc agaatttcag a                      41

SEQ ID NO: 93          moltype = DNA  length = 18
FEATURE                Location/Qualifiers
misc_feature           1..18
                       note = Synthetic: atoBintrecomb- R
source                 1..18
                       mol_type = other DNA
                       organism = synthetic construct
SEQUENCE: 93
gccagcccgc tttttaac                                                18

SEQ ID NO: 94          moltype = DNA  length = 35
FEATURE                Location/Qualifiers
misc_feature           1..35
                       note = Synthetic: maqu_250 7-f2
source                 1..35
                       mol_type = other DNA
                       organism = synthetic construct
SEQUENCE: 94
aaggagatat acatatgaac tactttctga ccggt                             35

SEQ ID NO: 95          moltype = DNA  length = 38
FEATURE                Location/Qualifiers
misc_feature           1..38
                       note = Synthetic: maqu_250 7-r2
source                 1..38
                       mol_type = other DNA
                       organism = synthetic construct
SEQUENCE: 95
ttgagatctg ccatatgtta ccagtaaatg ccacgcat                          38

SEQ ID NO: 96          moltype = DNA  length = 56
FEATURE                Location/Qualifiers
misc_feature           1..56
                       note = Synthetic: maqu_250 7-r3
source                 1..56
                       mol_type = other DNA
                       organism = synthetic construct
SEQUENCE: 96
ttaaattccg gcataattac tccttcactg ccatattacc agtaaatgcc acgcat      56

SEQ ID NO: 97          moltype = DNA  length = 39
FEATURE                Location/Qualifiers
misc_feature           1..39
                       note = Synthetic: cbjALD-f2
source                 1..39
                       mol_type = other DNA
                       organism = synthetic construct
SEQUENCE: 97
```

-continued

```
aaggagatat acatatgaat aaagacacac taataccta                          39

SEQ ID NO: 98           moltype = DNA  length = 37
FEATURE                 Location/Qualifiers
misc_feature            1..37
                        note = Synthetic: cbjALD-r2
source                  1..37
                        mol_type = other DNA
                        organism = synthetic construct
SEQUENCE: 98
ttgagatctg ccatatgtta gccggcaagt acacatc                            37

SEQ ID NO: 99           moltype = DNA  length = 55
FEATURE                 Location/Qualifiers
misc_feature            1..55
                        note = Synthetic: cbjALD-r3
source                  1..55
                        mol_type = other DNA
                        organism = synthetic construct
SEQUENCE: 99
ttaaattccg gcataattac tccttcactg ccatattagc cggcaagtac acatc       55

SEQ ID NO: 100          moltype = DNA  length = 39
FEATURE                 Location/Qualifiers
misc_feature            1..39
                        note = Synthetic: adhE2-f1
source                  1..39
                        mol_type = other DNA
                        organism = synthetic construct
SEQUENCE: 100
aaggagatat acatatgaaa gttacaaatc aaaaagaac                          39

SEQ ID NO: 101          moltype = DNA  length = 47
FEATURE                 Location/Qualifiers
misc_feature            1..47
                        note = Synthetic: adhE2-r1
source                  1..47
                        mol_type = other DNA
                        organism = synthetic construct
SEQUENCE: 101
ttgagatctg ccatatgtta aaatgatttt atatagatat ccttaag                 47

SEQ ID NO: 102          moltype = DNA  length = 33
FEATURE                 Location/Qualifiers
misc_feature            1..33
                        note = Synthetic: hmgs-f1
source                  1..33
                        mol_type = other DNA
                        organism = synthetic construct
SEQUENCE: 102
aggagatata ccatgaccat cggcatcgat aag                                33

SEQ ID NO: 103          moltype = DNA  length = 38
FEATURE                 Location/Qualifiers
misc_feature            1..38
                        note = Synthetic: hmgs-r1
source                  1..38
                        mol_type = other DNA
                        organism = synthetic construct
SEQUENCE: 103
cgccgagctc gaattcttat tccggacgat gatattcg                           38

SEQ ID NO: 104          moltype = DNA  length = 51
FEATURE                 Location/Qualifiers
misc_feature            1..51
                        note = Synthetic: aibA-f1
source                  1..51
                        mol_type = other DNA
                        organism = synthetic construct
SEQUENCE: 104
tccggaataa gaattgtagg aggaatacta catgaaaacc gcacgttggt g            51

SEQ ID NO: 105          moltype = DNA  length = 56
FEATURE                 Location/Qualifiers
misc_feature            1..56
                        note = Synthetic: aibA-r1
source                  1..56
                        mol_type = other DNA
                        organism = synthetic construct
```

-continued

```
SEQUENCE: 105
cagggttgcg ctcatggttt attcctcctt aaaatcttat gctgcacgac gggtca      56

SEQ ID NO: 106          moltype = DNA  length = 20
FEATURE                 Location/Qualifiers
misc_feature            1..20
                        note = Synthetic: aibB-f1
source                  1..20
                        mol_type = other DNA
                        organism = synthetic construct
SEQUENCE: 106
atgagcgcaa ccctggatat                                              20

SEQ ID NO: 107          moltype = DNA  length = 40
FEATURE                 Location/Qualifiers
misc_feature            1..40
                        note = Synthetic: aibB-r1
source                  1..40
                        mol_type = other DNA
                        organism = synthetic construct
SEQUENCE: 107
cctgcaggcg cgccgagctc ttatgcacca accagtgcat                        40

SEQ ID NO: 108          moltype = DNA  length = 36
FEATURE                 Location/Qualifiers
misc_feature            1..36
                        note = Synthetic: liuC-f1
source                  1..36
                        mol_type = other DNA
                        organism = synthetic construct
SEQUENCE: 108
aaggagatat acatatgccg gaatttaaag ttgatg                            36

SEQ ID NO: 109          moltype = DNA  length = 37
FEATURE                 Location/Qualifiers
misc_feature            1..37
                        note = Synthetic: liuC-r1
source                  1..37
                        mol_type = other DNA
                        organism = synthetic construct
SEQUENCE: 109
ttgagatctg ccatattaac gacctttata aaccggt                           37

SEQ ID NO: 110          moltype = DNA  length = 50
FEATURE                 Location/Qualifiers
misc_feature            1..50
                        note = Synthetic: chnD-f2
source                  1..50
                        mol_type = other DNA
                        organism = synthetic construct
SEQUENCE: 110
ttaatatggc agatcaggag gaatagctga tgcactgcta ttgtgttacc             50

SEQ ID NO: 111          moltype = DNA  length = 37
FEATURE                 Location/Qualifiers
misc_feature            1..37
                        note = Synthetic: chnD-r2
source                  1..37
                        mol_type = other DNA
                        organism = synthetic construct
SEQUENCE: 111
ctttaccaga ctcgagtcaa ttttcgtgca tcagaac                           37

SEQ ID NO: 112          moltype = DNA  length = 51
FEATURE                 Location/Qualifiers
misc_feature            1..51
                        note = Synthetic: yjgB-f1
source                  1..51
                        mol_type = other DNA
                        organism = synthetic construct
SEQUENCE: 112
ttaatatggc agatcaggag gaatagctga tgtcgatgat aaaaagctat g           51

SEQ ID NO: 113          moltype = DNA  length = 37
FEATURE                 Location/Qualifiers
misc_feature            1..37
                        note = Synthetic: yjgB-r1
source                  1..37
                        mol_type = other DNA
```

```
                        organism = synthetic construct
SEQUENCE: 113
ctttaccaga ctcgagtcaa aaatcggctt tcaacac                          37

SEQ ID NO: 114          moltype = DNA  length = 51
FEATURE                 Location/Qualifiers
misc_feature            1..51
                        note = Synthetic: yahK-f1
source                  1..51
                        mol_type = other DNA
                        organism = synthetic construct
SEQUENCE: 114
ttaatatggc agatcaggag gaatagctga tgaagatcaa agctgttggt g          51

SEQ ID NO: 115          moltype = DNA  length = 37
FEATURE                 Location/Qualifiers
misc_feature            1..37
                        note = Synthetic: yahK-r1
source                  1..37
                        mol_type = other DNA
                        organism = synthetic construct
SEQUENCE: 115
ctttaccaga ctcgagtcag tctgttagtg tgcgatt                          37

SEQ ID NO: 116          moltype = DNA  length = 70
FEATURE                 Location/Qualifiers
misc_feature            1..70
                        note = Synthetic: Reverse primer
source                  1..70
                        mol_type = other DNA
                        organism = synthetic construct
SEQUENCE: 116
gcattggcgg cggtcaggga attgcgatgg tgattgaacg gttgaattaa aaaatgagac  60
gttgatcggc                                                        70

SEQ ID NO: 117          moltype = DNA  length = 70
FEATURE                 Location/Qualifiers
misc_feature            1..70
                        note = Synthetic: Forward primer
source                  1..70
                        mol_type = other DNA
                        organism = synthetic construct
SEQUENCE: 117
caacaaacag acaatctggt ctgtttgtat tatgaacgaa ggagagatct atgacgcgtg  60
aagtggtagt                                                        70

SEQ ID NO: 118          moltype = DNA  length = 70
FEATURE                 Location/Qualifiers
misc_feature            1..70
                        note = Synthetic: Reverse primer
source                  1..70
                        mol_type = other DNA
                        organism = synthetic construct
SEQUENCE: 118
gatgttcaag aaaacacccg ataactttcg ctatcgggtg tttttattga tcagatacgc  60
tcgaagatgg                                                        70

SEQ ID NO: 119          moltype = DNA  length = 71
FEATURE                 Location/Qualifiers
misc_feature            1..71
                        note = Synthetic: Forward primer
source                  1..71
                        mol_type = other DNA
                        organism = synthetic construct
SEQUENCE: 119
ttgacggcgg tttcagcatt gctgcaatga acgaactcga actgaaataa gtgtaggctg  60
gagctgcttc g                                                      71

SEQ ID NO: 120          moltype = DNA  length = 90
FEATURE                 Location/Qualifiers
misc_feature            1..90
                        note = Synthetic: Reverse primer
source                  1..90
                        mol_type = other DNA
                        organism = synthetic construct
SEQUENCE: 120
aacagagata acgggcggca gaacgccgcc catctttacc aacagaacga ttatttcagt  60
tcgagttcgt tttattgctg tgctgcggac                                  90
```

```
SEQ ID NO: 121          moltype = DNA  length = 70
FEATURE                 Location/Qualifiers
misc_feature            1..70
                        note = Synthetic: Forward primer
source                  1..70
                        mol_type = other DNA
                        organism = synthetic construct
SEQUENCE: 121
caacaaacag acaatctggt ctgtttgtat tatgaacgaa ggagagatct atggcaatgt  60
ttaccacgac                                                         70

SEQ ID NO: 122          moltype = DNA  length = 69
FEATURE                 Location/Qualifiers
misc_feature            1..69
                        note = Synthetic: Reverse primer
source                  1..69
                        mol_type = other DNA
                        organism = synthetic construct
SEQUENCE: 122
ttaaacccgc tcaaacaccg tcgcaatacc ctgacccaga ccgatacaca ttattgctgt  60
gctgcggac                                                          69

SEQ ID NO: 123          moltype = DNA  length = 72
FEATURE                 Location/Qualifiers
misc_feature            1..72
                        note = Synthetic: F1 primer
source                  1..72
                        mol_type = other DNA
                        organism = synthetic construct
SEQUENCE: 123
atcctccggt tgagccagcc cgtccggttg gcgacctgaa aacggcttaa atgattgaac  60
aagatggatt gc                                                      72

SEQ ID NO: 124          moltype = DNA  length = 42
FEATURE                 Location/Qualifiers
misc_feature            1..42
                        note = Synthetic: R1 primer
source                  1..42
                        mol_type = other DNA
                        organism = synthetic construct
SEQUENCE: 124
taaggggtga cgccaaagta tcagaagaac tcgtcaagaa gg                     42

SEQ ID NO: 125          moltype = DNA  length = 42
FEATURE                 Location/Qualifiers
misc_feature            1..42
                        note = Synthetic: F2 primer
source                  1..42
                        mol_type = other DNA
                        organism = synthetic construct
SEQUENCE: 125
ccttcttgac gagttcttct gatactttgg cgtcacccct ta                     42

SEQ ID NO: 126          moltype = DNA  length = 73
FEATURE                 Location/Qualifiers
misc_feature            1..73
                        note = Synthetic: R2 primer
source                  1..73
                        mol_type = other DNA
                        organism = synthetic construct
SEQUENCE: 126
atcggggtgc gaattgcatc gacaatgaca acctgttcca ttgtgactcc atcaaaggga  60
aaactgtcca tat                                                     73

SEQ ID NO: 127          moltype = DNA  length = 69
FEATURE                 Location/Qualifiers
misc_feature            1..69
                        note = Synthetic: Forward primer
source                  1..69
                        mol_type = other DNA
                        organism = synthetic construct
SEQUENCE: 127
ttgagccagc ccgtccggtt ggcgacctga aaacggctta aggagtcaca atggccaagt  60
tgaccagtg                                                          69

SEQ ID NO: 128          moltype = DNA  length = 68
FEATURE                 Location/Qualifiers
misc_feature            1..68
                        note = Synthetic: Reverse primer
```

```
source                  1..68
                        mol_type = other DNA
                        organism = synthetic construct
SEQUENCE: 128
ttaaacccgc tcaaacaccg tcgcaatacc ctgacccaga ccgatacaca tcagtcctgc  60
tcctctgc                                                           68

SEQ ID NO: 129          moltype = DNA  length = 40
FEATURE                 Location/Qualifiers
misc_feature            1..40
                        note = Synthetic: fadM-f1
source                  1..40
                        mol_type = other DNA
                        organism = synthetic construct
SEQUENCE: 129
ttaaagagga gaaaggtacc atgcaaacac aaatcaaagt                        40

SEQ ID NO: 130          moltype = DNA  length = 73
FEATURE                 Location/Qualifiers
misc_feature            1..73
                        note = Synthetic: Forward primer
source                  1..73
                        mol_type = other DNA
                        organism = synthetic construct
SEQUENCE: 130
gatgttcaag aaaacacccg ataactttcg ctatcgggtg tttttattga atcaaaggga  60
aaactgtcca tat                                                     73

SEQ ID NO: 131          moltype = DNA  length = 30
FEATURE                 Location/Qualifiers
misc_feature            1..30
                        note = Synthetic: MK-IF-fwd
source                  1..30
                        mol_type = other DNA
                        organism = synthetic construct
SEQUENCE: 131
aggagatata ccatgagcct gccgtttctg                                   30

SEQ ID NO: 132          moltype = DNA  length = 34
FEATURE                 Location/Qualifiers
misc_feature            1..34
                        note = Synthetic: MK-IF-rev
source                  1..34
                        mol_type = other DNA
                        organism = synthetic construct
SEQUENCE: 132
cgccgagctc gaattcttag ctggtccacg gcag                              34

SEQ ID NO: 133          moltype = DNA  length = 37
FEATURE                 Location/Qualifiers
misc_feature            1..37
                        note = Synthetic: PMK-IF-fwd
source                  1..37
                        mol_type = other DNA
                        organism = synthetic construct
SEQUENCE: 133
gaccagctaa gaatttagga ggaataactc atgagcg                           37

SEQ ID NO: 134          moltype = DNA  length = 41
FEATURE                 Location/Qualifiers
misc_feature            1..41
                        note = Synthetic: PMK-IF-rev
source                  1..41
                        mol_type = other DNA
                        organism = synthetic construct
SEQUENCE: 134
cgccgagctc gaattcattc ctcctttaat tgttatttgt c                      41

SEQ ID NO: 135          moltype = DNA  length = 35
FEATURE                 Location/Qualifiers
misc_feature            1..35
                        note = Synthetic: PMD-IF-fwd
source                  1..35
                        mol_type = other DNA
                        organism = synthetic construct
SEQUENCE: 135
aaggaggaat gaattatgac cgtttatacc gcaag                             35

SEQ ID NO: 136          moltype = DNA  length = 34
```

```
FEATURE                Location/Qualifiers
misc_feature           1..34
                       note = Synthetic: PMD-IF-rev
source                 1..34
                       mol_type = other DNA
                       organism = synthetic construct
SEQUENCE: 136
cgccgagctc gaattcttat tctttcggca gacc                        34

SEQ ID NO: 137         moltype = DNA  length = 43
FEATURE                Location/Qualifiers
misc_feature           1..43
                       note = Synthetic: idi-GB-fwd
source                 1..43
                       mol_type = other DNA
                       organism = synthetic construct
SEQUENCE: 137
gtttaacttt aagaaggaga tatacatgca aacggaacac gtc              43

SEQ ID NO: 138         moltype = DNA  length = 43
FEATURE                Location/Qualifiers
misc_feature           1..43
                       note = Synthetic: idi-GB-rev
source                 1..43
                       mol_type = other DNA
                       organism = synthetic construct
SEQUENCE: 138
atggtttatt cctccttaaa ttatttaagc tgggtaaatg cag              43

SEQ ID NO: 139         moltype = DNA  length = 47
FEATURE                Location/Qualifiers
misc_feature           1..47
                       note = Synthetic: trGPPS2-IF-fwd
source                 1..47
                       mol_type = other DNA
                       organism = synthetic construct
SEQUENCE: 139
tttaaggagg aataaaccat ggtggaattt gactttaaca aatatat          47

SEQ ID NO: 140         moltype = DNA  length = 36
FEATURE                Location/Qualifiers
misc_feature           1..36
                       note = Synthetic: GPPS2-GB-rev
source                 1..36
                       mol_type = other DNA
                       organism = synthetic construct
SEQUENCE: 140
gtgatggctg ctgccttagt tctgacgaaa tgcaac                      36

SEQ ID NO: 141         moltype = DNA  length = 38
FEATURE                Location/Qualifiers
misc_feature           1..38
                       note = Synthetic: CymR-GB-fwd
source                 1..38
                       mol_type = other DNA
                       organism = synthetic construct
SEQUENCE: 141
ctgcaggtcg acaagcttgc aggcgtatca cgaggcag                    38

SEQ ID NO: 142         moltype = DNA  length = 50
FEATURE                Location/Qualifiers
misc_feature           1..50
                       note = Synthetic: CymR-GB-rev
source                 1..50
                       mol_type = other DNA
                       organism = synthetic construct
SEQUENCE: 142
catctgctgc ttcgctcata tgagatctct ccttcgttca taatacaaac       50

SEQ ID NO: 143         moltype = DNA  length = 25
FEATURE                Location/Qualifiers
misc_feature           1..25
                       note = Synthetic: NphB- cumate-GB- fwd
source                 1..25
                       mol_type = other DNA
                       organism = synthetic construct
SEQUENCE: 143
tctcatatga gcgaagcagc agatg                                  25
```

-continued

```
SEQ ID NO: 144         moltype = DNA  length = 48
FEATURE                Location/Qualifiers
misc_feature           1..48
                       note = Synthetic: NphB- cumate-GB- rev
source                 1..48
                       mol_type = other DNA
                       organism = synthetic construct
SEQUENCE: 144
agcagcggtt tctttaccag actcgaggtc aatcttccag gctatcaa              48

SEQ ID NO: 145         moltype = DNA  length = 33
FEATURE                Location/Qualifiers
misc_feature           1..33
                       note = Synthetic: NphB-IF-fwd
source                 1..33
                       mol_type = other DNA
                       organism = synthetic construct
SEQUENCE: 145
aaggagatat acataatgag cgaagcagca gat                              33

SEQ ID NO: 146         moltype = DNA  length = 35
FEATURE                Location/Qualifiers
misc_feature           1..35
                       note = Synthetic: NphB-IF-rev
source                 1..35
                       mol_type = other DNA
                       organism = synthetic construct
SEQUENCE: 146
ttaccagact cgaggtcaat cttccaggct atcaa                            35
```